US010906899B2

(12) United States Patent
Plemper et al.

(10) Patent No.: US 10,906,899 B2
(45) Date of Patent: Feb. 2, 2021

(54) BICYCLIC FUSED PYRAZOLE DERIVATIVES FOR THE TREATMENT OF RSV

(71) Applicants: GEORGIA STATE UNIVERSITY RESEARCH FOUNDATION, INC., Atlanta, GA (US); AVIRAGEN THERAPEUTICS, INC., Alpharetta, GA (US)

(72) Inventors: Richard K. Plemper, Decatur, GA (US); Eddy Lee, Alpharetta, GA (US); John Vernachio, Alpharetta, GA (US); Elyse Bourque, L'etang-du Nord (CA)

(73) Assignee: GEORGIA STATE UNIVERSITY RESEARCH FOUNDATION, INC., Atlanta, GA (US)

(*) Notice: Subject to any disclaimer, the term of this patent is extended or adjusted under 35 U.S.C. 154(b) by 0 days.

(21) Appl. No.: 16/099,969

(22) PCT Filed: May 10, 2017

(86) PCT No.: PCT/US2017/031961
§ 371 (c)(1),
(2) Date: Nov. 8, 2018

(87) PCT Pub. No.: WO2017/196982
PCT Pub. Date: Nov. 16, 2017

(65) Prior Publication Data
US 2019/0144441 A1 May 16, 2019

Related U.S. Application Data

(60) Provisional application No. 62/359,894, filed on Jul. 8, 2016, provisional application No. 62/333,992, filed on May 10, 2016.

(51) Int. Cl.
*C07D 471/02* (2006.01)
*C07D 471/04* (2006.01)
*C07D 413/12* (2006.01)
*C07D 491/12* (2006.01)
*C07D 491/02* (2006.01)
*C07D 231/08* (2006.01)
*A61K 31/444* (2006.01)
*A61K 31/437* (2006.01)
*A61P 31/12* (2006.01)
*C07D 519/00* (2006.01)

(52) U.S. Cl.
CPC ......... *C07D 471/04* (2013.01); *A61K 31/437* (2013.01); *A61K 31/444* (2013.01); *A61P 31/12* (2018.01); *C07D 519/00* (2013.01); *C12N 2760/18511* (2013.01)

(58) Field of Classification Search
CPC .. C07D 471/02; C07D 471/04; C07D 413/12; C07D 491/02; C07D 231/08
See application file for complete search history.

(56) References Cited

U.S. PATENT DOCUMENTS

| | | | |
|---|---|---|---|
| 2,841,582 A | 7/1958 | Zimmermann | |
| 3,767,653 A | 10/1973 | Krapcho | |
| 4,397,849 A | 8/1983 | Teraji et al. | |
| 8,389,518 B2 | 3/2013 | Page et al. | |
| 9,073,919 B2 | 7/2015 | Page et al. | |
| 2004/0147546 A1 | 7/2004 | Tanaka et al. | |
| 2004/0254200 A1 | 12/2004 | Davis et al. | |
| 2008/0280881 A1 | 11/2008 | Bonfanti et al. | |
| 2010/0048560 A1* | 2/2010 | Page .................... | C07D 471/04 514/234.2 |
| 2011/0269757 A1 | 11/2011 | Page et al. | |
| 2013/0123256 A1 | 5/2013 | Page et al. | |

FOREIGN PATENT DOCUMENTS

WO    WO-2004080466    9/2004

OTHER PUBLICATIONS

International Search Report for PCT/US17/31961, dated August Jul. 9, 2017.
Written Opinion of the International Search Authority for PCT/US17/31961, dated Jul. 9, 2017.
International Preliminary Report on Patentability for PCT/US17/31961 dated Nov. 13, 2018.
Office Action dated Dec. 27, 2019 in Canadian Application No. 3,023,922.
STN Colombus-RN: 1115981-40-2, Aurora Fine Chemicals, Mar. 5, 2009.
Extended Search Report dated Dec. 17, 2019 in corresponding European Application No. 17796764.3.
Russo, F, et al. "Pyrazolothiazolopyrimidine Derivatives as a Novel Class of Anti-Inflammatory or Antinociceptive Agents: Synthesis, Structural Characterization and Pharmacological Evaluation." European Journal of Medicinal Chemistry, vol. 28, No. 5, Jan. 1, 1993, pp. 363-376., doi:10.1016/0223-5234(93)90123-v.
Bookser, Brett C., and Nicholas B. Raffaele. "High-Throughput Five Minute Microwave Accelerated Glycosylation Approach to the Synthesis of Nucleoside Libraries." The Journal of Organic Chemistry, vol. 72, No. 1, Jan. 1, 2007, pp. 173-179., doi:10.1021/jo061885I.
Komarova, E. S., et al. "4,5-Diamino-1-Phenyl-1,7-Dihydro-6H-Pyrazolo[3,4-b]Pyridin-6-One in the Synthesis of Fused Tricyclic Systems." Russian Chemical Bulletin, vol. 56, No. 11, Nov. 1, 2007, pp. 2337-2343., doi:10.1007/s11172-007-0369-5.

(Continued)

Primary Examiner — Bruck Kifle
(74) Attorney, Agent, or Firm — B. Aaron Schulman, Esq.; Stites & Harbison, PLLC

(57) ABSTRACT

Disclosed herein are compounds and compositions for treating or inhibiting RSV and related members of the pneumovirus and paramyxovirus families such as human metapneumovirus, mumps virus, human parainfluenzaviruses, and Nipah and hendra virus, and methods of treatment or prevention thereof.

19 Claims, 6 Drawing Sheets

(56) References Cited

OTHER PUBLICATIONS

Kidwai, Mazaahir, and Kavita Singhal. "Green Synthesis of Fused Pyrimido Derivatives in Aqueous Medium." Journal of Heterocyclic Chemistry, vol. 44, No. 6, Nov. 1, 2007, pp. 1253-1257., doi:10.1002/jhet.5570440605.

Quiroga, Jairo, et al. "Preparation of 6-Chloropyrazolo[3,4-b]Pyridine-5-Carbaldehydes by Vilsmeier—Haack Reaction and Its Use in the Synthesis of Heterocyclic Chalcones and Dipyrazolopyridines." Tetrahedron Letters, vol. 51, No. 21, May 26, 2010, pp. 2928-2930., doi:10.1016/j.tetlet.2010.03.117.

Fink, Karin, et al. "Dual Role of NOX2 in Respiratory Syncytial Virus- and Sendai Virus-Induced Activation of NF-KB in Airway Epithelial Cells." The Journal of Immunology, vol. 180, No. 10, May 15, 2008, pp. 6911-6922., doi:10.4049/jimmunol.180.10.6911.

Office Action dated Nov. 26, 2019 in corresponding Canadian Application No. 3,027,097.

Canadian Office Action dated Sep. 18, 2020 in Canadian Application No. 3,027,097.

Fink, et al, "Dual Role of NOX2 in Respiratory Syncytial Virus-and Sendai Virus-Induced Activation of NF-KB in Airway Epithelial Cells", May 15, 2008, pp. 6911-6922, vol. 180, No. 10, J. Immunology.

* cited by examiner

FIGURE 6

BICYCLIC FUSED PYRAZOLE DERIVATIVES FOR THE TREATMENT OF RSV

CROSS-REFERENCE TO RELATED APPLICATIONS

This application claims the benefit of U.S. Provisional Application Ser. No 62/359,894, filed Jul. 8, 2016, and Ser. No. 62/333,992, filed May 10, 2016, the disclosures of which are incorporated herein in their entirety.

STATEMENT REGARDING FEDERALLY SPONSORED RESEARCH AND DEVELOPMENT

This invention was made with government support under grants HD079327 and AI071002 awarded by the National Institutes of Health (NIH). The government has certain rights in the invention.

FIELD OF THE INVENTION

The invention relates to the use of small molecule therapeutics for the treatment of respiratory syncytial virus (RSV) and related members of the pneumovirus and paramyxovirus family such as human metapneumovirus, mumps virus, human parainfluenzaviruses, and Nipah and hendra virus.

BACKGROUND

Respiratory syncytial virus (RSV) is a member of the paramyxovirus family, which consists of mostly highly contagious nonsegmented, negative polarity RNA viruses that spread through the respiratory route. Specifically, RSV is a member of the order Mononegavirales, which consists of the non-segmented negative strand RNA viruses in the Families Paramyxoviridae, Pneumoviridae; Bunyaviridae, Rhabdoviridae and Filoviridae. RSV of humans (often also termed RSV or HRSV) is a member of the Pneumoviridae. Based on genetic and antigenic variations in the structural proteins, RSV is classified into two subgroups, A and B (Mufson, M. et al., J. Gen. Virol. 66:2111-2124). Other members of the Pneumovirus family include viruses such as bovine RSV (BRSV), ovine RSV (ORSV), pneumonia virus of mice (PVM), and the human metapneumoviruses amongst others.

In addition to the genome features described above, family characteristics include a lipid envelope containing one or more glycoprotein species considered to be associated with attachment and entry of the host cell. Entry is considered to require a process by which the viral envelope fuses with the membrane of the host cell. Fusion of infected cells with, for example, their neighbors, can also result in the formation of fused multinucleate cells known as syncytia in some cases. The fusion process is believed to be glycoprotein mediated and is a feature shared with diverse enveloped viruses in other taxonomic groups. In the case of the pneumo- and paramyxoviruses, virions characteristically express a fusion glycoprotein (F), which mediates membrane fusion.

Respiratory syncytial virus (RSV) is the leading cause of acute upper and lower respiratory tract infections (LRTI) in adults, young children and infants. Although at risk populations include the hospitalized, elderly and high-risk adults, RSV is primarily considered to be a pediatric disease due to the prevalence and severity of unfavorable outcomes in infants. Acute LRTI infections are a leading cause of global childhood mortality and morbidity. Serological evidence indicates that in the western world approximately 95% of all children have been infected with RSV by the age of two and 100% of children have been exposed by the time they reach adulthood.

RSV disease is thus the leading cause of virus infection-induced death among children less than 1 year of age and can be life-threatening to the elderly and the immunocompromised. Reinfection with RSV can occur throughout life, but infants born prematurely, or with bronchopulmonary dysplasia or a congenital heart defect, are at highest risk of developing severe disease. In a typical case, initial RSV infection of airway epithelia cells is followed by rapid spread from the nasopharynx to the lower airways that can affect respiratory function through excessive mucus, necrotic epithelial debris, and inflammatory cells obstructing the airways.

RSV is a seasonal infectious disease that generally runs from November to March/April in the Northern Hemisphere. In more tropical climates, the annual epidemics are more variable, often coinciding with the wet season. In most cases the RSV infections will only cause minor upper respiratory illness with symptoms resembling that of the common cold. However, severe infection with the virus may result in bronchiolitis or pneumonia, which may result in hospitalization or death. Further, since the immune response to RSV infection is not protective, RSV infections reoccur throughout adulthood. Annual re-infection rates in adults of 3-6% have been observed.

RSV infections place a significant burden on the healthcare system. This is particularly so in the case of infants such as, for example, immunodeficient infants, which on average spend twice as long in hospital as other patients with an RSV infection (7-8 days compared to 3-4 days). Hospitalization of infants with acute RSV-related bronchiolitis or RSV-related pneumonia involves supportive care management with oxygen therapy, fluids to prevent dehydration, nasal suctioning and respiratory support. There is also an economic impact associated with parents taking time away from work to care for their child.

Attempts to develop an effective RSV vaccine have been fruitless thus far, because the virus is poorly immunogenic overall and neutralizing antibody titers wane quickly after infection. Although ribavirin has been approved for RSV treatment, it has not been widely adopted in clinical use due to efficacy and toxicity issues. The humanized neutralizing antibody palivizumab is used for immunoprophylaxis of high-risk pediatric patients, but high costs prohibit broad-scale implementation.

Accordingly, there remains an urgent and unmet need for new compounds that are useful in the treatment and prevention of RSV infections. Small-molecule drug-like therapeutics have high promise to provide a novel avenue towards RSV disease management and prevention. It is therefore an object of the present invention to provide new small-molecule therapeutics classes for the treatment of human patients and other hosts infected with RSV.

SUMMARY

Disclosed herein are compounds, compositions, and methods of inhibiting RSV, or treating or preventing RSV infection in a patient in need thereof. RSV can be inhibited, and RSV infection can be treated or prevented by administering to a patient in need thereof a composition containing an anti-RSV compound of Formula 1:

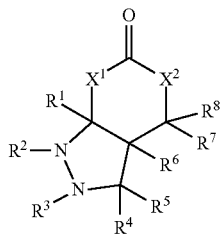

[Formula 1]

or a pharmaceutically acceptable salt thereof, wherein
$X^1$ and $X^2$ are independently selected from —$NR^0$ and —$CR^aR^b$;
$R^1$, $R^4$, $R^5$, $R^6$, $R^7$, $R^8$, $R^a$ and $R^b$ are independently selected from —$R^c$, —$OR^{c'}$, —$N(R^c)_2$, —$SR^c$, —$SO_2R^c$, —$SO_2N(R^c)_2$; —$C(O)R^c$, $OC(O)R^c$, —$COOR^c$, —$C(O)N(R^c)_2$, —$OC(O)N(R^c)_2$, —$N(R^c)C(O)$, —$N(R^c)C(O)N(R^c)_2$, —F, —Cl, —Br, —I, —CN, —$NO_2$;
$R^0$, $R^2$, and $R^3$ are independently selected from —$R^c$, —$SO_2R^c$, —$SO_2N(R^c)_2$; —$C(O)R^c$, —$COOR^c$, —$C(O)N(R^c)_2$;
wherein two or more of $R^0$, $R^1$, $R^2$, $R^3$, $R^4$, $R^5$, $R^6$, $R^7$, $R^8$, $R^a$ and $R^b$ can together form a ring;
wherein any two of the aforementioned R groups, when adjacent, can together form a double bond;
wherein two of the aforementioned R groups, when geminal, can together form a carbonyl, olefin or imine;
wherein $R^c$ is in each case independently selected from hydrogen, $C_{1-8}$ alkyl, $C_{3-8}$ cycloalkyl, $C_{2-8}$ heterocyclyl, $C_{6-12}$ aryl, $C_{3-12}$ heteroaryl, $C_{1-8}$ alkyl-$C_{3-8}$ cycloalkyl, $C_{1-8}$ alkyl-$C_{2-8}$ heterocyclyl, $C_{1-8}$ alkyl-$C_{6-12}$ aryl, and $C_{1-8}$ alkyl-$C_{3-12}$ heteroaryl; wherein one or more of $R^c$ can together form a ring with any one or more of $R^0$, $R^1$, $R^2$, $R^3$, $R^4$, $R^5$, $R^6$, $R^7$, $R^8$, $R^a$, $R^b$ and $R^c$.

The details of one or more embodiments are set forth in the descriptions below. Other features, objects, and advantages will be apparent from the description and from the claims.

BRIEF DESCRIPTION OF THE FIGURES

Figure 6:
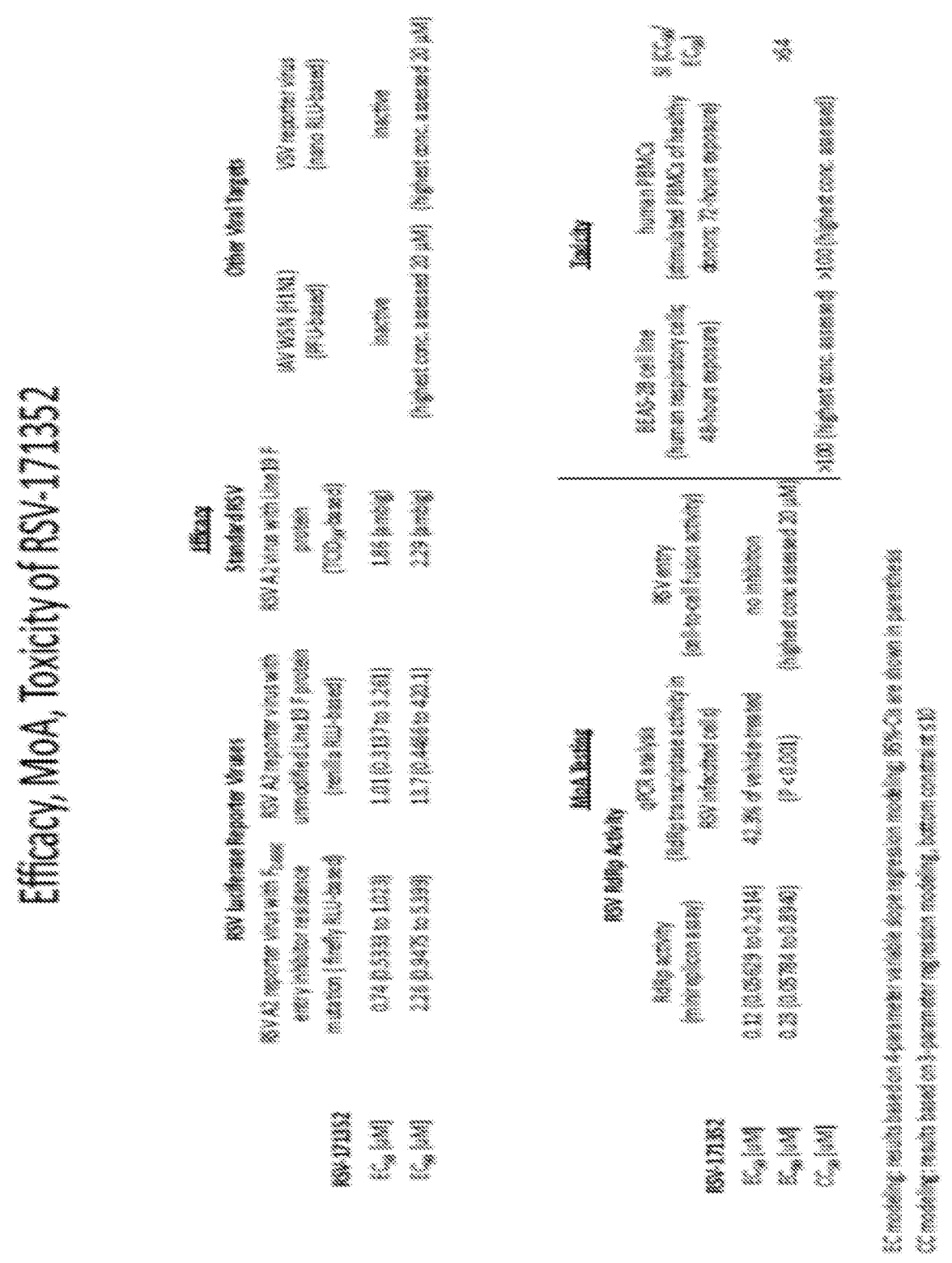

FIG. 6 depicts activity of an RSV inhibitor in accordance with the invention [RSVP-171352] in tabular format.

DETAILED DESCRIPTION

Figure 1:
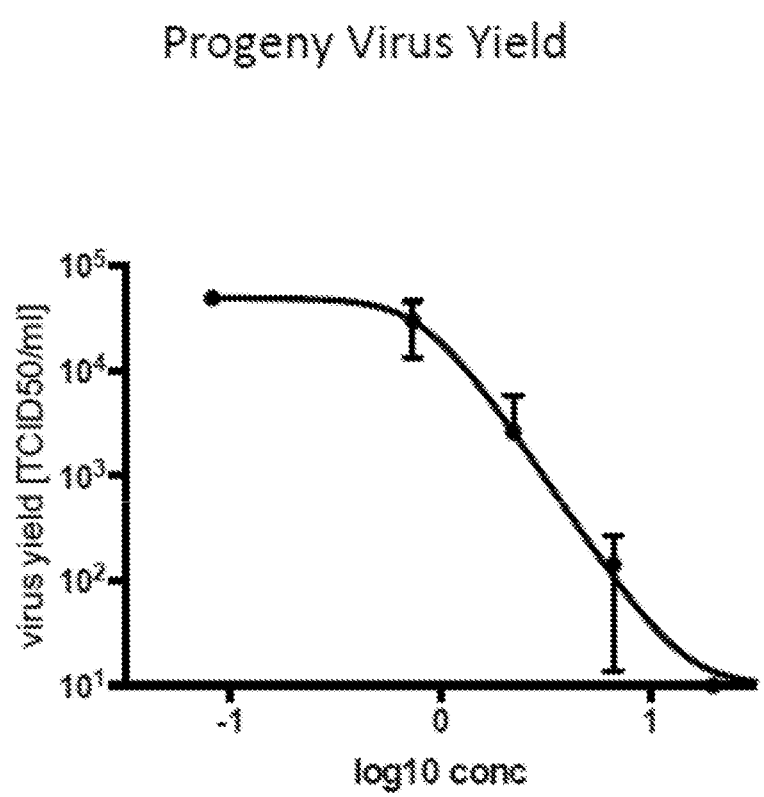
FIG. 1 includes a depiction of the virus yield of an RSV inhibitor in accordance with the invention [RSVP-156784] as a function of concentration.

Before the present compounds, compositions, methods and systems are disclosed and described, it is to be understood that the methods and systems are not limited to specific synthetic methods, specific compounds, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

The term "alkyl" as used herein is a branched or unbranched hydrocarbon group such as methyl, ethyl, n-propyl, isopropyl, n-butyl, isobutyl, t-butyl, pentyl, hexyl, heptyl, octyl, nonyl, decyl, dodecyl, and the like. The alkyl group can also be substituted or unsubstituted. Unless stated otherwise, the term "alkyl" contemplates both substituted and unsubstituted alkyl groups. The alkyl group can be substituted with one or more groups including, but not limited to, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol as described herein. An alkyl group which contains no double or triple carbon-carbon bonds is designated a saturated alkyl group, whereas an alkyl group having one or more such bonds is designated an unsaturated alkyl group. Unsaturated alkyl groups having a double bond can be designated alkenyl groups, and unsaturated alkyl groups having a triple bond can be designated alkynyl groups. Unless specified to the contrary, the term alkyl embraces both saturated and unsaturated groups.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is replaced with a heteroatom such as, but not limited to, nitrogen, oxygen, sulfur, selenium or phosphorus. The cycloalkyl group and heterocycloalkyl group can be substituted or unsubstituted. Unless stated otherwise, the terms "cycloalkyl" and "heterocycloalkyl" contemplate both substituted and unsubstituted cyloalkyl and heterocycloalkyl groups. The cycloalkyl group and heterocycloalkyl group can be substituted with one or more groups including, but not limited to, alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol as described herein. A cycloalkyl group which contains no double or triple carbon-carbon bonds is designated a saturated cycloalkyl group, whereas an cycloalkyl group having one or more such bonds (yet is still not aromatic) is designated an unsaturated cycloalkyl group. Unless specified to the contrary, the term alkyl embraces both saturated and unsaturated groups.

The term "aryl" as used herein is an aromatic ring composed of carbon atoms. Examples of aryl groups include, but are not limited to, phenyl and naphthyl, etc. The term "heteroaryl" is an aryl group as defined above where at least one of the carbon atoms of the ring is replaced with a heteroatom such as, but not limited to, nitrogen, oxygen, sulfur, selenium or phosphorus. The aryl group and heteroaryl group can be substituted or unsubstituted. Unless stated otherwise, the terms "aryl" and "heteroaryl" contemplate both substituted and unsubstituted aryl and heteroaryl groups. The aryl group and heteroaryl group can be substituted with one or more groups including, but not limited to, alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol as described herein.

Exemplary heteroaryl and heterocyclyl rings include: benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyL cirrnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, IH-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl.

The terms "alkoxy," "cycloalkoxy," "heterocycloalkoxy," "cycloalkoxy," "aryloxy," and "heteroaryloxy" have the aforementioned meanings for alkyl, cycloalkyl, heterocycloalkyl, aryl and heteroaryl, further providing said group is connected via an oxygen atom.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Unless specifically stated, a substituent that is said to be "substituted" is meant that the substituent is substituted with one or more of the following: alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol as described herein. In a specific example, groups that are said to be substituted are substituted with a protic group, which is a group that can be protonated or deprotonated, depending on the pH.

Unless specified otherwise, the term "patient" refers to any mammalian organism, including but not limited to, humans.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate.

Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

Disclosed herein are compounds, compositions and methods of inhibiting RSV or treating or preventing RSV infection in a patient in need thereof by administering to the patient an effective amount of at least one RSV inhibiting compound. In certain embodiments, the RSV inhibiting compound has the structure of Formula I:

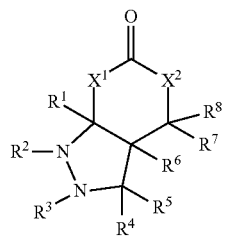

[Formula 1]

or a pharmaceutically acceptable salt thereof, wherein
$X^1$ and $X^2$ are independently selected from —$NR^0$ and —$CR^aR^b$;
$R^1, R^4, R^5, R^6, R^7, R^8, R^a$ and $R^b$ are independently selected from —$R^0$, —$OR^{c'}$, —$N(R^c)_2$, —$SR^c$, —$SO_2R^c$, —$SO_2N(R^c)_2$; —$C(O)R^c$, $OC(O)R^c$, —$COOR^c$, —$C(O)N(R^c)_2$, —$OC(O)N(R^c)_2$, —$N(R^c)C(O)$, —$N(R^c)C(O)N(R^c)_2$, —F, —Cl, —Br, —I, —CN, —$NO_2$;
$R^0, R^2,$ and $R^3$ are independently selected from —$R^0$, —$SO_2R^c$, —$SO_2N(R^c)_2$; —$C(O)R^c$, —$COOR^c$, —$C(O)N(R^c)_2$;
wherein two or more of $R^0, R^1, R^2, R^3, R^4, R^5, R^6, R^7, R^8, R^a$ and $R^b$ can together form a ring;
wherein any two of the aforementioned R groups, when adjacent (e.g., $R^1$ and $R^2$, $R^2$ and $R^3$, $R^3$ and $R^4$, $R^4$ and $R^6$, $R^6$ and $R^1$, $R^6$ and $R^7$, $R^1$ and $R^a$ or $R^0$, and $R^7$ and $R^a$ or $R^0$) groups can together form a double bond;
wherein any two of the aforementioned R groups, when geminal (e.g., $R^4$ and $R^5$, $R^7$ and $R^8$, $R^a$ and $R^b$) can together form a carbonyl, imine or olefin;
wherein $R^c$ is in each case independently selected from hydrogen, $C_{1-8}$ alkyl, $C_{3-8}$ cycloalkyl, $C_{2-8}$ heterocyclyl, $C_{6-12}$ aryl, $C_{3-12}$ heteroaryl, $C_{1-8}$alkyl-$C_{3-8}$ cycloalkyl, $C_{1-8}$ alkyl-$C_{2-8}$ heterocyclyl, $C_{1-6}$ alkyl-$C_{6-12}$ aryl, and $C_{1-6}$ alkyl-$C_{3-12}$ heteroaryl, $C_{1-8}$ alkyl-$C_{1-8}$ alkoxy, $C_{1-8}$ alkyl-$C_{3-8}$ cycloalkoxy, $C_{1-8}$ alkyl-$C_{2-8}$ heterocycloalkoxy, $C_{1-8}$ alkyl-$C_{6-12}$ aryloxy, and $C_{1-8}$ alkyl-$C_{3-12}$ heteroaryloxy;
wherein one or more of $R^c$ can together form a ring with any one or more of $R^0, R^1, R^2, R^3, R^4, R^5, R^6, R^7, R^8, R^a, R^b$ or other $R^c$ group.

As used herein, the term olefin includes unsubstituted methylene (e.g., =$CH_2$), as well as substituted groups including the functional groups falling with the definitions of $R^1, R^4, R^5, R^6, R^7, R^8, R^a$ and $R^b$. The term imine includes the primary imine (e.g., =NH) as well as substituted imines including the functional groups falling with the definitions of $R^0, R^2,$ and $R^3$.

In certain embodiments, one of $X^1$ or $X^2$ is $NR^0$, and the other is $CR^aR^b$. The RSV inhibiting compound can have the structure of Formula 1a or 1b:

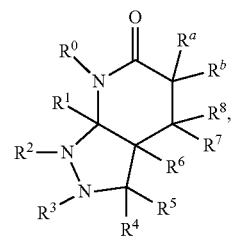

[Formula 1a]

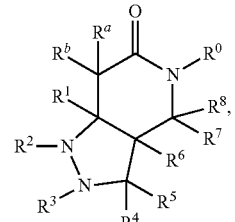

[Formula 1b]

wherein $R^0$-$R^8$, $R^a$ and $R^b$ have the meanings given for the compound of Formula 1.

In some cases, the $R^1$ and $R^2$ and/or $R^5$ and $R^6$ can be double bonds, while in other embodiments, $R^3$ and $R^4$ and/or $R^1$ and $R^6$ can be double bonds:

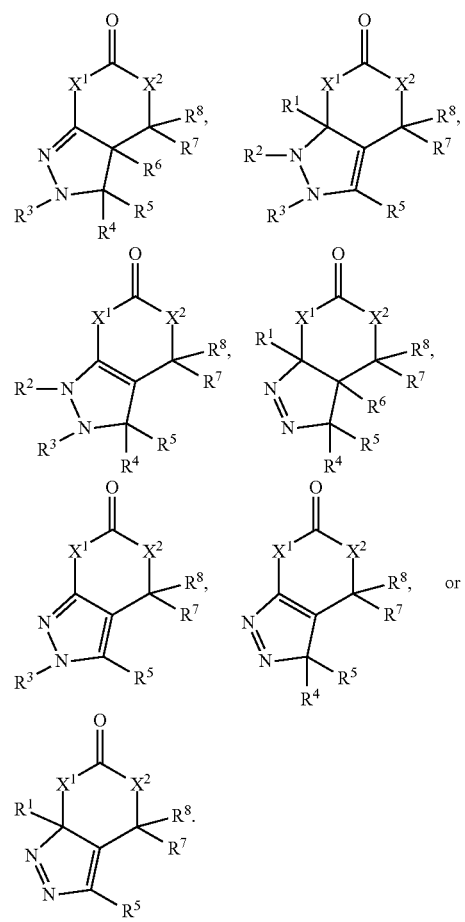

In some embodiments, the RSV inhibiting compound can be characterized by any of Formula 1a-i, 1a-ii, 1a-iii, 1a-iv, 1a-v, 1a-vi, or 1a-vii:

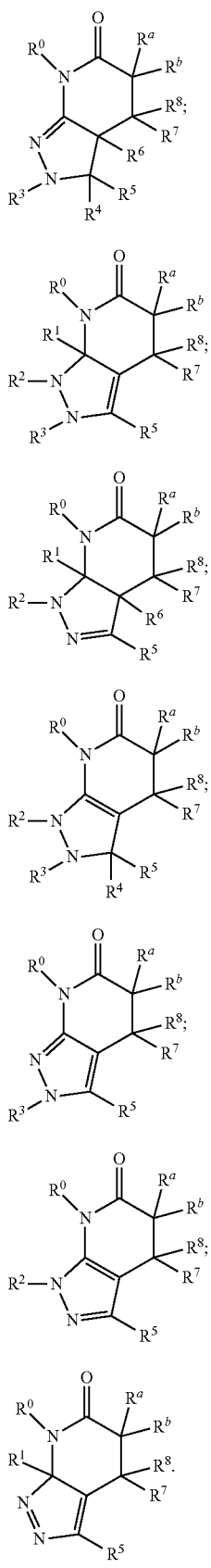
[Formula 1a-i]
[Formula 1a-ii]
[Formula 1a-iii]
[Formula 1a-iv]
[Formula 1a-v]
[Formula 1a-vi]
[Formula 1a-vii]
[Formula 1a-viii]
In other embodiments, the RSV inhibiting compound can be characterized by any of Formula 1b-i, 1b-ii, 1b-iii, 1b-iv, 1b-v, 1b-vi, or 1b-vii:
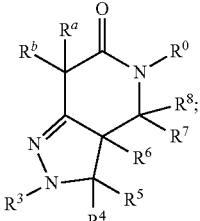
[Formula 1b-i]
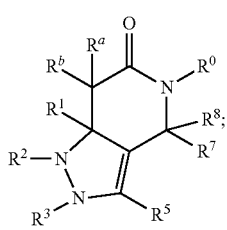
[Formula 1b-ii]
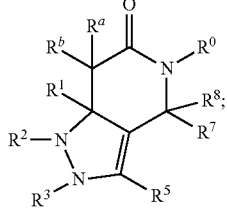
[Formula 1b-iii]
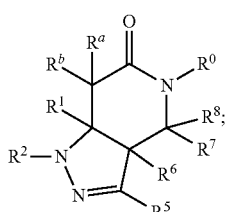
[Formula 1b-iv]
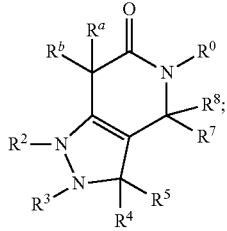
[Formula 1b-v]
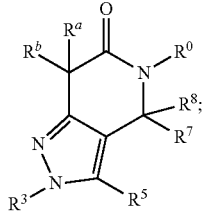
[Formula 1b-vi]
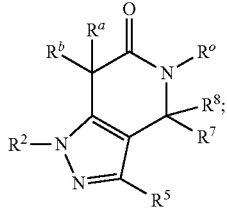

-continued

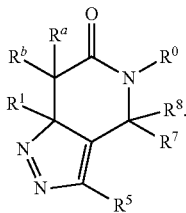
[Formula 1b-vii]

In some embodiments of the compound of Formula 1, for instance, embodiments of the compound of Formula 1a, 1b, 1a-i, 1a-ii, 1a-iii, 1a-iv, 1a-v, 1a-vi, 1a-vii, 1b, 1b-i, 1b-ii, 1b-iii, 1b-iv, 1b-v, 1b-vi, or 1b-vii, it is preferred that $R^2$ is a $C_{3-12}$ heteroaryl group.

In some embodiment, the heteroaryl group can be selected from the following:

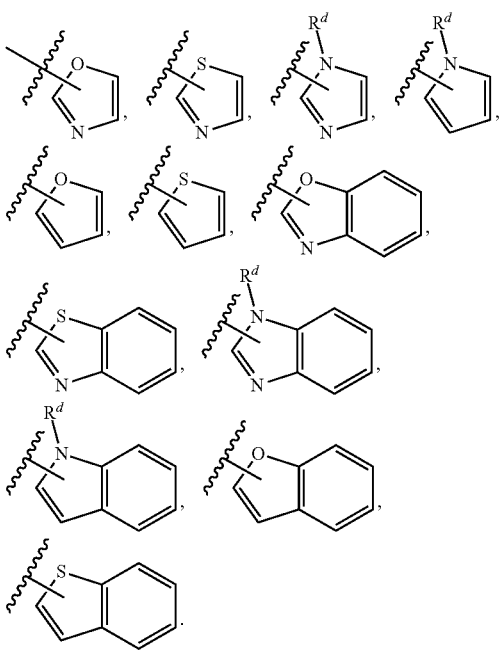

wherein $R^d$ is hydrogen, $C_{1-6}$ alkyl, or the point of attachment to the compound of Formula 1. Any of the above heteroaryl groups may be attached to the compound of Formula 1 via any atom permitted by the rules of valency. For instance, when $R^2$ is an oxazole, thiazole, or imidazole ring, it may be connected at the 2, 4 or 5 position, as well as the 1 position in the case of imidazole. When $R^2$ is pyrrole, furan, or thiophene ring, it may be connected at the 2, 3, 4, or 5 position, as well as the 1 position in the case of pyrrole. When $R^2$ is benzoxazole, benzthioazole, or benzimidazole, it may be connected at the 2, 4, 5, 6, or 7 position, as well as the 1 position in the case of benzimidazole. When $R^2$ is indole, benzofuran, or benzothiophene, it may be connected at the 2, 4, 3, 5, 6, or 7 position, as well as the 1 position in the case of indole.

Any of the heteroaryl groups may be substituted one or more times by —F, —Cl, —Br, —I, —CN, —NO$_2$, OH, COOH, $C_{1-8}$ alkyl, $C_{3-8}$ cycloalkyl, $C_{2-8}$ heterocyclyl, $C_{6-12}$ aryl, $C_{3-12}$ heteroaryl, $C_{1-8}$ alkyl-$C_{3-8}$ cycloalkyl, $C_{1-8}$ alkyl-$C_{2-8}$ heterocyclyl, $C_{1-8}$ alkyl-$C_{6-12}$ aryl, and $C_{1-8}$ alkyl-$C_{3-12}$ heteroaryl, $C_{1-6}$ alkyl-$C_{1-8}$ alkoxy, $C_{1-6}$ alkyl-$C_{3-8}$ cycloalkoxy, $C_1$ is alkyl-$C_{2-8}$ heterocycloalkoxy, $C_{1-8}$ alkyl-$C_{6-12}$ aryloxy, and $C_{1-8}$ alkyl-$C_{3-12}$ heteroaryloxy. The substitution may occur at any atomic position permitted by valency. Any of the above mentioned groups may be unsubstituted or substituted one or more times by —F, —Cl, —Br, —I, —CN, —NO$_2$, OH, COOH The above definitions of $R^2$ are particularly preferred for the compounds of Formula 1a, 1a-ii, 1a-iii, 1a-iv, and 1a-vi, especially for compounds of Formula 1a-vi. In these embodiments, $R^2$ is preferably a benzthiazole, preferably connected at the 2 position:

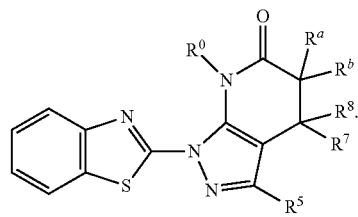
[Formula 1c]

In some embodiments of the compound of Formula 1, for instance, embodiments of the compound of Formula 1a, 1b, 1a-i, 1a-ii, 1a-iii, 1a-iv, 1a-v, 1a-vi, 1a-vii, 1b, 1b-i, 1b-ii, 1b-iii, 1b-iv, 1b-v, 1b-vi, or 1b-vii, it is preferred that $R^3$ is a $C_{3-12}$ heteroaryl group.

In some embodiment, the heteroaryl group can be selected from the following:

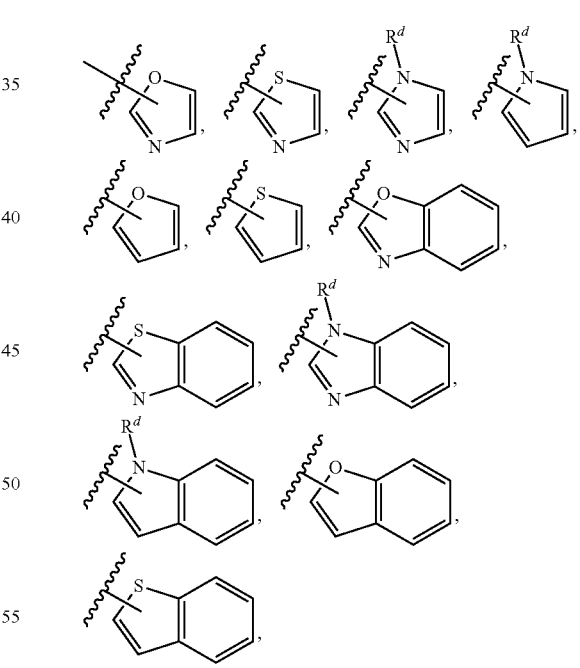

wherein $R^d$ is hydrogen, $C_{1-6}$alkyl or a point of attachment to the compound of Formula 1. Any of the above heteroaryl groups may be attached via any atom permitted by the rules of valency. For instance, when $R^3$ is an oxazole, thiazole, or imidazole ring, it may be connected at the 2, 4 or 5 position, as well as the 1 position in the case of imidazole. When $R^3$ is pyrrole, furan, or thiophene ring, it may be connected at the 2, 3, 4, or 5 position, as well as the 1 position in the case of pyrrole. When $R^3$ is benzoxazole, benzthioazole, or benzimidazole, it may be connected at the 2, 4, 5, 6, or 7 position, as well as the 1 position in the case of benzimidazole. When $R^3$ is indole, benzofuran, or benzothiophene, it may be connected at the 2, 4, 3, 5, 6, or 7 position, as well as the 1 position in the case of indole.

Any of the heteroaryl groups may be substituted one or more times by —F, —Cl, —Br, —I, —CN, —NO$_2$, $C_{1-8}$ alkyl, $C_{3-8}$ cycloalkyl, $C_{2-8}$ heterocyclyl, $C_{6-12}$ aryl, $C_{3-12}$ heteroaryl, $C_{1-8}$alkyl-$C_{3-8}$ cycloalkyl, $C_{1-8}$alkyl-$C_{2-8}$ heterocyclyl, $C_{1-8}$alkyl-$C_{6-12}$ aryl, and $C_{1-8}$alkyl-$C_{3-12}$ heteroaryl, $C_{1-8}$alkyl-$C_{1-8}$ alkoxy, $C_{1-8}$alkyl-$C_{3-8}$ cycloalkoxy, $C_{1-8}$alkyl-$C_{2-8}$ heterocycloalkoxy, $C_{1-8}$alkyl-$C_{6-12}$ aryloxy, and $C_{1-8}$alkyl-$C_{3-12}$ heteroaryloxy. The substitution may occur at any atomic position permitted by valency.

The above definitions of $R^3$ are particularly preferred for the compounds of Formula 1b, 1b-I, 1b-ii, 1a-iv, and 1a-vi, especially for compounds of Formula 1b, especially when $R^4$ and $R^5$ together form a carbonyl:

[Formula 1d]

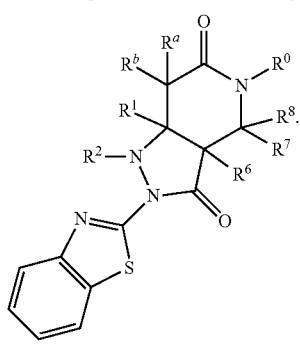

In some embodiments of the compound of Formula 1, for instance, embodiments of the compound of Formula 1a, 1b, 1a-i, 1a-ii, 1a-iii, 1a-iv, 1a-v, 1a-vi, 1a-vii, 1b, 1b-i, 1b-ii, 1b-iii, 1b-iv, 1b-v, 1b-vi, 1b-vii, 1c, or 1d, it is preferred that $R^7$ is a $C_{6-12}$ aryl or $C_{1-8}$ alkyl-$C_{6-12}$ aryl. When $R^7$ contains a $C_{1-8}$ alkyl group, it is preferred that it is a $C_{1-4}$alkyl group. In some embodiments, $R^7$ is a $C_6$ aryl ring optionally substituted 1, 2, 3, 4, or 5 times by —$R^e$, —$OR^e$, —$N(R^e)_2$, —$SR^e$, —$SO_2R^e$, —$SO_2N(R^e)_2$; —$C(O)R^e$, $OC(O)R^e$, —$COOR^e$, —$C(O)N(R^e)_2$, —$OC(O)N(R^e)_2$, —$N(R^e)C(O)$, —$N(R^e)C(O)N(R^e)_2$, —F, —Cl, —Br, —I, —CN, —NO$_2$; wherein $R^e$ is in each case independently selected from hydrogen, $C_{1-8}$ alkyl, $C_{3-8}$ cycloalkyl, $C_{2-8}$ heterocyclyl, $C_{6-12}$ aryl, $C_{3-12}$ heteroaryl, $C_{1-8}$ alkyl-$C_{3-8}$ cycloalkyl, $C_{1-8}$alkyl-$C_{2-8}$ heterocyclyl, $C_{1-8}$ alkyl-$C_{6-12}$ aryl, and $C_{1-8}$ alkyl-$C_{3-12}$ heteroaryl, $C_{1-8}$ alkyl-$C_{1-8}$ alkoxy, $C_{1-8}$ alkyl-$C_{3-8}$ cycloalkoxy, $C_{1-8}$ alkyl-$C_{2-8}$ heterocycloalkoxy, $C_{1-8}$ alkyl-$C_{6-12}$ aryloxy, and $C_{1-8}$ alkyl-$C_{3-12}$ heteroaryloxy.

In certain preferred embodiments, especially for compounds of Formula 1a, 1a-i, 1a-ii, 1a-iii, 1a-iv, 1a-v, 1a-vi, 1a-vii, 1c, and 1d, it is preferred that $R^7$ is a $C_6$ aryl ring optionally substituted one or more times (e.g., 1, 2, 3, 4 or 5) by —$R^e$, —$OR^e$, —$N(R^e)_2$, —$SR^e$, —$SO_2R^e$, —$SO_2N(R^e)_2$; —$C(O)R^e$, $OC(O)R^e$, —$COOR^e$, —$C(O)N(R^e)_2$, —$OC(O)N(R^e)_2$, —$N(R^e)C(O)$, —$N(R^e)C(O)N(R^e)_2$, —F, —Cl, —Br, —I, —CN, —NO$_2$, wherein $R^e$ is in each case independently selected from hydrogen, $C_{1-6}$ alkyl or $C_{3-8}$ cycloalkyl. In certain preferred cases, $R^7$ is a $C_6$ aryl ring substituted 2 times by —$OR^e$, wherein $R^e$ has the meanings given above. Exemplary $OR^e$ groups include methoxy, ethoxy, isopropoxy, cyclopentyloxy, cyclohexyloxy and the like.

In certain embodiments, especially in compounds of Formula 1b, it is preferred that $R^0$ is $C_{1-8}$ alkyl-$C_{3-8}$ cycloalkyl, $C_{1-8}$ alkyl-$C_{2-8}$ heterocyclyl, $C_{1-8}$ alkyl-$C_{6-12}$ aryl, and $C_{1-8}$ alkyl-$C_{3-12}$ heteroaryl. Especially preferred are $C_{1-3}$ alkyl-$C_{3-8}$ cycloalkyl, $C_{1-3}$ alkyl-$C_{2-8}$ heterocyclyl, $C_{1-3}$ alkyl-$C_{6-12}$ aryl, and $C_{1-3}$ alkyl-$C_{3-12}$ heteroaryl, and even more preferably CH$_2$—$C_{3-8}$ cycloalkyl, CH$_2$—$C_{2-8}$ heterocyclyl, CH$_2$—$C_{6-12}$ aryl, and CH$_2$—$C_{3-12}$ heteroaryl. $C_{1-8}$ alkyl-$C_{3-12}$ heteroaryl groups can be preferred; in some such embodiment, the heteroaryl group can be selected from the following:

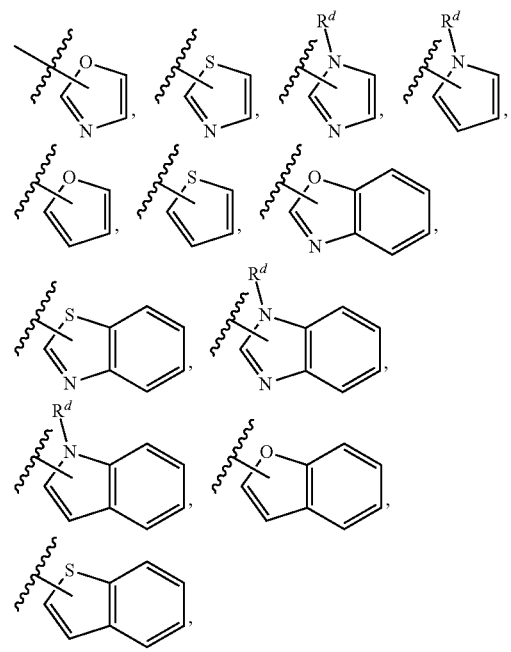

wherein $R^d$ is hydrogen, $C_{1-6}$alkyl or a point of attachment to $C_{1-8}$ alkyl. Any of the above heteroaryl groups may be attached via any atom permitted by the rules of valency. For instance, when the heteroaryl is an oxazole, thiazole, or imidazole ring, it may be connected at the 2, 4 or 5 position, as well as the 1 position in the case of imidazole. When the heteroaryl is pyrrole, furan, or thiophene ring, it may be connected at the 2, 3, 4, or 5 position, as well as the 1 position in the case of pyrrole. When the heteroaryl is benzoxazole, benzthioazole, or benzimidazole, it may be connected at the 2, 4, 5, 6, or 7 position, as well as the 1 position in the case of benzimidazole. When the heteroaryl is indole, benzofuran, or benzothiophene, it may be connected at the 2, 4, 3, 5, 6, or 7 position, as well as the 1 position in the case of indole.

Any of the heteroaryl groups may be substituted one or more times by —F, —Cl, —Br, —I, —CN, —NO$_2$, $C_{1-8}$ alkyl, $C_{3-8}$ cycloalkyl, $C_{2-8}$ heterocyclyl, $C_{6-12}$ aryl, $C_{3-12}$ heteroaryl, $C_{1-8}$alkyl-$C_{3-8}$ cycloalkyl, $C_{1-8}$alkyl-$C_{2-8}$ heterocyclyl, $C_{1-8}$alkyl-$C_{6-12}$ aryl, and $C_{1-8}$alkyl-$C_{3-12}$ heteroaryl, $C_{1-8}$alkyl-$C_{1-8}$ alkoxy, $C_{1-8}$alkyl-$C_{3-8}$ cycloalkoxy, $C_{1-8}$alkyl-$C_{2-8}$ heterocycloalkoxy, $C_{1-8}$alkyl-$C_{6-12}$ aryloxy, and $C_{1-8}$alkyl-$C_{3-12}$ heteroaryloxy. The substitution may occur at any atomic position permitted by valency. In preferred embodiments, the heteroaryl is selected from:

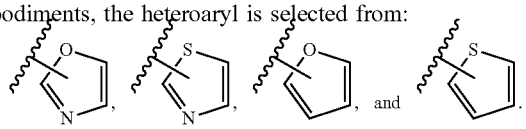

The following compounds in accordance with the present invention are grouped into series "A" and "B" in Table 1 below:

TABLE 1

| Compounds of the Invention | | |
|---|---|---|
| CP-target list | Series | Structure |
| AVG-001 | A | |
| AVG-001-b | A | |
| AVG-002 | A | |
| AVG-003 | A | |
| AVG-004 | A | |

TABLE 1-continued

Compounds of the Invention

| CP-target list | Series | Structure |
|---|---|---|
| AVG-005 | A | 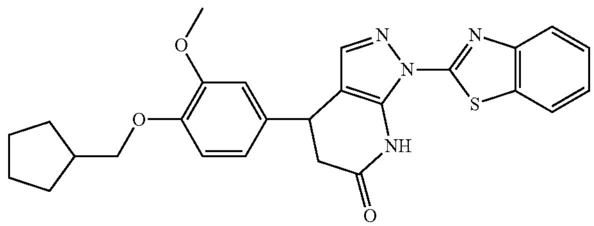 [SMILES: COc1cc(C2CC(=O)Nc3c2cnn3-c2nc3ccccc3s2)ccc1OCC1CCCC1] |
| AVG-006 (171352) | A | 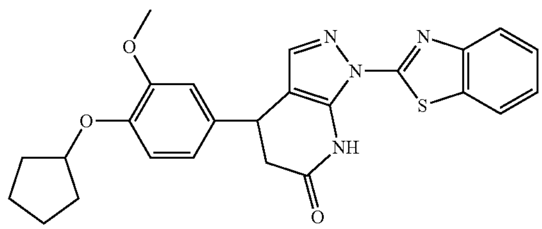 |
| AVG-006b | A | 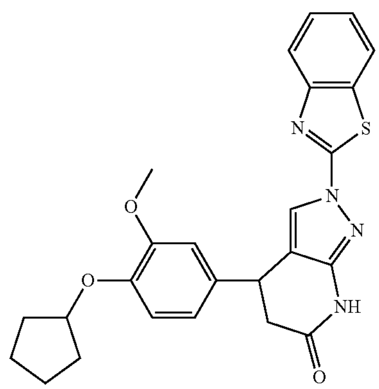 [SMILES: COc1cc(C2CC(=O)Nc3nn(-c4nc5ccccc5s4)cc32)ccc1OC1CCCC1] |
| AVG-007 | A | 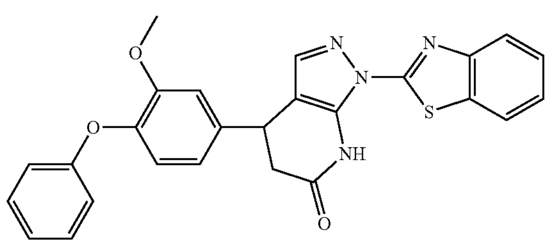 [SMILES: COc1cc(C2CC(=O)Nc3c2cnn3-c2nc3ccccc3s2)ccc1Oc1ccccc1] |
| AVG-010 | A | 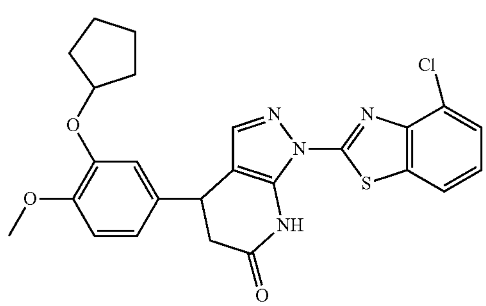 [SMILES: COc1ccc(C2CC(=O)Nc3c2cnn3-c2nc3c(Cl)cccc3s2)cc1OC1CCCC1] |

TABLE 1-continued
Compounds of the Invention
| CP-target list | Series | Structure |
|---|---|---|
| AVG-011 | A | 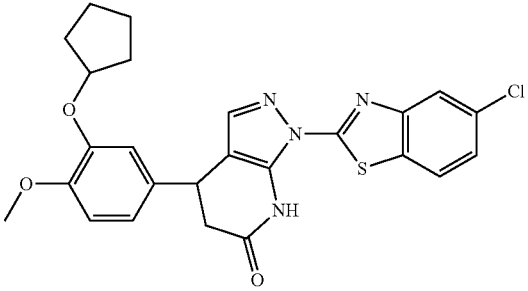 [SMILES: COc1ccc(C2CC(=O)Nc3c2cnn3-c2nc3cc(Cl)ccc3s2)cc1OC1CCCC1] |
| AVG-012 | A | 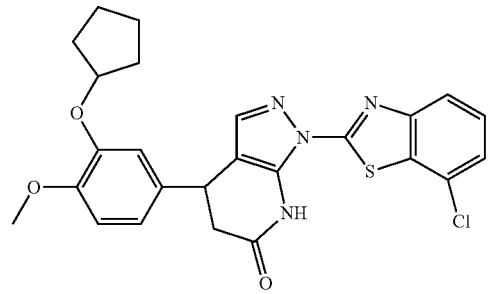 [SMILES: COc1ccc(C2CC(=O)Nc3c2cnn3-c2nc3cccc(Cl)c3s2)cc1OC1CCCC1] |
| AVG-013 | A | 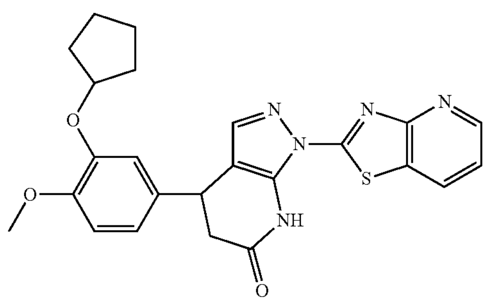 [SMILES: COc1ccc(C2CC(=O)Nc3c2cnn3-c2nc3ncccc3s2)cc1OC1CCCC1] |
| AVG-014 | A | 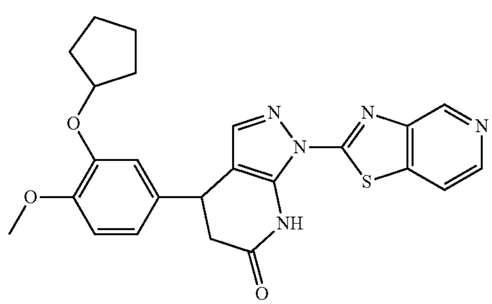 [SMILES: COc1ccc(C2CC(=O)Nc3c2cnn3-c2nc3cnccc3s2)cc1OC1CCCC1] |
| AVG-015 | A | 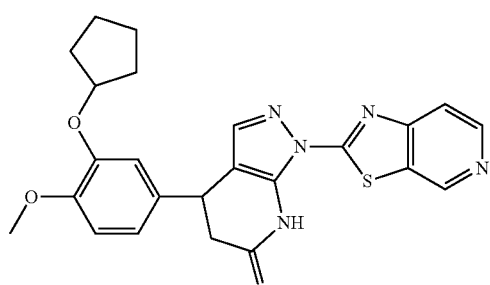 |

TABLE 1-continued

Compounds of the Invention

| CP-target list | Series | Structure |
|---|---|---|
| AVG-016 | A | 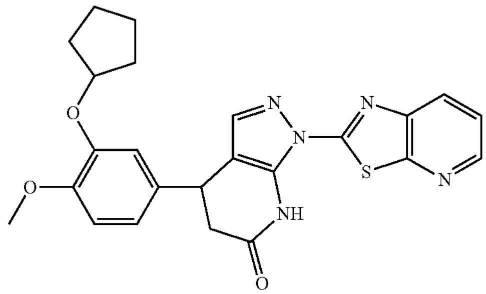 [SMILES: COc1ccc(C2CC(=O)Nc3c2cnn3-c2nc3cccnc3s2)cc1OC1CCCC1] |
| AVG-017 | A | 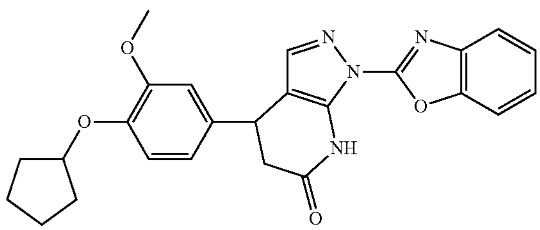 [SMILES: COc1cc(C2CC(=O)Nc3c2cnn3-c2nc3ccccc3o2)ccc1OC1CCCC1] |
| AVG-018 | A | 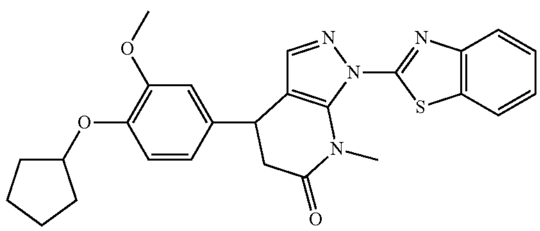 [SMILES: COc1cc(C2CC(=O)N(C)c3c2cnn3-c2nc3ccccc3s2)ccc1OC1CCCC1] |
| AVG-021 (156784) | B | 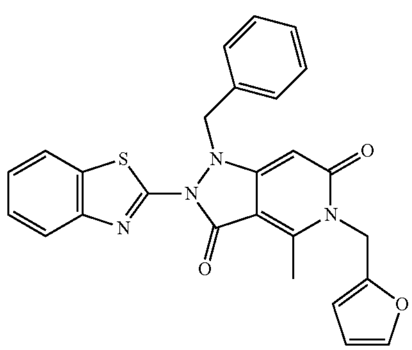 |
| AVG-022 | B | 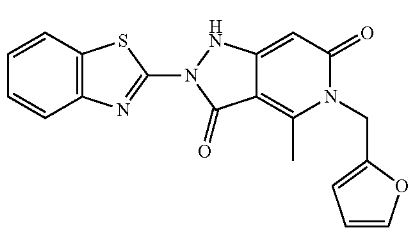 [SMILES: Cc1c2c(=O)n(-c3nc4ccccc4s3)[nH]c2cc(=O)n1Cc1ccco1] |

TABLE 1-continued

Compounds of the Invention

| CP-target list | Series | Structure |
|---|---|---|
| AVG-023 | B | 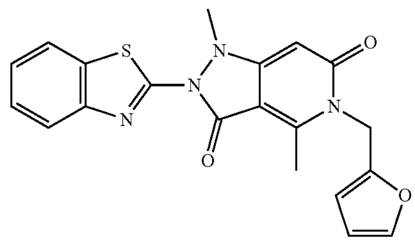 [SMILES: Cc1c2c(=O)n(-c3nc4ccccc4s3)n(C)c2cc(=O)n1Cc1ccco1] |
| AVG-024 | B | 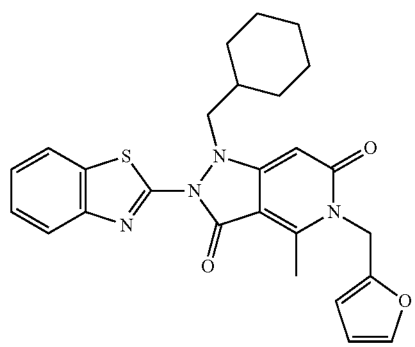 |
| AVG-025 | B | 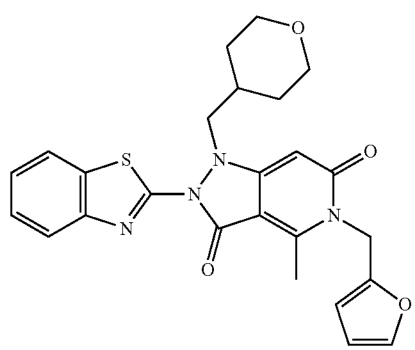 [SMILES: Cc1c2c(=O)n(-c3nc4ccccc4s3)n(CC3CCOCC3)c2cc(=O)n1Cc1ccco1] |
| AVG-026 | B | 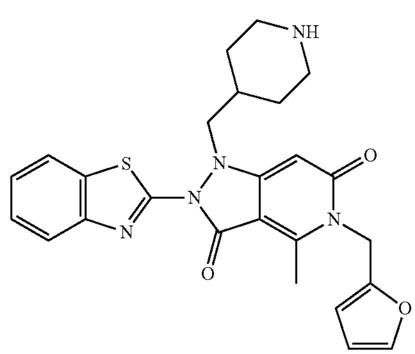 [SMILES: Cc1c2c(=O)n(-c3nc4ccccc4s3)n(CC3CCNCC3)c2cc(=O)n1Cc1ccco1] |

TABLE 1-continued

Compounds of the Invention

| CP-target list | Series | Structure |
|---|---|---|
| AVG-027 | B | 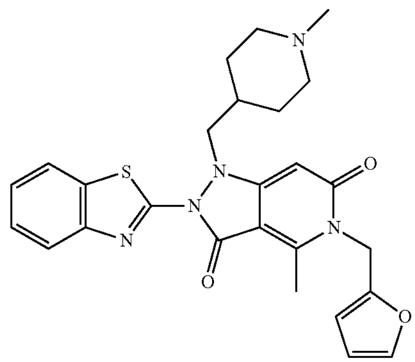 [SMILES: Cc1c2c(=O)n(-c3nc4ccccc4s3)n(CC3CCN(C)CC3)c2cc(=O)n1Cc1ccco1] |
| AVG-028 | B | 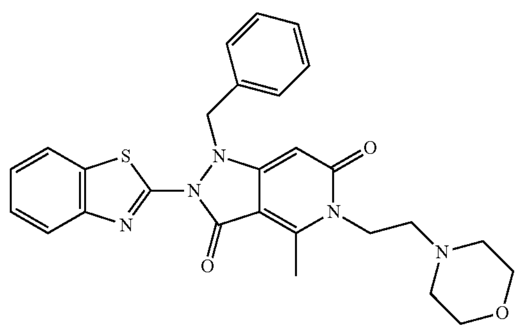 [SMILES: Cc1c2c(=O)n(-c3nc4ccccc4s3)n(Cc3ccccc3)c2cc(=O)n1CCN1CCOCC1] |
| AVG-029 | B | 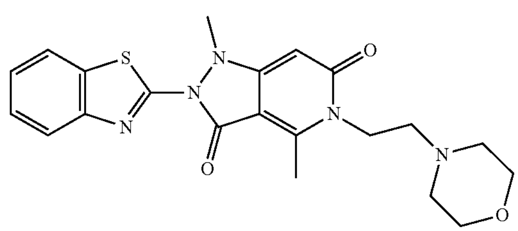 [SMILES: Cc1c2c(=O)n(-c3nc4ccccc4s3)n(C)c2cc(=O)n1CCN1CCOCC1] |
| AVG-030 | B | 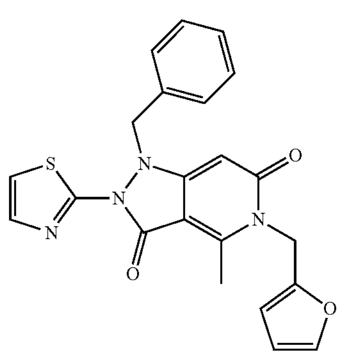 [SMILES: Cc1c2c(=O)n(-c3nccs3)n(Cc3ccccc3)c2cc(=O)n1Cc1ccco1] |

TABLE 1-continued
Compounds of the Invention
| CP-target list | Series | Structure |
|---|---|---|
| AVG-031 | B | 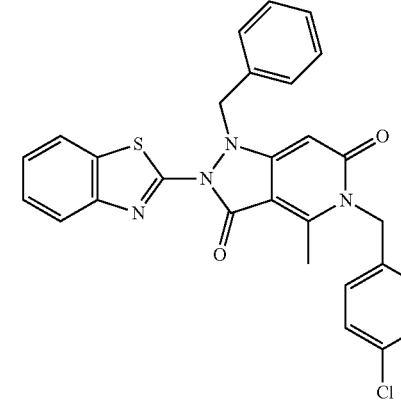 |
| AVG-032 | B | 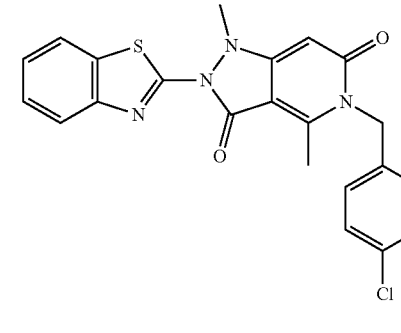 |
| AVG-033 | B | 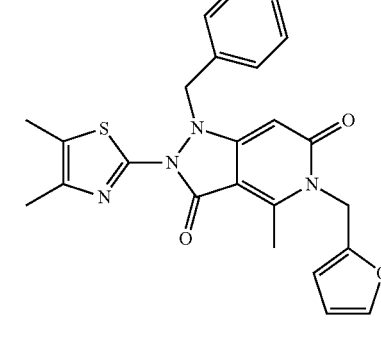 |
| AVG-034 | B | 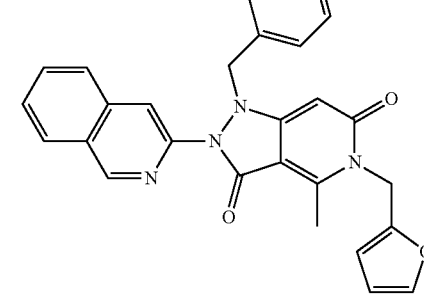 |

TABLE 1-continued
Compounds of the Invention
| CP-target list | Series | Structure |
|---|---|---|
| AVG-035 | B | 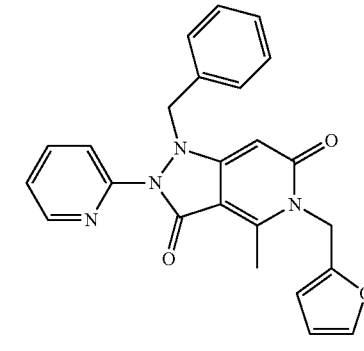 |
| AVG-036 | B | 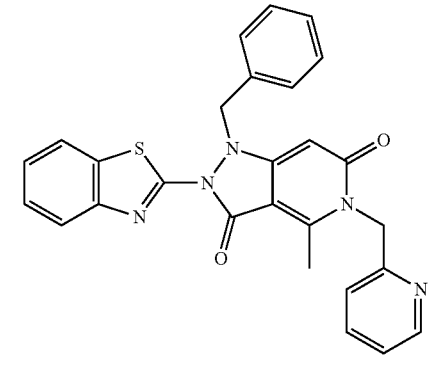 [SMILES: Cc1c2c(=O)n(-c3nc4ccccc4s3)n(Cc3ccccc3)c2cc(=O)n1Cc1ccccn1] |
| AVG-037 | B | 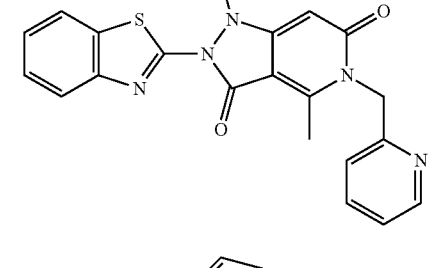 |
| AVG-038 | B | 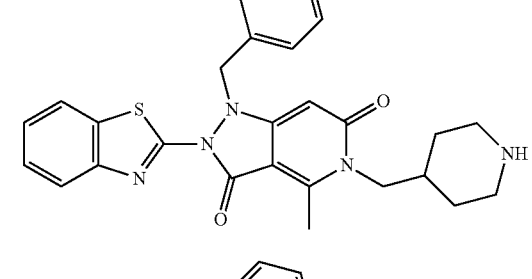 |
| AVG-039 | B | 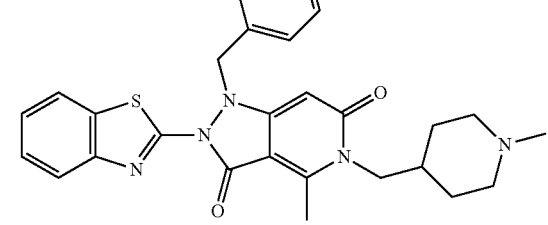 |

TABLE 1-continued
Compounds of the Invention
| CP-target list | Series | Structure |
|---|---|---|
| AVG-040 | B | 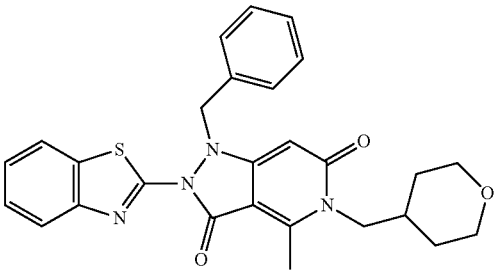 [SMILES: Cc1c2c(=O)n(-c3nc4ccccc4s3)n(Cc3ccccc3)c2cc(=O)n1CC1CCOCC1] |
| AVG-041 | B | 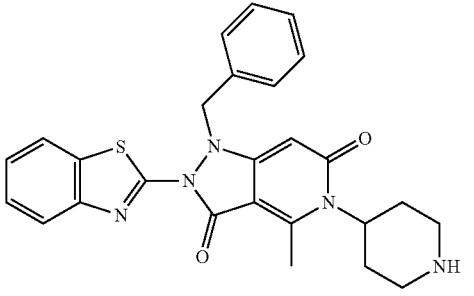 [SMILES: Cc1c2c(=O)n(-c3nc4ccccc4s3)n(Cc3ccccc3)c2cc(=O)n1C1CCNCC1] |
| AVG-042 | B | 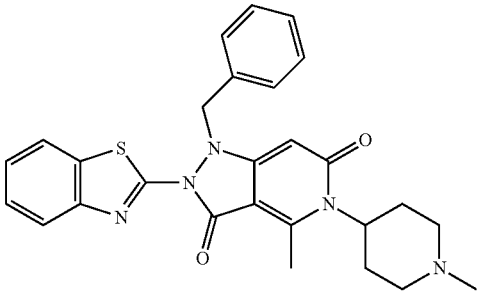 [SMILES: Cc1c2c(=O)n(-c3nc4ccccc4s3)n(Cc3ccccc3)c2cc(=O)n1C1CCN(C)CC1] |
| AVG-043 | B | 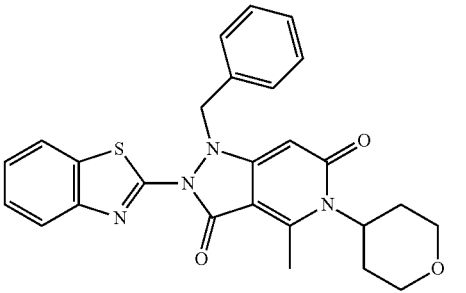 [SMILES: Cc1c2c(=O)n(-c3nc4ccccc4s3)n(Cc3ccccc3)c2cc(=O)n1C1CCOCC1] |
| AVG-065 | A | 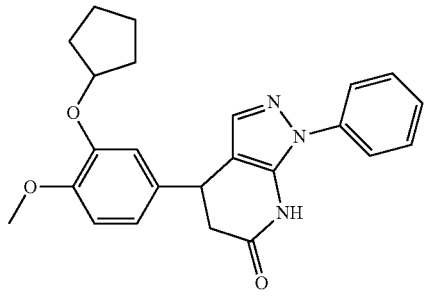 [SMILES: COc1ccc(C2CC(=O)Nc3c2cnn3-c2ccccc2)cc1OC1CCCC1] |

TABLE 1-continued
Compounds of the Invention
| CP-target list | Series | Structure |
|---|---|---|
| AVG-065b | A | 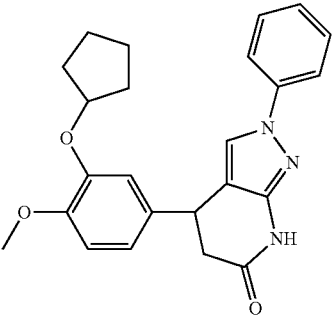 [SMILES: COc1ccc(C2CC(=O)Nc3nn(-c4ccccc4)cc32)cc1OC1CCCC1] |
| AVG-066 | A | 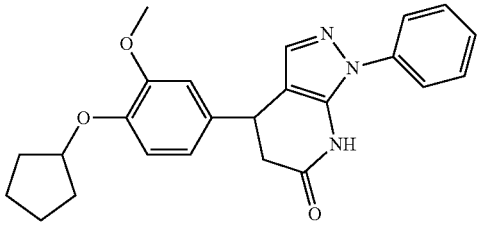 |
| AVG-067 | A | 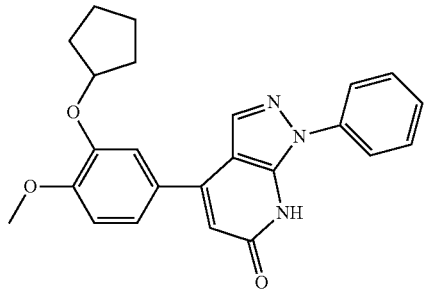 [SMILES: COc1ccc(-c2cc(=O)[nH]c3c2cnn3-c2ccccc2)cc1OC1CCCC1] |
| AVG-068 | A | 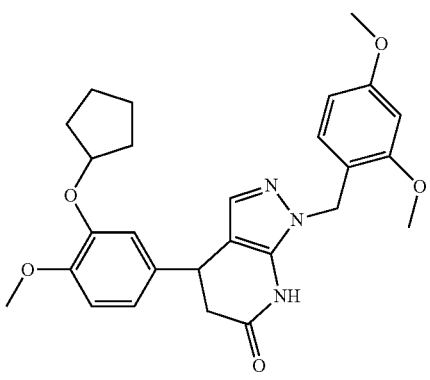 [SMILES: COc1ccc(Cn2ncc3c2NC(=O)CC3c2ccc(OC)c(OC3CCCC3)c2)c(OC)c1] |

TABLE 1-continued
Compounds of the Invention
| CP-target list | Series | Structure |
|---|---|---|
| AVG-068-II | A | 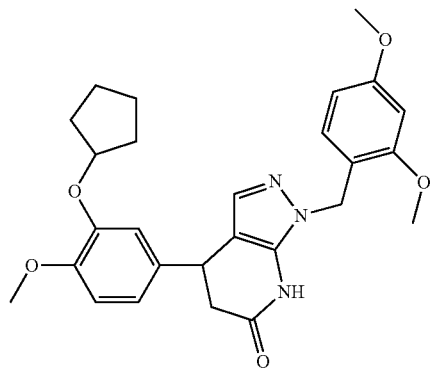 [SMILES: COc1ccc(Cn2ncc3c2NC(=O)CC3c2ccc(OC)c(OC3CCCC3)c2)c(OC)c1] |
| AVG-069 | A | 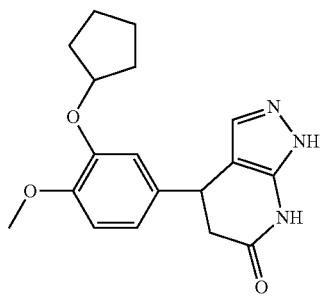 [SMILES: COc1ccc(C2CC(=O)Nc3[nH]ncc32)cc1OC1CCCC1] |
| AVG-070 | B | 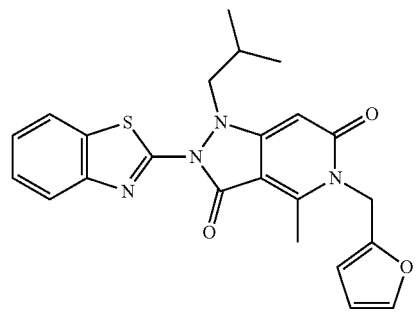 [SMILES: Cc1c2c(=O)n(-c3nc4ccccc4s3)n(CC(C)C)c2cc(=O)n1Cc1ccco1] |
| AVG-071 | B | 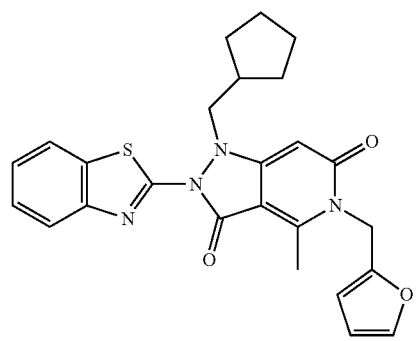 [SMILES: Cc1c2c(=O)n(-c3nc4ccccc4s3)n(CC3CCCC3)c2cc(=O)n1Cc1ccco1] |

TABLE 1-continued

Compounds of the Invention

| CP-target list | Series | Structure |
|---|---|---|
| AVG-072 | B | 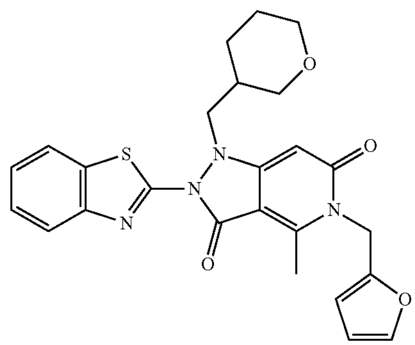 [SMILES: Cc1c2c(=O)n(-c3nc4ccccc4s3)n(CC3CCCOC3)c2cc(=O)n1Cc1ccco1] |
| AVG-073 | B | 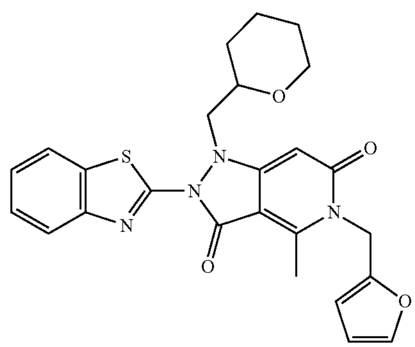 |
| AVG-074 | B | 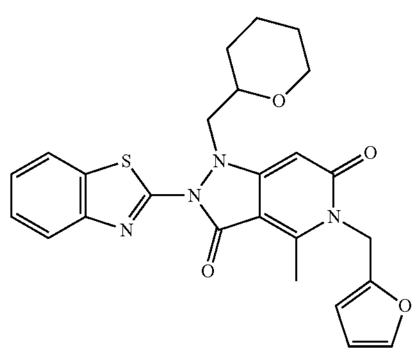 [SMILES: Cc1c2c(=O)n(-c3nc4ccccc4s3)n(CC3CCCCO3)c2cc(=O)n1Cc1ccco1] |
| AVG-075 | B | 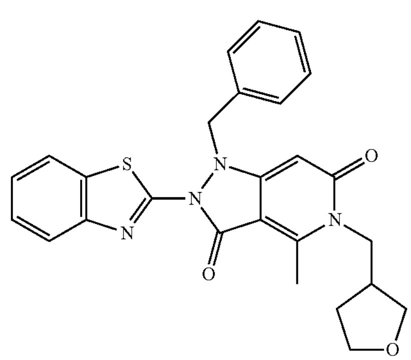 [SMILES: Cc1c2c(=O)n(-c3nc4ccccc4s3)n(Cc3ccccc3)c2cc(=O)n1CC1CCOC1] |

TABLE 1-continued
Compounds of the Invention
| CP-target list | Series | Structure |
|---|---|---|
| AVG-076 | B | 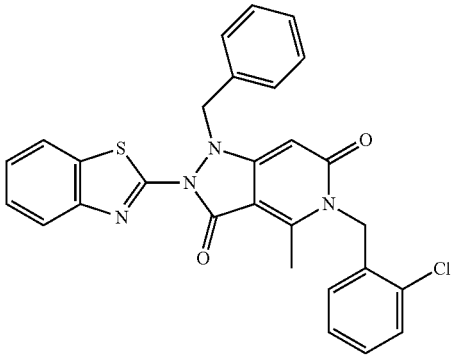 [SMILES: Cc1c2c(=O)n(-c3nc4ccccc4s3)n(Cc3ccccc3)c2cc(=O)n1Cc1ccccc1Cl] |
| AVG-077 | B | 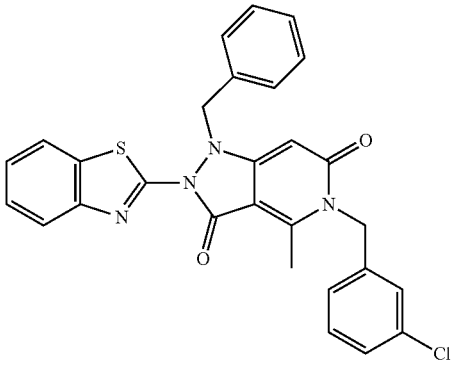 [SMILES: Cc1c2c(=O)n(-c3nc4ccccc4s3)n(Cc3ccccc3)c2cc(=O)n1Cc1cccc(Cl)c1] |
| AVG-078 | B | 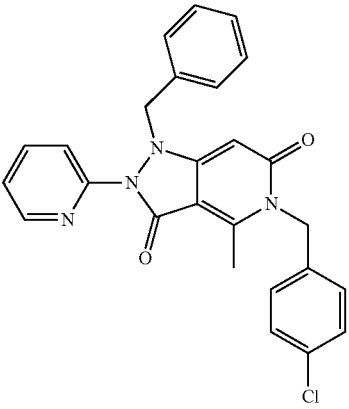 [SMILES: Cc1c2c(=O)n(-c3ccccn3)n(Cc3ccccc3)c2cc(=O)n1Cc1ccc(Cl)cc1] |
| AVG-079 | B | 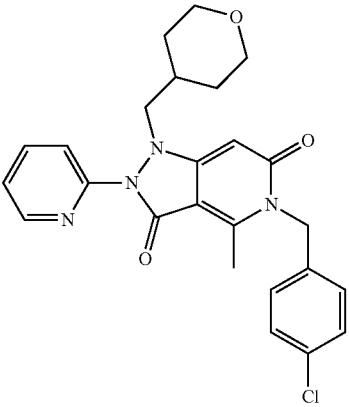 [SMILES: Cc1c2c(=O)n(-c3ccccn3)n(CC3CCOCC3)c2cc(=O)n1Cc1ccc(Cl)cc1] |

TABLE 1-continued

Compounds of the Invention

| CP-target list | Series | Structure |
|---|---|---|
| AVG-080 | B | 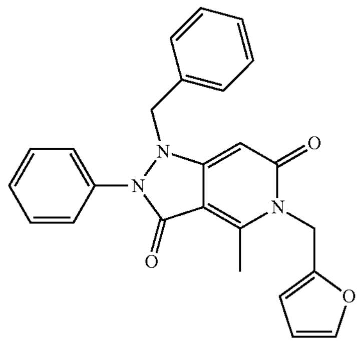 [SMILES: Cc1c2c(=O)n(-c3ccccc3)n(Cc3ccccc3)c2cc(=O)n1Cc1ccco1] |
| AVG-081 | B | 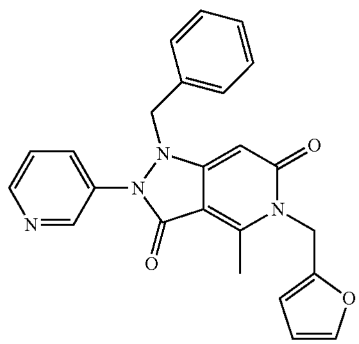 [SMILES: Cc1c2c(=O)n(-c3cccnc3)n(Cc3ccccc3)c2cc(=O)n1Cc1ccco1] |
| AVG-082 | B | 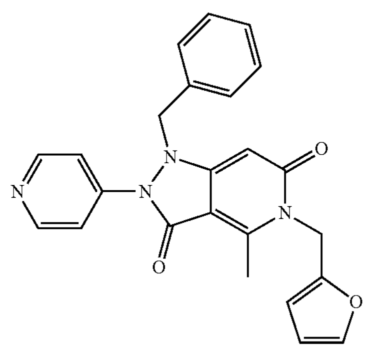 [SMILES: Cc1c2c(=O)n(-c3ccncc3)n(Cc3ccccc3)c2cc(=O)n1Cc1ccco1] |
| AVG-088 | B | 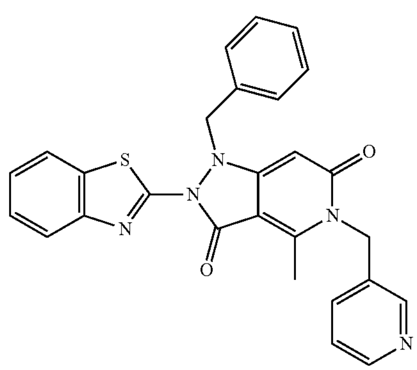 |

TABLE 1-continued
| Compounds of the Invention | | |
|---|---|---|
| CP-target list | Series | Structure |
| AVG-089 | B | 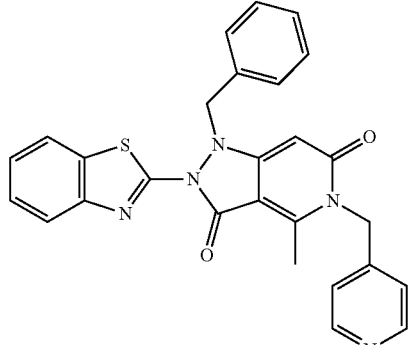 |
| AVG-090 | B | 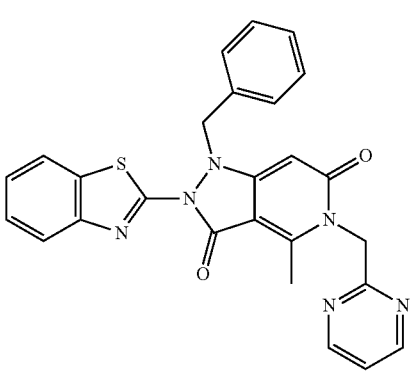 [SMILES: Cc1c2c(=O)n(-c3nc4ccccc4s3)n(Cc3ccccc3)c2cc(=O)n1Cc1ncccn1] |
| AVG-091 | B | 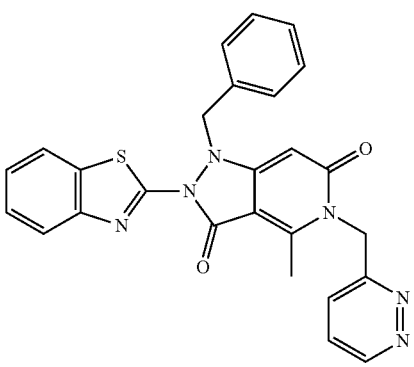 [SMILES: Cc1c2c(=O)n(-c3nc4ccccc4s3)n(Cc3ccccc3)c2cc(=O)n1Cc1cccnn1] |
| AVG-092 | B | 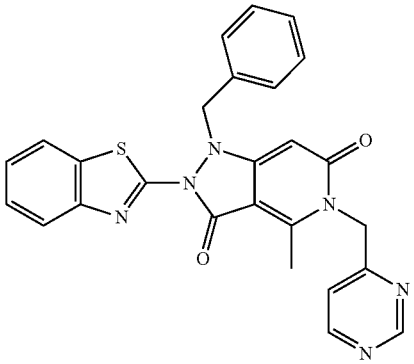 [SMILES: Cc1c2c(=O)n(-c3nc4ccccc4s3)n(Cc3ccccc3)c2cc(=O)n1Cc1ccncn1] |

TABLE 1-continued

| Compounds of the Invention | | |
|---|---|---|
| CP-target list | Series | Structure |
| AVG-093 | B | |
| AVG-094 | B | |
| AVG-095 | B | |
| AVG-096 | B | |

TABLE 1-continued

Compounds of the Invention

| CP-target list | Series | Structure |
|---|---|---|
| AVG-097 | B | 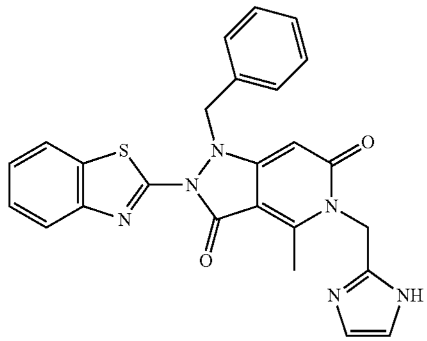 [SMILES: Cc1c2c(=O)n(-c3nc4ccccc4s3)n(Cc3ccccc3)c2cc(=O)n1Cc1ncc[nH]1] |
| AVG-098 | B | 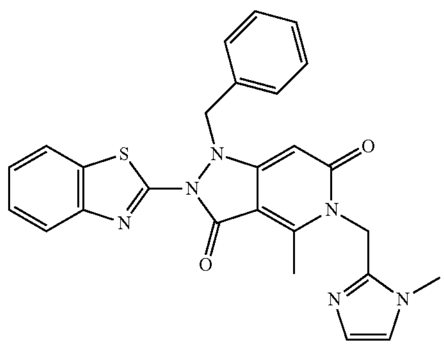 [SMILES: Cc1c2c(=O)n(-c3nc4ccccc4s3)n(Cc3ccccc3)c2cc(=O)n1Cc1nccn1C] |
| AVG-099 | B | 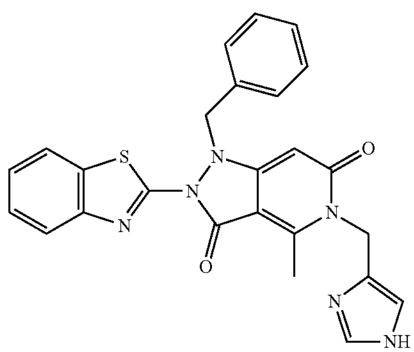 [SMILES: Cc1c2c(=O)n(-c3nc4ccccc4s3)n(Cc3ccccc3)c2cc(=O)n1Cc1c[nH]cn1] |
| AVG-100 | B | 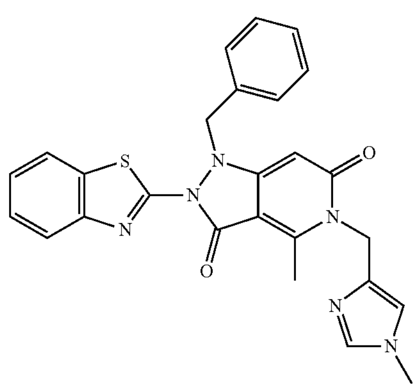 [SMILES: Cc1c2c(=O)n(-c3nc4ccccc4s3)n(Cc3ccccc3)c2cc(=O)n1Cc1cn(C)cn1] |

TABLE 1-continued
Compounds of the Invention
| CP-target list | Series | Structure |
|---|---|---|
| AVG-101 | B | 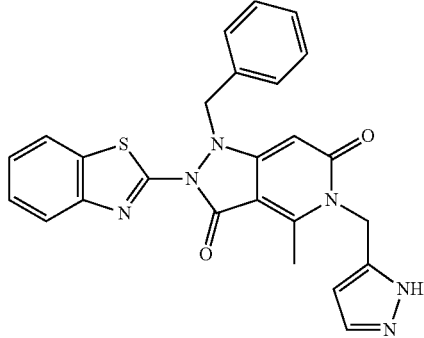 [SMILES: Cc1c2c(=O)n(-c3nc4ccccc4s3)n(Cc3ccccc3)c2cc(=O)n1Cc1ccn[nH]1] |
| AVG-102 | B | 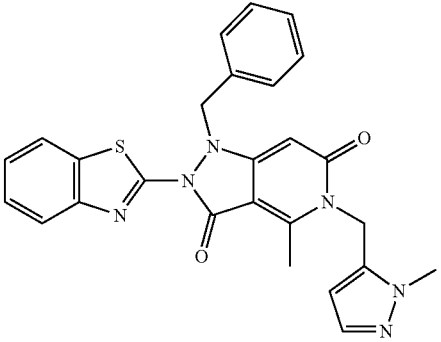 [SMILES: Cc1c2c(=O)n(-c3nc4ccccc4s3)n(Cc3ccccc3)c2cc(=O)n1Cc1ccnn1C] |
| AVG-103 | B | 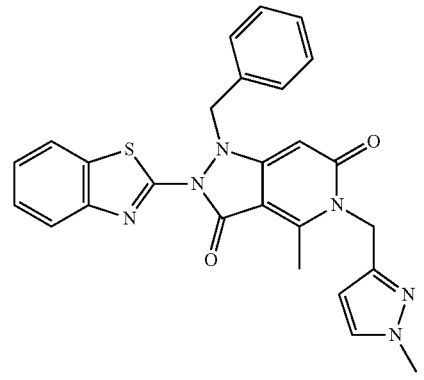 [SMILES: Cc1c2c(=O)n(-c3nc4ccccc4s3)n(Cc3ccccc3)c2cc(=O)n1Cc1ccn(C)n1] |
| AVG-104 | B | 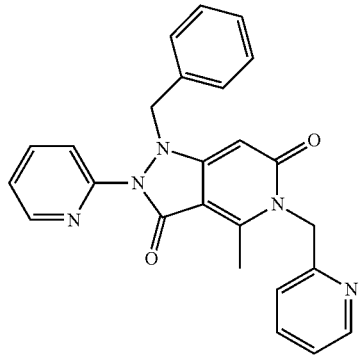 |

TABLE 1-continued

Compounds of the Invention

| CP-target list | Series | Structure |
|---|---|---|
| AVG-105 | B | 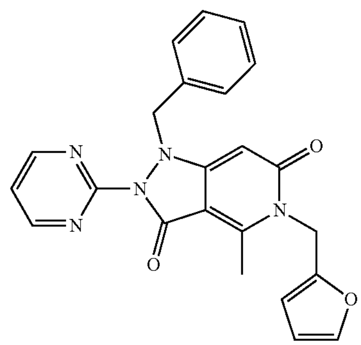 [SMILES: Cc1c2c(=O)n(-c3ncccn3)n(Cc3ccccc3)c2cc(=O)n1Cc1ccco1] |
| AVG-106 | B | 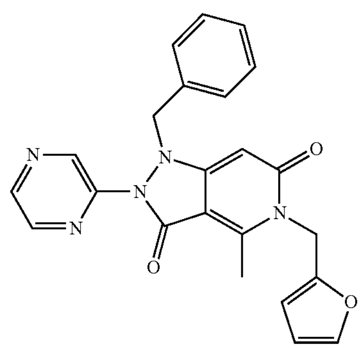 [SMILES: Cc1c2c(=O)n(-c3cnccn3)n(Cc3ccccc3)c2cc(=O)n1Cc1ccco1] |
| AVG-107 | B | 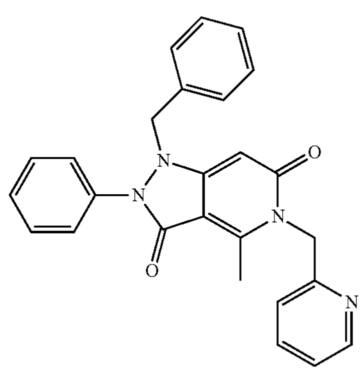 [SMILES: Cc1c2c(=O)n(-c3ccccc3)n(Cc3ccccc3)c2cc(=O)n1Cc1ccccn1] |
| AVG-108 | B | 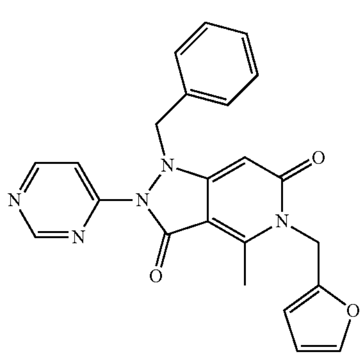 [SMILES: Cc1c2c(=O)n(-c3ccncn3)n(Cc3ccccc3)c2cc(=O)n1Cc1ccco1] |

TABLE 1-continued
Compounds of the Invention
| CP-target list | Series | Structure |
|---|---|---|
| AVG-109 | B | 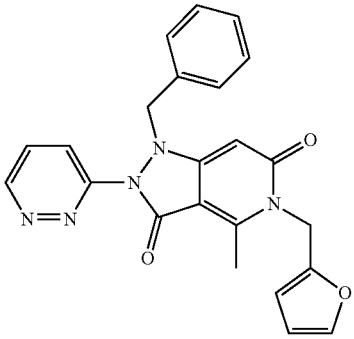 [SMILES: Cc1c2c(=O)n(-c3cccnn3)n(Cc3ccccc3)c2cc(=O)n1Cc1ccco1] |
| AVG-110 | B | 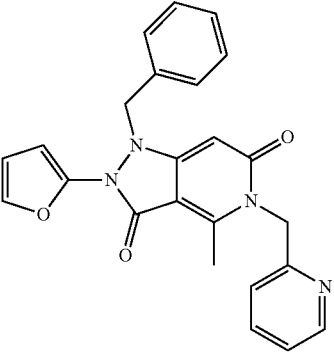 [SMILES: Cc1c2c(=O)n(-c3ccco3)n(Cc3ccccc3)c2cc(=O)n1Cc1ccccn1] |
| AVG-116 | A | 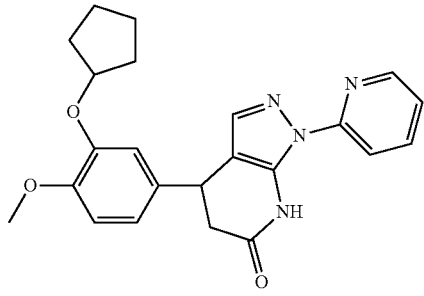 [SMILES: COc1ccc(C2CC(=O)Nc3c2cnn3-c2ccccn2)cc1OC1CCCC1] |
| AVG-117 | A | 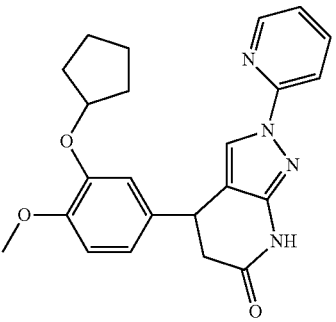 [SMILES: COc1ccc(C2CC(=O)Nc3nn(-c4ccccn4)cc32)cc1OC1CCCC1] |

TABLE 1-continued
Compounds of the Invention
| CP-target list | Series | Structure |
|---|---|---|
| AVG-118 | A | 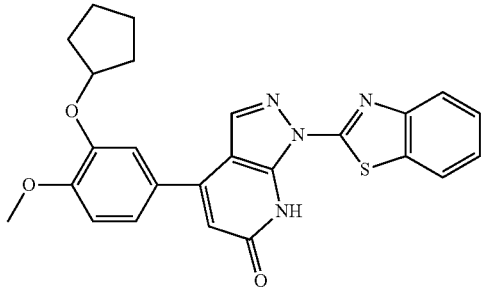 [SMILES: COc1ccc(-c2cc(=O)[nH]c3c2cnn3-c2nc3ccccc3s2)cc1OC1CCCC1] |
| AVG-119 | B | 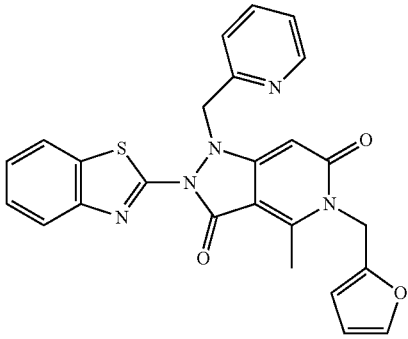 |
| AVG-120 | B | 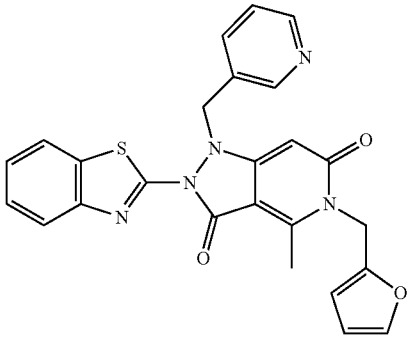 |
| AVG-121 | B | 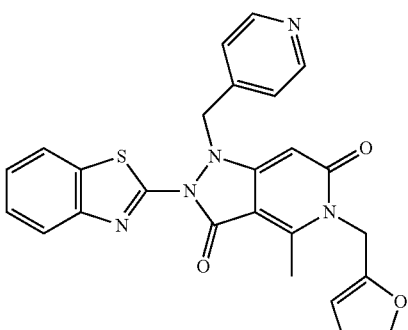 |

TABLE 1-continued
| Compounds of the Invention | | |
|---|---|---|
| CP-target list | Series | Structure |
| AVG-122 | B | 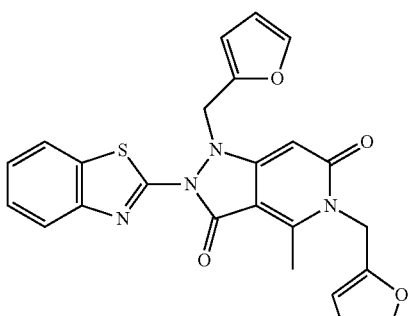 |
| AVG-123 | B | 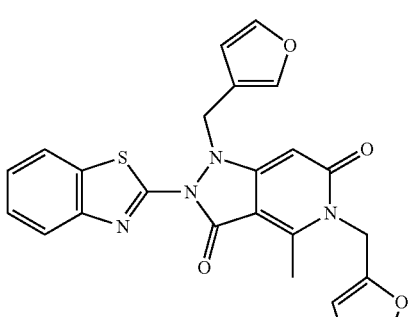 |
| AVG-124 | B | 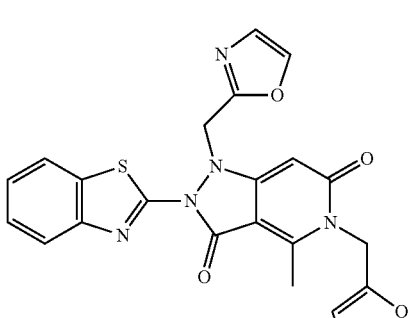 |
| AVG-125 | B | 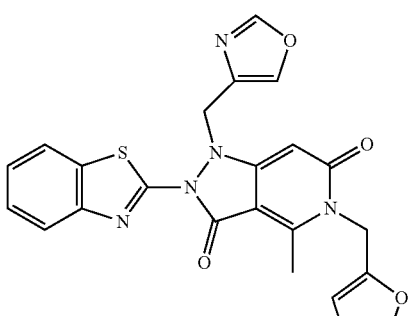 |

TABLE 1-continued
| | Compounds of the Invention | |
|---|---|---|
| CP-target list | Series | Structure |
| AVG-126 | B | 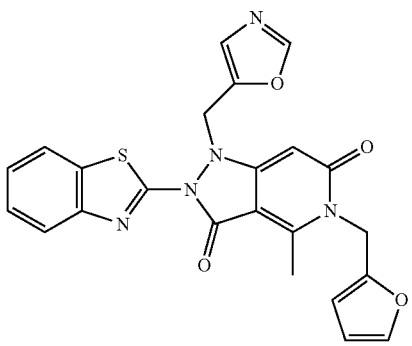 [SMILES: Cc1c2c(=O)n(-c3nc4ccccc4s3)n(Cc3cnco3)c2cc(=O)n1Cc1ccco1] |
| AVG-127 | B | 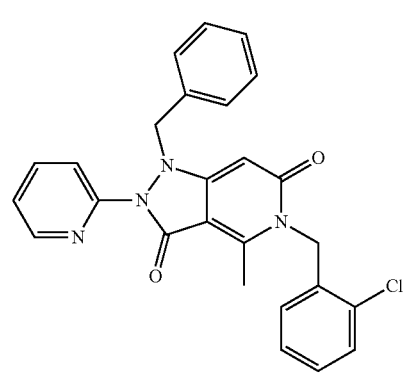 [SMILES: Cc1c2c(=O)n(-c3ccccn3)n(Cc3ccccc3)c2cc(=O)n1Cc1ccccc1Cl] |
| AVG-128 | B | 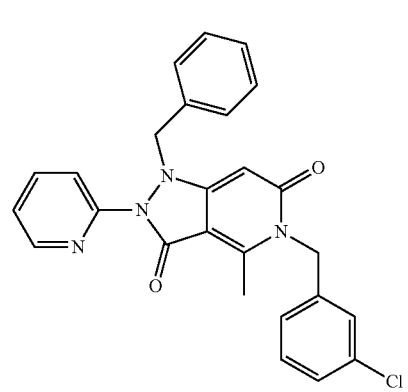 [SMILES: Cc1c2c(=O)n(-c3ccccn3)n(Cc3ccccc3)c2cc(=O)n1Cc1cccc(Cl)c1] |
| AVG-129 | B | 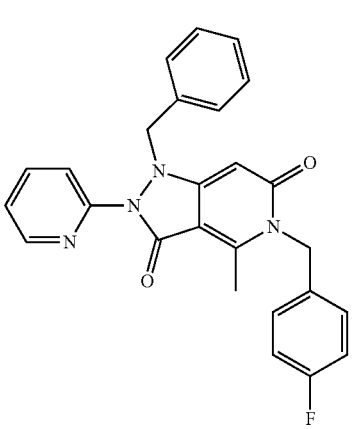 [SMILES: Cc1c2c(=O)n(-c3ccccn3)n(Cc3ccccc3)c2cc(=O)n1Cc1ccc(F)cc1] |

TABLE 1-continued

| Compounds of the Invention | | |
|---|---|---|
| CP-target list | Series | Structure |
| AVG-130 | B | (structure: 1-benzyl-2-(pyridin-2-yl)-4-methyl-5-(2-fluorobenzyl)-pyrazolo[4,3-c]pyridine-3,6-dione) |
| AVG-131 | B | (structure: 1-benzyl-2-(pyridin-2-yl)-4-methyl-5-(3-fluorobenzyl)-pyrazolo[4,3-c]pyridine-3,6-dione) |
| AVG-132 | B | (structure: 1-benzyl-2-(pyridin-2-yl)-4-methyl-5-(4-methoxybenzyl)-pyrazolo[4,3-c]pyridine-3,6-dione) |
| AVG-133 | B | (structure: 1-benzyl-2-(pyridin-2-yl)-4-methyl-5-(2-methoxybenzyl)-pyrazolo[4,3-c]pyridine-3,6-dione) |

TABLE 1-continued

Compounds of the Invention

| CP-target list | Series | Structure |
|---|---|---|
| AVG-134 | B | 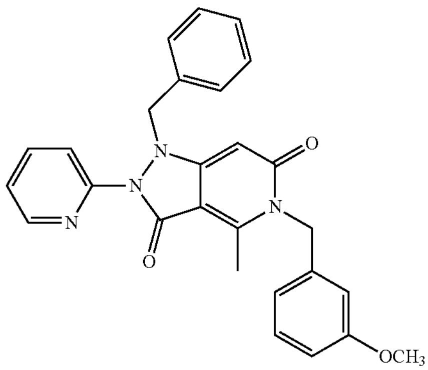 [SMILES: COc1cccc(Cn2c(C)c3c(=O)n(-c4ccccn4)n(Cc4ccccc4)c3cc2=O)c1] |
| AVG-135 | B | 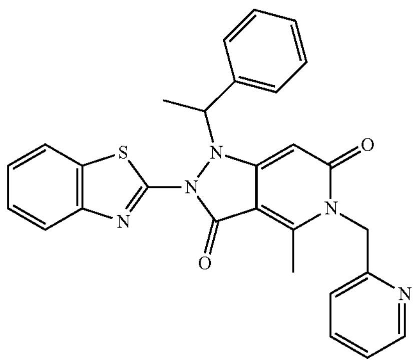 [SMILES: Cc1c2c(=O)n(-c3nc4ccccc4s3)n(C(C)c3ccccc3)c2cc(=O)n1Cc1ccccn1] |
| AVG-136 | B | 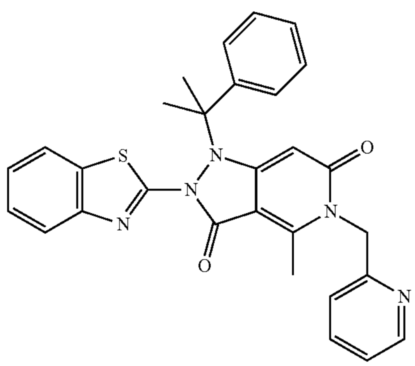 [SMILES: Cc1c2c(=O)n(-c3nc4ccccc4s3)n(C(C)(C)c3ccccc3)c2cc(=O)n1Cc1ccccn1] |
| AVG-157 | B | 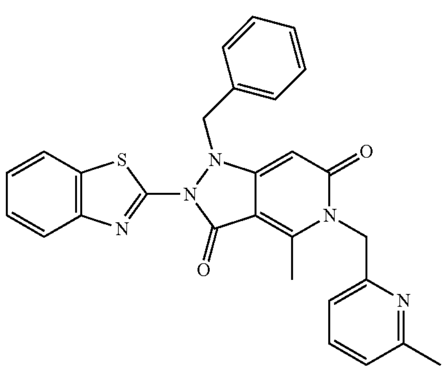 [SMILES: Cc1cccc(Cn2c(C)c3c(=O)n(-c4nc5ccccc5s4)n(Cc4ccccc4)c3cc2=O)n1] |

TABLE 1-continued

Compounds of the Invention

| CP-target list | Series | Structure |
|---|---|---|
| AVG-158 | B | 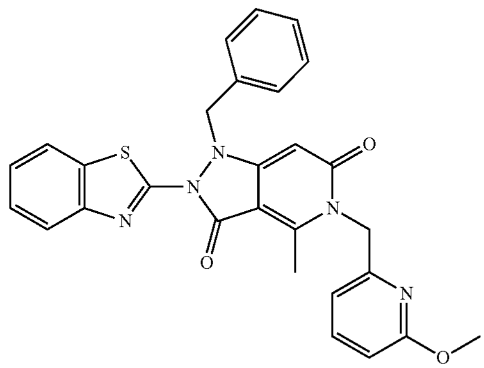 [SMILES: COc1cccc(Cn2c(C)c3c(=O)n(-c4nc5ccccc5s4)n(Cc4ccccc4)c3cc2=O)n1] |
| AVG-159 | B | 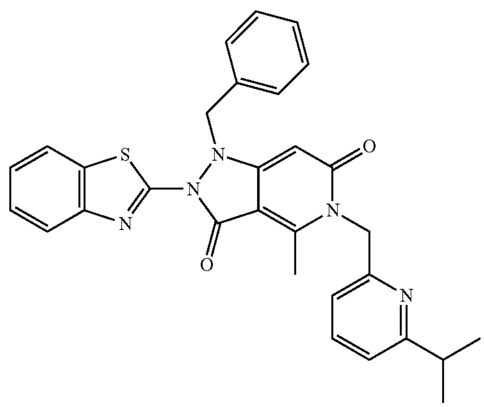 [SMILES: Cc1c2c(=O)n(-c3nc4ccccc4s3)n(Cc3ccccc3)c2cc(=O)n1Cc1cccc(C(C)C)n1] |
| AVG-160 | B | 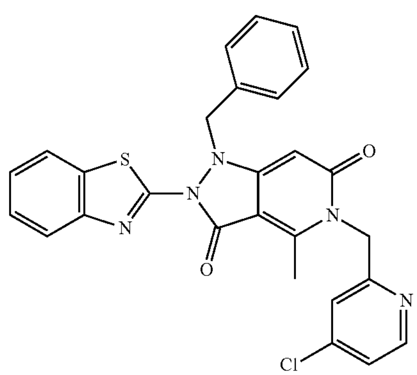 [SMILES: Cc1c2c(=O)n(-c3nc4ccccc4s3)n(Cc3ccccc3)c2cc(=O)n1Cc1cc(Cl)ccn1] |
| AVG-161 | B | 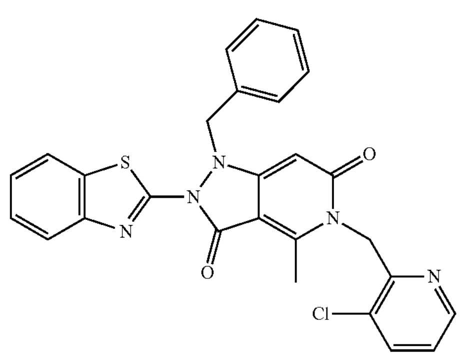 [SMILES: Cc1c2c(=O)n(-c3nc4ccccc4s3)n(Cc3ccccc3)c2cc(=O)n1Cc1ncccc1Cl] |

TABLE 1-continued

| Compounds of the Invention | | |
|---|---|---|
| CP-target list | Series | Structure |
| AVG-162 | B | |
| AVG-163 | B | |
| AVG-164 | B | |
| AVG-165 | B | |

TABLE 1-continued
| Compounds of the Invention | | |
|---|---|---|
| CP-target list | Series | Structure |
| AVG-166 | B | 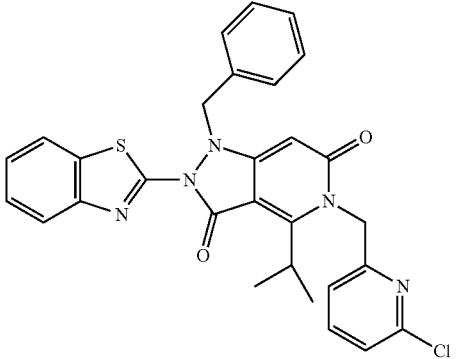 [SMILES: CC(C)c1c2c(=O)n(-c3nc4ccccc4s3)n(Cc3ccccc3)c2cc(=O)n1Cc1cccc(Cl)n1] |
| AVG-167 | B | 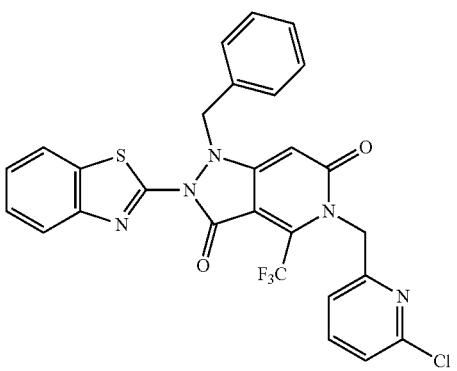 [SMILES: O=c1cc2c(c(C(F)(F)F)n1Cc1cccc(Cl)n1)c(=O)n(-c1nc3ccccc3s1)n2Cc1ccccc1] |
| AVG-168 | B | 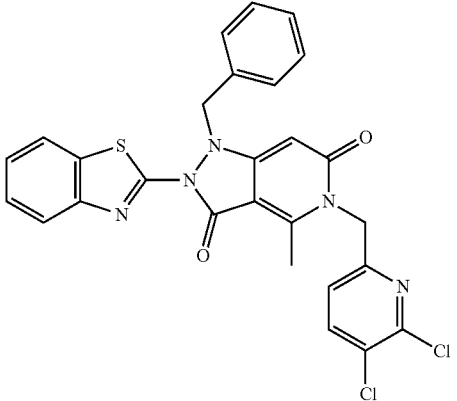 [SMILES: Cc1c2c(=O)n(-c3nc4ccccc4s3)n(Cc3ccccc3)c2cc(=O)n1Cc1ccc(Cl)c(Cl)n1] |
| AVG-169 | B | 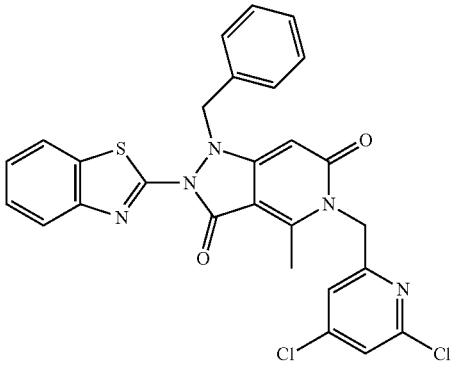 [SMILES: Cc1c2c(=O)n(-c3nc4ccccc4s3)n(Cc3ccccc3)c2cc(=O)n1Cc1cc(Cl)cc(Cl)n1] |

TABLE 1-continued

Compounds of the Invention

| CP-target list | Series | Structure |
|---|---|---|
| AVG-170 | B | 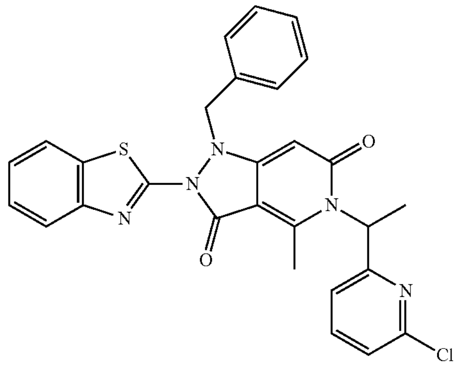 [SMILES: Cc1c2c(=O)n(-c3nc4ccccc4s3)n(Cc3ccccc3)c2cc(=O)n1C(C)c1cccc(Cl)n1] |
| AVG-171 | B | 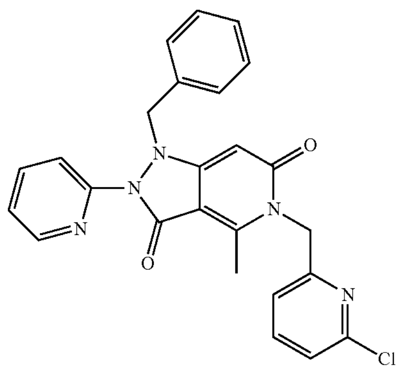 [SMILES: Cc1c2c(=O)n(-c3ccccn3)n(Cc3ccccc3)c2cc(=O)n1Cc1cccc(Cl)n1] |
| AVG-172 | B | 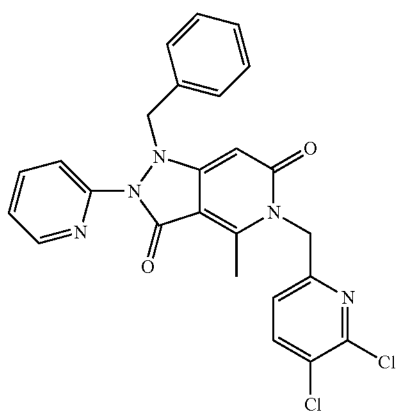 [SMILES: Cc1c2c(=O)n(-c3ccccn3)n(Cc3ccccc3)c2cc(=O)n1Cc1ccc(Cl)c(Cl)n1] |
| AVG-173 | B | 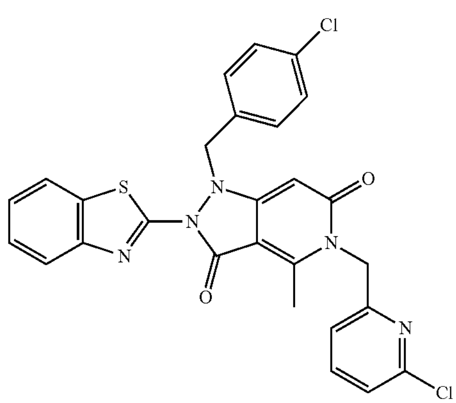 [SMILES: Cc1c2c(=O)n(-c3nc4ccccc4s3)n(Cc3ccc(Cl)cc3)c2cc(=O)n1Cc1cccc(Cl)n1] |

TABLE 1-continued
Compounds of the Invention
| CP-target list | Series | Structure |
|---|---|---|
| AVG-174 | B | 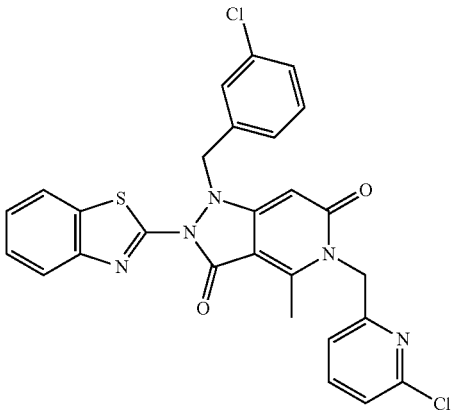 [SMILES: Cc1c2c(=O)n(-c3nc4ccccc4s3)n(Cc3cccc(Cl)c3)c2cc(=O)n1Cc1cccc(Cl)n1] |
| AVG-175 | B | 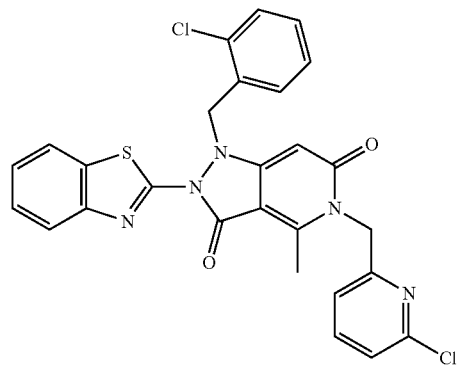 [SMILES: Cc1c2c(=O)n(-c3nc4ccccc4s3)n(Cc3ccccc3Cl)c2cc(=O)n1Cc1cccc(Cl)n1] |
| AVG-176 | B | 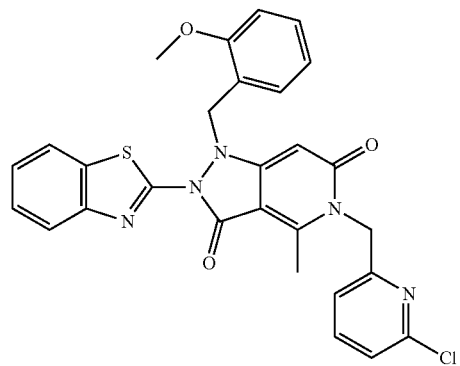 [SMILES: COc1ccccc1Cn1c2cc(=O)n(Cc3cccc(Cl)n3)c(C)c2c(=O)n1-c1nc2ccccc2s1] |

TABLE 1-continued

Compounds of the Invention

| CP-target list | Series | Structure |
|---|---|---|
| AVG-177 | B | 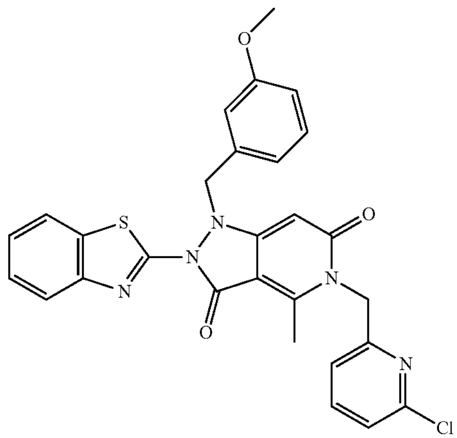 [SMILES: COc1cccc(Cn2c3cc(=O)n(Cc4cccc(Cl)n4)c(C)c3c(=O)n2-c2nc3ccccc3s2)c1] |
| AVG-178 | B | 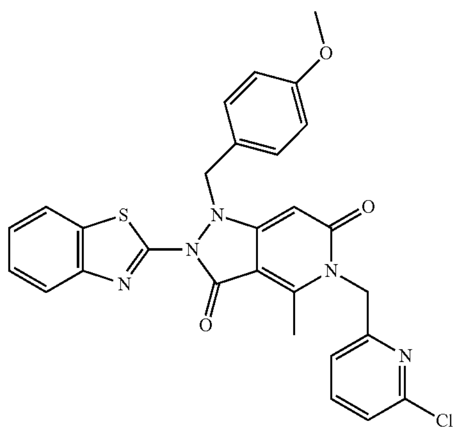 [SMILES: COc1ccc(Cn2c3cc(=O)n(Cc4cccc(Cl)n4)c(C)c3c(=O)n2-c2nc3ccccc3s2)cc1] |
| AVG-179 | A | 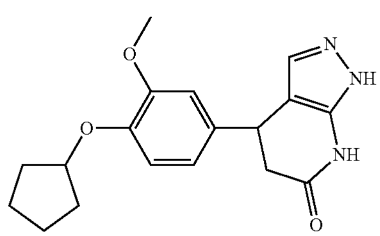 [SMILES: COc1cc(C2CC(=O)Nc3[nH]ncc32)ccc1OC1CCCC1] |
| AVG-180 | A | 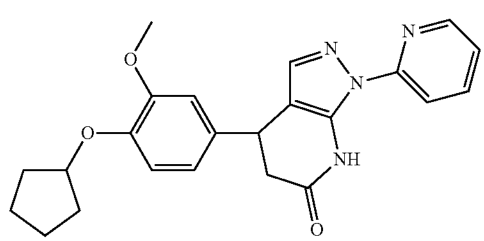 [SMILES: COc1cc(C2CC(=O)Nc3c2cnn3-c2ccccn2)ccc1OC1CCCC1] |

TABLE 1-continued
Compounds of the Invention
| CP-target list | Series | Structure |
|---|---|---|
| AVG-180b | A | 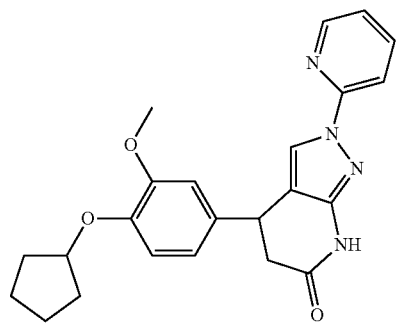 [SMILES: COc1cc(C2CC(=O)Nc3nn(-c4ccccn4)cc32)ccc1OC1CCCC1] |
| AVG-181 | A | 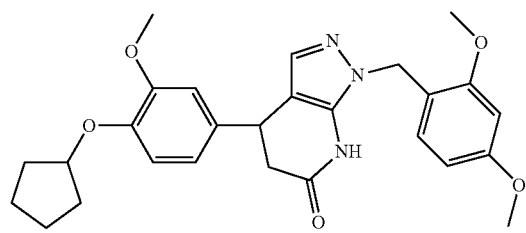 [SMILES: COc1ccc(Cn2ncc3c2NC(=O)CC3c2ccc(OC3CCCC3)c(OC)c2)c(OC)c1] |
| AVG-183 | B | 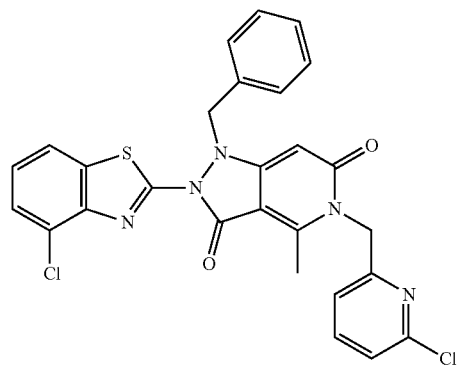 [SMILES: Cc1c2c(=O)n(-c3nc4c(Cl)cccc4s3)n(Cc3ccccc3)c2cc(=O)n1Cc1cccc(Cl)n1] |
| AVG-184 | B | 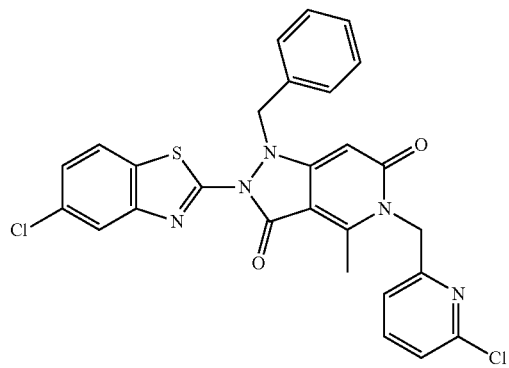 [SMILES: Cc1c2c(=O)n(-c3nc4cc(Cl)ccc4s3)n(Cc3ccccc3)c2cc(=O)n1Cc1cccc(Cl)n1] |

TABLE 1-continued

Compounds of the Invention

| CP-target list | Series | Structure |
|---|---|---|
| AVG-185 | B | 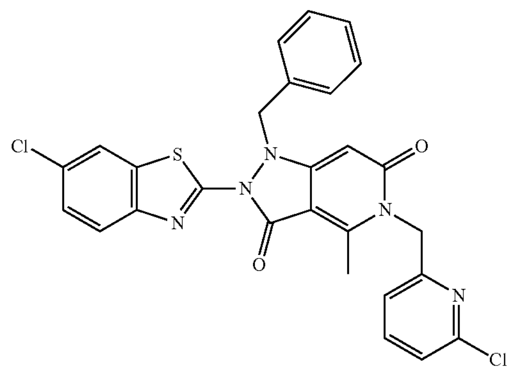 [SMILES: Cc1c2c(=O)n(-c3nc4ccc(Cl)cc4s3)n(Cc3ccccc3)c2cc(=O)n1Cc1cccc(Cl)n1] |
| AVG-186 | B | 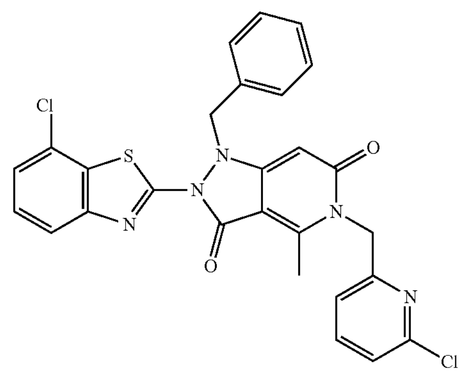 [SMILES: Cc1c2c(=O)n(-c3nc4cccc(Cl)c4s3)n(Cc3ccccc3)c2cc(=O)n1Cc1cccc(Cl)n1] |
| AVG-187 | B | 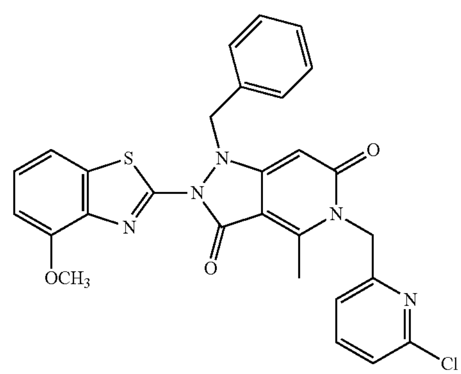 [SMILES: COc1cccc2sc(-n3c(=O)c4c(C)n(Cc5cccc(Cl)n5)c(=O)cc4n3Cc3ccccc3)nc12] |
| AVG-188 | B | 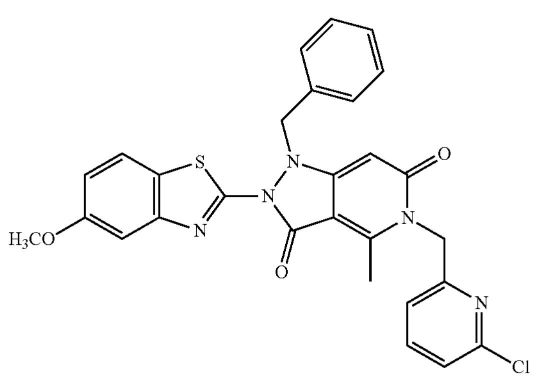 [SMILES: COc1ccc2sc(-n3c(=O)c4c(C)n(Cc5cccc(Cl)n5)c(=O)cc4n3Cc3ccccc3)nc2c1] |

TABLE 1-continued

Compounds of the Invention

| CP-target list | Series | Structure |
|---|---|---|
| AVG-189 | B | 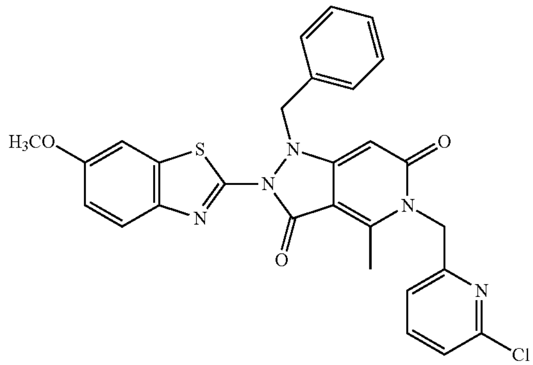 [SMILES: COc1ccc2nc(-n3c(=O)c4c(C)n(Cc5cccc(Cl)n5)c(=O)cc4n3Cc3ccccc3)sc2c1] |
| AVG-190 | B | 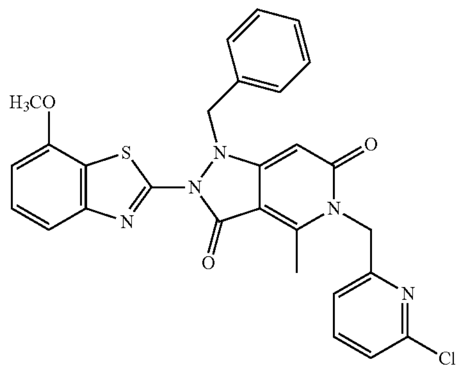 [SMILES: COc1cccc2nc(-n3c(=O)c4c(C)n(Cc5cccc(Cl)n5)c(=O)cc4n3Cc3ccccc3)sc12] |
| AVG-191 | B | 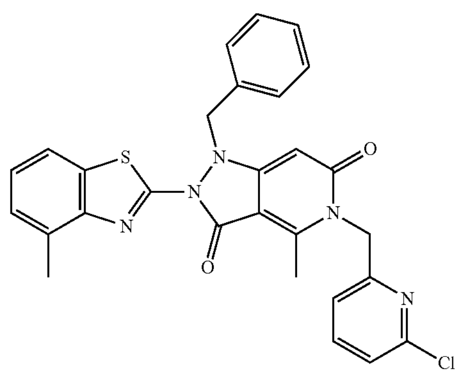 [SMILES: Cc1cccc2sc(-n3c(=O)c4c(C)n(Cc5cccc(Cl)n5)c(=O)cc4n3Cc3ccccc3)nc12] |
| AVG-192 | B | 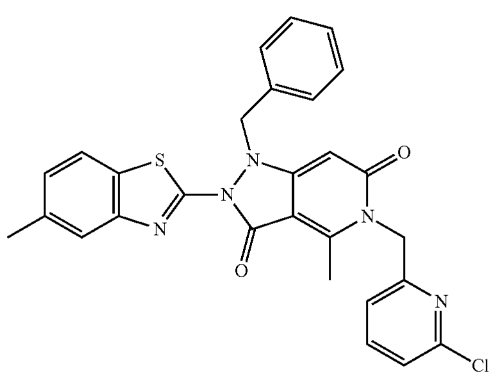 [SMILES: Cc1ccc2sc(-n3c(=O)c4c(C)n(Cc5cccc(Cl)n5)c(=O)cc4n3Cc3ccccc3)nc2c1] |

TABLE 1-continued
Compounds of the Invention
| CP-target list | Series | Structure |
|---|---|---|
| AVG-193 | B | 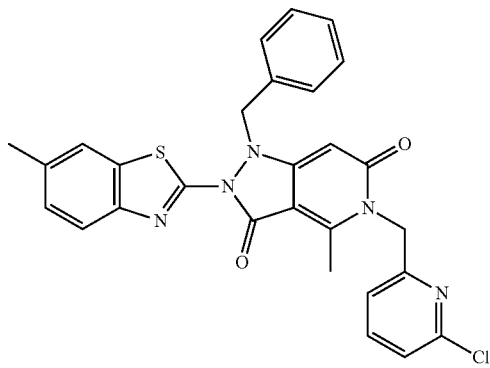 [SMILES: Cc1ccc2nc(-n3c(=O)c4c(C)n(Cc5cccc(Cl)n5)c(=O)cc4n3Cc3ccccc3)sc2c1] |
| AVG-194 | B | 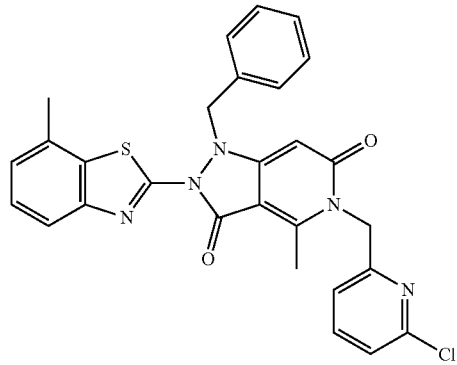 [SMILES: Cc1cccc2nc(-n3c(=O)c4c(C)n(Cc5cccc(Cl)n5)c(=O)cc4n3Cc3ccccc3)sc12] |
| AVG-195 | B | 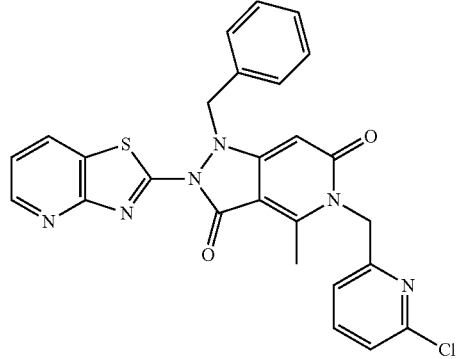 [SMILES: Cc1c2c(=O)n(-c3nc4ncccc4s3)n(Cc3ccccc3)c2cc(=O)n1Cc1cccc(Cl)n1] |
| AVG-196 | B | 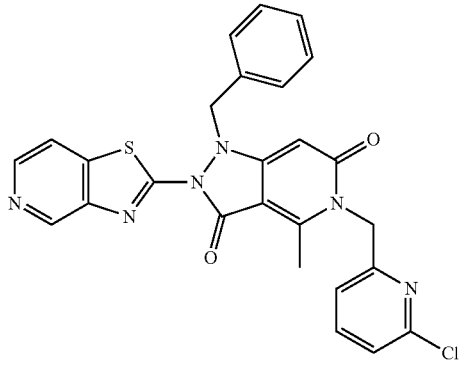 [SMILES: Cc1c2c(=O)n(-c3nc4cnccc4s3)n(Cc3ccccc3)c2cc(=O)n1Cc1cccc(Cl)n1] |

TABLE 1-continued
Compounds of the Invention
| CP-target list | Series | Structure |
|---|---|---|
| AVG-197 | B | 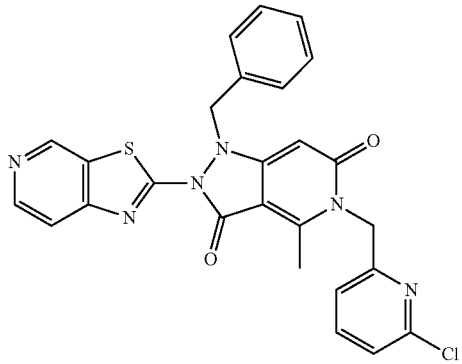 [SMILES: Cc1c2c(=O)n(-c3nc4ccncc4s3)n(Cc3ccccc3)c2cc(=O)n1Cc1cccc(Cl)n1] |
| AVG-198 | B | 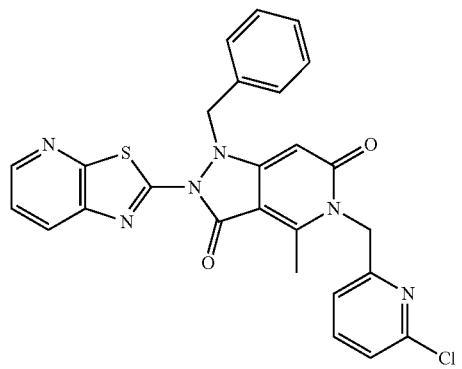 [SMILES: Cc1c2c(=O)n(-c3nc4cccnc4s3)n(Cc3ccccc3)c2cc(=O)n1Cc1cccc(Cl)n1] |
| AVG-199 | B | 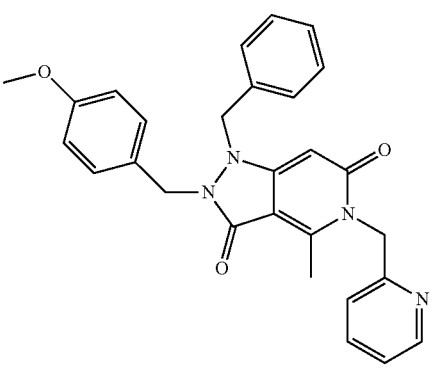 [SMILES: COc1ccc(Cn2c(=O)c3c(C)n(Cc4ccccn4)c(=O)cc3n2Cc2ccccc2)cc1] |
| AVG-200 | B | 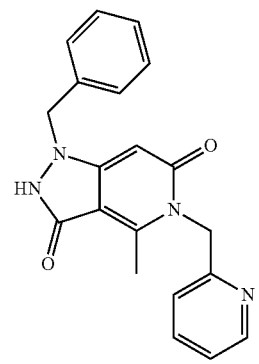 [SMILES: Cc1c2c(=O)[nH]n(Cc3ccccc3)c2cc(=O)n1Cc1ccccn1] |

TABLE 1-continued
Compounds of the Invention
| CP-target list | Series | Structure |
|---|---|---|
| AVG-201 | B | 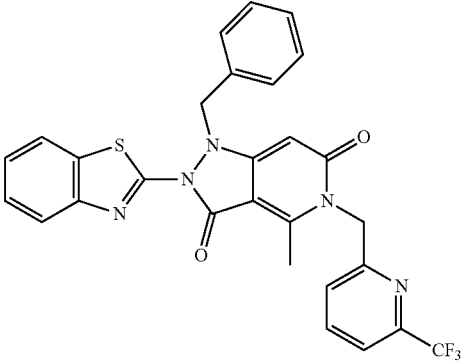 [SMILES: Cc1c2c(=O)n(-c3nc4ccccc4s3)n(Cc3ccccc3)c2cc(=O)n1Cc1cccc(C(F)(F)F)n1] |
| AVG-202 | B | 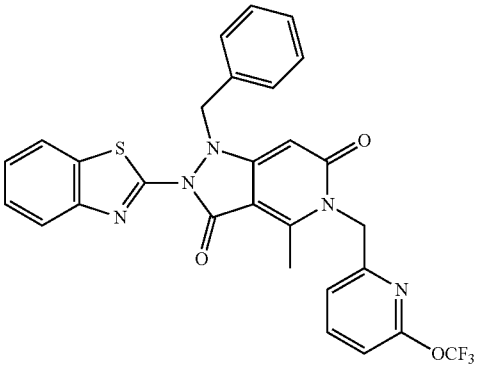 [SMILES: Cc1c2c(=O)n(-c3nc4ccccc4s3)n(Cc3ccccc3)c2cc(=O)n1Cc1cccc(OC(F)(F)F)n1] |
| AVG-203 | B | 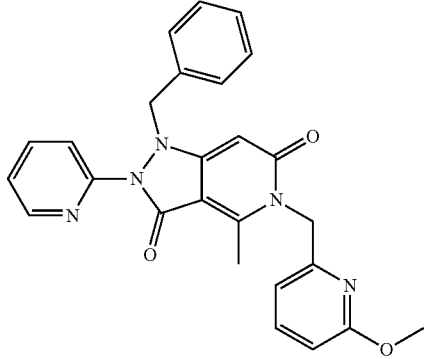 [SMILES: COc1cccc(Cn2c(C)c3c(=O)n(-c4ccccn4)n(Cc4ccccc4)c3cc2=O)n1] |
| AVG-204 | B | 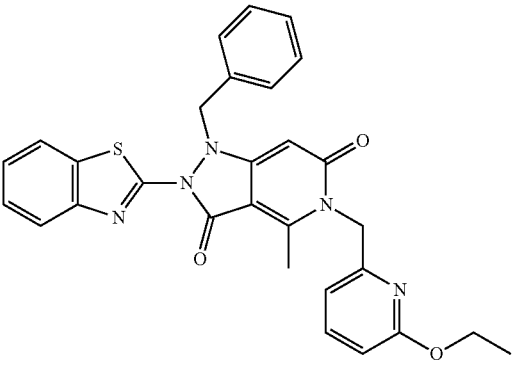 [SMILES: CCOc1cccc(Cn2c(C)c3c(=O)n(-c4nc5ccccc5s4)n(Cc4ccccc4)c3cc2=O)n1] |

TABLE 1-continued
Compounds of the Invention
| CP-target list | Series | Structure |
|---|---|---|
| AVG-205 | B | 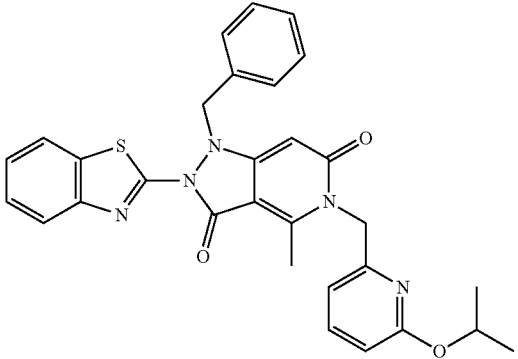 [SMILES: Cc1c2c(=O)n(-c3nc4ccccc4s3)n(Cc3ccccc3)c2cc(=O)n1Cc1cccc(OC(C)C)n1] |
| AVG-206 | B | 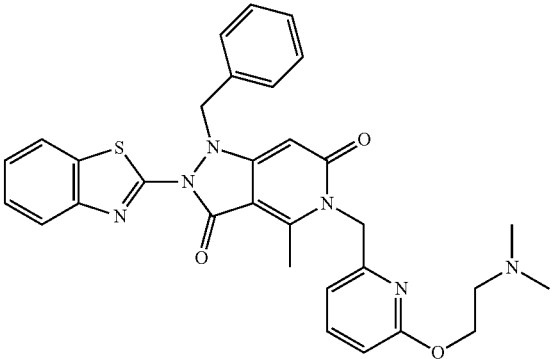 [SMILES: Cc1c2c(=O)n(-c3nc4ccccc4s3)n(Cc3ccccc3)c2cc(=O)n1Cc1cccc(OCCN(C)C)n1] |
| AVG-207 | B | 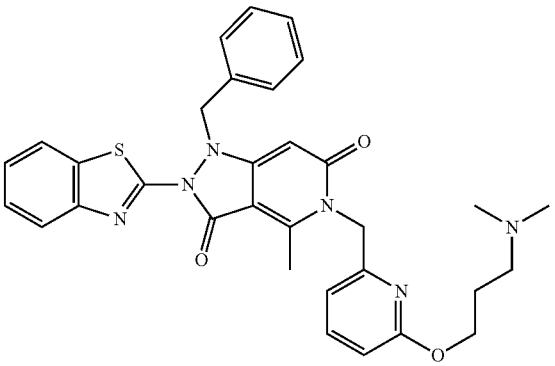 [SMILES: Cc1c2c(=O)n(-c3nc4ccccc4s3)n(Cc3ccccc3)c2cc(=O)n1Cc1cccc(OCCCN(C)C)n1] |
| AVG-208 | B | 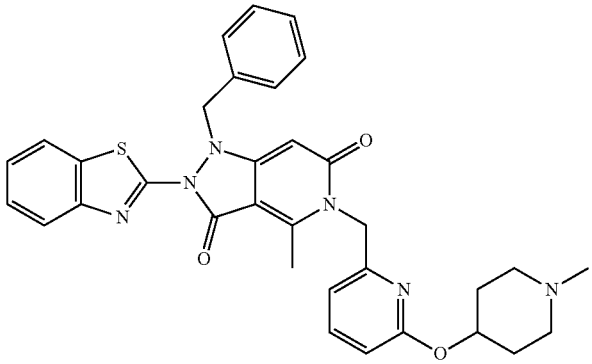 [SMILES: Cc1c2c(=O)n(-c3nc4ccccc4s3)n(Cc3ccccc3)c2cc(=O)n1Cc1cccc(OC2CCN(C)CC2)n1] |

TABLE 1-continued

Compounds of the Invention

| CP-target list | Series | Structure |
|---|---|---|
| AVG-209 | B | 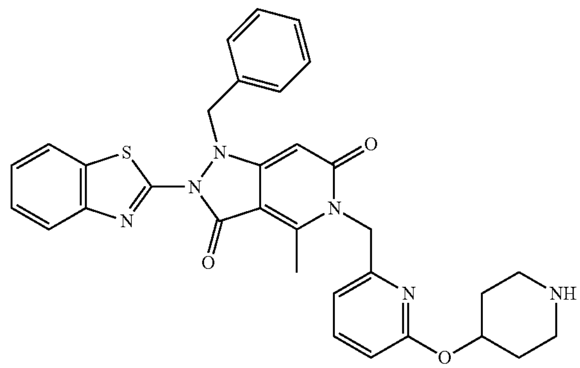 [SMILES: Cc1c2c(=O)n(-c3nc4ccccc4s3)n(Cc3ccccc3)c2cc(=O)n1Cc1cccc(OC2CCNCC2)n1] |
| AVG-210 | B | 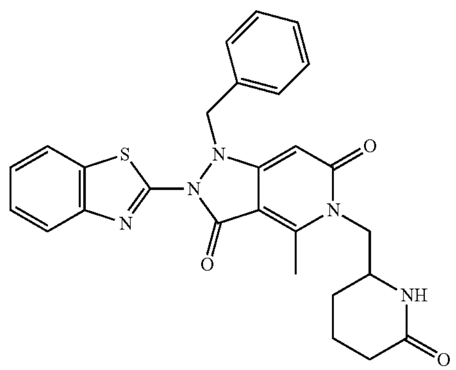 [SMILES: Cc1c2c(=O)n(-c3nc4ccccc4s3)n(Cc3ccccc3)c2cc(=O)n1CC1CCCC(=O)N1] |
| AVG-211 | B | 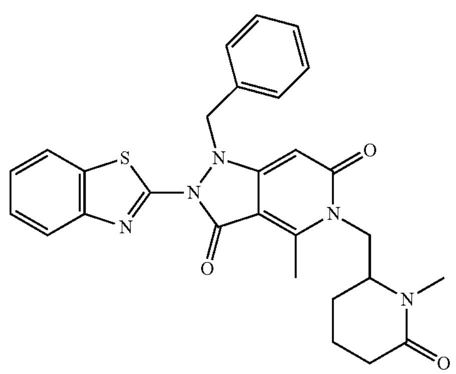 [SMILES: Cc1c2c(=O)n(-c3nc4ccccc4s3)n(Cc3ccccc3)c2cc(=O)n1CC1CCCC(=O)N1C] |
| AVG-212 | B | 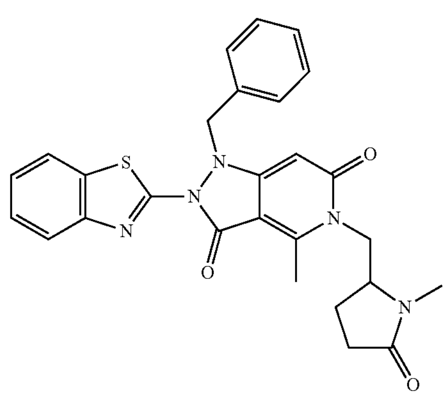 [SMILES: Cc1c2c(=O)n(-c3nc4ccccc4s3)n(Cc3ccccc3)c2cc(=O)n1CC1CCC(=O)N1C] |

TABLE 1-continued
Compounds of the Invention
| CP-target list | Series | Structure |
|---|---|---|
| AVG-213 | B | 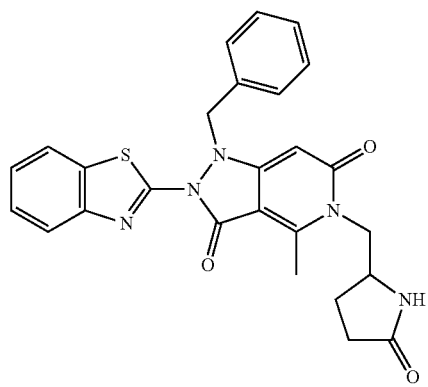 [SMILES: Cc1c2c(=O)n(-c3nc4ccccc4s3)n(Cc3ccccc3)c2cc(=O)n1CC1CCC(=O)N1] |
| AVG-214 | B | 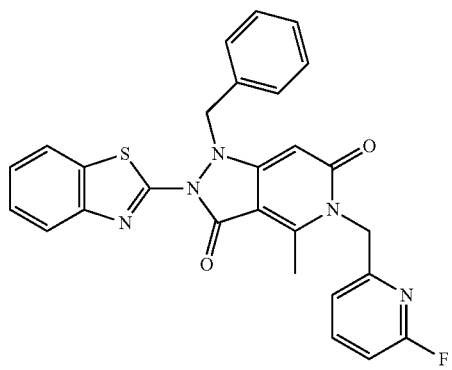 [SMILES: Cc1c2c(=O)n(-c3nc4ccccc4s3)n(Cc3ccccc3)c2cc(=O)n1Cc1cccc(F)n1] |
| AVG-225 | B | 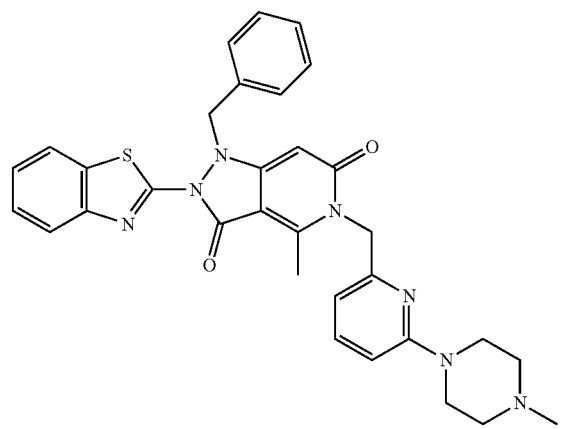 [SMILES: Cc1c2c(=O)n(-c3nc4ccccc4s3)n(Cc3ccccc3)c2cc(=O)n1Cc1cccc(N2CCN(C)CC2)n1] |

TABLE 1-continued
Compounds of the Invention
| CP-target list | Series | Structure |
|---|---|---|
| AVG-226 | B | 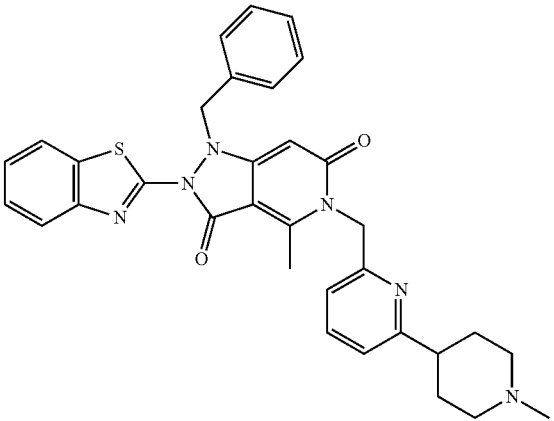 [SMILES: Cc1c2c(=O)n(-c3nc4ccccc4s3)n(Cc3ccccc3)c2cc(=O)n1Cc1cccc(C2CCN(C)CC2)n1] |
| AVG-227 | B | 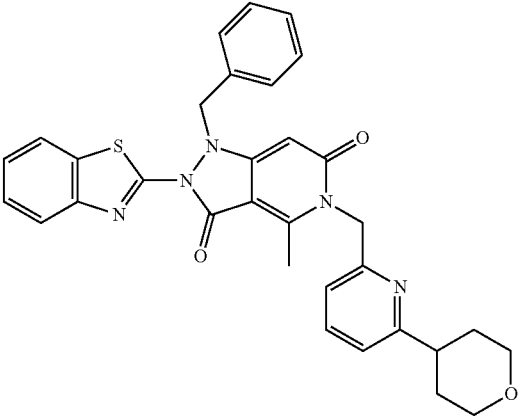 [SMILES: Cc1c2c(=O)n(-c3nc4ccccc4s3)n(Cc3ccccc3)c2cc(=O)n1Cc1cccc(C2CCOCC2)n1] |
| AVG-228 | B | 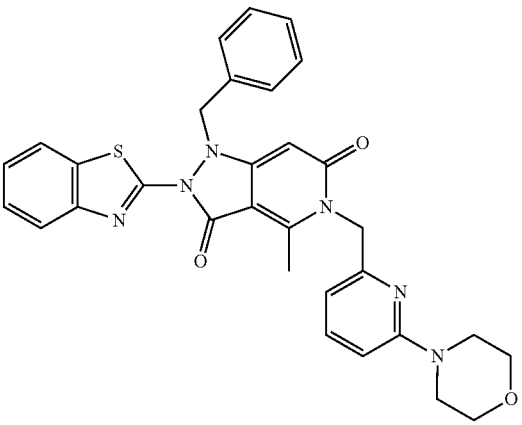 [SMILES: Cc1c2c(=O)n(-c3nc4ccccc4s3)n(Cc3ccccc3)c2cc(=O)n1Cc1cccc(N2CCOCC2)n1] |

TABLE 1-continued
Compounds of the Invention
| CP-target list | Series | Structure |
|---|---|---|
| AVG-229 | B | 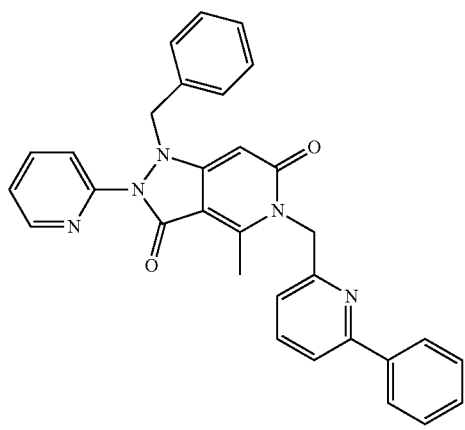 [SMILES: Cc1c2c(=O)n(-c3ccccn3)n(Cc3ccccc3)c2cc(=O)n1Cc1cccc(-c2ccccc2)n1] |
| AVG-230 | B | 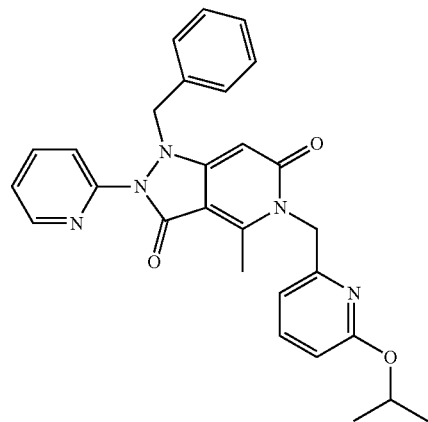 [SMILES: Cc1c2c(=O)n(-c3ccccn3)n(Cc3ccccc3)c2cc(=O)n1Cc1cccc(OC(C)C)n1] |
| AVG-231 | B | 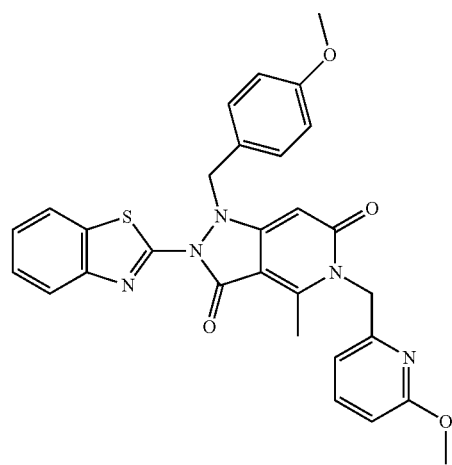 [SMILES: COc1ccc(Cn2c3cc(=O)n(Cc4cccc(OC)n4)c(C)c3c(=O)n2-c2nc3ccccc3s2)cc1] |

TABLE 1-continued
Compounds of the Invention
| CP-target list | Series | Structure |
|---|---|---|
| AVG-232 | B | 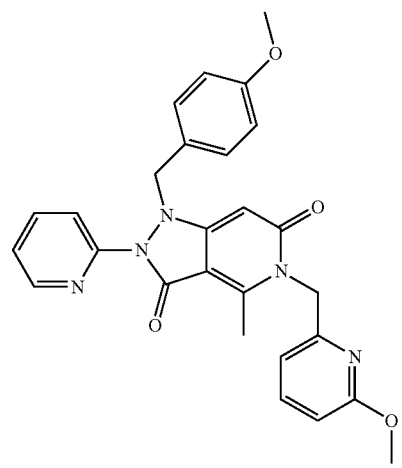 [SMILES: COc1ccc(Cn2c3cc(=O)n(Cc4cccc(OC)n4)c(C)c3c(=O)n2-c2ccccn2)cc1] |
| AVG-233 | B | 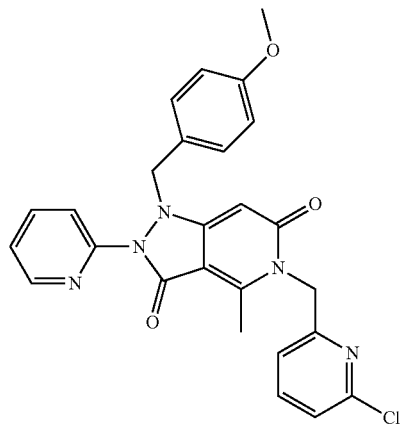 [SMILES: COc1ccc(Cn2c3cc(=O)n(Cc4cccc(Cl)n4)c(C)c3c(=O)n2-c2ccccn2)cc1] |
| AVG-234 | B | 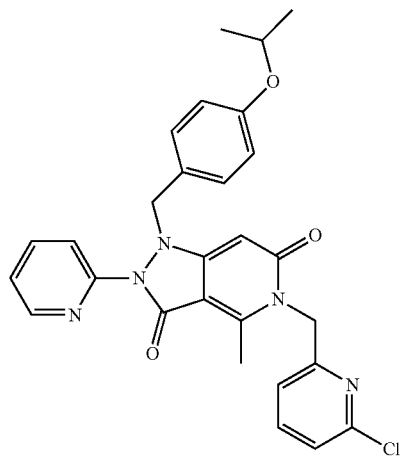 [SMILES: Cc1c2c(=O)n(-c3ccccn3)n(Cc3ccc(OC(C)C)cc3)c2cc(=O)n1Cc1cccc(Cl)n1] |

TABLE 1-continued
Compounds of the Invention
| CP-target list | Series | Structure |
|---|---|---|
| AVG-239 | B | 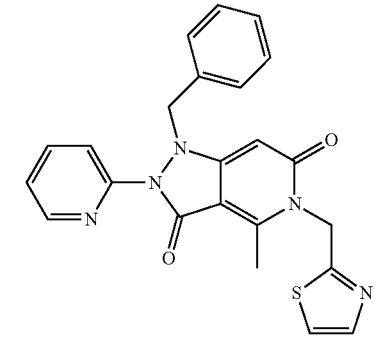 [SMILES: Cc1c2c(=O)n(-c3ccccn3)n(Cc3ccccc3)c2cc(=O)n1Cc1nccs1] |
| AVG-240 | B | 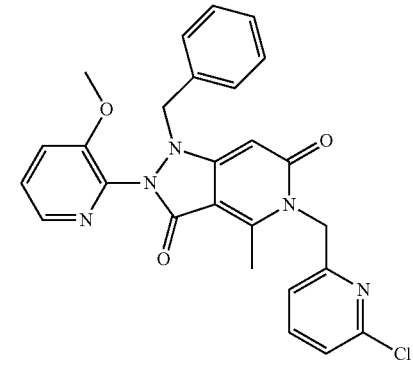 [SMILES: COc1cccnc1-n1c(=O)c2c(C)n(Cc3cccc(Cl)n3)c(=O)cc2n1Cc1ccccc1] |
| AVG-241 | B | 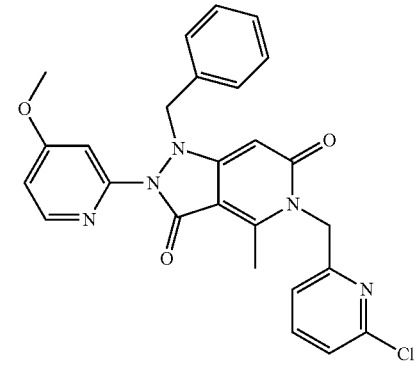 [SMILES: COc1ccnc(-n2c(=O)c3c(C)n(Cc4cccc(Cl)n4)c(=O)cc3n2Cc2ccccc2)c1] |
| AVG-242 | B | 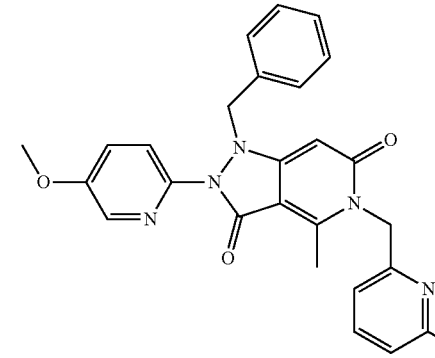 |

TABLE 1-continued

Compounds of the Invention

| CP-target list | Series | Structure |
|---|---|---|
| AVG-243 | B | 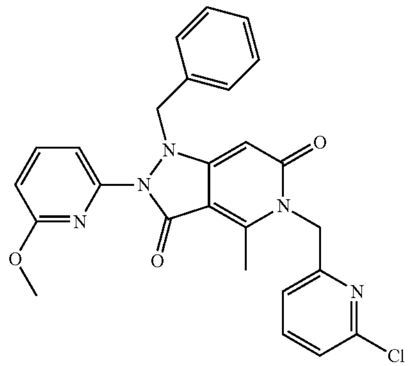 [SMILES: COc1cccc(-n2c(=O)c3c(C)n(Cc4cccc(Cl)n4)c(=O)cc3n2Cc2ccccc2)n1] |
| AVG-244 | B | 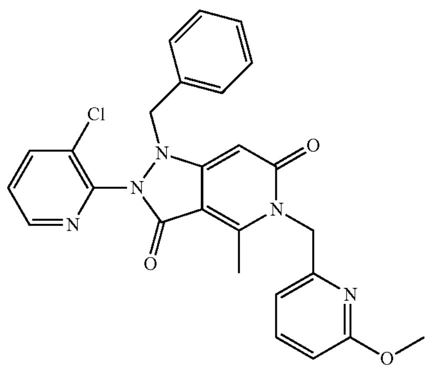 [SMILES: COc1cccc(Cn2c(C)c3c(=O)n(-c4ncccc4Cl)n(Cc4ccccc4)c3cc2=O)n1] |
| AVG-245 | B | 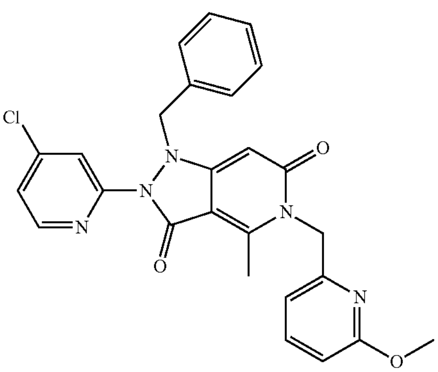 [SMILES: COc1cccc(Cn2c(C)c3c(=O)n(-c4cc(Cl)ccn4)n(Cc4ccccc4)c3cc2=O)n1] |
| AVG-246 | B | 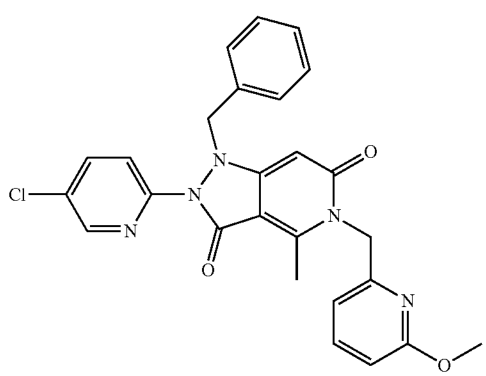 [SMILES: COc1cccc(Cn2c(C)c3c(=O)n(-c4ccc(Cl)cn4)n(Cc4ccccc4)c3cc2=O)n1] |

TABLE 1-continued

Compounds of the Invention

| CP-target list | Series | Structure |
|---|---|---|
| AVG-247 | B | 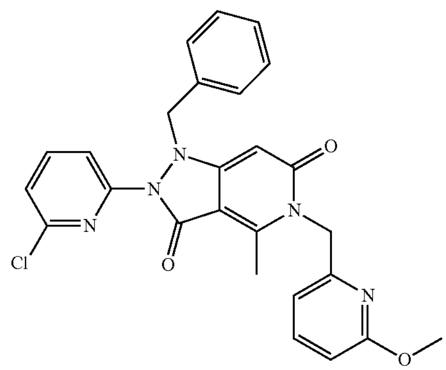 [SMILES: COc1cccc(Cn2c(C)c3c(=O)n(-c4cccc(Cl)n4)n(Cc4ccccc4)c3cc2=O)n1] |
| AVG-248 | B | 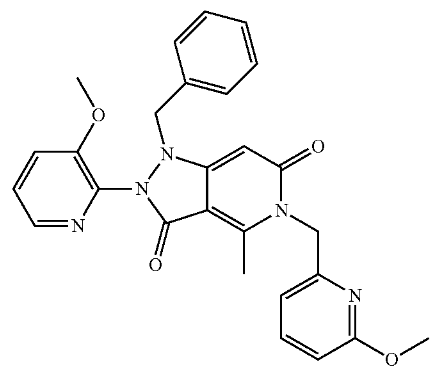 [SMILES: COc1cccc(Cn2c(C)c3c(=O)n(-c4ncccc4OC)n(Cc4ccccc4)c3cc2=O)n1] |
| AVG-249 | B | 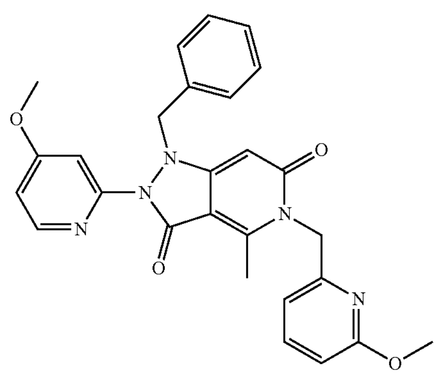 [SMILES: COc1ccnc(-n2c(=O)c3c(C)n(Cc4cccc(OC)n4)c(=O)cc3n2Cc2ccccc2)c1] |
| AVG-250 | B | 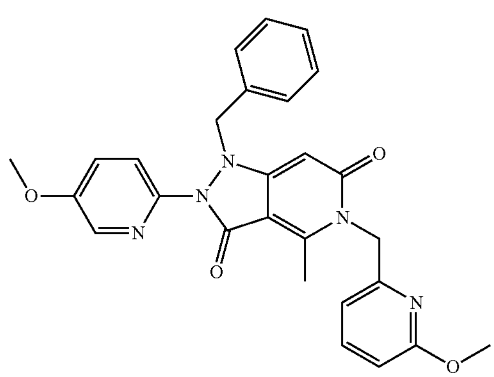 |

TABLE 1-continued
Compounds of the Invention
| CP-target list | Series | Structure |
|---|---|---|
| AVG-251 | B | 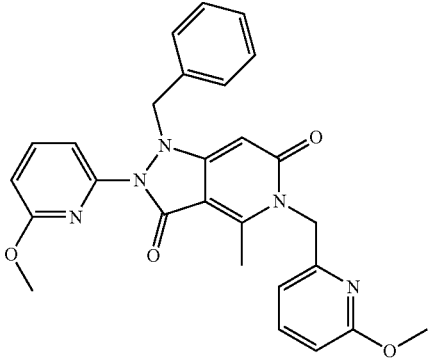 [SMILES: COc1cccc(Cn2c(C)c3c(=O)n(-c4cccc(OC)n4)n(Cc4ccccc4)c3cc2=O)n1] |
| AVG-252 | B | 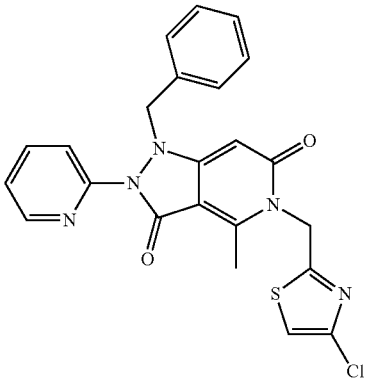 |
| AVG-253 | B | 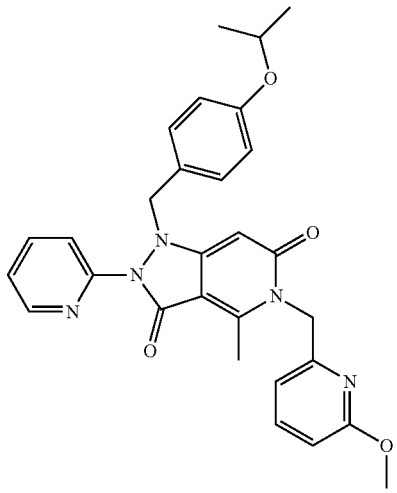 [SMILES: COc1cccc(Cn2c(C)c3c(=O)n(-c4ccccn4)n(Cc4ccc(OC(C)C)cc4)c3cc2=O)n1] |

TABLE 1-continued
Compounds of the Invention
| CP-target list | Series | Structure |
|---|---|---|
| AVG-254 | B | 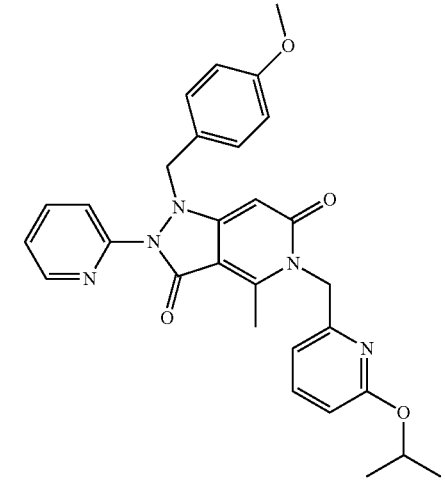 [SMILES: COc1ccc(Cn2c3cc(=O)n(Cc4cccc(OC(C)C)n4)c(C)c3c(=O)n2-c2ccccn2)cc1] |
| AVG-255 | B | 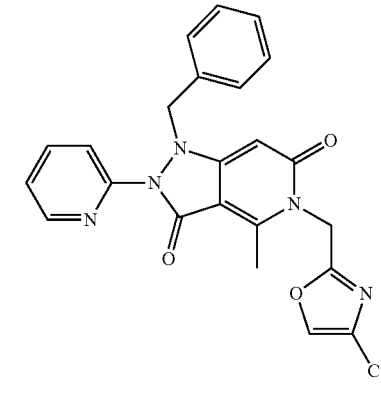 |
| AVG-256 | B | 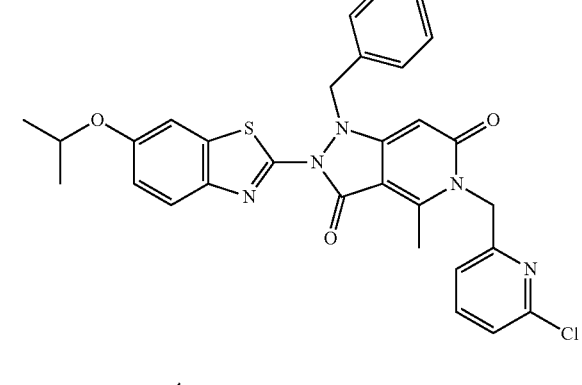 |
| AVG-257 | B | 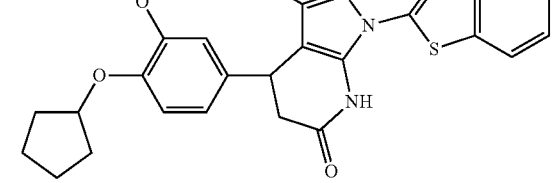 |

TABLE 1-continued
Compounds of the Invention
| CP-target list | Series | Structure |
|---|---|---|
| AVG-258 | B | 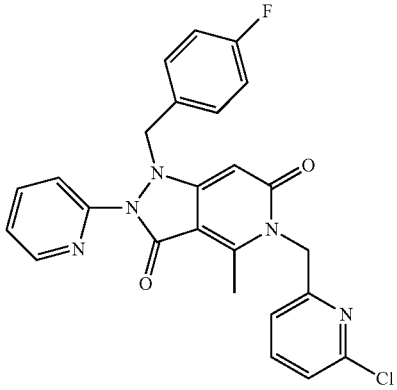 [SMILES: Cc1c2c(=O)n(-c3ccccn3)n(Cc3ccc(F)cc3)c2cc(=O)n1Cc1cccc(Cl)n1] |
| AVG-259 | B | 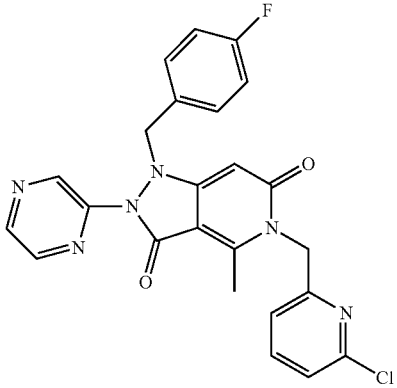 [SMILES: Cc1c2c(=O)n(-c3cnccn3)n(Cc3ccc(F)cc3)c2cc(=O)n1Cc1cccc(Cl)n1] |
| AVG-260 | B | 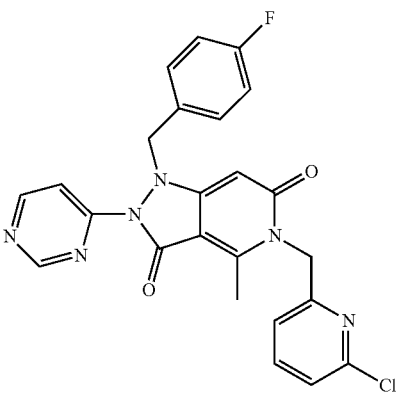 [SMILES: Cc1c2c(=O)n(-c3ccncn3)n(Cc3ccc(F)cc3)c2cc(=O)n1Cc1cccc(Cl)n1] |
| AVG-261 | B | 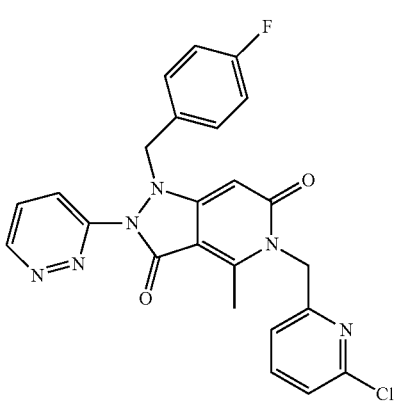 [SMILES: Cc1c2c(=O)n(-c3cccnn3)n(Cc3ccc(F)cc3)c2cc(=O)n1Cc1cccc(Cl)n1] |

TABLE 1-continued

Compounds of the Invention

| CP-target list | Series | Structure |
|---|---|---|
| AVG-262 | B | 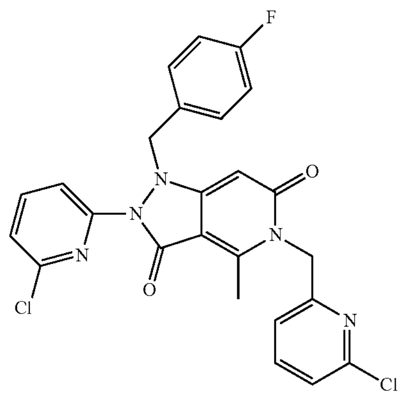 [SMILES: Cc1c2c(=O)n(-c3cccc(Cl)n3)n(Cc3ccc(F)cc3)c2cc(=O)n1Cc1cccc(Cl)n1] |

The compounds defined in the above aspects are RSV antiviral agents and are useful in the treatment of RSV infections. Accordingly, these compounds of the invention are useful in the treatment of RSV disease, such as bronchiolitis or pneumonia, or in reducing exacerbation of underlying or pre-existing respiratory diseases or conditions wherein RSV infection is a cause of said exacerbation. The underlying or pre-existing respiratory diseases or conditions may include asthma, chronic obstructive pulmonary disease (COPD) and immunosuppression such as immunosuppression experienced by bone marrow transplant recipients. The compounds above may also be combined with one or more other RSV antiviral agents.

The compounds of the invention may be formulated as pharmaceutical compositions and administered to a human patient as set forth in more detail below. The compounds can be delivered in a number of suitable ways including orally, intravenously, topically, parentally, subcutaneously, intradermally, or by inhalation. Exemplary routes of administration include buccal, oral, intravenous, intramuscular, topical, subcutaneous, rectal, vaginal, parenteral, pulmonary, intranasal, ophthalmic, and the like, as set forth in more detail below.

Useful dosages of the compounds of the invention for inclusion in the pharmaceutical compositions of the invention can be determined by comparing in vitro activity and in vivo activity of the compounds in appropriate animal models. Generally, the concentration of the compound(s) of the invention in a liquid composition will range from about 0.1% to about 95% by weight, preferably from about 0.5% to about 25% by weight. The concentration in a semi-solid or solid composition will range from about 0.1% to 100% by weight, preferably about 0.5% to about 5% by weight. Single doses for intravenous injection, subcutaneous, intramuscular or topical administration, infusion, ingestion or suppository will generally be from about 0.001 to about 5000 mg, and be administered from about 1 to about 3 times daily, to yield levels of about 0.01 to about 500 mg/kg, for adults.

The compounds can be co-administered with one or more other agents for the treatment or prevention of RSV infection. The other agents can be formulated separately, and administered either at the same or different time as the compounds of the instant invention. The other agents can be co-formulated with the compounds of the instant invention to give a combination dosage form.

Pharmaceutical Compositions and Modes of Administration

The invention also provides a pharmaceutical composition comprising a compound of formula (I) and a pharmaceutically acceptable vehicle, excipient or carrier, and the form of this composition can be suitable for a number of different modes of administration to a patient as set forth below.

The pharmaceutical composition may further comprise or be administered in combination with one or more other RSV antiviral agents such as Virazole®, BMS-4337715, TMC3531216, MDT-637 (formerly VP-14637), GS-5806, RSV604, ALNRSV01, AL-8176 (or ALS-8176) and/or other agents that may be developed as inhibitors of viral entry, assembly, replication, egress or host-virus interactions The term "composition" is intended to include the formulation of an active ingredient with conventional vehicles, carriers and excipients, and also with encapsulating materials as the carrier, to give a capsule in which the active ingredient (with or without other carriers) is surrounded by the encapsulation carrier. Any carrier must be "pharmaceutically acceptable" meaning that it is compatible with the other ingredients of the composition and is not deleterious to a subject. The compositions of the present invention may contain other therapeutic agents as described above, and may be formulated, for example, by employing conventional solid or liquid vehicles or diluents, as well as pharmaceutical additives of a type appropriate to the mode of desired administration (for example, excipients, binders, preservatives, stabilizers, flavours and the like) according to techniques such as those well known in the art of pharmaceutical formulation (see, for example, Remington: *The Science and Practice of Pharmacy,* 21st Ed., 2005, Lippincott Williams & Wilkins).

The pharmaceutical composition includes those suitable for oral, rectal, nasal, topical (including buccal and sublingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilizers, lubricants, suspending agents, binders, preservatives, tablet disintegrating agents, or an encapsulating material.

Suitable vehicles, carriers or excipients include magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with an encapsulating material as the carrier by providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compositions according to the present invention may thus be formulated for parenteral administration (for example, by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, for example, sterile, pyrogen-free water, before use.

Pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

The solvent or dispersion medium for the injectable solution or dispersion may contain any of the conventional solvent or carrier systems for the compounds, and may contain, for example, water, ethanol, polyol (for example, glycerol, propylene glycol and liquid polyethylene glycol and the like), suitable mixtures thereof, and vegetable oils.

Pharmaceutical forms suitable for injectable use may be delivered by any appropriate route including intravenous, intramuscular, intracerebral, intrathecal, epidural injection or infusion.

Sterile injectable solutions are prepared by incorporating the active compounds in the required amount in the appropriate solvent with various other ingredients such as these enumerated above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

When the active ingredients are suitably protected they may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compound may be incorporated with excipients and used in the form of ingestible tablets, buccal tablets, troches, capsules, elixirs, suspensions, syrups, wafers and the like.

The amount of active compound in therapeutically useful compositions should be sufficient that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin; or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations, including those that allow specific delivery of the active peptide to specific regions of the gut.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well-known suspending agents.

Pharmaceutically acceptable carriers and/or diluents include any and all solvents, dispersion media, coatings, antibacterial and antifungal agents, isotonic and absorption delaying agents and the like.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension.

In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, a hydrofluorocarbon (HFC) for example hydrofluoroalkanes (HFA), carbon dioxide, or other suitable gas.

The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, for example gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of viral infection in living subjects having a diseased condition in which bodily health is impaired as herein disclosed in detail.

The invention also includes the compounds in the absence of carrier where the compounds are in unit dosage form.

Liquids or powders for intranasal administration, tablets or capsules for oral administration and liquids for intravenous administration are the preferred compositions.

The compounds as set forth above can be useful in a method of inhibiting RSV or in treating or preventing an RSV infection of other infections caused by related members of the paramyxovirus family such as mumps virus, human parainfluenzaviruses, and Nipah and hendra virus. The reference to RSV as used hereinbelow also include these related members or the paramyxovirus family compounds can also be used to treat an RSV disease or reduce exacerbation of an underlying or pre-existing respiratory disease wherein RSV infection is a cause of said exacerbation. The RSV disease may include bronchiolitis or pneumonia. The underlying or pre-existing respiratory diseases or conditions may include asthma, chronic obstructive pulmonary disease (COPD) and immunosuppression such as immunosuppression experienced by bone marrow transplant recipients.

Treatment may be therapeutic treatment or prophylactic treatment or prevention. Generally, the term "treating" means affecting a subject, tissue or cell to obtain a desired pharmacological and/or physiological effect and includes: (a) inhibiting the viral infection or RSV disease, such as by arresting its development or further development; (b) relieving or ameliorating the effects of the viral infection or RSV disease, such as by causing regression of the effects of the viral infection or RSV disease; (c) reducing the incidence of the viral infection or RSV disease or (d) preventing the viral infection or RSV disease from occurring in a subject, tissue or cell predisposed to the viral infection or RSV disease or at risk thereof, but has not yet been diagnosed with a protective pharmacological and/or physiological effect so that the viral infection or RSV disease does not develop or occur in the subject, tissue or cell.

The term "subject" refers to any animal, in particular mammals such as humans, having a disease which requires treatment with the compound of formula (I). Particularly preferred treatment groups include at risk populations such as hospitalised subjects, the elderly, high-risk adults and infants. In one embodiment of the invention, an effective amount of the above compounds, or pharmaceutical compositions thereof, is administered to a patient or subject in need thereof.

The term "administering" or "administered" should be understood to mean providing a compound or pharmaceutical composition of the invention to a subject suffering from or at risk of the disease or condition to be treated or prevented.

As indicated above, although the invention has been described with particular reference to treating RSV infections and diseases, more particularly human and animal RSV infections or diseases, it will be appreciated that the invention may also be useful in the treatment of other viruses of the sub-family Pneumovirinae, more particularly, the genera Pneumovirus and Metapneumovirus.

Dosages

The term "therapeutically effective amount" refers to the amount of the compound of formula (I) that will elicit the biological or medical response of a subject, tissue or cell that is being sought by the researcher, veterinarian, medical doctor or other clinician.

By "effective amount" is generally considered that amount that will be effective to treat the condition sought to be treated, or to inhibit RSV, and this effective amount is variable based on a variety of factors including age, size and condition of the patient being treated. Accordingly, one skilled in the art would be readily able to determine the specific effective amount for each patient being treated for RSV, an RSV-related condition, or to inhibit RSV in a given case.

In the treatment of RSV infections or diseases, an appropriate dosage level will generally be about 0.01 to about 500 mg per kg subject body weight per day which can be administered in single or multiple doses. The dosage may be selected, for example, to any dose within any of these ranges, for therapeutic efficacy and/or symptomatic adjustment of the dosage to the subject to be treated.

As indicated above, it will be understood that the specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the subject undergoing therapy.

Methods of Preparation

The compounds of the invention may generally be prepared by one skilled in the art using at least the following methods. Unless otherwise stated, the groups of each of the compounds are as previously defined.

With regard to the series "A" compounds as identified above, there are at least three general methods that may be employed, identified herein as general method "A1", "A2" and "A3", respectively.

General Information Regarding Method of Preparation:

In the syntheses of the present invention, all evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. 1H chemical shifts are reported in b values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration.

These general methods A1, A2 and A3 are shown schematically as follows:

General Synthetic Method A1

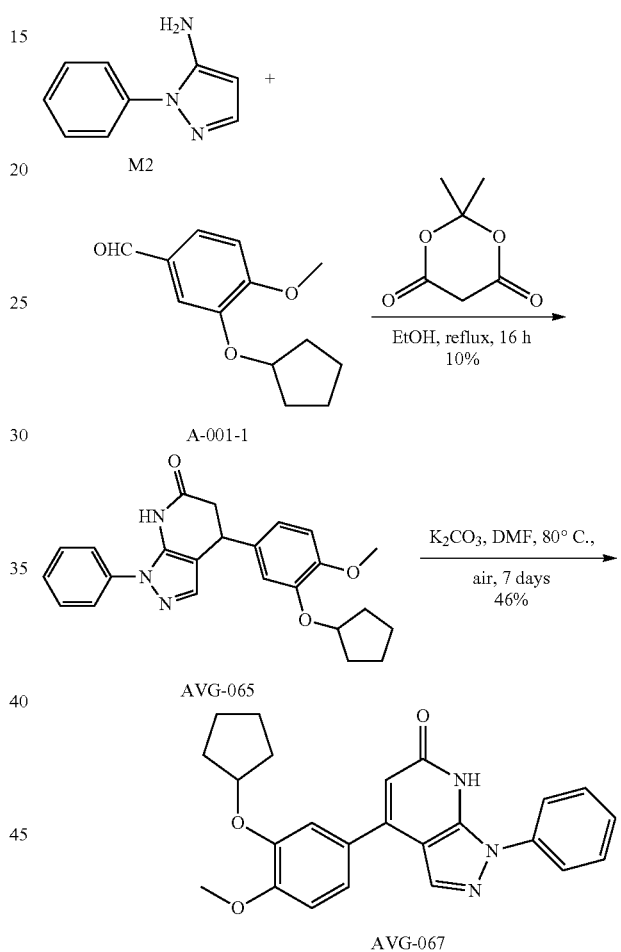

General Synthetic Method A2

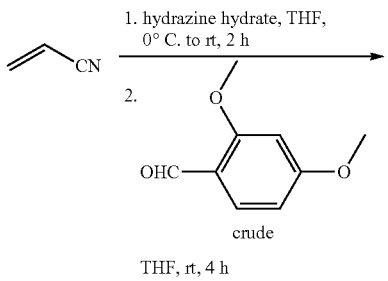

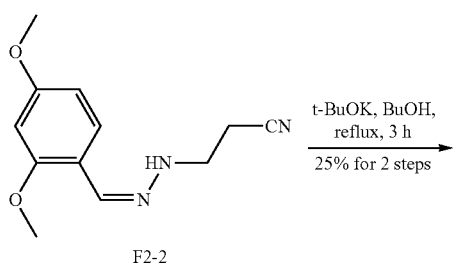
F2-2
t-BuOK, BuOH,
reflux, 3 h
25% for 2 steps
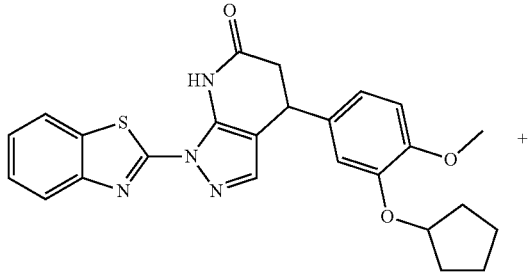
AVG-001-b
(minor isomer)
1% yield
+
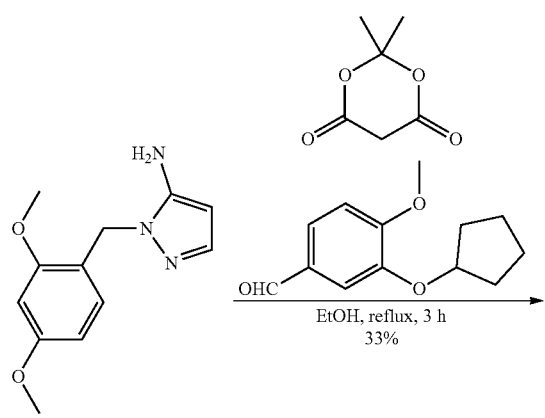
F2
EtOH, reflux, 3 h
33%
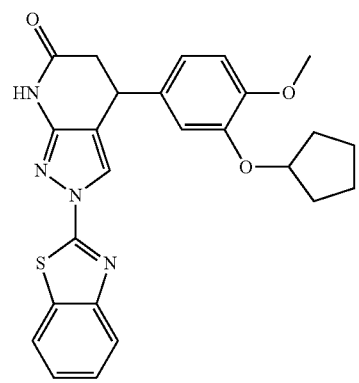
AVG-001
(major isomer)
15% yield
General Synthetic Method A3
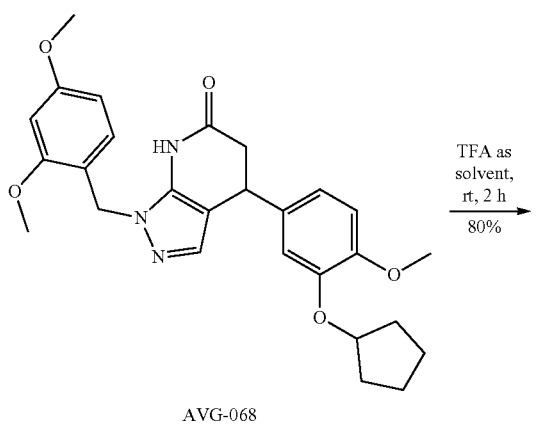
AVG-068
TFA as solvent, rt, 2 h
80%
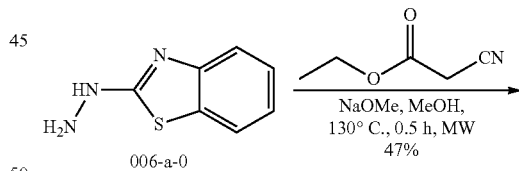
006-a-0
NaOMe, MeOH,
130° C., 0.5 h, MW
47%
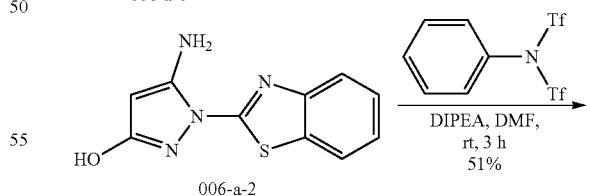
006-a-2
DIPEA, DMF,
rt, 3 h
51%
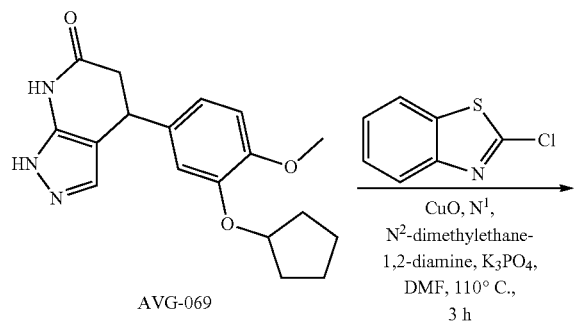
AVG-069
CuO, N$^1$,
N$^2$-dimethylethane-
1,2-diamine, K$_3$PO$_4$,
DMF, 110° C.,
3 h
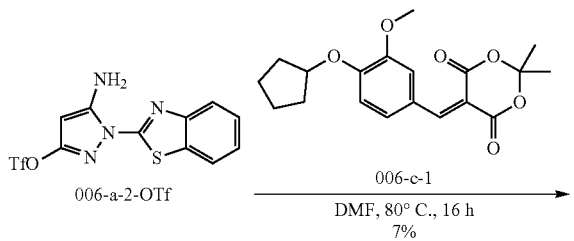
006-a-2-OTf
006-c-1
DMF, 80° C., 16 h
7%

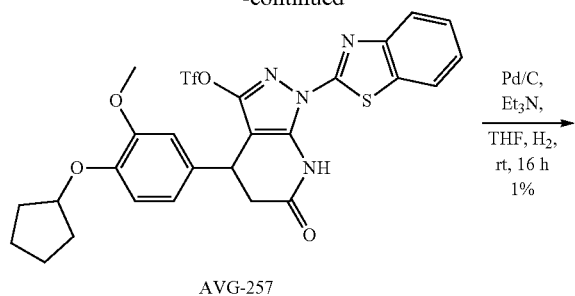
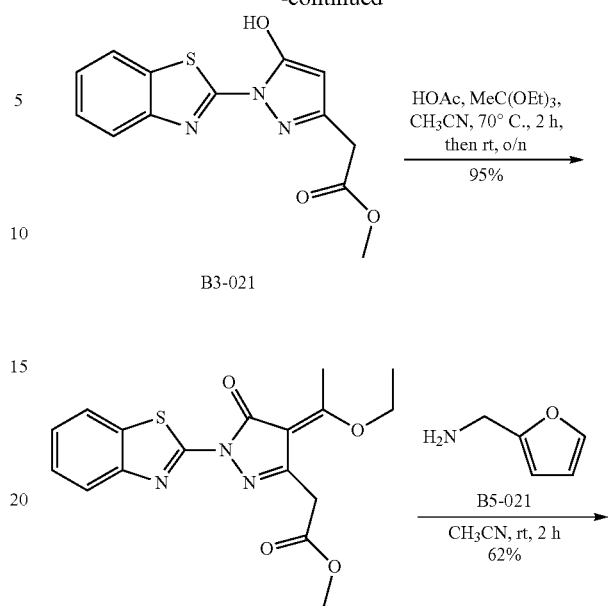
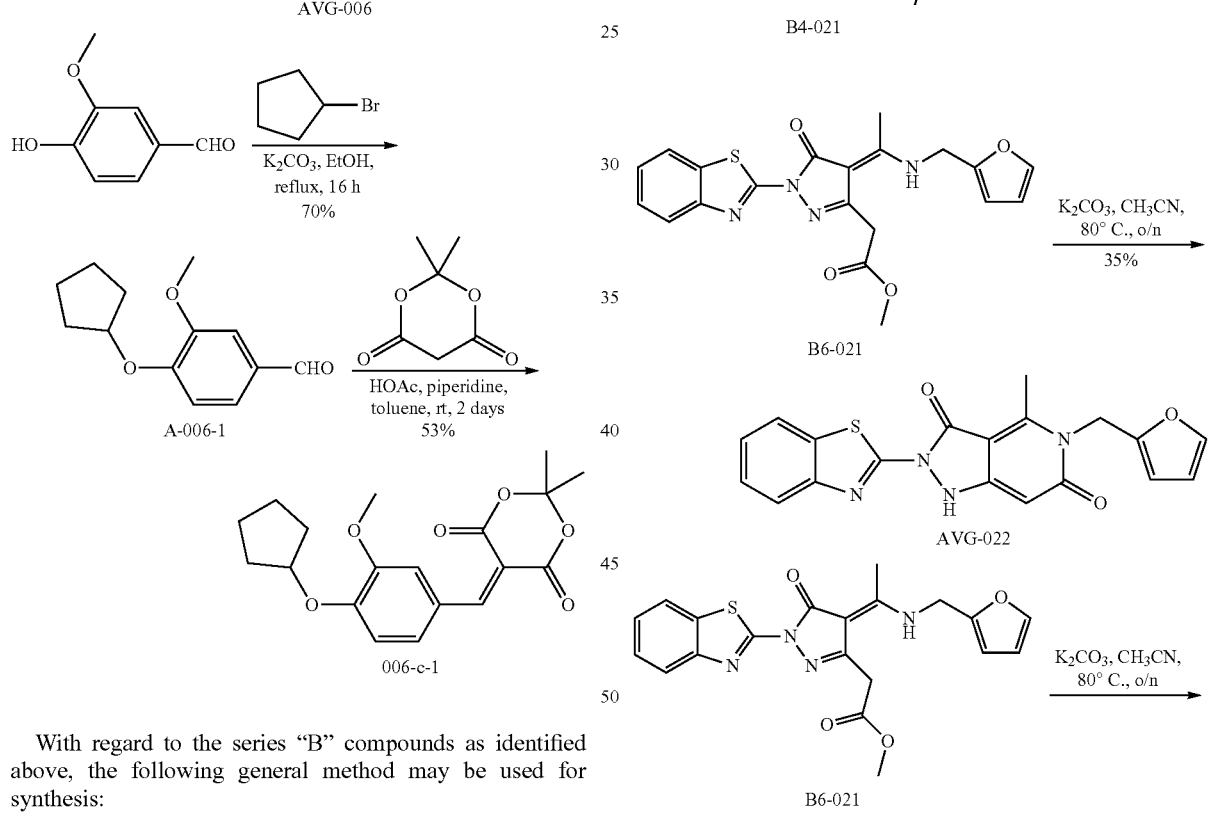
With regard to the series "B" compounds as identified above, the following general method may be used for synthesis:
General Synthetic Method B
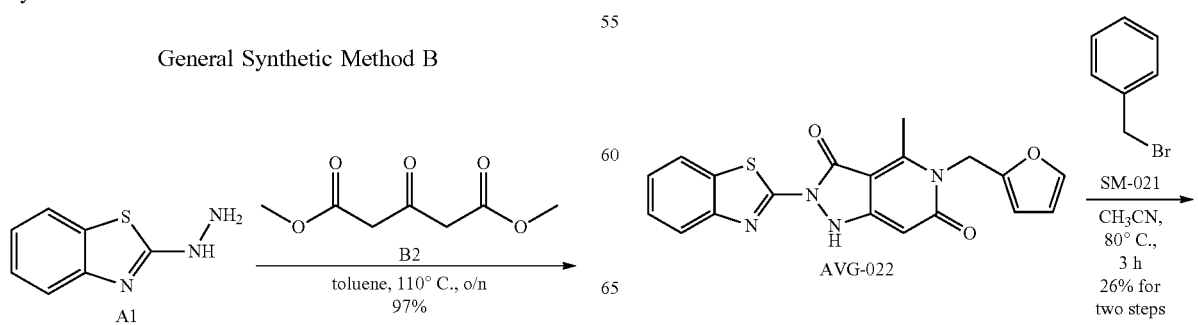

125

-continued

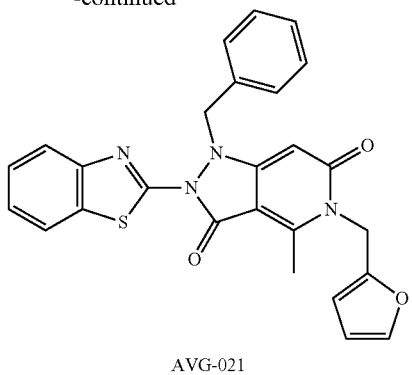

AVG-021

Additional information regarding these general methods is included in the Examples below.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

Methods or Preparation of Series a Compounds

In all of the experimental data as reported below, the following abbreviations are used:
rt: room temperature
UV: ultra violet
HPLC: high pressure liquid chromatography
Rt: retention time
LCMS: Liquid chromatography mass spectroscopy
NMR: Nuclear magnetic resonance spectroscopy
CC: column chromatography
TLC: thin layer chromatography
sat: saturated
aq: aqueous
DCM: dichloromethane
DCE: dichloroethane
DMF: dimethylformamide
DIPEA: diisopropylethylamine
EtOAc: ethyl acetate
TEA: triethylamine
THF: tetrahydrofurane
TFA: trifluoroacetic acid
t-BuOK: Potassium tert-butoxide

126 n-BuOH: n-Butanol
EtOH: Ethanol
HOAc: acetic acid
o/n: overnight
MW: microwave
h: hour(s)
min: minutes
General Information:

In all of the general methods of synthesis of series "A" compounds described herein, all evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. 1H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration.

As indicated above, the first general synthetic method (A1) is shown schematically below:

Example 1A: General Synthetic Method A1

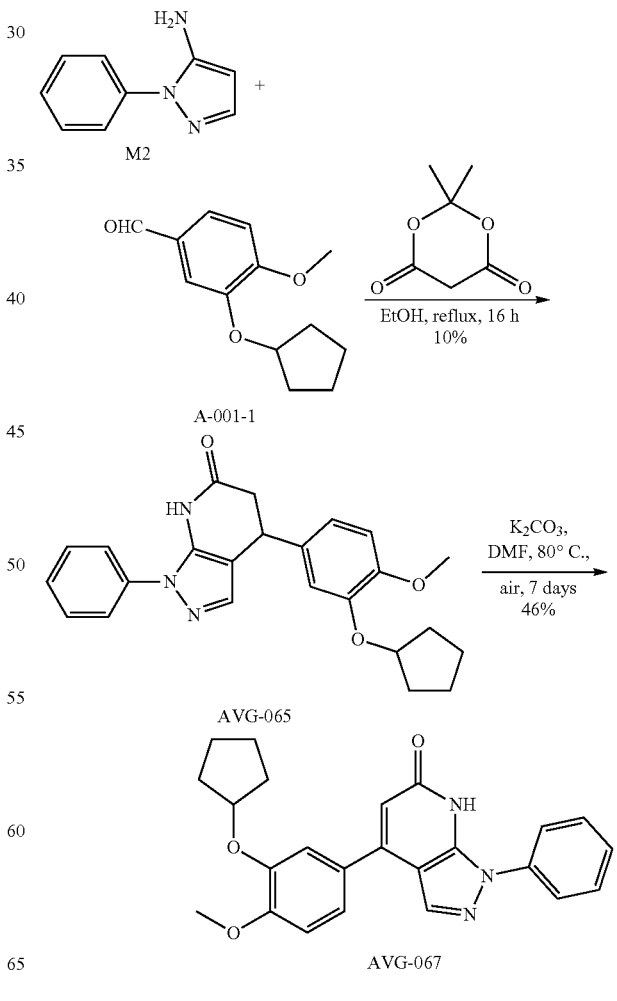

127

Exemplary Experimental Procedures for General Method A1

1. The synthesis of 4-(3-(cyclopentyloxy)-4-methoxyphenyl)-1-phenyl-4,5-dihydro-1H-pyrazolo[3,4-b] pyridin-6(7H)-one (AVG-065) is conducted as follows:

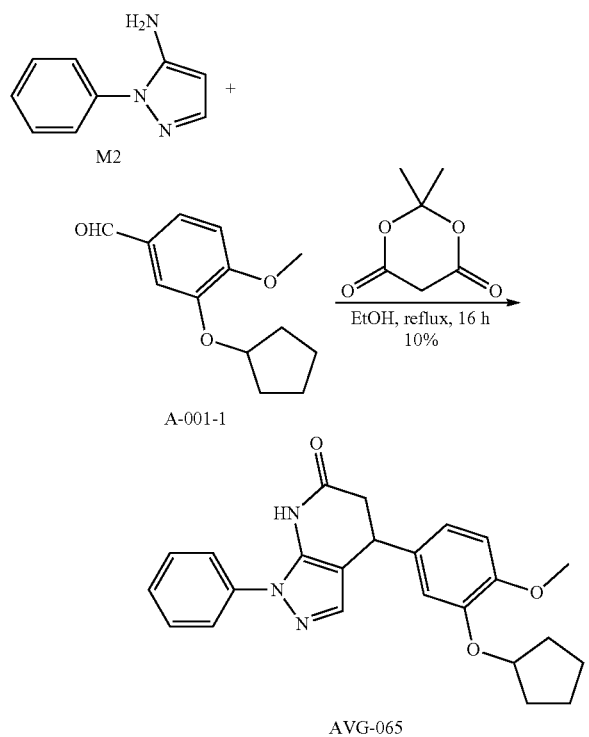

A mixture of compound M2 (200 mg, 1.3 mmol) 2,2-dimethyl-1,3-dioxane-4,6-dione (272 mg, 1.9 mmol) and 3-(cyclopentyloxy)-4-methoxybenzaldehyde (415 mg, 1.9 mmol) in EtOH (10 mL) was refluxed for 16 h. After cooling to room temperature, the mixture was concentrated in vacuum. The residue was diluted with water and extracted with EtOAc (30 mL×2). The organic layer was washed with water and brine, dried over $Na_2SO_4$, filtered and concentrated to give a crude product, which was purified by Pre-TLC to give compound AVG-065 (50 mg, 10% yield) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 3.0 min, then under this condition for 1.0 min, finally changed to 95% [water+0.05% TFA] and 5% [$CH_3CN$+0.05% TFA] in 0.05 min and under this condition for 0.7 min. Purity is 100%, Rt=2.470 min; MS Calcd.: 403.2; MS Found: 404.1 [M+H]$^+$.

Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [$CH_3CN$+0.1% TFA] to 0% [water+0.1% TFA] and 100% [$CH_3CN$+0.1% TFA] in 10 min, then under this condition for 5 min, finally changed to 95% [water+0.1% TFA] and 5% [$CH_3CN$+0.1% TFA] in 0.1 min and under this condition for 5 min. Purity is 100%, Rt=9.298 min.

128

$^1$H NMR (400 MHz, $CDCl_3$) δ 7.66 (s, 1H), 7.56-7.48 (m, 4H), 7.46-7.41 (m, 1H), 7.32 (s, 1H), 6.86-6.80 (m, 3H), 4.78-4.73 (m, 1H), 4.24 (dd, J=9.6, 6.4 Hz, 1H), 3.85 (s, 3H), 2.97 (dd, J=16.0, 6.4 Hz, 1H), 2.83 (dd, J=16.0, 10.0 Hz, 1H), 1.93-1.86 (m, 6H), 1.85-1.77 (m, 2H).

2. The synthesis of 4-(3-(cyclopentyloxy)-4-methoxyphenyl)-1-phenyl-1H-pyrazolo[3,4-b]pyridine-6(7H)-one (AVG-067) is conducted as follows:

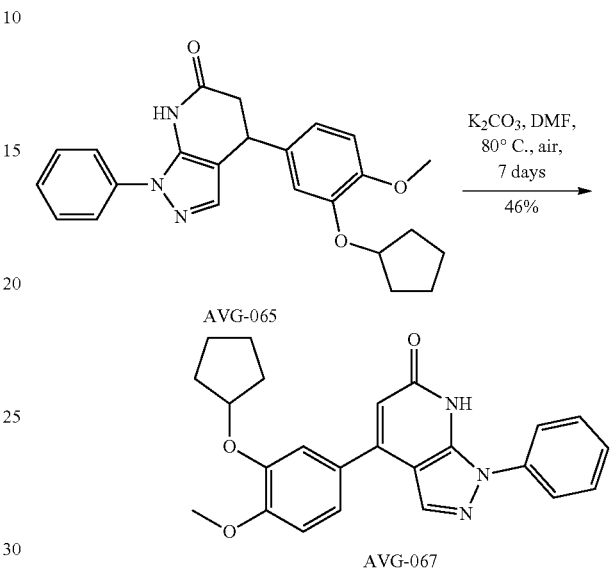

The mixture of AVG-065 (35 mg, 0.09 mmol) and $K_2CO_3$ (36 mg, 0.27 mmol) in DMF (2 mL) was stirred at 80° C. for 7 days under air. The mixture was diluted with water (10 mL) and extracted with EtOAc (10 mL×3). The combined organic layer was washed with water and brine, dried over $Na_2SO_4$, filtered and concentrated in vacuum. The residue was purified by Pre-TLC to give AVG-067 (16 mg, 46% yield) as a yellow solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM $AcONH_4$) water/$CH_3CN$=900/100 (v/v)] and 10% [(total 10 mM $AcONH_4$) water/$CH_3CN$=100/900 (v/v)] to 10% [(total 10 mM $AcONH_4$) water/$CH_3CN$=900/100 (v/v)] and 90% [(total 10 mM $AcONH_4$) water/$CH_3CN$=100/900 (v/v)] in 1.6 min, then under this condition for 2.4 min, finally changed to 90% [(total 10 mM $AcONH_4$) water/$CH_3CN$=900/100 (v/v)] and 10% [(total 10 mM $AcONH_4$) water/$CH_3CN$=100/900 (v/v)] in 0.1 min and under this condition for 0.7 min. Purity is 98.1%, Rt=2.663 min; MS Calcd.: 401.2; MS Found: 402.2 [M+H]$^+$.

Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM $AcONH_4$) water/$CH_3CN$=900/100 (v/v)] and 10% [total 10 mM $AcONH_4$) water/$CH_3CN$=100/900 (v/v)] to 15% [total 10 mM $AcONH_4$) water/$CH_3CN$=900/100 (v/v)] and 85% [total 10 mM $AcONH_4$) water/$CH_3CN$=100/900 (v/v)] in 5 min, then under this condition for 10 min, finally changed to 90% [(total 10 mM $AcONH_4$) water/$CH_3CN$=900/100 (v/v)] and 10% [total 10 mM $AcONH_4$) water/$CH_3CN$=100/900 (v/v)] in 0.1 min and under this condition for 5 min. Purity is 100%, Rt=7.485 min.

$^1$H NMR (400 MHz, $CDCl_3$) δ 8.07 (s, 1H), 7.76 (d, J=7.6 Hz, 2H), 7.49 (dd, J=8.0, 7.6 Hz, 2H), 7.35 (t, J=7.8 Hz, 1H), 7.30 (dd, J=8.4, 2.0 Hz, 1H), 7.26-7.23 (m, 1H), 7.03 (d, J=8.4 Hz, 1H), 6.55 (s, 1H), 4.88-4.84 (m, 1H), 3.94 (s, 3H), 2.05-1.95 (m, 4H), 1.90-1.84 (m, 2H), 1.70-1.60 (m, 2H).
Example 1B: General Synthetic Method A2
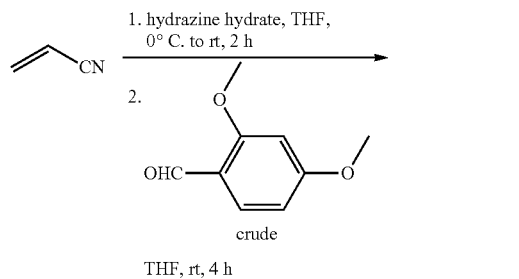
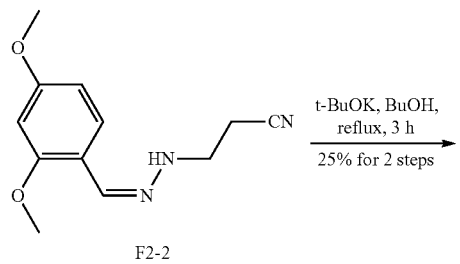
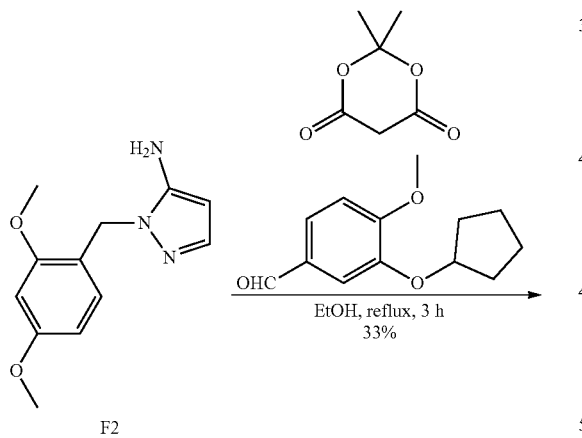
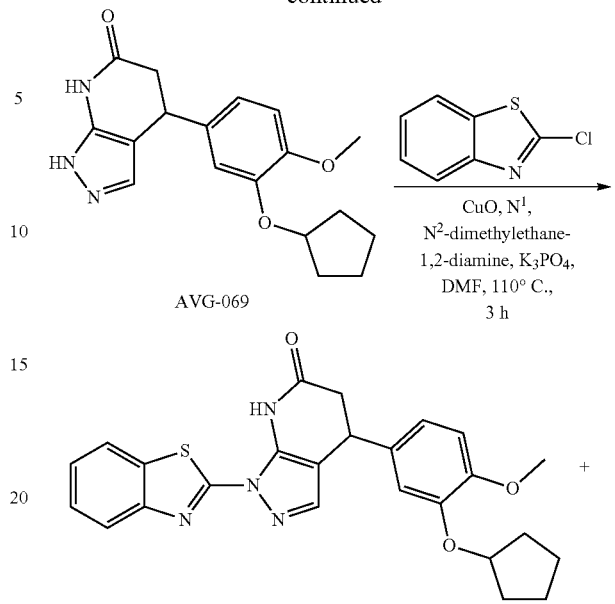
Exemplary Experimental Procedures for General Method A2
1. The Synthesis of 3-(2-(2,4-dimethoxybenzylidene)hydrazinyl)propanenitrile (F2-2)
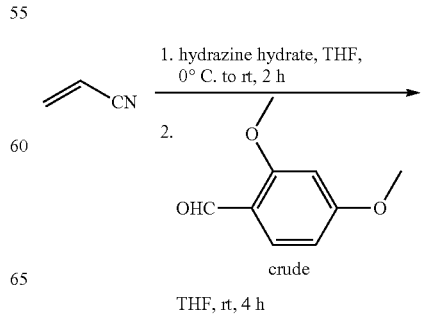

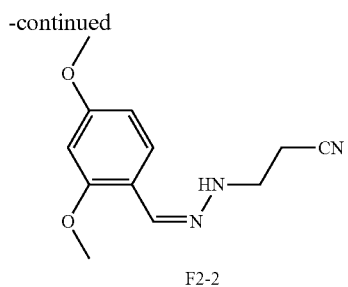

F2-2

To a stirred solution of acrylonitrile (6.0 g, 113 mmol) in THF (50 mL) cooled at 0° C., hydrazine hydrate (80%, 5.0 g, 124 mmol) was added over a period of about 20 min and the reaction mixture was stirred at room temperature for 2 h. To the reaction mixture, 2,4-dimethoxybenzaldehyde (19.7 g, 119 mmol) was added over a period of about 15 min and the reaction mixture was stirred for 4 h at room temperature. Then the crude oil was obtained by concentration, which was used for next step directly.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 0% [water+0.05% TFA] and 100% [CH₃CN+0.05% TFA] in 1.6 min, then under this condition for 1.4 min, finally changed to 95% [water+0.05% TFA] and 5% [CH₃CN+0.05% TFA] in 0.05 min and under this condition for 0.7 min. Rt=1.222 min; MS Calcd.: 233.1; MS Found: 234.2 [M+H]$^+$.

2. The Synthesis of tert-butyl 4-(2-ethoxy-2-oxo-ethyl)-4-(nitromethyl)piperidine-1-carboxylate (F2)

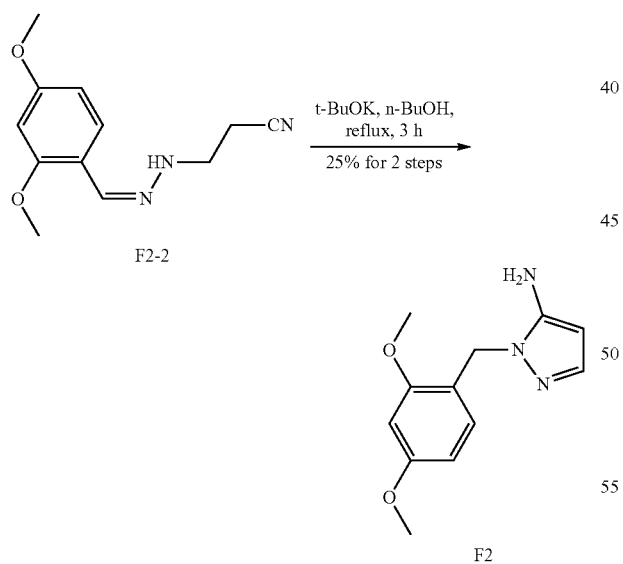

A mixture of F2-2 (crude from last step) in n-BuOH (100 mL) was added the solid t-BuOK (12.7 g, 113 mmol) in several portions at room temperature, then the reaction mixture was refluxed for 3 h. After being cooled to room temperature, the mixture was quenched with ice-water, and then the mixture was concentrated in vacuum. The residue was diluted with water and extracted with EtOAc (100 mL×3). The organic layer was washed with water and brine, dried over Na₂SO₄, filtered and concentrated to give a crude product, which was purified by column chromatography (petrol ether/EtOAc=10/1 to 3/1) to give compound F2 (6.6 g, 25% yield) as a yellow solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 0% [water+0.05% TFA] and 100% [CH₃CN+0.05% TFA] in 1.6 min, then under this condition for 1.4 min, finally changed to 95% [water+0.05% TFA] and 5% [CH₃CN+0.05% TFA] in 0.05 min and under this condition for 0.7 min. Purity is 84.3%, Rt=1.225 min; MS Calcd.: 233.1; MS Found: 234.1 [M+H]$^+$.

3. The Synthesis of 4-(3-(cyclopentyloxy)-4-methoxyphenyl)-1-(2,4-dimethoxybenzyl)-4,5-di-hydro-1H-pyrazolo[3,4-b]pyridin-6(7H)-one (AVG-068)

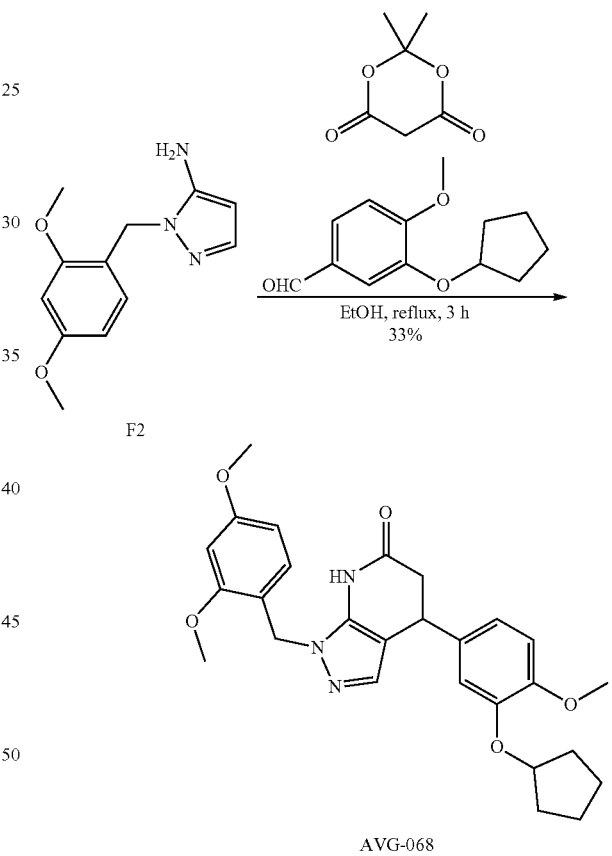

A mixture of compound F2 (250 mg, 1.1 mmol) 2,2-dimethyl-1,3-dioxane-4,6-dione (185 mg, 1.3 mmol) and 3-(cyclopentyloxy)-4-methoxybenzaldehyde (283 mg, 1.3 mmol) in EtOH (10 mL) was refluxed for 3 h. After being cooled to room temperature, the mixture was concentrated in vacuum. The residue was diluted with water and extracted with EtOAc (30 mL×3). The organic layer was washed with water and brine, dried over Na₂SO₄, filtered and concentrated to give a crude product, which was purified by column chromatography (petrol ether/EtOAc=4/1 to 3/1) then further purification by Pre-TLC to give compound AVG-068 (170 mg, 33% yield) as an off-white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 3.0 min, then under this condition for 1.0 min, finally changed to 95% [water+0.05% TFA] and 5% [CH$_3$CN+0.05% TFA] in 0.05 min and under this condition for 0.7 min. Purity is 99.0%, Rt=2.468 min; MS Calcd.: 477.2; MS Found: 478.1 [M+H]$^+$.

Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min. Purity is 100%, Rt=9.033 min.

$^1$H NMR (400 MHz, DMSO-d$_6$) δ 10.71 (s, 1H), 7.05 (s, 1H), 6.87 (d, J=8.4 Hz, 1H), 6.75 (d, J=2.0 Hz, 1H), 6.68 (dd, J=8.2, 1.8 Hz, 1H), 6.63 (d, J=8.4 Hz, 1H), 6.57 (d, J=2.4 Hz, 1H), 6.44 (dd, J=8.4, 2.4 Hz, 1H), 5.13 (s, 2H), 4.71-4.65 (m, 1H), 4.14 (dd, J=6.8, 6.4 Hz, 1H), 3.78 (s, 3H), 3.74 (s, 3H), 3.70 (s, 3H), 2.83 (dd, J=16.0, 6.8 Hz, 1H), 2.58 (dd, J=16.0, 6.4 Hz, 1H), 1.88-1.75 (m, 2H), 1.72-1.62 (m, 4H), 1.59-1.50 (m, 2H).

4. The Synthesis of 4-(3-(cyclopentyloxy)-4-methoxyphenyl)-4,5-dihydro-1H-pyrazolo[3,4-b]pyridin-6(7H)-one (AVG-069)

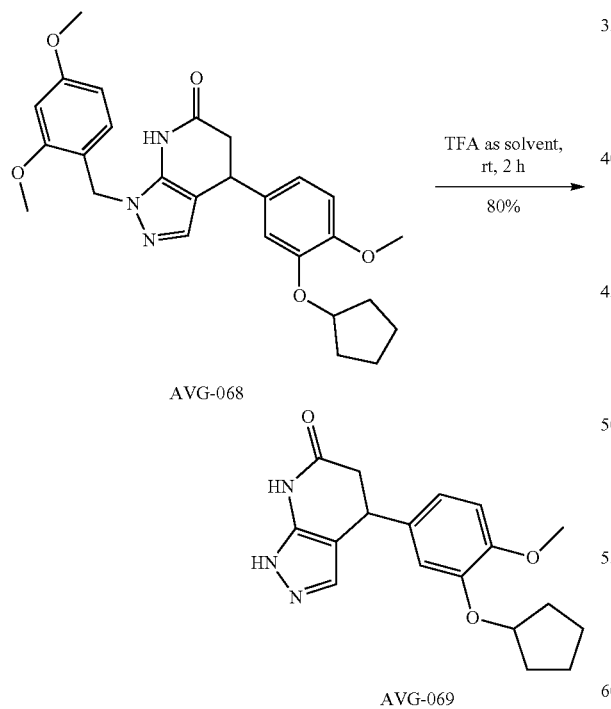

AVG-068 (97 mg, 0.2 mmol) was added to TFA (2 mL) at room temperature, then the mixture was stirred at room temperature for 2 h. Excess TFA was removed in vacuum, then the residue was neutralized to pH=8 with sat. NaHCO$_3$ and extracted with EtOAc (20 mL×3). The combined organic layer was washed with water and brine, dried over Na$_2$SO$_4$, filtered and concentrated in vacuum. The residue was purified by Pre-TLC to give AVG-069 (53 mg, 80% yield) as a yellow solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 3.0 min, then under this condition for 1.0 min, finally changed to 95% [water+0.05% TFA] and 5% [CH$_3$CN+0.05% TFA] in 0.05 min and under this condition for 0.7 min. Purity is 98.1%, Rt=1.973 min; MS Calcd.: 327.2; MS Found: 328.0 [M+H]$^+$.

Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min. Purity is 90.7%, Rt=7.398 min.

$^1$H NMR (400 MHz, DMSO-d$_6$) δ 12.06 (s, 1H), 10.36 (s, 1H), 7.28 (s, 1H), 6.86 (d, J=8.4 Hz, 1H), 6.79 (d, J=2.0 Hz, 1H), 6.70 (dd, J=8.0, 2.0 Hz, 1H), 4.72-4.67 (m, 1H), 4.13 (dd, J=7.2, 6.4 Hz, 1H), 3.70 (s, 3H), 2.69 (dd, J=15.6, 6.4 Hz, 1H), 2.56 (dd, J=15.8, 7.8 Hz, 1H), 1.88-1.76 (m, 2H), 1.74-1.61 (m, 4H), 1.59-1.49 (m, 2H).

5. The Synthesis of 1-(benzo[d]thiazol-2-yl)-4-(3-(cyclopentyloxy)-4-methoxyphenyl)-4,5-dihydro-1H-pyrazolo[3,4-b]pyridin-6(7H)-one (AVG-001) and 2-(benzo[d]thiazol-2-yl)-4-(3-(cyclopentyloxy)-4-m ethoxyphenyl)-4,5-dihydro-2H-pyrazolo[3,4-b]pyridin-6(7H)-one (AVG-001-b)

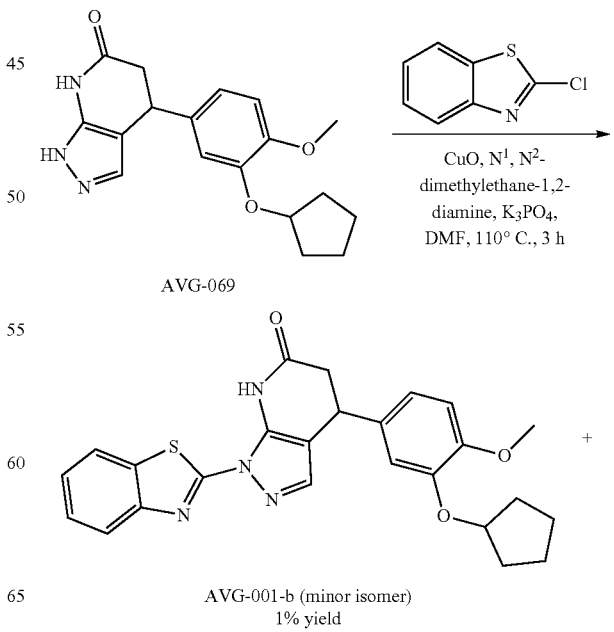

-continued

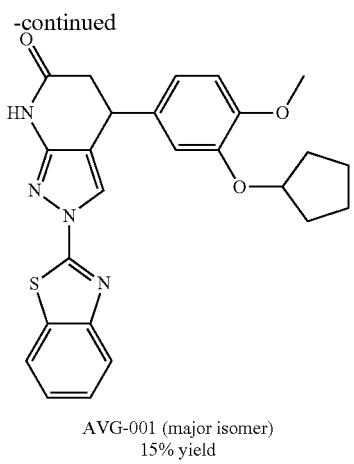

AVG-001 (major isomer)
15% yield

To a mixture of AVG-069 (200 mg, 0.61 mmol), CuO (10 mg, 0.12 mmol), $N^1,N^2$-dimethylethane-1,2-diamine (11 mg, 0.12 mmol) and $K_3PO_4$ (301 mg, 1.83 mmol) in DMF (8 mL) was added 2-chlorobenzo[d]thiazole (114 mg, 0.67 mmol) under nitrogen. The mixture was stirred at 110° C. for 3 h under nitrogen. After being cooled to room temperature, the mixture was filtered and washed with EtOAc (20 mL). The filtrate was washed with brine (20 mL), dried over $Na_2SO_4$, filtered and concentrated in vacuum. The residue was purified by Pre-TLC, and then further purified by Pre-HPLC to give AVG-001 (42 mg, 15% yield) as an off-white solid and AVG-001-b (3 mg, 1% yield) as an off-white solid.

AVG-001

Prep-HPLC Condition:

1.1 Chromatographic Equipment

Gilson Prep-HPLC system: GX-281 sample manager, 306 pump, 806 Manometric module, 811D DYNAMIC Mixer, UV/VIS-156

1.2 Chromatographic Condition

Column: Waters X-Bridge™ Prep C18 5 μm OBD™, 30×100 mm

Flowrate: 20 mL/min

Gradient:

| Time(min) | MeOH | Water (0.04% $NH_4HCO_3$) |
|---|---|---|
| 0 | 55 | 45 |
| 8.0 | 80 | 20 |
| 9 | 95 | 5 |
| 13.5 | 95 | 5 |
| 13.6 | 55 | 45 |
| 17.6 | 55 | 45 |

Wavelength: 214 nm and 254 nm.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min. Purity is 94.2%, Rt=2.955 min; MS Calcd.: 460.2; MS Found: 461.2 [M+H]$^+$.

Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity is 100%, Rt=10.529 min.

$^1$H NMR (400 MHz, DMSO-$d_6$) δ 11.07 (s, 1H), 8.20 (s, 1H), 8.04 (d, J=8.0 Hz, 1H), 7.80 (d, J=8.0 Hz, 1H), 7.49 (ddd, J=8.4, 8.0, 1.0 Hz, 1H), 7.37 (dd, J=8.0, 7.6 Hz, 1H), 6.90-6.93 (m, 2H), 6.78 (dd, J=8.2, 1.8 Hz, 1H), 4.79-4.73 (m, 1H), 4.33 (dd, J=7.2, 6.8 Hz, 1H), 3.72 (s, 3H), 2.86 (dd, J=15.8, 6.6 Hz, 1H), 2.78 (dd, J=16.0, 7.6 Hz, 1H), 1.92-1.80 (m, 2H), 1.74-1.64 (m, 4H), 1.60-1.50 (m, 2H).

AVG-001-b

Prep-HPLC Condition:

1.1 Chromatographic Equipment

Gilson Prep-HPLC system: GX-281 sample manager, 306 pump, 806 Manometric module, 811D DYNAMIC Mixer, UV/VIS-156

1.2 Chromatographic Condition

Column: Waters X-Bridge™ Prep C18 5 μm OBD™, 30×100 mm

Flowrate: 20 mL/min

Gradient:

| Time(min) | MeOH | Water (0.04% $NH_4HCO_3$) |
|---|---|---|
| 0 | 65 | 35 |
| 8.0 | 80 | 20 |
| 9 | 95 | 5 |
| 13.5 | 95 | 5 |
| 13.6 | 65 | 35 |
| 17.6 | 65 | 35 |

Wavelength: 214 nm and 254 nm.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min. Purity is 100%, Rt=3.045 min; MS Calcd.: 460.2; MS Found: 461.1 [M+H]$^+$.

Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity is 100%, Rt=11.372 min.

$^1$H NMR (400 MHz, DMSO-$d_6$) δ 10.03 (s, 1H), 8.11 (d, J=8.0 Hz, 1H), 8.02 (d, J=8.0 Hz, 1H), 7.58-7.52 (m, 2H), 7.44 (dd, J=8.0, 7.2 Hz, 1H), 6.90 (d, J=8.4 Hz, 1H), 6.89 (s, 1H), 6.76 (d, J=8.4 Hz, 1H), 4.79-4.71 (m, 1H), 4.30 (dd, J=7.6, 6.8 Hz, 1H), 3.72 (s, 3H), 2.99 (dd, J=16.2, 7.0 Hz, 1H), 2.81 (dd, J=16.2, 7.8 Hz, 1H), 1.90-1.78 (m, 2H), 1.74-1.64 (m, 4H), 1.60-1.50 (m, 2H).

Example 1C: General Synthetic Method A3
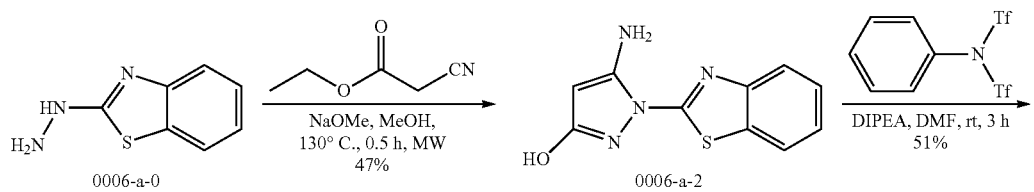
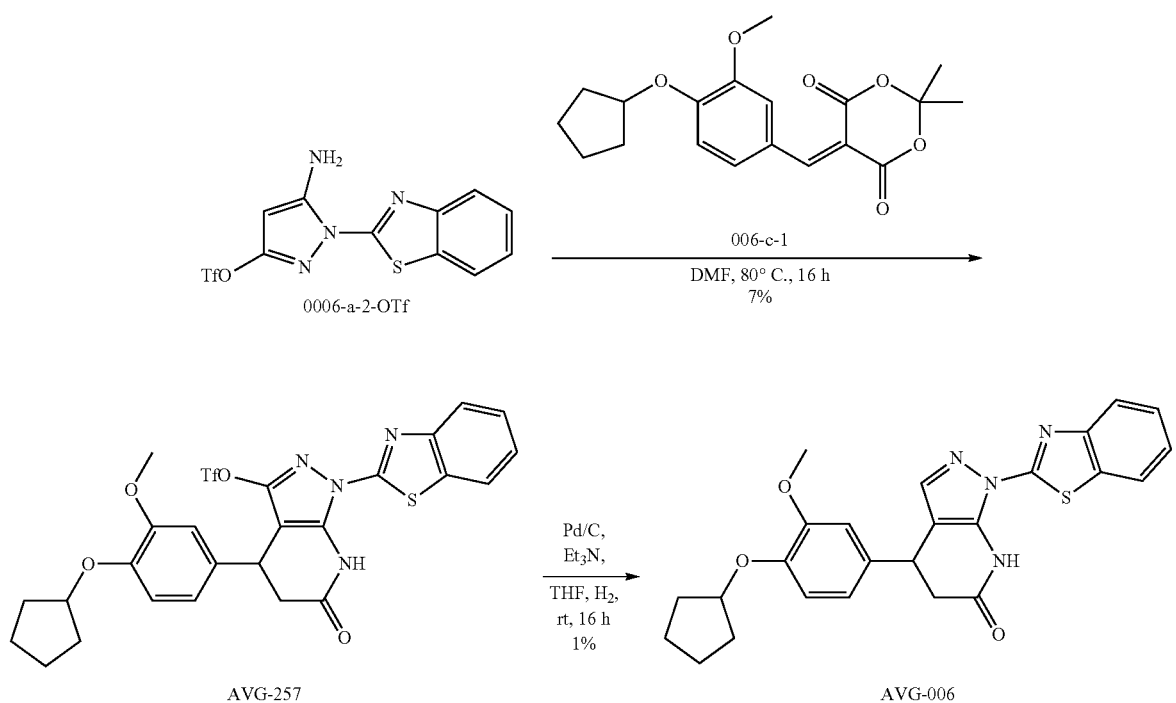
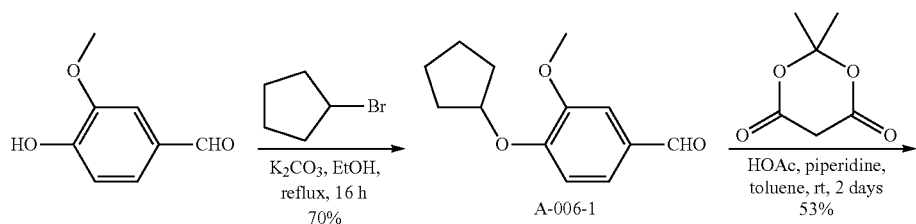
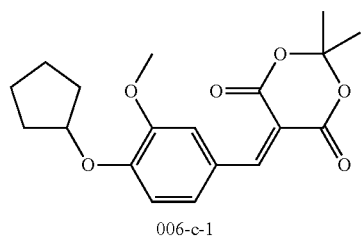

Exemplary Experimental Procedures for General Method A3

1. The Synthesis of 5-amino-1-(benzo[d]thiazol-2-yl)-1H-pyrazol-3-ol (006-a-2)

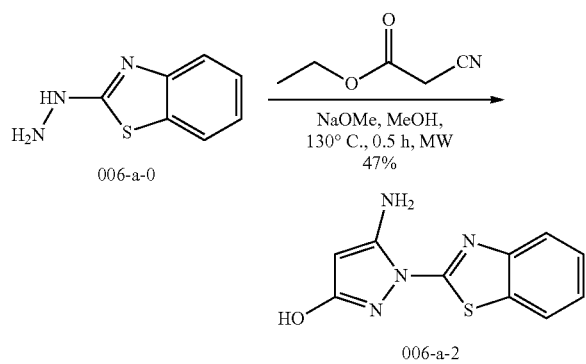

To a mixture of 006-a-0 (3.0 g, 18.2 mmol) and ethylcyanoacetate (2.1 g, 18.6 mmol) was added the solution of NaOMe in MeOH (4 N, 9.1 mL, 36.4 mmol) at room temperature, then the reaction mixture was irradiated in microwave at 130° C. for 0.5 h. The resulting solid was obtained by filtration and washed with diethyl ether, then recrystallized in EtOH to get 006-a-2 (2.0 g, 47% yield) as a brown solid.

Agilent LCMS 1200-6110, Column: Waters X-Bridge C18 (50 mm*4.6 mm*3.5 µm); Column Temperature: 40° C.; Flow Rate: 2.0 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 1.6 min, then under this condition for 1.4 min, finally changed to 95% [water+0.05% TFA] and 5% [$CH_3CN$+0.05% TFA] in 0.05 min and under this condition for 0.7 min. Purity is 98.7%, Rt=1.533 min; MS Calcd.: 232.0; MS Found: 233.1 [M+H]$^+$.

2. The Synthesis of 5-amino-1-(benzo[d]thiazol-2-yl)-1H-pyrazol-3-yl trifluoromethanesulfonate (006-2-OTf)

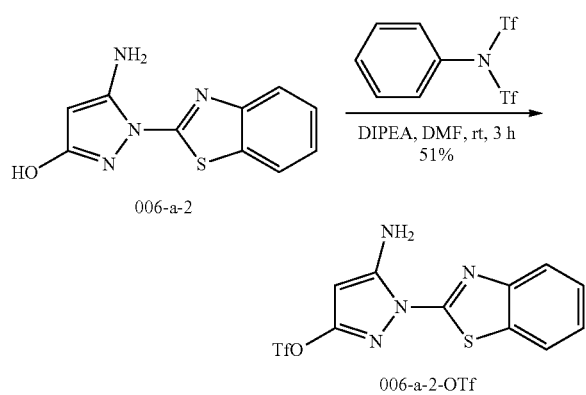

To a mixture of 006-a-2 (1.0 g, 4.3 mmol) in DMF (10 mL) was added 1,1,1-trifluoro-N-phenyl-N-(trifluoromethylsulfonyl)methanesulfonamidethe (1.5 g, 4.3 mmol) and DIPEA (1.1 g, 8.6 mmol) at room temperature, and then the reaction mixture was stirred at room temperature for 3 h. The mixture was diluted with water and extracted with EtOAc (30 mL×3). The organic layer was washed with water and brine, dried over $Na_2SO_4$, filtered and concentrated to give a crude product, which was purified by column chromatography (petrol ether/EtOAc=10/1 to 5/1) to get 006-a-2-OTf (0.8 g, 51% yield) as a white solid.

Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 90% [(total 10 mM $AcONH_4$) water/$CH_3CN$=900/100 (v/v)] and 10% [(total 10 mM $AcONH_4$) water/$CH_3CN$=100/900 (v/v)] to 10% [(total 10 mM $AcONH_4$) water/$CH_3CN$=900/100 (v/v)] and 90% [(total 10 mM $AcONH_4$) water/$CH_3CN$=100/900 (v/v)] in 1.6 min, then under this condition for 2.4 min, finally changed to 90% [(total 10 mM $AcONH_4$) water/$CH_3CN$=900/100 (v/v)] and 10% [(total 10 mM $AcONH_4$) water/$CH_3CN$=100/900 (v/v)] in 0.1 min and under this condition for 0.7 min. Purity is 94.7%, Rt=2.448 min; MS Calcd.: 364.0; MS Found: 365.0 [M+H]$^+$.

$^1$H NMR (400 MHz, DMSO-$d_6$) δ 8.09 (d, J=7.2 Hz, 1H), 7.92 (d, J=8.0 Hz, 1H), 7.54 (ddd, J=8.4, 8.0, 1.0 Hz, 1H), 7.50 (s, 2H), 7.43 (ddd, J=8.4, 8.0, 1.2 Hz, 1H), 5.60 (s, 1H).

3. The Synthesis of 1-(benzo[d]thiazol-2-yl)-4-(4-(cyclopentyloxy)-3-methoxyphenyl)-6-oxo-4,5,6,7-tetrahydro-1H-pyrazolo[3,4-b]pyridin-3-yl trifluoromethanesulfonate (AVG-257)

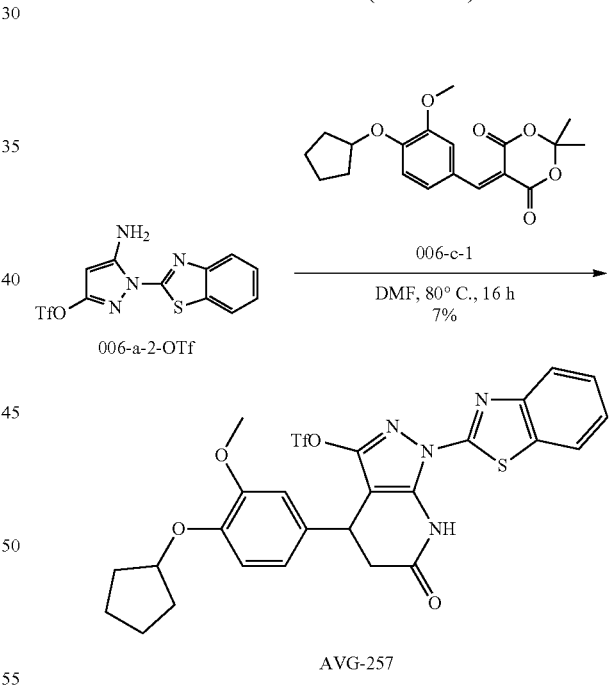

To a mixture of 006-a-2-OTf (1.0 g, 2.7 mmol) in DMF (10 mL) was added 006-c-1 (1.4 g, 4.1 mmol) at room temperature, then the reaction mixture was stirred at 80° C. for 16 h. The mixture was diluted with water and extracted with EtOAc (35 mL×3). The organic layer was washed with water and brine, dried over $Na_2SO_4$, filtered and concentrated to give a crude product, which was purified by column chromatography (reverse, Water/$CH_3CN$) to get AVG-257 (120 mg, 7% yield) as a yellow solid.

Agilent LCMS 1200-6110, Column: Waters X-Bridge C18 (50 mm*4.6 mm*3.5 µm); Column Temperature: 40°

C.; Flow Rate: 2.0 mL/min; Mobile Phase: from 95% [water+0.05% TFA] and 5% [CH₃CN+0.05% TFA] to 0% [water+0.05% TFA] and 100% [CH₃CN+0.05% TFA] in 3.0 min, then under this condition for 1.0 min, finally changed to 95% [water+0.05% TFA] and 5% [CH₃CN+0.05% TFA] in 0.05 min and under this condition for 0.7 min. Purity is >99%, Rt=3.379 min; MS Calcd.: 608.1; MS Found: 609.1 [M+H]⁺.

Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH₃CN+0.1% TFA] to 0% [water+0.1% TFA] and 100% [CH₃CN+0.1% TFA] in 10 min, then under this condition for 5 min, finally changed to 95% [water+0.1% TFA] and 5% [CH₃CN+0.1% TFA] in 0.1 min and under this condition for 5 min. Purity is 97.9%, Rt=12.103 min.

$^1$H NMR (400 MHz, DMSO-$d_6$) δ 10.45 (s, 1H), 8.14 (d, J=7.6 Hz, 1H), 8.07 (d, J=7.6 Hz, 1H), 7.59 (dd, J=7.6, 7.6 Hz, 1H), 7.48 (dd, J=7.6, 7.2 Hz, 1H), 6.95 (d, J=1.6 Hz, 1H), 6.88 (d, J=8.4 Hz, 1H), 6.78 (dd, J=8.2, 1.8 Hz, 1H), 4.79-4.73 (m, 1H), 4.34 (dd, J=8.0, 7.2 Hz, 1H), 3.72 (s, 3H), 3.05-2.89 (m, 2H), 1.90-1.78 (m, 2H), 1.76-1.64 (m, 4H), 1.60-1.52 (m, 2H).

Notes: 006-a-2-OTf was not consumed up and should be recovered.

4. The Synthesis of 1-(benzo[d]thiazol-2-yl)-4-(4-(cyclopentyloxy)-3-methoxyphenyl)-4,5-dihydro-1H-pyrazolo[3,4-b]pyridin-6(7H)-one (AVG-006)

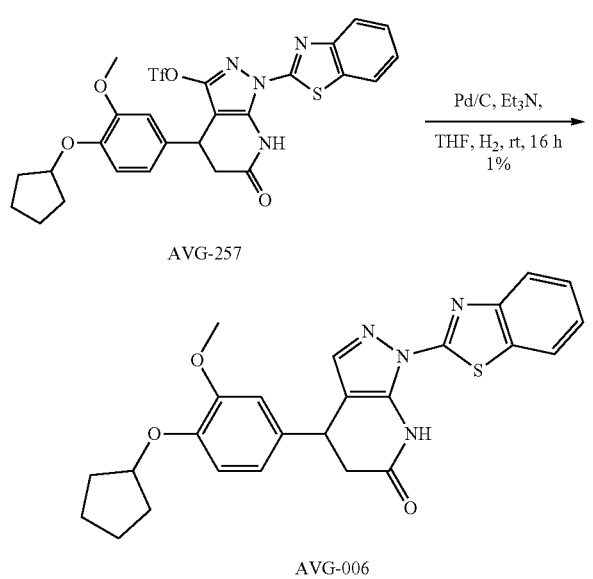

To a solution of AVG-257 (100 mg, 0.16 mmol) THF (3 mL) was added Et₃N (32 mg, 0.32 mmol) and Pd/C (10%, 100 mg) at room temperature. The mixture was stirred at room temperature for 16 h under hydrogen (Note: we conducted this reaction for four times (100 mg of AVG-257 for each) in parallel and combined all the reaction mixtures to do work-up together). The catalyst was filtered and washed with EtOAc (20 mL), and the obtained filtrate was concentrated in vacuum. The residue was purified by Pre-TLC and then by Pre-HPLC to give AVG-006 (3 mg, 1% yield) as a gray solid.

Prep-HPLC condition:
1.1 Chromatographic Equipment
Gilson Prep-HPLC system: GX-281 sample manager, 306 pump, 806 Manometric module, 811D DYNAMIC Mixer, UV/VIS-156
1.2 Chromatographic Condition
Column: Waters X-Bridge™ Prep C18 5 μm OBD™, 30×100 mm
Flowrate: 20 mL/min
Gradient:

| Time(min) | MeOH | Water (0.04% NH₄HCO₃) |
|---|---|---|
| 0 | 55 | 45 |
| 8.0 | 80 | 20 |
| 9 | 95 | 5 |
| 13.5 | 95 | 5 |
| 13.6 | 55 | 45 |
| 17.6 | 55 | 45 |

Wavelength: 214 nm and 254 nm.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 3.0 min, then under this condition for 1.0 min, finally changed to 95% [water+10 mM NH₄HCO₃] and 5% [CH₃CN] in 0.1 min and under this condition for 0.7 min. Purity is 95.7%, Rt=3.313 min; MS Calcd.: 460.2; MS Found: 461.2 [M+H]⁺.

Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min. Purity is 92.4%, Rt=11.446 min.

$^1$H NMR (400 MHz, DMSO-$d_6$) δ 10.01 (brs, 1H), 8.11 (d, J=8.0 Hz, 1H), 8.02 (d, J=8.0 Hz, 1H), 7.58-7.52 (m, 2H), 7.44 (dd, J=7.6, 7.2 Hz, 1H), 6.93 (d, J=1.6 Hz, 1H), 6.87 (d, J=8.4 Hz, 1H), 6.73 (dd, J=8.2, 1.8 Hz, 1H), 4.77-4.70 (m, 1H), 4.30 (dd, J=7.2, 7.2 Hz, 1H), 3.73 (s, 3H), 3.00 (dd, J=13.2, 6.6 Hz, 1H), 2.82 (dd, J=14.4, 7.6 Hz, 1H), 1.90-1.79 (m, 2H), 1.75-1.65 (m, 4H), 1.60-1.50 (m, 2H).

5. The Synthesis of 4-(cyclopentyloxy)-3-methoxybenzaldehyde (A-006-1)

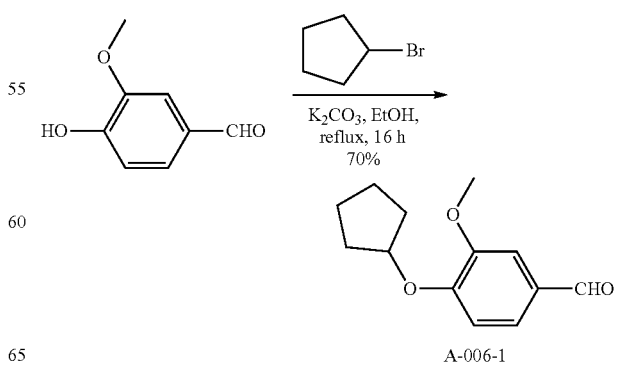

To a stirred mixture of 4-hydroxy-3-methoxybenzaldehyde (5.0 g, 33 mmol) and $K_2CO_3$ (9.1 g, 66 mmol) in EtOH (50 ml) was added bromocyclopentane (5.1 g, 35 mmol) over a period of about 10 min and the reaction mixture was refluxed for 16 h. The reaction mixture was filtered and washed with EtOAc, and the filtrate was concentrated to give a crude product, which was purified by column chromatography (petrol ether/EtOAc=10/1) to give compound A-006-1 (5.1 g, 70% yield) as a yellow solid.

Notes: The reaction was monitored by TLC.

6. The Synthesis of 5-(4-(cyclopentyloxy)-3-methoxybenzylidene)-2,2-dimethyl-1,3-dioxane-4,6-dione (006-c-1)

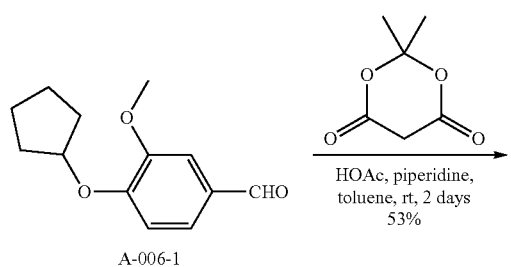

To a stirred mixture of A-006-1 (3.0 g, 13.6 mmol) and 2,2-dimethyl-1,3-dioxane-4,6-dione (2.1 g, 14.3 mmol) in toluene (40 ml) was added HOAc (0.8 g, 13.6 mmol) and piperidine (0.2 g, 2.7 mmol) at room temperature and the reaction mixture was stirred at room temperature for 2 days. The yellow solid was obtained by filtration and washed with diethyl ether, then the solid was dried in vacuum to give compound 006-c-1 (2.5 g, 53% yield) as a yellow solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 1.6 min, then under this condition for 1.4 min, finally changed to 95% [water+0.05% TFA] and 5% [$CH_3CN$+0.05% TFA] in 0.05 min and under this condition for 0.7 min. Purity is 98.7%, Rt=1.966 min; MS Calcd.: 346.1; MS Found: 369.3 [M+Na]$^+$.

Example 1D: General Synthetic Method B

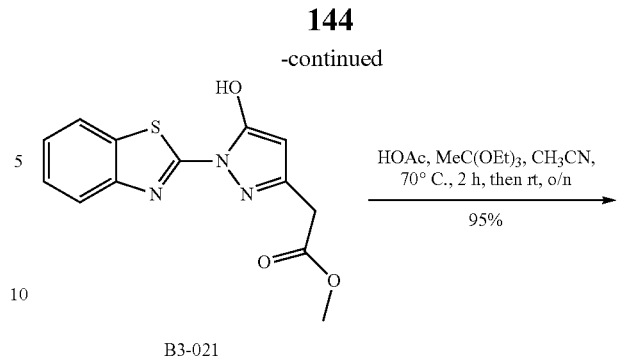

-continued

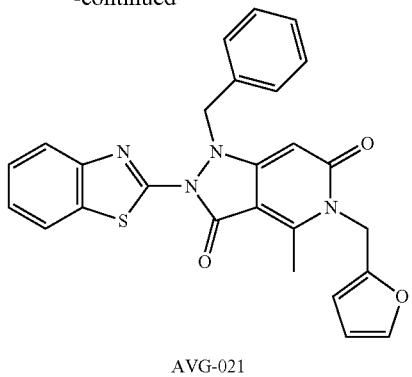

AVG-021

Exemplary Experimental Procedures for General Method B

1. The Synthesis of methyl 2-(1-(benzo[d]thiazol-2-yl)-5-hydroxy-1H-pyrazol-3-yl)acetate (B3-021)

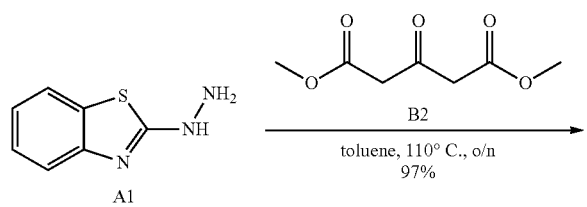

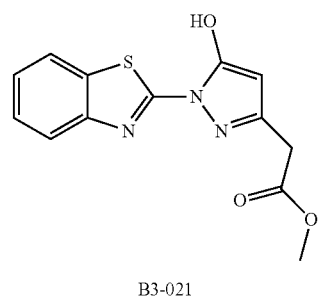

B3-021

To a solution of A1 (3.3 g, 19.97 mmol) in toluene (30 mL) was added B2 (3.5 g, 19.97 mmol), then the reaction mixture was stirred at 110° C. overnight. After cooling the reaction mixture to room temperature, the resulting solid was filtered, washed with toluene and dried in vacuum to give B3-021 (5.6 g, 97% yield) as a white solid.

Agilent LCMS 1200-6120, Column: Waters X-Bridge C18 (30 mm*4.6 mm*3.5 μm); Column Temperature: 40° C.; Flow Rate: 2.0 mL/min; Mobile Phase: from 90% [water+10 mM NH$_4$HCO$_3$] and 10% [CH$_3$CN] to 5% [water+10 mM NH$_4$HCO$_3$] and 95% [CH$_3$CN] in 0.5 min, then under this condition for 1.5 min, finally changed to 90% [water+10 mM NH$_4$HCO$_3$] and 10% [CH$_3$CN] in 0.1 min and under this condition for 0.5 min. Purity is 97.2%, Rt=0.874 min; MS Calcd.: 289.1; MS Found: 290.0 [M+H]$^+$.

2. The Synthesis of (E)-methyl 2-(1-(benzo[d]thiazol-2-yl)-4-(1-ethoxyethylidene)-5-oxo-4,5-dihydro-1H-pyrazol-3-yl)acetate (B4-021)

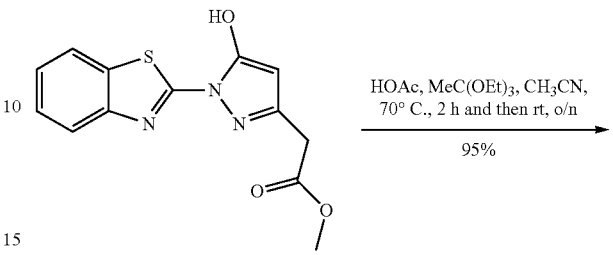

B3-021

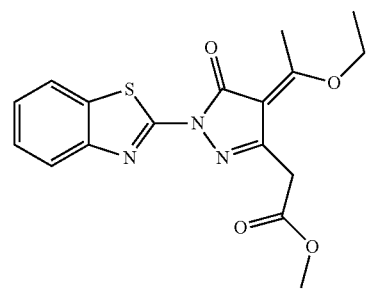

B4-021

To a mixture of B3-021 (4.5 g, 15.49 mmol) and MeC(OEt)$_3$ (7.5 g, 46.46 mmol) in CH$_3$CN (50 mL) was added HOAc (186 mg, 3.10 mmol) and then the reaction mixture was stirred at 70° C. for 2 h, then the reaction mixture was stirred at room temperature overnight. After the reaction was complete, the resulting solid was filtered, then washed with CH$_3$CN and dried in vacuum to give B4-021 (5.3 g, 95% yield) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min. Purity is 100%. Rt=1.353 min; MS Calcd.: 359.1; MS Found: 332.1 [M−28+H]$^+$.

$^1$H NMR (400 MHz, DMSO-d$_6$) δ 8.04 (d, J=7.6 Hz, 1H), 7.84 (d, J=7.6 Hz, 1H), 7.48 (ddd, J=8.4, 8.4, 1.2 Hz, 1H), 7.35 (ddd, J=8.4, 8.0, 1.2 Hz, 1H), 4.47 (q, J=7.2 Hz, 2H), 3.83 (s, 2H), 3.67 (s, 3H), 2.84 (s, 3H), 1.33 (t, J=6.8 Hz, 3H).

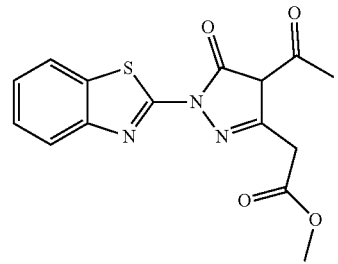

B4-021a

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 0% [water+0.05% TFA] and 100% [CH₃CN+0.05% TFA] in 1.6 min, then under this condition for 1.4 min, finally changed to 95% [water+0.05% TFA] and 5% [CH₃CN+0.05% TFA] in 0.05 min and under this condition for 0.7 min. Purity is 100%. Rt=1.353 min; MS Calcd.: 331.1; MS Found: 332.1 [M+H]⁺.

¹H NMR (400 MHz, DMSO-d₆) δ 8.08 (d, J=8.0 Hz, 1H), 7.84 (d, J=8.0 Hz, 1H), 7.52 (dd, J=7.6, 7.6 Hz, 1H), 7.39 (dd, J=7.6, 7.6 Hz, 1H), 3.81 (s, 2H), 3.62 (s, 3H), 2.33 (s, 3H).

3. The Synthesis of (E)-methyl 2-(1-(benzo[d]thiazol-2-yl)-4-(1-(furan-2-ylmethylamino)ethylidene)-5-oxo-4,5-dihydro-1H-pyrazol-3-yl)acetate (B6-021)

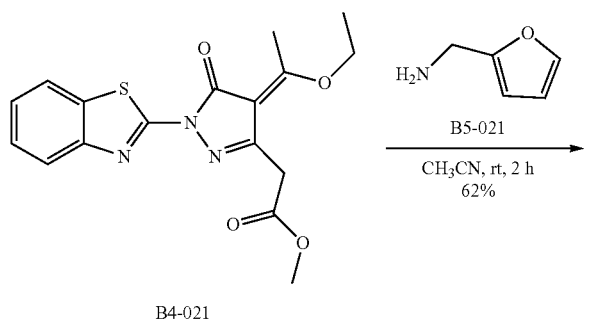

B4-021

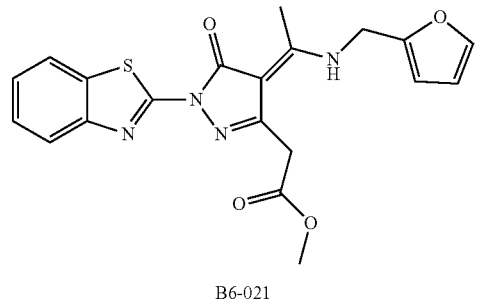

B6-021

To a solution of B4-021 (4.9 g, 13.75 mmol) in CH₃CN (30 mL) was added B5-021 (1.6 g, 16.49 mmol), then the reaction mixture was stirred at room temperature for 2 h. The resulting solid was collected by filtration, washed with CH₃CN and dried in vacuum to give B6-021 (3.5 g, 62% yield) as a white solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 0% [water+0.05% TFA] and 100% [CH₃CN+0.05% TFA] in 1.6 min, then under this condition for 1.4 min, finally changed to 95% [water+0.05% TFA] and 5% [CH₃CN+0.05% TFA] in 0.05 min and under this condition for 0.7 min. Purity is 100%. Rt=1.741 min; MS Calcd.: 410.1; MS Found: 411.1 [M+H]⁺.

4. The Synthesis of 2-(benzo[d]thiazol-2-yl)-5-(furan-2-ylmethyl)-4-methyl-1H-pyrazolo[4,3-c]pyridine-3,6(2H, 5H)-dione (AVG-022)

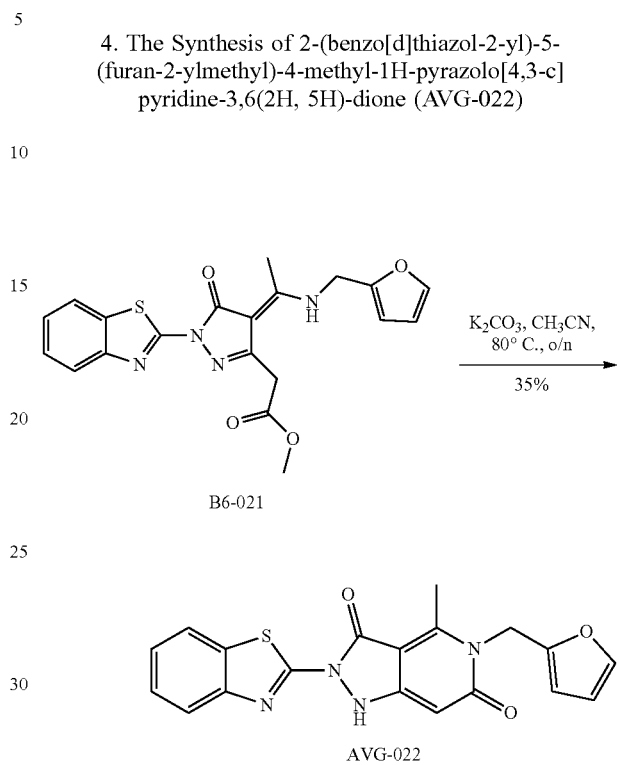

To a solution of B6-021 (0.5 g, 1.22 mmol) in CH₃CN (20 mL) was added K₂CO₃ (337 mg, 2.44 mmol), then the reaction mixture was stirred at 80° C. overnight. The mixture was concentrated to dryness and the residue was diluted with water (20 mL). The pH value of this mixture was adjusted to 7 with hydrochloric acid (1 N). The resulting solid was filtered, washed with water and dried in vacuum to give AVG-022 (160 mg, 35% yield) as a brown solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 3.0 min, then under this condition for 1.0 min, finally changed to 95% [water+10 mM NH₄HCO₃] and 5% [CH₃CN] in 0.1 min and under this condition for 0.7 min. Purity is 98.7%, Rt=1.827 min; MS Calcd.: 378.1; MS Found: 379.1 [M+H]⁺.

Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min. Purity is 100.0%, Rt=6.429 min.

¹H NMR (400 MHz, DMSO-d₆) δ 11.90 (s, 1H), 8.07 (d, J=8.0 Hz, 1H), 7.84 (d, J=8.0 Hz, 1H), 7.61 (s, 1H), 7.50 (dd, J=7.6, 7.2 Hz, 1H), 7.37 (dd, J=7.6, 7.6 Hz, 1H), 6.43 (s, 1H), 6.37 (d, J=2.8 Hz, 1H), 5.73 (s, 1H), 5.34 (s, 2H), 2.96 (s, 3H).

4. The Synthesis of 2-(benzo[d]thiazol-2-yl)-1-benzyl-5-(furan-2-ylmethyl)-4-methyl-1H-pyrazolo[4,3-c] pyridine-3,6(2H,5H)-dione (AVG-021)

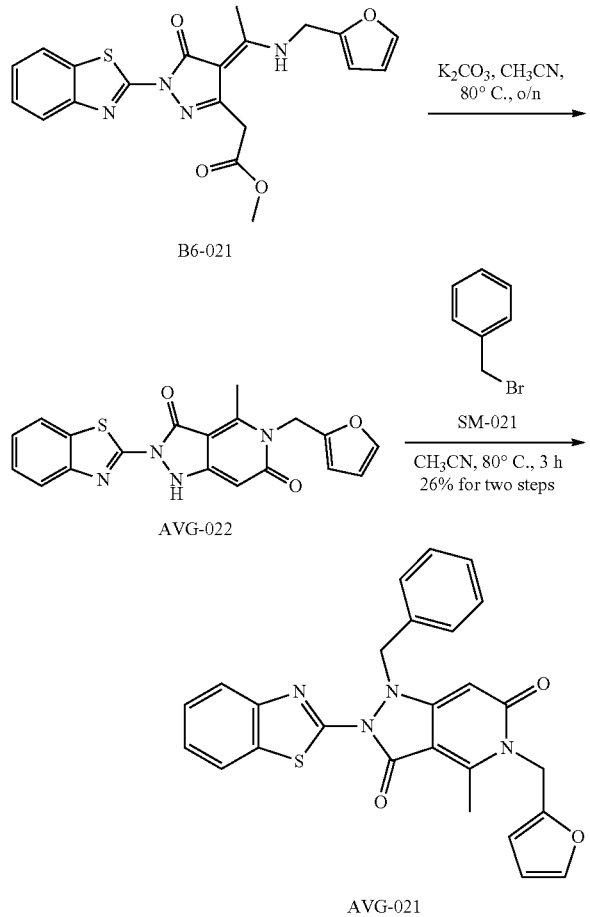

To a solution of B6-021 (205 mg, 0.50 mmol) in CH₃CN (10 mL) was added K₂CO₃ (138 mg, 1.00 mmol), then the reaction mixture was stirred at 80° C. overnight. After being cooled to room temperature, SM-021 (85 mg, 0.50 mmol) was added and then the mixture was stirred at 80° C. for 3 h. After being cooled to room temperature, the reaction system was diluted with water (20 mL) and extracted with ethyl acetate (20 mL×3). The combined organic layers were washed with brine (20 mL×2), dried over sodium sulfate, and concentrated to dryness. The residue was purified by Prep-TLC (petrol ether/EtOAc=1/1) to give AVG-021 (60 mg, 26% yield) as a white solid.

Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 3.0 min, then under this condition for 1.0 min, finally changed to 95% [water+10 mM NH₄HCO₃] and 5% [CH₃CN] in 0.1 min and under this condition for 0.7 min. Purity is 98.5%, Rt=2.909 min; MS Calcd.: 468.1; MS Found: 469.2 [M+H]⁺.

Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min. Purity is 100.0%, Rt=10.392 min.

$^1$H NMR (400 MHz, DMSO-$d_6$) δ 8.09 (d, J=7.6 Hz, 1H), 7.97 (d, J=8.0 Hz, 1H), 7.61 (dd, J=1.8, 1.0 Hz, 1H), 7.54 (ddd, J=8.0, 7.2, 1.2 Hz, 1H), 7.41 (ddd, J=8.4, 8.0, 1.2 Hz, 1H), 7.24-7.19 (m, 3H), 7.04-7.01 (m, 2H), 6.48 (s, 1H), 6.43 (dd, J=3.2, 2.0 Hz, 1H), 6.36 (d, J=2.4 Hz, 1H), 5.54 (s, 2H), 5.32 (s, 2H), 2.89 (s, 3H).

Example 2: Testing of the Compounds of the Invention Against RSV

Cell Lines and Transfections

Human carcinoma (HEp-2, ATCC CCL-23), human lung carcinoma (A549, ATCC CCL-185), human bronchial epithelial (BEAS-2B, ATCC CRL-9609), human embryonic kidney (293T, ATCC CRL-3216), and Madin Darby canine kidney (MDCK, ATCC CCL-34) cells were maintained at 37° C. and 5% CO2 in Dulbecco's modified Eagle's medium (DMEM) supplemented with 7.5% fetal bovine serum. Lipofectamine 2000 or GeneJuice were used for all transient transfection reactions.

RSV Amplification and Virion Purification recRSV stocks were grown on HEp-2 cells inoculated at a multiplicity of infection (MOI) of 0.01 pfu/cell. Infected cells were kept for 16 hours at 37° C., followed by incubation at 32° C. for five to seven days. Cell-associated progeny virus was released through one freeze/thaw cycle and titers determined by TCID50 titration on HEp-2 cells. Two alternative strategies were explored to remove contaminating luciferase proteins from virus stocks. Progeny virions in culture supernatants (IAV stocks) or released through one freeze/thaw cycle from infected cells (RSV stocks) were cleared (4,000×g for 20 minutes at 4° C.), then pelleted (60,000×g for 30 minutes at 4° C.). Pelleted material was resuspended in TNE buffer (50 mM Tris/Cl pH 7.2, 10 mM EDTA) and purified through a 20/60% one-step sucrose gradient in TNE buffer (100,000×g for 90 minutes at 4° C.). Virions were harvested from the gradient intersection.

Automated HTS Protocol in 384-Well Plate Format

BEAS-2B cells (8×10³/well) were injected in 30 µl/well into barcoded white wall/clear bottom 384-well plates using a MultiFlo automated dispenser (BioTek) equipped with dual 10-µl peristaltic pump manifolds, collected (150×g for 90 seconds at 25° C.), and incubated for five hours at 37° C. and 5% CO₂. Compound was added to a final concentration of 5 µM (20 nl/well) using a high-density pin tool (V&P Scientific) attached to the pipetting head of Hamilton Nimbus liquid handler, followed by infection in 10 µl/well using the MultiFlo dispenser unit, spin collection (150×g for 90 seconds at 25° C.), and incubation for 40 hours at 37° C. and 5% CO₂. Final vehicle (DMSO) concentration was 0.05%. Barcodes of source and assay plates were automatically detected and recorded by the Nimbus unit at the time of stamping. Using a stacker unit with integrated barcode reader (Biotek) attached to an H1 Biotek synergy plate reader, plates were automatically loaded, luciferase substrates (15 µl/well) injected, and bioluminescence recorded after a three minute lag time. Readouts were automatically saved by plate barcode. For analysis of primary screen raw data, normalized relative inhibition values were calculated for each compound by subtracting each value from the average of the plate vehicle controls, followed by dividing the results by the difference between the means of plate vehicle and positive controls. Hits candidates were defined as compounds showing ≥75% inhibition of normalized signal intensity against either or both viral targets.

Dose-Response Counterscreens

Two-fold serial dilutions of hit candidates were prepared in 384-well plates in three replicates each using the Nimbus liquid handler. BEAS-2B cells ($8 \times 10^3$/well) were then plated as before, serial dilutions transferred using the pintool, and cells infected with recombinant virus strains expressing distinct luciferase reporter proteins or left uninfected for cell viability assessment. Reporter signals were recorded as outlined above. To determine cell viability, PrestoBlue substrate (life technologies) was added after 40-hour incubation of cells at 37° C. (5 μl/well) and top-read fluorescence (excitation 560 nm; emission 590 nm; instrument gain 85) recorded after 45 minutes of incubation at 37° C. using the H1 synergy plate reader. Four-parameter variable slope regression modeling was applied to determine 50% active ($EC_{50}$) and toxic ($CC_{50}$) concentrations.

RSV Minigenome Reporter Assays

An RSV minigenome reporter plasmid (pHH-RSV-repI-firefly) was constructed under the control of the constitutive RNA pol I promoter by generating a firefly luciferase open reading frame flanked by the 5'- and 3'-non-coding regions and transfer into a pHH plasmid backbone harboring an RNA pol I promoter. Huh-7 cells were co-transfected with this plasmid and expression plasmids pRSV-L, pRSV-M2-1, pRSV-N and pRSV-P, which encode the RSV polymerase protein subunits. Test compounds were added in serial dilutions, luciferase reporter activities determined 40 hours post-transfection, and $EC_{50}$ concentrations calculated if possible.

Virus Yield Reduction Assay

Hep2 cells were seeded in a 12-well plate format and exposed to serial dilutions of compound (3-fold, 20 μM highest), followed by infection with recombinant RSV-A2 harboring the fusion protein of the L19F isolate at a multiplicity of infection (MOI) of 0.1. Cell-associated progeny virions were harvested after 48-hour incubation at 37° C. and subjected to $TCID_{50}$ titration on Hep2 cells. Viral titers were calculated based on the Spearman Karber method and inhibitory concentrations based on virus yields determined through four-parameter variable slope regression modeling.

Statistical Analysis

The Excel and Prism 6 (GraphPad) software packages were used for data analysis.

Statistical significance of differences between sample groups were assessed by unpaired two-tailed t tests or one-way analysis of variance (ANOVA) in combination with Tukey's multiple comparison post-tests, respectively.

Figure 2:
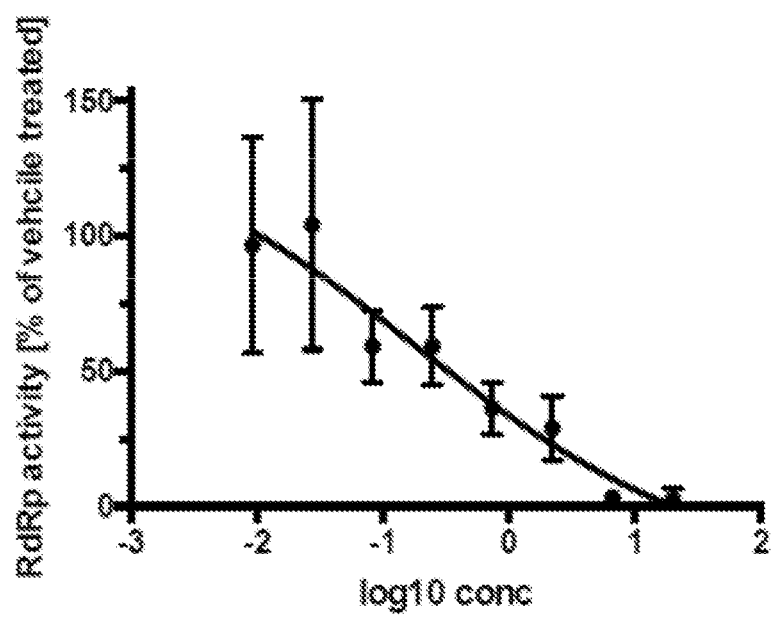
FIG. 2 includes a depiction of the RdRp activity of an RSV inhibitor in accordance with the invention [RSVP-156784] as a function of concentration.
Figure 3:
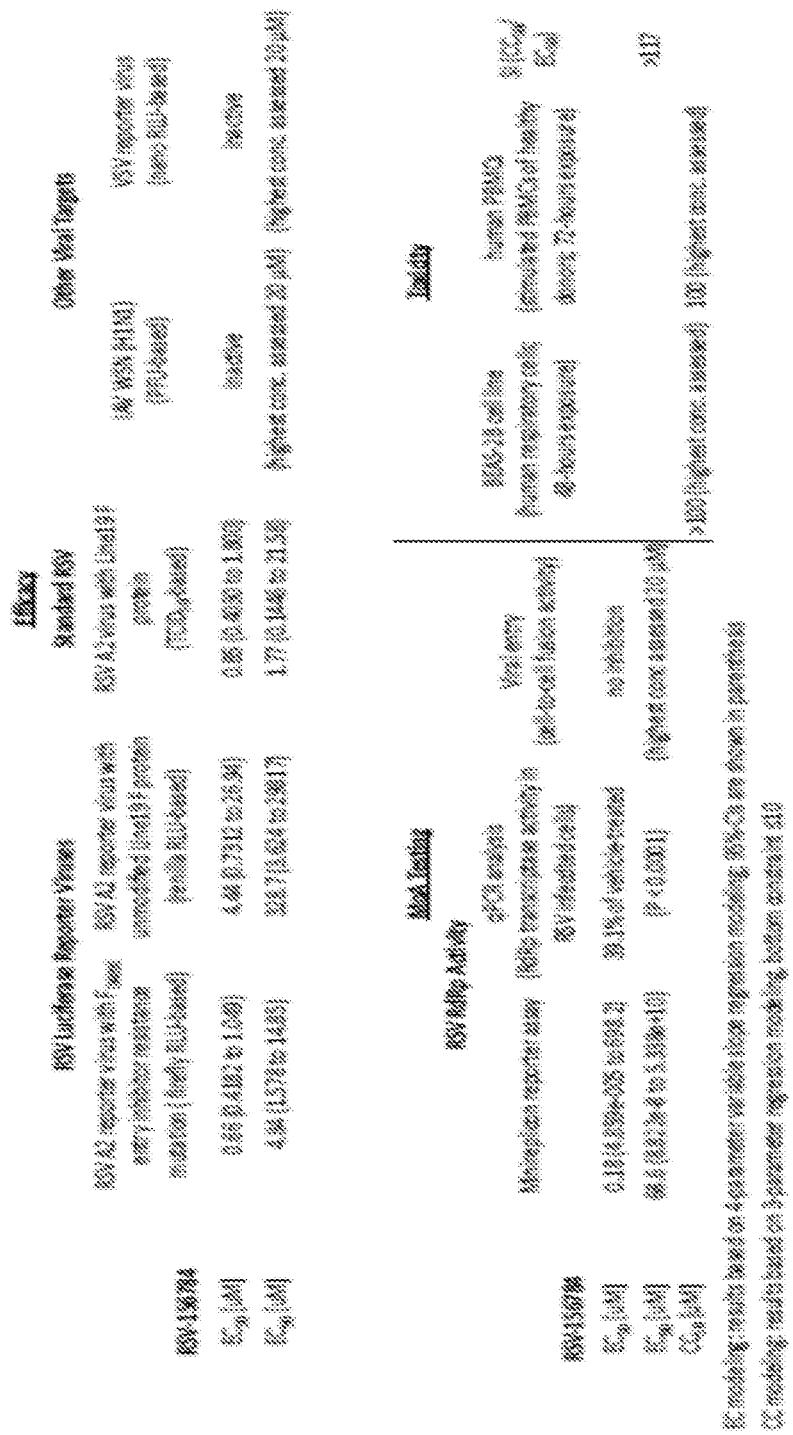
FIG. 3 depicts activity of in accordance with the invention [RSVP-156784] in tabular format.
Figure 4:
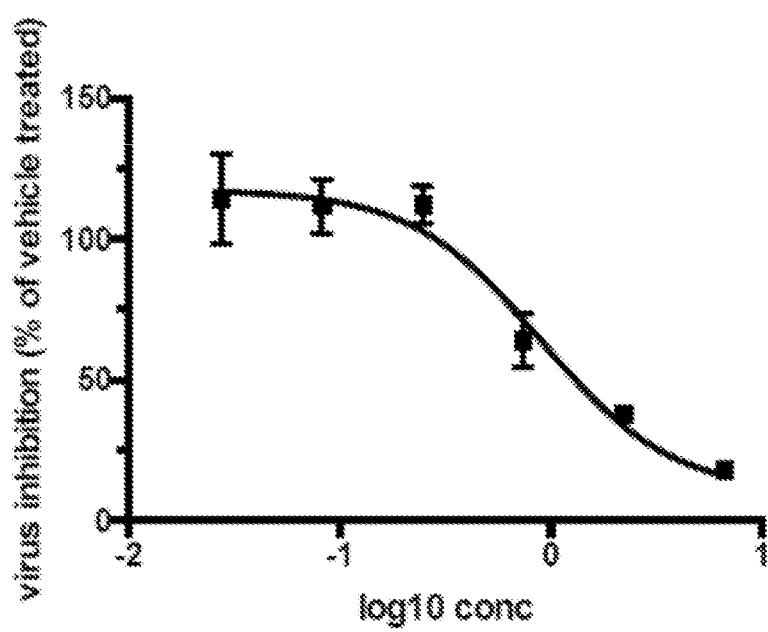
FIG. 4 includes a depiction of the virus yield of an RSV inhibitor in accordance with the invention [RSVP-171352] as a function of concentration.
Figure 5:
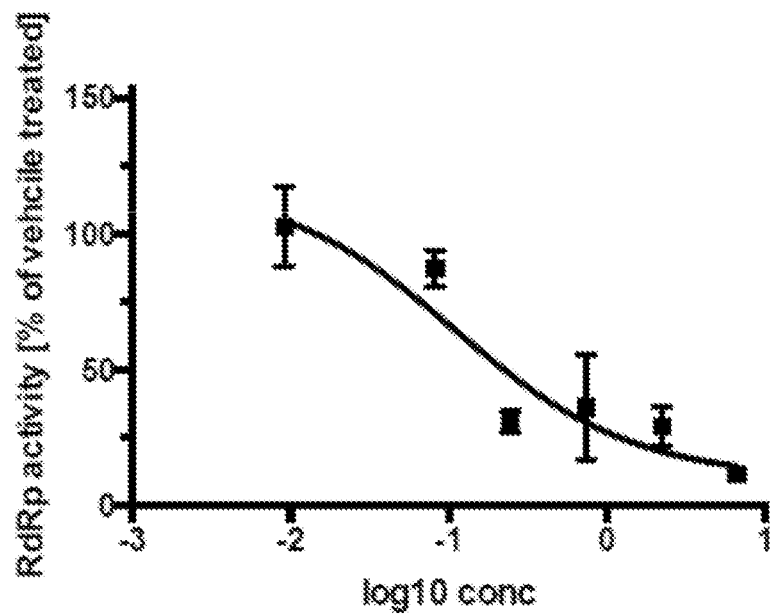
FIG. 5 includes a depiction of the RdRp activity of an RSV inhibitor in accordance with the invention [RSVP-171352] as a function of concentration.

Assay results for two compounds: RSV-156784 and RSV-171352 are presented in FIGS. 1-4.

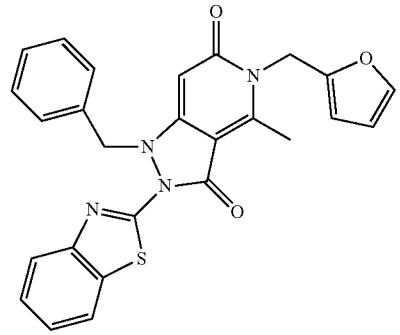

RSV 156784

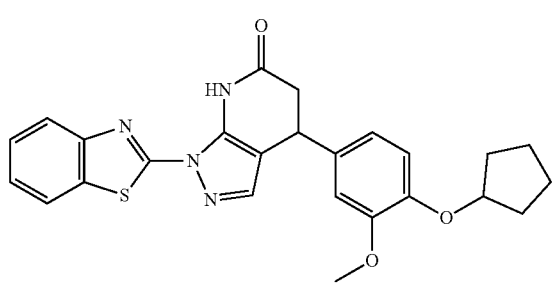

RSV 171352

Example 3: Additional Testing of Compounds of the A Series

Additional testing was conducted to determine additional parameters of the compounds of the invention. In the following Table, a group of selected A series compounds was analyzed with regard to MS, LC, and NMR, and the results are provided below.

| Compound ID | Structure | M + 1 | Rt (min) (LCMS) | Rt (Min) (HPLC) | Method | 1HNMR (400 MHz) |
|---|---|---|---|---|---|---|
| AVG-001 | 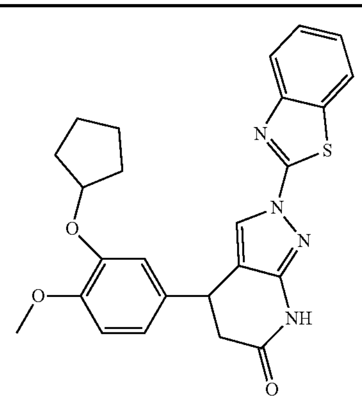 | 461.2 | 2.96 | 10.53 | A2 | (DMSO-$d_6$) • 11.07 (s, 1H), 8.20 (s, 1H), 8.04 (d, J = 8.0 Hz, 1H), 7.80 (d, J = 8.0 Hz, 1H), 7.49 (ddd, J = 8.4, 8.0, 1.0 Hz, 1H), 7.37 (dd, J = 8.0, 7.6 Hz, 1H), 6.90-6.93 (m, 2H), 6.78 (dd, J = 8.2, 1.8 Hz, 1H), 4.79-4.73 (m, 1H), 4.33 (dd, J = 7.2, 6.8 Hz, 1H), 3.72 (s, 3H), 2.86 (dd, J = 15.8, 6.6 Hz, 1H), 2.78 (dd, J = 16.0, 7.6 Hz, 1H), 1.92-1.80 (m, 2H), 1.74-1.64 (m, 4H), 1.60-1.50 (m, 2H) |

-continued

| Compound ID | Structure | M + 1 | Rt (min) (LCMS) | Rt (Min) (HPLC) | Method | 1HNMR (400 MHz) |
|---|---|---|---|---|---|---|
| AVG-001-b | 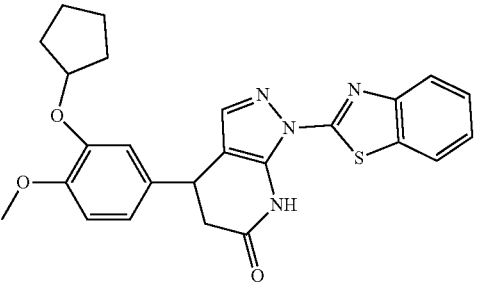 [SMILES: COc1ccc(C2CC(=O)Nc3c2cnn3-c2nc3ccccc3s2)cc1OC1CCCC1] | 461.2 | 3.05 | 11.37 | A2 | (DMSO-d$_6$) • 10.03 (s, 1H), 8.11 (d, J = 8.0 Hz, 1H), 8.02 (d, J = 8.0 Hz, 1H), 7.58-7.52 (m, 2H), 7.44 (dd, J = 8.0, 7.2 Hz, 1H), 6.90 (d, J = 8.4 Hz, 1H), 6.89 (s, 1H), 6.76 (d, J = 8.4 Hz, 1H), 4.79-4.71 (m, 1H), 4.30 (dd, J = 7.6, 6.8 Hz, 1H), 3.72 (s, 3H), 2.99 (dd, J = 16.2, 7.0 Hz, 1H), 2.81 (dd, J = 16.2, 7.8 Hz, 1H), 1.90-1.78 (m, 2H), 1.74-1.64 (m, 4H), 1.60-1.50 (m, 2H) |
| AVG-006 | 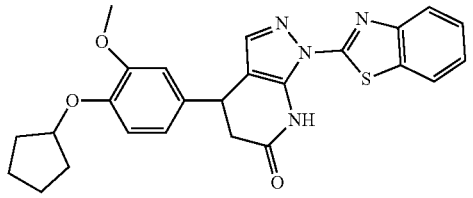 [SMILES: COc1cc(C2CC(=O)Nc3c2cnn3-c2nc3ccccc3s2)ccc1OC1CCCC1] | 461.2 | 3.31 | 11.45 | A3 | (DMSO-d$_6$) • 10.01 (brs, 1H), 8.11 (d, J = 8.0 Hz, 1H), 8.02 (d, J = 8.0 Hz, 1H), 7.58-7.52 (m, 2H), 7.44 (dd, J = 7.6, 7.2 Hz, 1H), 6.93 (d, J = 1.6 Hz, 1H), 6.87 (d, J = 8.4 Hz, 1H), 6.73 (dd, J = 8.2, 1.8 Hz, 1H), 4.77-4.70 (m, 1H), 4.30 (dd, J = 7.2, 7.2 Hz, 1H), 3.73 (s, 3H), 3.00 (dd, J = 13.2, 6.6 Hz, 1H), 2.82 (dd, J = 14.4, 7.6 Hz, 1H), 1.90-1.79 (m, 2H), 1.75-1.65 (m, 4H), 1.60-1.50 (m, 2H) |
| AVG-006b | 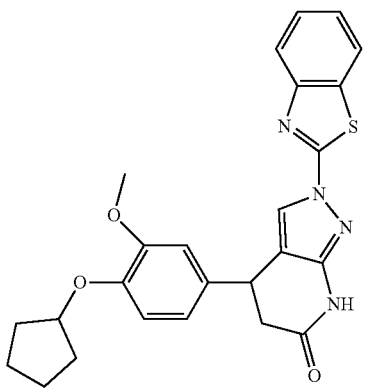 [SMILES: COc1cc(C2CC(=O)Nc3nn(-c4nc5ccccc5s4)cc32)ccc1OC1CCCC1] | 461.1 | 2.92 | 10.89 | A2 | (DMSO-d$_6$) • 11.07 (s, 1H), 8.19 (s, 1H), 8.04 (d, J = 7.6 Hz, 1H), 7.80 (d, J = 8.0 Hz, 1H), 7.48 (ddd, J = 8.4, 8.4, 1.2 Hz, 1H), 7.37 (ddd, J = 8.4, 8.0, 1.2 Hz, 1H), 6.98 (d, J = 2.0 Hz, 1H), 6.89 (d, J = 8.4 Hz, 1H), 6.75 (dd, J = 8.4, 2.0 Hz, 1H), 4.78-4.71 (m, 1H), 4.32 (dd, J = 7.2, 6.8 Hz, 1H), 3.74 (s, 3H), 2.87-2.80 (m, 2H), 1.90-1.80 (m, 2H), 1.75-1.65 (m, 4H), 1.60-1.50 (m, 2H). |
| AVG-065 | 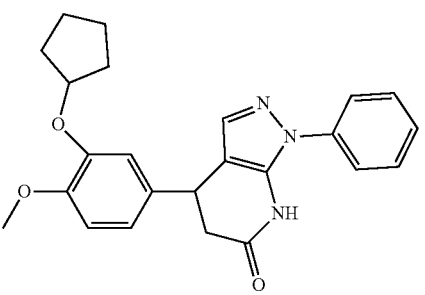 [SMILES: COc1ccc(C2CC(=O)Nc3c2cnn3-c2ccccc2)cc1OC1CCCC1] | 404.1 | 2.47 | 9.30 | A1 | (CDCl$_3$) • 7.66 (s, 1H), 7.56-7.48 (m, 4H), 7.46-7.41 (m, 1H), 7.32 (s, 1H), 6.86-6.80 (m, 3H), 4.78-4.73 (m, 1H), 4.24 (dd, J = 9.6, 6.4 Hz, 1H), 3.85 (s, 3H), 2.97 (dd, J = 16.0, 6.4 Hz, 1H), 2.83 (dd, J = 16.0, 10.0 Hz, 1H), 1.93-1.86 (m, 6H), 1.85-1.77 (m, 2H). |
| AVG-065b | 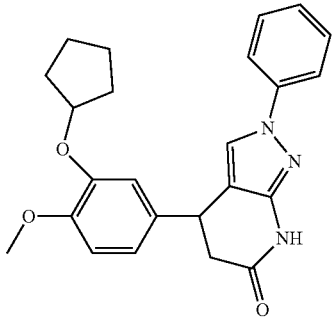 [SMILES: COc1ccc(C2CC(=O)Nc3nn(-c4ccccc4)cc32)cc1OC1CCCC1] | 404.2 | 2.62 | 9.78 | A2 | (CDCl$_3$) • 8.29 (s, 1H), 7.54 (dd, J = 8.6, 1.0 Hz, 2H), 7.46 (s, 1H), 7.40 (dd, J = 8.4, 7.2 Hz, 2H), 7.23 (t, J = 7.4 Hz, 1H), 6.86-6.80 (m, 3H), 4.77-4.71 (m, 1H), 4.23 (dd, J = 10.4, 6.4 Hz, 1H), 3.85 (s, 3H), 2.94 (dd, J = 16.0, 6.4 Hz, 1H), 2.81 (dd, J = 16.2, 10.6 Hz, 1H), 1.93-1.77 (m, 6H), 1.62-1.56 (m, 2H). |

| Compound ID | Structure | M + 1 | Rt (min) (LCMS) | Rt (Min) (HPLC) | Method | 1HNMR (400 MHz) |
|---|---|---|---|---|---|---|
| AVG-066 | 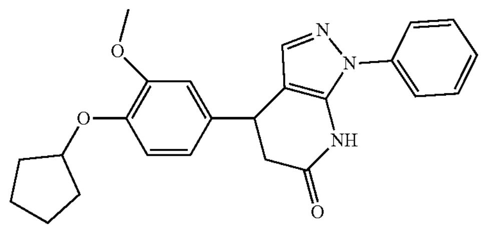 [SMILES: COc1cc(C2CC(=O)Nc3c2cnn3-c2ccccc2)ccc1OC1CCCC1] | 404.2 | 2.52 | 9.44 | A1 | (CDCl$_3$) • 7.61 (s, 1H), 7.56-7.49 (m, 4H), 7.45-7.41 (m, 1H), 7.32 (s, 1H), 6.86-6.78 (m, 3H), 4.78-4.74 (m, 1H), 4.25 (dd, J = 9.6, 6.4 Hz, 1H), 3.84 (s, 3H), 2.97 (dd, J = 16.4, 6.4 Hz, 1H), 2.85 (dd, J = 16.0, 9.6 Hz, 1H), 1.96-1.89 (m, 4H), 1.88-1.81 (m, 2H), 1.64-1.59 (m, 2H). |
| AVG-067 | 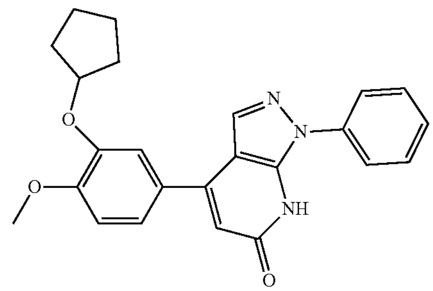 [SMILES: COc1ccc(-c2cc(=O)[nH]c3c2cnn3-c2ccccc2)cc1OC1CCCC1] | 402.2 | 2.66 | 7.49 | A1 | (CDCl$_3$) • 8.07 (s, 1H), 7.76 (d, J = 7.6 Hz, 2H), 7.49 (dd, J = 8.0, 7.6 Hz, 2 H), 7.35 (t, J = 7.8 Hz, 1H), 7.30 (dd, J = 8.4, 2.0 Hz, 1H), 7.26-7.23 (m, 1H), 7.03 (d, J = 8.4 Hz, 1H), 6.55 (s, 1H), 4.88-4.84 (m, 1H), 3.94 (s, 3H), 2.05-1.95 (m, 4H), 1.90-1.84 (m, 2H), 1.70-1.60 (m, 2H). |
| AVG-068 | 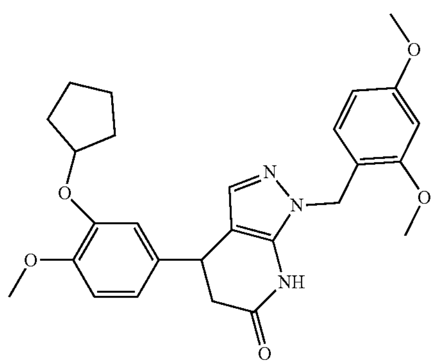 [SMILES: COc1ccc(Cn2ncc3c2NC(=O)CC3c2ccc(OC)c(OC3CCCC3)c2)c(OC)c1] | 478.1 | 2.47 | 9.03 | A2 | (DMSO-d$_6$) • 10.71 (s, 1H), 7.05 (s, 1H), 6.87 (d, J = 8.4 Hz, 1H), 6.75 (d, J = 2.0 Hz, 1H), 6.68 (dd, J = 8.2, 1.8 Hz, 1H), 6.63 (d, J = 8.4 Hz, 1H), 6.57 (d, J = 2.4 Hz, 1H), 6.44 (dd, J = 8.4, 2.4 Hz, 1H), 5.13 (s, 2H), 4.71-4.65 (m, 1H), 4.14 (dd, J = 6.8, 6.4 Hz, 1H), 3.78 (s, 3H), 3.74 (s, 3H), 3.70 (s, 3H), 2.83 (dd, J = 16.0, 6.8 Hz, 1H), 2.58 (dd, J = 16.0, 6.4 Hz, 1H), 1.88-1.75 (m, 2H), 1.72-1.62 (m, 4H), 1.59-1.50 (m, 2H) |
| AVG-069 | 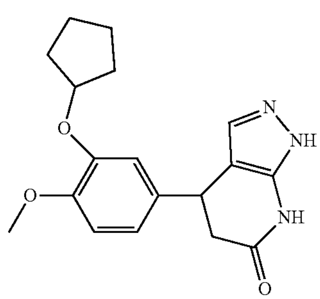 [SMILES: COc1ccc(C2CC(=O)Nc3[nH]ncc32)cc1OC1CCCC1] | 328 | 1.97 | 7.39 | A2 | (DMSO-d$_6$) • 12.06 (s, 1H), 10.36 (s, 1H), 7.28 (s, 1H), 6.86 (d, J = 8.4 Hz, 1H), 6.79 (d, J = 2.0 Hz, 1H), 6.70 (dd, J = 8.0, 2.0 Hz, 1H), 4.72-4.67 (m, 1H), 4.13 (dd, J = 7.2, 6.4 Hz, 1H), 3.70 (s, 3H), 2.69 (dd, J = 15.6, 6.4 Hz, 1H), 2.56 (dd, J = 15.8, 7.8 Hz, 1H), 1.88-1.76 (m, 2H), 1.74-1.61 (m, 4H), 1.59-1.49 (m, 2H) |
| AVG-116 | 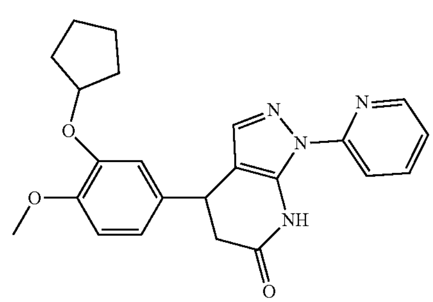 [SMILES: COc1ccc(C2CC(=O)Nc3c2cnn3-c2ccccn2)cc1OC1CCCC1] | 405.2 | 2.68 | 10.12 | A1 | (DMSO-d$_6$) • 10.28 (s, 1H), 8.51 (dd, J = 5.0, 1.0 Hz, 1 H), 8.02 (ddd, J = 8.8, 8.4, 1.6 Hz, 1H), 7.87 (d, J = 8.4 Hz, 1H), 7.41 (s, 1H), 7.36 (dd, J = 7.2, 4.8 Hz, 1 H), 6.90-6.86 (m, 2H), 6.74 (dd, J = 8.2, 1.8 Hz, 1 H), 4.77-4.71 (m, 1H), 4.26 (dd, J = 7.2, 6.8 Hz, 1H), 3.71 (s, 3H), 2.93 (dd, J = 16.0, 7.2 Hz, 1H), 2.76 (dd, J = 16.2, 7.8 Hz, 1H), 1.89-1.78 (m, 2H), 1.74-1.64 (m, 4H), 1.60-1.50 (m, 2H). |

| Compound ID | Structure | M + 1 | Rt (min) (LCMS) | Rt (Min) (HPLC) | Method | 1HNMR (400 MHz) |
|---|---|---|---|---|---|---|
| AVG-117 | 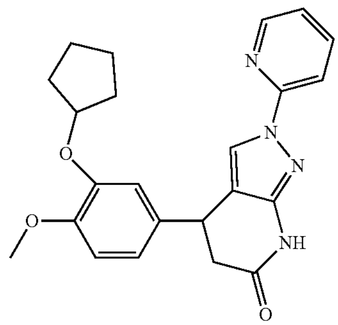 [SMILES: COc1ccc(C2CC(=O)Nc3nn(-c4ccccn4)cc32)cc1OC1CCCC1] | 405.2 | 2.52 | 9.47 | A1 | (DMSO-d$_6$) • 10.85 (s, 1H), 8.36 (dd, J = 4.8, 0.8 Hz, 1H), 8.14 (s, 1H), 7.93 (ddd, J = 9.2, 8.4, 2.0 Hz, 1H), 7.67 (d, J = 8.4 Hz, 1H), 7.24 (dd, J = 6.4, 4.8 Hz, 1H), 6.92-6.88 (m, 2H), 6.77 (dd, J = 8.4, 2.0 Hz, 1H), 4.78-4.71 (m, 1H), 4.28 (dd, J = 7.2, 7.2 Hz, 1H), 3.71 (s, 3H), 2.84-2.68 (m, 2H), 1.90-1.78 (m, 2H), 1.74-1.62 (m, 4H), 1.60-1.50 (m, 2H). |
| AVG-179 | 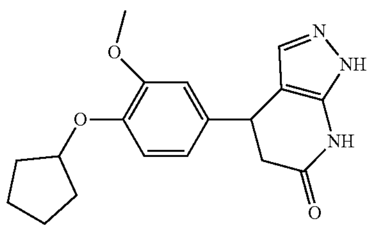 [SMILES: COc1cc(C2CC(=O)Nc3[nH]ncc32)ccc1OC1CCCC1] | 328.2 | 2.05 | 7.61 | A2 | (DMSO-d$_6$) • 12.07 (s, 1H), 10.37 (s, 1H), 7.29 (s, 1H), 6.86-6.82 (m, 2H), 6.66 (dd, J = 8.0, 2.0 Hz, 1H), 4.75-4.68 (m, 1H), 4.13 (dd, J = 7.2, 7.2 Hz, 1H), 3.70 (s, 3H), 2.70-2.55 (m, 2H), 1.88-1.78 (m, 2H), 1.74-1.64 (m, 4H), 1.60-1.50 (m, 2H). |
| AVG-180 | 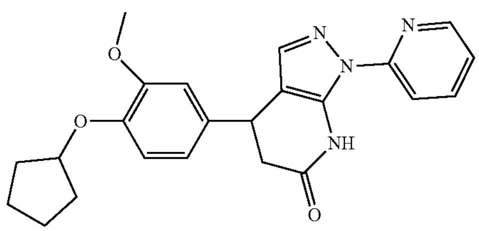 | 405.2 | 2.86 | 9.96 | A1 | (CDCl$_3$) • 10.39 (s, 1H), 8.37 (dd, J = 4.8, 0.8 Hz, 1H), 7.95 (d, J = 8.4 Hz, 1H), 7.87-7.83 (m, 1H), 7.30 (s, 1H), 7.21-7.17 (m, 1H), 6.85-6.77 (m, 3H), 4.78-4.73 (m, 1H), 4.23 (dd, J = 9.6, 6.8 Hz, 1H), 3.82 (s, 3H), 2.98 (dd, J = 16.4, 6.8 Hz, 1H), 2.83 (dd, J = 16.4, 9.6 Hz, 1H), 1.97-1.78 (m, 6H), 1.65-1.58 (m, 2H). |
| AVG-180b | 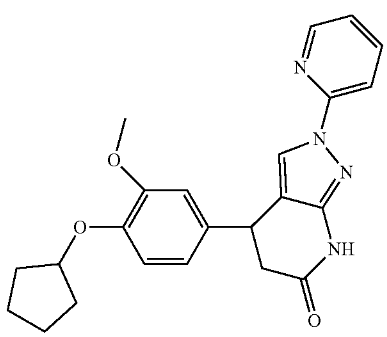 [SMILES: COc1cc(C2CC(=O)Nc3nn(-c4ccccn4)cc32)ccc1OC1CCCC1] | 405.3 | 2.706 | 9.454 | A1 | (DMSO-d$_6$) • 10.85 (s, 1H), 8.36 (d, J = 3.6 Hz, 1H), 8.12 (s, 1H), 7.93 (ddd, J = 8.8, 8.4, 1.8 Hz, 1H), 7.68 (d, J = 8.0 Hz, 1H), 7.24 (dd, J = 6.8, 5.2 Hz, 1H), 6.95 (d, J = 1.6 Hz, 1H), 6.88 (d, J = 8.4 Hz, 1H), 6.74 (dd, J = 8.4, 1.6 Hz, 1H), 4.71-4.76 (m, 1H), 4.28 (dd, J = 7.6, 7.2 Hz, 1H), 3.72 (s, 3H), 2.77-2.79 (m, 2H), 1.88-1.80 (m, 2H), 1.72-1.66 (m, 4H), 1.59-1.53 (m, 2H). |
| AVG-181 | 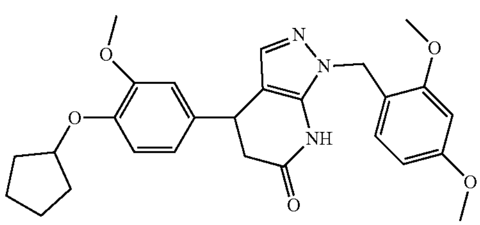 [SMILES: COc1ccc(Cn2ncc3c2NC(=O)CC3c2ccc(OC3CCCC3)c(OC)c2)c(OC)c1] | 478.2 | 2.53 | 9.39 | A2 | (DMSO-d$_6$) • 10.73 (s, 1H), 7.05 (s, 1H), 6.87-6.80 (m, 2H), 6.66-6.61 (m, 2H), 6.56 (s, 1H), 6.45 (d, J = 8.4 Hz, 1H), 5.13 (s, 2H), 4.76-4.69 (m, 1H), 4.15 (dd, J = 6.4, 6.4 Hz, 1H), 3.78 (s, 3H), 3.74 (s, 3H), 3.70 (s, 3H), 2.81 (dd, J = 16.0, 9.2 Hz, 1H), 2.62 (dd, J = 9.6, 6.8 Hz, 1H), 1.88-1.80 (m, 2H), 1.74-1.64 (m, 4H), 1.60-1.50 (m, 2H). |

| Compound ID | Structure | M + 1 | Rt (min) (LCMS) | Rt (Min) (HPLC) | Method | 1HNMR (400 MHz) |
|---|---|---|---|---|---|---|
| AVG-257 | 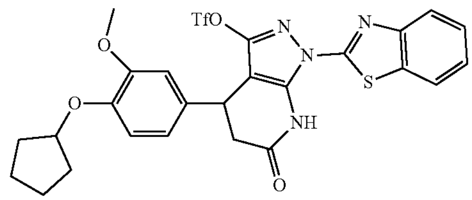 [SMILES: COc1cc(C2CC(=O)Nc3c2c(OS(=O)(=O)C(F)(F)F)nn3-c2nc3ccccc3s2)ccc1OC1CCCC1] | 609.1 | 3.38 | 12.10 | A3 | (DMSO-d$_6$) • 10.45 (s, 1H), 8.14 (d, J = 7.6 Hz, 1H), 8.07 (d, J = 7.6 Hz, 1H), 7.59 (dd, J = 7.6, 7.6 Hz, 1H), 7.48 (dd, J = 7.6, 7.2 Hz, 1H), 6.95 (d, J = 1.6 Hz, 1H), 6.88 (d, J = 8.4 Hz, 1H), 6.78 (dd, J = 8.2, 1.8 Hz, 1H), 4.79-4.73 (m, 1H), 4.34 (dd, J = 8.0, 7.2 Hz, 1H), 3.72 (s, 3H), 3.05-2.89 (m, 2H), 1.90-1.78 (m, 2H), 1.76-1.64 (m, 4H), 1.60-1.52 (m, 2H) |

Example 4: Additional Testing of Compounds of the B Series

Additional testing was conducted to determine additional parameters of the compounds of the invention. In the following Table, a group of selected B series compounds was analyzed with regard to MS, LC, and NMR, and the results are provided below.

| Compound ID | Structure | M + 1 | Rt (min) (LCMS) | Rt (Min) (HPLC) | Method | 1HNMR (400 MHz) |
|---|---|---|---|---|---|---|
| AVG-021 | 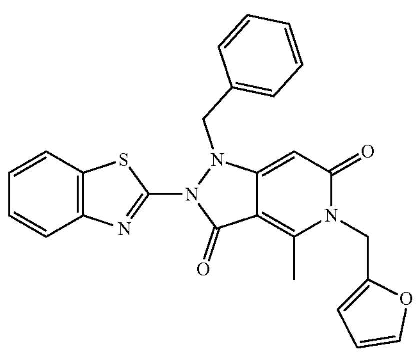 [SMILES: Cc1c2c(=O)n(-c3nc4ccccc4s3)n(Cc3ccccc3)c2cc(=O)n1Cc1ccco1] | 469.2 | 2.91 | 10.39 | B | (DMSO-d$_6$) • 8.09 (d, J = 7.6 Hz, 1H), 7.97 (d, J = 8.0 Hz, 1H), 7.61 (dd, J = 1.8, 1.0 Hz, 1H), 7.54 (ddd, J = 8.0, 7.2, 1.2 Hz, 1H), 7.41 (ddd, J = 8.4, 8.0, 1.2 Hz, 1H), 7.24-7.19 (m, 3H), 7.04-7.01 (m, 2H), 6.48 (s, 1H), 6.43 (dd, J = 3.2, 2.0 Hz, 1H), 6.36 (d, J = 2.4 Hz, 1H), 5.54 (s, 2H), 5.32 (s, 2H), 2.89 (s, 3H). |
| AVG-022 | 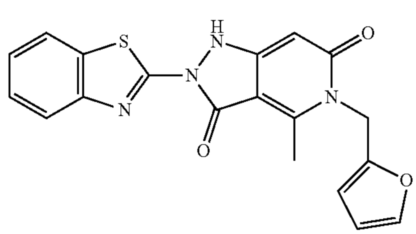 [SMILES: Cc1c2c(=O)n(-c3nc4ccccc4s3)[nH]c2cc(=O)n1Cc1ccco1] | 379.1 | 1.83 | 6.43 | B | (DMSO-d$_6$) • 11.90 (s, 1H), 8.07 (d, J = 8.0 Hz, 1H), 7.84 (d, J = 8.0 Hz, 1H), 7.61 (s, 1H), 7.50 (dd, J = 7.6, 7.2 Hz, 1H), 7.37 (dd, J = 7.6, 7.6 Hz, 1H), 6.43 (s, 1H), 6.37 (d, J = 2.8 Hz, 1H), 5.73 (s, 1H), 5.34 (s, 2H), 2.96 (s, 3H). |
| AVG-023 | 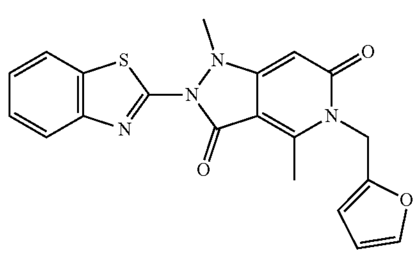 [SMILES: Cc1c2c(=O)n(-c3nc4ccccc4s3)n(C)c2cc(=O)n1Cc1ccco1] | 393.2 | 2.62 | 9.42 | B | (DMSO-d$_6$) • 8.07 (d, J = 8.4 Hz, 1H), 7.88 (d, J = 7.6 Hz, 1H), 7.62 (s, 1H), 7.50 (ddd, J = 8.4, 8.4, 1.2 Hz, 1H), 7.38 (dd, J = 7.2, 6.8 Hz, 1H), 6.44-6.40 (m, 2H), 6.23 (s, 1H), 5.34 (s, 2H), 3.65 (s, 3H), 2.98 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-024 | 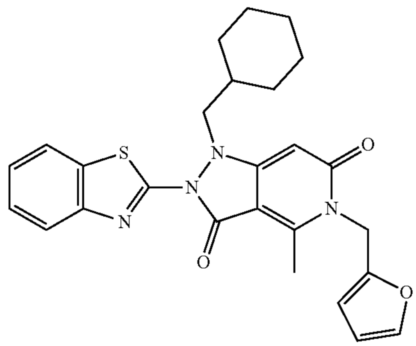 [SMILES: Cc1c2c(=O)n(-c3nc4ccccc4s3)n(CC3CCCCC3)c2cc(=O)n1Cc1ccco1] | 475.1 | 3018 | 11.87 | B | (DMSO-d$_6$) • 8.08 (d, J = 8.0 Hz, 1H), 7.88 (d, J = 8.0 Hz, 1H), 7.61 (d, J = 1.2 Hz, 1H), 7.50 (ddd, J = 7.8, 7.6, 1.2 Hz, 1H), 7.39 (dd, J = 7.6, 7.4 Hz, 1H), 6.43 (dd, J = 3.2, 2.0 Hz, 1H), 6.38 (d, J = 2.8 Hz, 1H), 6.17 (s, 1H), 5.34 (s, 2H), 4.28 (d, J = 7.2 Hz, 2H), 2.97 (s, 3H), 1.61-1.43 (m, 4H), 1.42-1.34 (m, 2H), 1.08-0.98 (m, 3H), 0.95-0.83 (m, 2H) |
| AVG-025 | 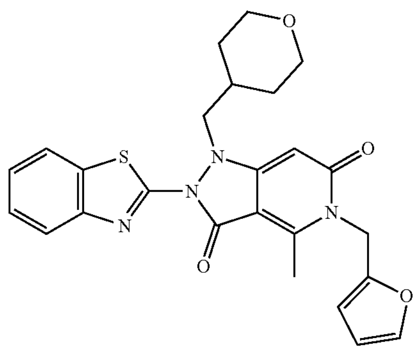 [SMILES: Cc1c2c(=O)n(-c3nc4ccccc4s3)n(CC3CCOCC3)c2cc(=O)n1Cc1ccco1] | 477.1 | 2.63 | 9.91 | B | (DMSO-d$_6$) • 8.08 (d, J = 7.2 Hz, 1H), 7.88 (d, J = 8.0 Hz, 1H), 7.62 (d, J = 0.8 Hz, 1H), 7.50 (ddd, J = 8.4, 8.0, 1.0 Hz, 1H), 7.39 (ddd, J = 8.0, 8.0, 0.8 Hz, 1H), 6.43 (dd, J = 3.2, 2.0 Hz, 1H), 6.39 (d, J = 8.0 Hz, 1H), 6.22 (s, 1H), 5.34 (s, 2H), 4.33 (d, J = 6.8 Hz, 2H), 3.71-3.67 (m, 2H), 3.15-3.10 (m, 2H), 2.97 (s, 3H), 1.89-1.87 (m, 1H), 1.30-1.15 (m, 4H). |
| AVG-026 | 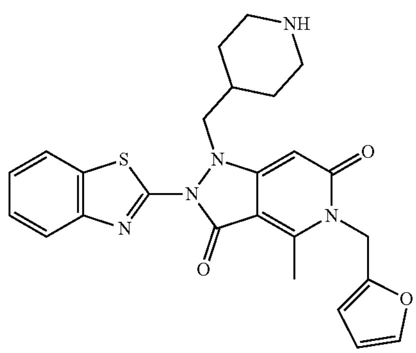 [SMILES: Cc1c2c(=O)n(-c3nc4ccccc4s3)n(CC3CCNCC3)c2cc(=O)n1Cc1ccco1] | 476.0 | 2.07 | 7.25 | B | (DMSO-d$_6$) • 8.08 (d, J = 8.0 Hz, 1H), 7.88 (d, J = 8.0 Hz, 1H), 7.62 (dd, J = 1.6, 0.8 Hz, 1H), 7.50 (ddd, J = 8.4, 8.4, 1.2 Hz, 1H), 7.39 (ddd, J = 8.4, 8.0, 1.2 Hz, 1H), 6.43 (dd, J = 3.2, 1.6 Hz, 1H), 6.39 (d, J = 3.6 Hz, 1H), 6.19 (s, 1H), 5.34 (s, 2H), 4.30 (d, J = 7.2 Hz, 2H), 2.97 (s, 3H), 2.78-2.74 (m, 2H), 2.27-2.20 (m, 2H), 1.71-1.60 (m, 1H), 1.30-1.23 (m, 3H), 1.01-0.97 (m, 2H). |
| AVG-027 | 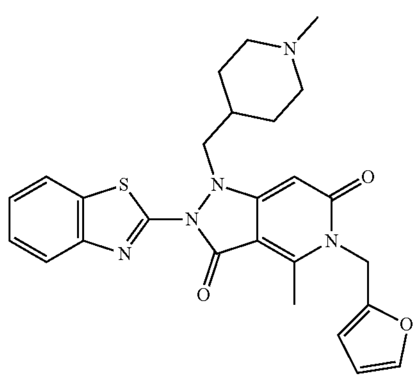 [SMILES: Cc1c2c(=O)n(-c3nc4ccccc4s3)n(CC3CCN(C)CC3)c2cc(=O)n1Cc1ccco1] | 490.3 | 2.47 | 8.90 | B | (DMSO-d$_6$) • 8.08 (d, J = 7.6 Hz, 1H), 7.88 (d, J = 8.0 Hz, 1H), 7.62 (d, J = 0.8 Hz, 1H), 7.50 (ddd, J = 8.4, 8.0, 1.0 Hz, 1H), 7.39 (ddd, J = 8.4, 7.2, 0.8 Hz, 1H), 6.43 (dd, J = 3.4, 1.8 Hz, 1H), 6.39 (d, J = 3.2 Hz, 1H), 6.20 (s, 1H), 5.34 (s, 2H), 4.32 (d, J = 6.8 Hz, 2H), 2.98 (s, 3H), 2.70-2.60 (m, 1H), 2.08 (s, 3H), 1.80-1.55 (m, 3H), 1.38-1.33 (m, 2H), 1.26-1.12 (m, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-028 | 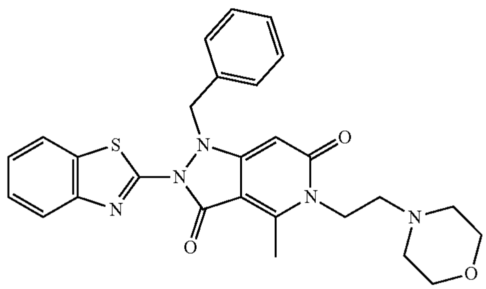 [SMILES: Cc1c2c(=O)n(-c3nc4ccccc4s3)n(Cc3ccccc3)c2cc(=O)n1CCN1CCOCC1] | 502.3 | 2.64 | 9.44 | B | (DMSO-$d_6$) • 8.09 (d, J = 7.6 Hz, 1H), 7.97 (d, J = 8.0 Hz, 1H), 7.54 (ddd, J = 8.4, 8.0, 1.0 Hz, 1H), 7.41 (ddd, J = 8.4, 7.6, 1.0 Hz, 1H), 7.25-7.17 (m, 3H), 7.02-6.99 (m, 2H), 6.45 (s, 1H), 5.52 (s, 2H), 4.13 (t, J = 6.6 Hz, 2H), 3.54-3.50 (m, 4H), 2.86 (s, 3H), 2.54 (t, J = 6.8 Hz, 2H), 2.48-2.40 (m, 4H). |
| AVG-029 | 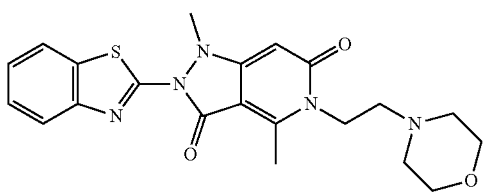 [SMILES: Cc1c2c(=O)n(-c3nc4ccccc4s3)n(C)c2cc(=O)n1CCN1CCOCC1] | 426.2 | 1.90 | 6.61 | B | (DMSO-$d_6$) • 8.07 (d, J = 7.6 Hz, 1H), 7.88 (d, J = 7.6 Hz, 1H), 750 (dd, J = 8.0, 7.2 Hz, 1H), 7.38 (dd, J = 7.6, 7.6 Hz, 1H), 6.19 (s, 1H), 4.16 (t, J = 6.4 Hz, 2H), 3.64 (s, 3H), 3.58-3.54 (m, 4H), 2.94 (s, 3H), 2.55 (t, J = 6.6 Hz, 2H), 2.50-2.44 (m, 4H). |
| AVG-031 | 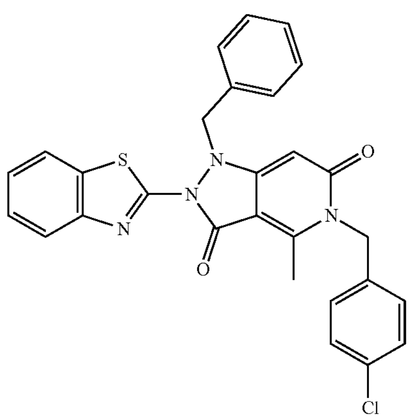 [SMILES: Cc1c2c(=O)n(-c3nc4ccccc4s3)n(Cc3ccccc3)c2cc(=O)n1Cc1ccc(Cl)cc1] | 513.0 | 3.11 | 11.60 | B | (DMSO-$d_6$) • 8.09 (d, J = 7.6 Hz, 1H), 7.98 (d, J = 8.0 Hz, 1H), 7.55-7.51 (m, 1H), 7.44-7.39 (m, 3H), 7.27-7.22 (m, 3H), 7.17 (d, J = 8.4 Hz, 2H), 7.07-7.03 (m, 2H), 6.55 (s, 1H), 5.56 (s, 2H), 5.35 (s, 2H), 2.69 (s, 3H). |
| AVG-033 | 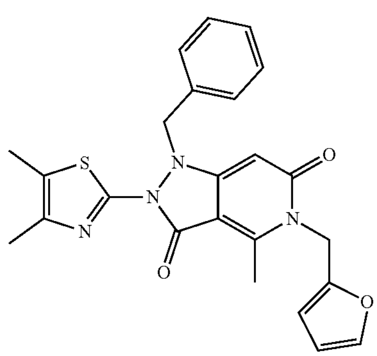 [SMILES: Cc1nc(-n2c(=O)c3c(C)n(Cc4ccco4)c(=O)cc3n2Cc2ccccc2)sc1C] | 447.1 | 2.73 | 10.18 | B | (CDCl$_3$) • 7.33 (dd, J = 1.8, 0.6 Hz, 1H), 7.26-7.18 (m, 3H), 7.06 (dd, J = 8.4, 1.6 Hz, 2H), 6.40 (d, J = 2.0 Hz, 1H), 6.33 (d, J = 2.0, 1.6 Hz, 1H), 6.12 (s, 1H), 5.29 (s, 2H), 5.26 (s, 2H), 2.95 (s, 3H), 2.35 (s, 6H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-034 | 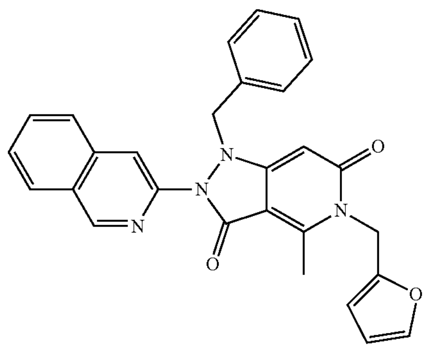 [SMILES: Cc1c2c(=O)n(-c3cc4ccccc4cn3)n(Cc3ccccc3)c2cc(=O)n1Cc1ccco1] | 463.2 | 2.53 | 9.06 | B | (CDCl$_3$) • 9.25 (s, 1H), 8.04 (s, 1H), 8.02 (d, J = 8.4 Hz, 1H), 7.90 (d, J = 8.0 Hz, 1H), 7.76-7.72 (m, 1H), 7.64-7.62 (m, 1H), 7.34 (d, J = 1.2 Hz, 1H), 7.22-7.15 (m, 3H), 7.01 (d, J = 7.2 Hz, 2H), 6.40 (d, J = 3.2 Hz, 1H), 6.33 (dd, J = 3.2, 1.6 Hz, 1H), 6.12 (s, 1H), 5.32 (s, 2H), 4.95 (s, 2H), 3.00 (s, 3H). |
| AVG-035 | 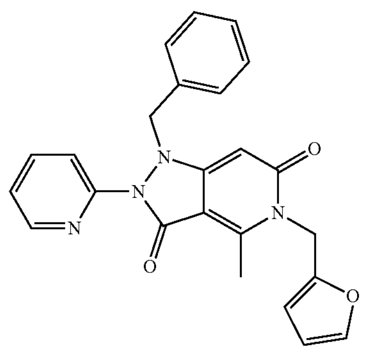 [SMILES: Cc1c2c(=O)n(-c3ccccn3)n(Cc3ccccc3)c2cc(=O)n1Cc1ccco1] | 413.1 | 2.27 | 8.51 | B | (CDCl$_3$) • 8.56 (ddd, J = 4.8, 0.8, 0.8 Hz, 1H), 7.82 (ddd, J = 8.4, 7.2, 2.0 Hz, 1H), 7.76 (ddd, J = 7.2, 1.2, 1.2 Hz, 1H), 7.33 (d, J = 6.0, 0.8 Hz, 1H), 7.25-7.14 (m, 4H), 6.98-6.94 (m, 2H), 6.39 (dd, J = 3.2, 0.8 Hz, 1H), 6.33 (dd, J = 3.2, 2.0 Hz, 1H), 6.10 (s, 1H), 5.31 (s, 2H), 4.96 (s, 2H), 2.97 (s, 3H) |
| AVG-036 | 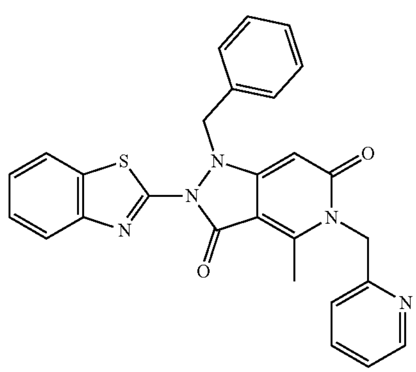 [SMILES: Cc1c2c(=O)n(-c3nc4ccccc4s3)n(Cc3ccccc3)c2cc(=O)n1Cc1ccccn1] | 480.2 | 2.79 | 9.93 | B | (DMSO-d$_6$) • 8.45 (d, J = 4.8 Hz, 1H), 8.09 (d, J = 7.6 Hz, 1H), 7.98 (d, J = 7.6 Hz, 1H), 7.80 (ddd, J = 7.6, 7.6, 1.8 Hz, 1H), 7.54 (ddd, J = 8.4, 8.0, 1.0 Hz, 1H), 7.42 (ddd, J = 8.4, 8.0, 1.2 Hz, 1H), 7.36-7.21 (m, 5H), 7.05 (dd, J = 7.6, 2.0 Hz, 2H), 6.47 (s, 1H), 5.55 (s, 2H), 5.42 (s, 2H), 2.79 (s, 3H). |
| AVG-037 | 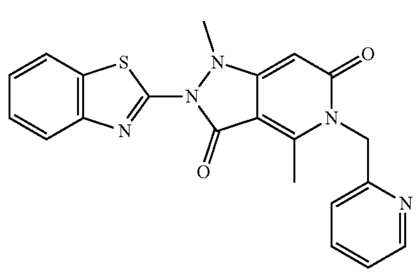 [SMILES: Cc1c2c(=O)n(-c3nc4ccccc4s3)n(C)c2cc(=O)n1Cc1ccccn1] | 404.1 | 2.44 | 8.73 | B | (DMSO-d$_6$) • 8.47 (d, J = 4.0 Hz, 1H), 8.08 (d, J = 7.6 Hz, 1H), 7.89 (d, J = 8.0 Hz, 1H), 7.80 (ddd, J = 7.6, 7.6, 2.0 Hz, 1H), 7.51 (ddd, J = 8.4, 8.0, 1.0 Hz, 1H), 7.41-7.36 (m, 2H), 7.31 (dd, J = 6.8, 5.2 Hz, 1H), 6.22 (s, 1H), 5.44 (s, 2H), 3.67 (s, 3H), 2.87 (s, 3H). |

| Compound ID | Structure | M + 1 | Rt (min) (LCMS) | Rt (Min) (HPLC) | Method | 1HNMR (400 MHz) |
|---|---|---|---|---|---|---|
| AVG-038 | 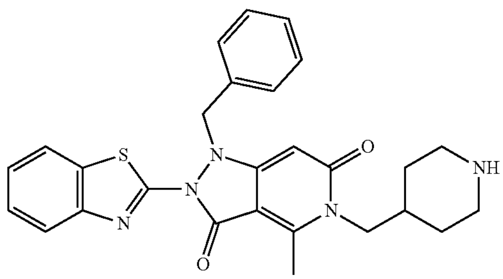 [SMILES: Cc1c2c(=O)n(-c3nc4ccccc4s3)n(Cc3ccccc3)c2cc(=O)n1CC1CCNCC1] | 486.3 | 2.41 | 8.33 | B | (DMSO-d$_6$) • 8.08 (d, J = 7.6 Hz, 1H), 7.97 (d, J = 8.0 Hz, 1H), 7.53 (ddd, J = 8.4, 8.0, 1.2 Hz, 1H), 7.41 (ddd, J = 8.4, 8.0, 1.2 Hz, 1H), 7.25-7.18 (m, 3H), 7.01 (dd, J = 8.2, 1.4 Hz, 2H), 6.43 (s, 1H), 5.52 (s, 2H), 3.94-3.90 (m, 2H), 2.91-2.77 (m, 2H), 2.67 (s, 3H), 2.43-2.32 (m, 2H), 1.87-1.79 (m, 1H), 1.40-1.35 (m, 2H), 1.30-1.23 (m, 1H) 1.18-1.13 (m, 2H). |
| AVG-039 | 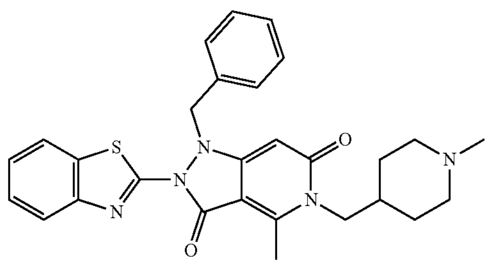 [SMILES: Cc1c2c(=O)n(-c3nc4ccccc4s3)n(Cc3ccccc3)c2cc(=O)n1CC1CCN(C)CC1] | 500.3 | 2.52 | 9.08 | B | (DMSO-d$_6$) • 8.08 (d, J = 8.0 Hz, 1H), 7.97 (d, J = 8.0 Hz, 1H), 7.53 (ddd, J = 8.0, 7.2, 0.8 Hz, 1H), 7.41 (dd, J = 7.2, 7.2 Hz, 1H), 7.24-7.17 (m, 3H), 7.01 (dd, J = 7.8, 1.8 Hz, 2H), 6.43 (s, 1H), 5.51 (s, 2H), 3.98-3.92 (m, 2H), 2.79 (s, 3H), 2.74-2.67 (m, 2H), 2.11 (s, 3H), 1.76-1.66 (m, 3H), 1.45-1.42 (m, 2H), 1.34-1.27 (m, 2H). |
| AVG-040 | 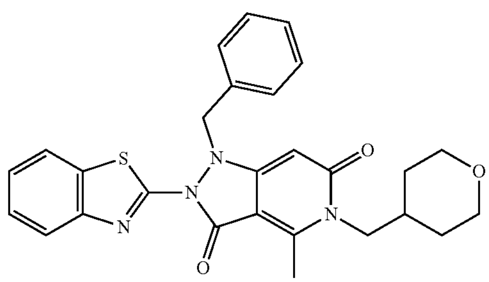 [SMILES: Cc1c2c(=O)n(-c3nc4ccccc4s3)n(Cc3ccccc3)c2cc(=O)n1CC1CCOCC1] | 487.1 | 2.71 | 10.20 | B | (CDCl$_3$) • 7.98 (d, J = 8.0 Hz, 1H), 7.88 (d, J = 8.0 Hz, 1H), 7.51 (ddd, J = 8.4, 8.4, 1.2 Hz, 1H), 7.38 (ddd, J = 8.4, 8.0, 1.0 Hz, 1H), 7.25-7.21 (m, 1H), 7.19-7.15 (m, 2H), 7.08 (dd, J = 8.4, 1.6 Hz, 2H), 6.16 (s, 1H), 5.40 (s, 2H), 4.00-3.96 (m, 4H), 3.37-3.31 (m, 2H), 2.84 (s, 3H), 2.20-2.11 (m, 1H), 1.56-1.41 (m, 4H). |
| AVG-041 | 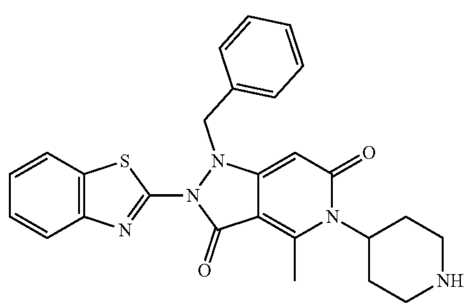 [SMILES: Cc1c2c(=O)n(-c3nc4ccccc4s3)n(Cc3ccccc3)c2cc(=O)n1C1CCNCC1] | 472.2 | 2.60 | 8.80 | B | (DMSO-d$_6$) • 8.09 (d, J = 8.0 Hz, 1H), 7.96 (d, J = 8.0 Hz, 1H), 7.53 (ddd, J = 8.4, 8.0, 1.2 Hz, 1H), 7.41 (ddd, J = 8.4, 8.0, 1.2 Hz, 1H), 7.27-7.20 (m, 3H), 7.05-7.03 (m, 2H), 6.32 (s, 1H), 5.50 (s, 2H), 4.20-4.13 (m, 1H), 3.32-3.31 (m, 2H), 3.02-2.91 (m, 2H), 2.86 (s, 3H), 2.74-2.67 (m, 2H), 2.55-2.54 (m, 1H), 1.55-1.53 (m, 2H). |
| AVG-042 | 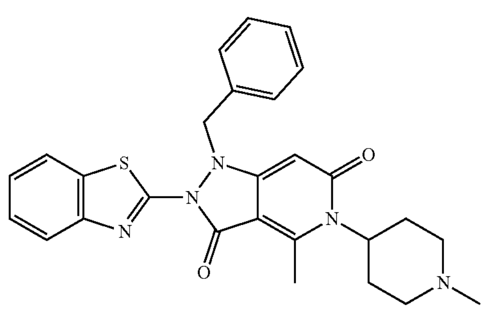 [SMILES: Cc1c2c(=O)n(-c3nc4ccccc4s3)n(Cc3ccccc3)c2cc(=O)n1C1CCN(C)CC1] | 486.2 | 2.29 | 7.67 | B | (CDCl$_3$) • 7.97 (d, J = 8.0 Hz, 1H), 7.87 (d, J = 7.6 Hz, 1H), 7.53-7.48 (m, 1H), 7.40-7.35 (m, 1H), 7.26-7.21 (m, 1H) 7.20-7.15 (m, 2H), 7.10-7.07 (m, 2H), 6.11 (s, 1H), 5.37 (s, 2H), 4.15-3.95 (m, 1H), 3.30-3.00 (m, 4H), 2.88 (s, 3H), 2.33 (s, 3H), 2.15-2.00 (m, 2H), 1.70-1.51 (m, 2H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-043 | 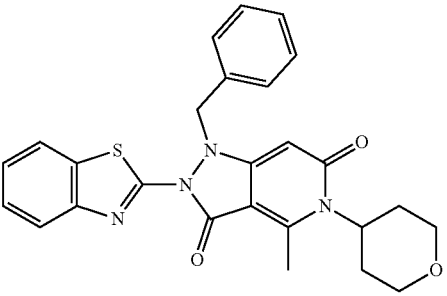 [SMILES: Cc1c2c(=O)n(-c3nc4ccccc4s3)n(Cc3ccccc3)c2cc(=O)n1C1CCOCC1] | 473.3 | 2.82 | 9.87 | B | (CDCl$_3$) • 7.97 (d, J = 8.0 Hz, 1H), 7.87 (d, J = 8.0 Hz, 1H), 7.51 (dd, J = 8.0, 7.2 Hz, 1H), 7.38 (dd, J = 7.6, 7.2 Hz, 1H), 7.26-7.22 (m, 1H), 7.21-7.16 (m, 2H), 7.11-7.08 (m, 2H), 6.09 (s, 1H), 5.38 (s, 2H), 4.60-4.20 (m, 1H), 4.17-4.12 (m, 2H), 3.50-3.44 (m, 2H), 3.35-3.05 (m, 2H), 2.91 (s, 3H), 1.64-1.56 (m, 2H). |
| AVG-070 | 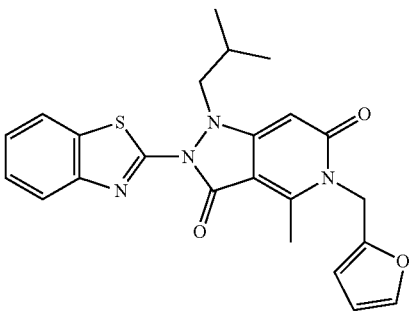 [SMILES: Cc1c2c(=O)n(-c3nc4ccccc4s3)n(CC(C)C)c2cc(=O)n1Cc1ccco1] | 435.2 | 2.97 | 10.66 | B | (DMSO-d$_6$) • 8.08 (d, J = 7.2 Hz, 1H), 7.88 (d, J = 8.0 Hz, 1H), 7.62 (dd, J = 1.6, 0.8 Hz, 1H), 7.50 (ddd, J = 8.4, 8.4, 1.2 Hz, 1H), 7.39 (ddd, J = 8.4, 8.4, 1.2 Hz, 1H), 6.43 (dd, J = 3.2, 2.0 Hz, 1H), 6.38 (d, 2.8 Hz, 1H), 6.18 (s, 1H), 5.34 (s, 2H), 4.24 (d, J = 7.2 Hz, 2H), 2.98 (s, 3H), 1.90-1.85 (m, 1H), 0.74 (d, J = 6.4 Hz, 6H). |
| AVG-071 | 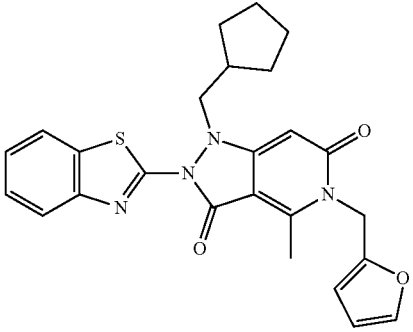 [SMILES: Cc1c2c(=O)n(-c3nc4ccccc4s3)n(CC3CCCC3)c2cc(=O)n1Cc1ccco1] | 461.2 | 3.05 | 11.39 | B | (DMSO-d$_6$) • 8.08 (d, J = 8.0 Hz, 1H), 7.88 (d, J = 8.0 Hz, 1H), 7.62 (s, 1H), 7.50 (dd, J = 8.0, 7.2 Hz, 1H), 7.39 (dd, J = 7.6, 7.6 Hz, 1H), 6.43 (dd, J = 3.2, 2.0 Hz, 1H), 6.40 (d, J = 3.2 Hz, 1H), 6.23 (s, 1H), 5.34 (s, 2H), 4.37 (d, J = 6.8 Hz, 2H), 2.98 (s, 3H), 1.96-1.88 (m, 1H), 1.47-1.37 (m, 4H), 1.35-1.33 (m, 2H), 1.04-1.03 (m, 2H). |
| AVG-072 | 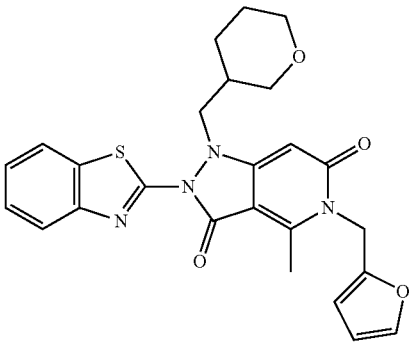 [SMILES: Cc1c2c(=O)n(-c3nc4ccccc4s3)n(CC3CCCOC3)c2cc(=O)n1Cc1ccco1] | 477.2 | 2.69 | 10.13 | B | (CDCl$_3$) • 7.89 (d, J = 8.4 Hz, 1H), 7.85 (d, J = 8.0 Hz, 1H), 7.48 (dd J = 7.2, 7.2 Hz, 1H), 7.38-7.35 (m, 2H), 6.46 (d, J = 2.8 Hz, 1H), 6.35 (dd, J = 3.2, 2.0 Hz, 1H), 5.97 (s, 1H), 5.34 (s, 2H), 4.22-4.19 (m, 2H), 3.76-3.73 (m, 1H), 3.66-3.62 (m, 1H), 3.34-3.27 (m, 1H), 3.13-3.08 (m, 4H), 2.05-2.00 (m, 1H), 1.65-1.62 (m, 1H), 1.55-1.47 (m, 2H), 1.22-1.18 (m, 1H). |

| Compound ID | Structure | M + 1 | Rt (min) (LCMS) | Rt (Min) (HPLC) | Method | 1HNMR (400 MHz) |
|---|---|---|---|---|---|---|
| AVG-073 | 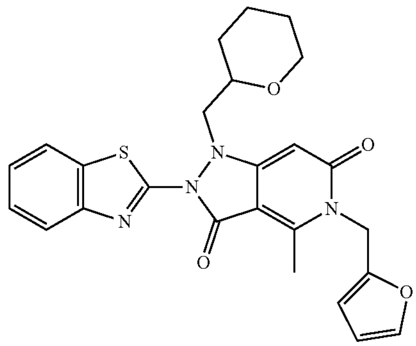 [SMILES: Cc1c2c(=O)n(-c3nc4ccccc4s3)n(CC3CCCCO3)c2cc(=O)n1Cc1ccco1] | 477.1 | 2.85 | 10.67 | B | (DMSO-d$_6$) • 8.07 (d, J = 8.0 Hz, 1H), 7.86 (d, J = 8.0 Hz, 1H), 7.62 (s, 1H), 7.50 (dd, J = 7.6, 7.6 Hz, 1H), 7.38 (dd, J = 8.0, 7.2 Hz, 1H), 6.43 (dd, J = 3.2, 1.6 Hz, 1H), 6.38 (d, J = 3.2 Hz, 1H), 6.17 (s, 1H), 5.34 (s, 2H), 4.41-4.36 (m, 1H), 4.24-4.18 (m, 1H), 3.67-3.63 (m, 1H), 3.57-3.51 (m, 1H), 3.16-3.09 (m, 1H), 2.97 (s, 3H), 1.69-1.66 (m, 1H), 1.47-1.39 (m, 1H), 1.34-1.30 (m, 3H), 1.18-1.15 (m, 1H). |
| AVG-074 | 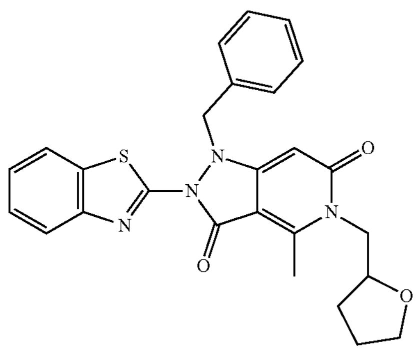 [SMILES: Cc1c2c(=O)n(-c3nc4ccccc4s3)n(Cc3ccccc3)c2cc(=O)n1CC1CCCO1] | 473.3 | 2.86 | 10.28 | B | (CDCl$_3$) • 7.97 (d, J = 8.0 Hz, 1H), 7.87 (d, J = 8.0 Hz, 1H), 7.50 (dd, J = 7.6 Hz, 1H), 7.38 (dd, J = 7.6 Hz, 1H), 7.24-7.21 (m, 1H), 7.20-7.16 (m, 2H), 7.10-7.08 (m, 2H), 6.15 (s, 1H), 5.50 (d, J = 14.4 Hz, 1H), 5.31 (d, J = 14.8 Hz, 1H), 4.50-4.46 (m, 1H), 4.29-4.21 (m, 1H), 3.89-3.78 (m, 2H), 3.74-3.66 (m, 1H), 2.92 (s, 3H), 2.22-2.13 (m, 1H), 1.98-1.85 (m, 2H), 1.68-1.60 (m, 1H). |
| AVG-075 | 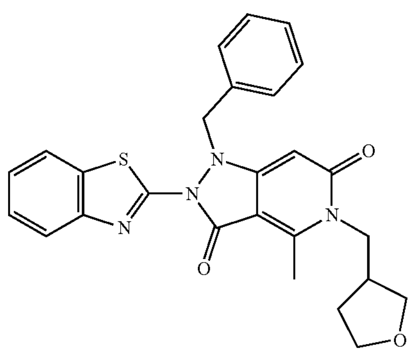 [SMILES: Cc1c2c(=O)n(-c3nc4ccccc4s3)n(Cc3ccccc3)c2cc(=O)n1CC1CCOC1] | 473.3 | 2.72 | 9.73 | B | (CDCl$_3$) • 7.98 (d, J = 8.0 Hz, 1H), 7.87 (d, J = 8.0 Hz, 1H), 7.51 (dd, J = 7.2 Hz, 1H), 7.39 (dd, J = 7.2 Hz, 1H), 7.24-7.22 (m, 1H), 7.20-7.16 (m, 2H), 7.09-7.07 (m, 2H), 6.16 (s, 1H), 5.44 (d, J = 14.8 Hz, 1H), 5.37 (d, J = 14.4 Hz, 1H), 4.23-4.18 (m, 1H), 4.01-3.95 (m, 2H), 3.82-3.76 (m, 1H), 3.71-3.67 (m, 1H), 3.56-3.52 (m, 1H), 2.89-2.80 (m, 1H), 2.85 (s, 3H), 2.11-2.02 (m, 1H), 1.77-1.69 (m, 1H). |
| AVG-076 | 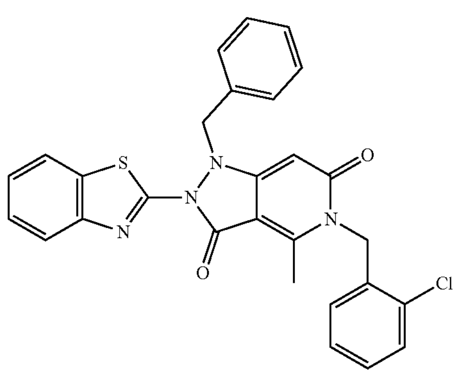 [SMILES: Cc1c2c(=O)n(-c3nc4ccccc4s3)n(Cc3ccccc3)c2cc(=O)n1Cc1ccccc1Cl] | 513.1 | 3.09 | 11.44 | B | (DMSO-d$_6$) • 8.10 (d, J = 8.0 Hz, 1H), 7.99 (d, J = 8.0 Hz, 1H), 7.44-7.57 (m, 2H), 7.42 (dd, J = 8.0, 7.2 Hz, 1H), 7.34 (dd, J = 7.6, 6.8 Hz, 1H), 7.30-7.25 (m, 4H), 7.07-7.05 (m, 2H), 6.62-6.59 (m, 2H), 5.58 (s, 2H), 5.36 (s, 2H), 2.66 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-077 | 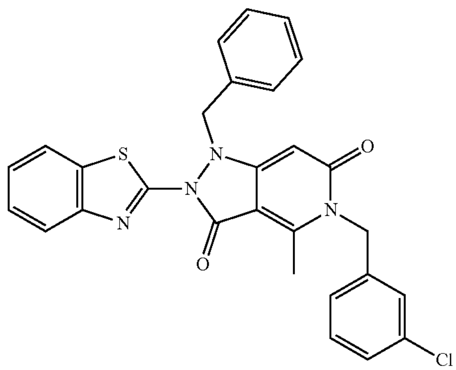 [SMILES: Cc1c2c(=O)n(-c3nc4ccccc4s3)n(Cc3ccccc3)c2cc(=O)n1Cc1cccc(Cl)c1] | 513.2 | 3.09 | 11.45 | B | (DMSO-d$_6$) • 8.09 (d, J = 8.0 Hz, 1H), 7.98 (d, J = 7.6 Hz, 1H), 7.54 (dd, J = 7.6, 7.6 Hz, 1H), 7.43-7.35 (m, 3H), 7.25-7.21 (m, 3H), 7.20-7.18 (m, 1H), 7.09-7.04 (m, 3H), 6.57 (s, 1H), 5.57 (s, 2H), 5.37 (s, 2H), 2.69 (s, 3H). |
| AVG-078 | 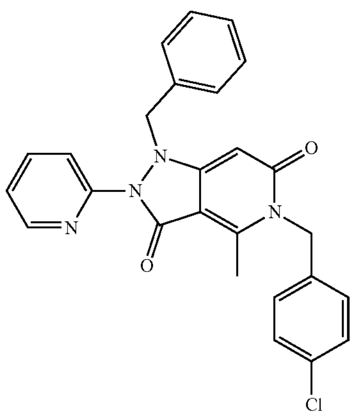 [SMILES: Cc1c2c(=O)n(-c3ccccn3)n(Cc3ccccc3)c2cc(=O)n1Cc1ccc(Cl)cc1] | 457.2 | 2.66 | 9.5 | B | (CDCl$_3$) • 8.58 (dd, J = 4.8, 1.2 Hz, 1H), 7.84-7.80 (m, 1H), 7.76 (d, J = 8.4 Hz, 1H), 7.31-7.28 (m, 2H), 7.26-7.22 (m, 2H), 7.22-7.17 (m, 2H), 7.08 (d, J = 8.4 Hz, 2H), 6.99 (d, J = 8.4 Hz, 2H), 6.19 (s, 1H), 5.36 (s, 2H), 5.00 (s, 2H), 2.72 (s, 3H). |
| AVG-079 | 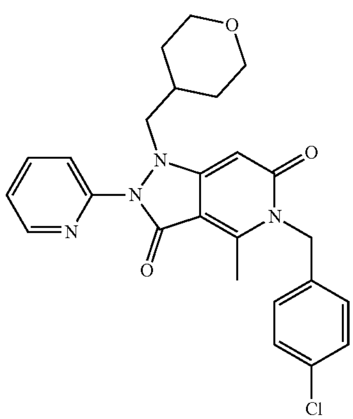 [SMILES: Cc1c2c(=O)n(-c3ccccn3)n(CC3CCOCC3)c2cc(=O)n1Cc1ccc(Cl)cc1] | 465.2 | 2.25 | 8.5 | B | (CDCl$_3$) • 8.52 (d, J = 4.4 Hz, 1H), 7.89-7.80 (m, 2H), 7.30 (d, J = 8.4 Hz, 2H), 7.24-7.20 (m, 1H), 7.13 (d, J = 8.4 Hz, 2H), 6.00 (s, 1H), 5.39 (s, 2H), 3.88-3.80 (m, 4H), 3.26-3.19 (m, 2H), 2.79 (s, 2H), 1.94-1.82 (m, 1H), 1.38-1.32 (m, 2H), 1.28-1.16 (m, 2H). |
| AVG-080 | 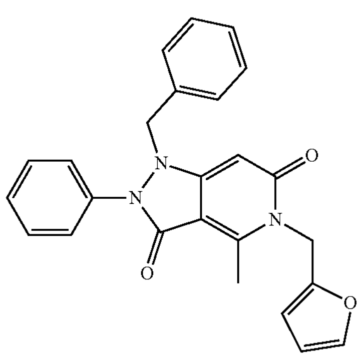 [SMILES: Cc1c2c(=O)n(-c3ccccc3)n(Cc3ccccc3)c2cc(=O)n1Cc1ccco1] | 412.2 | 2.50 | 8.93 | B | (CDCl$_3$) • 7.52-7.46 (m, 2H), 7.45-7.41 (m, 2H), 7.35-7.30 (m, 2H), 7.25-7.19 (m, 3H), 7.03 (d, J = 7.2 Hz, 2H), 6.40 (d, J = 3.2 Hz, 1H), 6.33 (s, 1H), 6.04 (s, 1H), 4.62 (s, 2H), 2.97 (s, 3H). |

| Compound ID | Structure | M + 1 | Rt (min) (LCMS) | Rt (Min) (HPLC) | Method | 1HNMR (400 MHz) |
|---|---|---|---|---|---|---|
| AVG-081 | 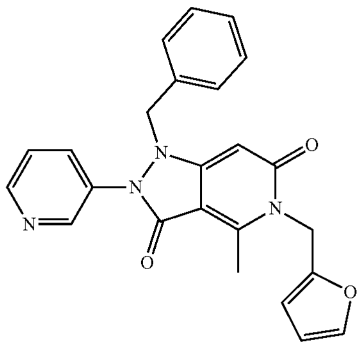 [SMILES: Cc1c2c(=O)n(-c3cccnc3)n(Cc3ccccc3)c2cc(=O)n1Cc1ccco1] | 413.2 | 2.11 | 7.53 | B | (CDCl$_3$) • 8.74 (d, J = 2.4 Hz, 1H), 8.55 (dd, J = 4.4, 0.8 Hz, 1H), 7.79 (dd, J = 8.4, 1.6 Hz, 1H), 7.42 (dd, J = 8.0, 4.4 Hz, 1H), 7.33 (d, J = 0.8 Hz, 1H), 7.29-7.21 (m, 3H), 7.00 (d, J = 6.8 Hz, 2H), 6.42 (d, J = 3.2 Hz, 1H), 6.33 (dd, J = 4.8, 1.6 Hz, 1H), 6.08 (s, 1H), 5.31 (s, 2H), 4.62 (s, 2H), 2.98 (s, 3H). |
| AVG-082 | 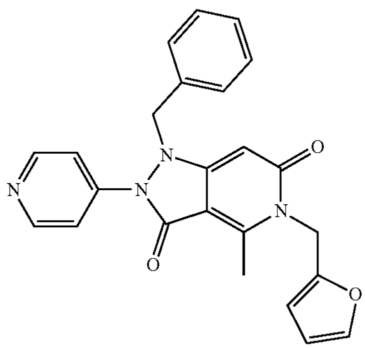 [SMILES: Cc1c2c(=O)n(-c3ccncc3)n(Cc3ccccc3)c2cc(=O)n1Cc1ccco1] | 413.2 | 2.42 | 7.6 | B | (CDCl$_3$) • 8.69 (d, J = 6.4 Hz, 2H), 7.47 (d, J = 6.4 Hz, 2H), 7.33 (d, J = 1.2 Hz, 1H), 7.28-7.21 (m, 3H), 7.01 (d, J = 7.2 Hz, 2H), 6.41 (d, J = 3.2 Hz, 1H), 6.33 (d, J = 4.8, 2.0 Hz, 1H), 6.09 (s, 1H), 5.30 (s, 2H), 4.64 (s, 2H), 2.96 (s, 3H). |
| AVG-088 | 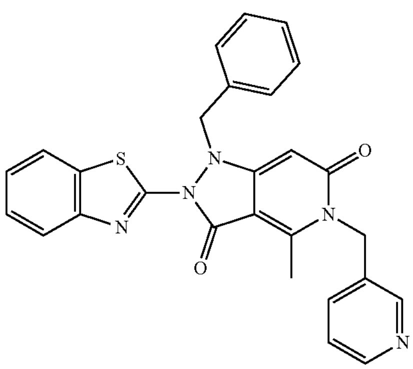 [SMILES: Cc1c2c(=O)n(-c3nc4ccccc4s3)n(Cc3ccccc3)c2cc(=O)n1Cc1cccnc1] | 480.1 | 2.25 | 7.59 | B | (DMSO-d$_6$) • 8.49 (dd, J = 4.6, 1.4 Hz, 1H), 8.46 (d, J = 2.0 Hz, 1H), 8.09 (d, J = 7.2 Hz, 1H), 7.98 (d, J = 8.0 Hz, 1H), 7.54-7.52 (m, 2H), 7.43-7.35 (m, 2H), 7.25-7.21 (m, 3H), 7.05 (dd, J = 7.4, 2.2 Hz, 2H), 6.55 (s, 1H), 5.57 (s, 2H), 5.39 (s, 2H), 2.74 (s, 3H). |
| AVG-089 | 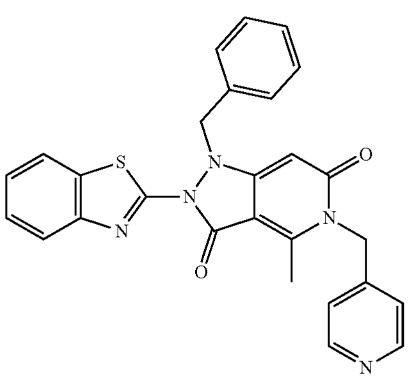 [SMILES: Cc1c2c(=O)n(-c3nc4ccccc4s3)n(Cc3ccccc3)c2cc(=O)n1Cc1ccncc1] | 480.2 | 2.59 | 9.29 | B | (DMSO-d$_6$) • 8.52 (dd, J = 4.4, 1.6 Hz, 1H), 8.09 (d, J = 7.6 Hz, 1H), 7.97 (d, J = 8.0 Hz, 1H), 7.55 (ddd, J = 8.4, 8.0, 1.2 Hz, 1H), 7.42 (ddd, J = 8.4, 8.0, 1.2 Hz, 1H), 7.29-7.22 (m, 3H), 7.10 (d, J = 6.0 Hz, 2H), 7.07-7.04 (m, 2H), 6.57 (s, 1H), 5.58 (s, 2H), 5.39 (s, 2H), 2.67 (s, 3H) |

-continued

| Compound ID | Structure | M + 1 | Rt (min) (LCMS) | Rt (Min) (HPLC) | Method | 1HNMR (400 MHz) |
|---|---|---|---|---|---|---|
| AVG-090 | 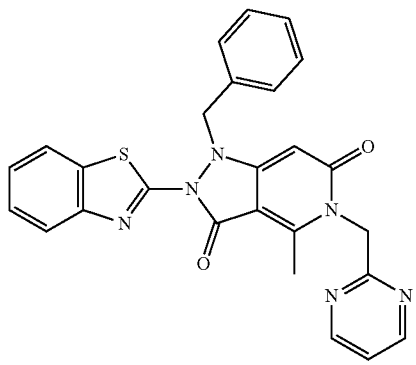 [SMILES: Cc1c2c(=O)n(-c3nc4ccccc4s3)n(Cc3ccccc3)c2cc(=O)n1Cc1ncccn1] | 481.2 | 2.61 | 9.40 | B | (DMSO-d$_6$) • 8.76 (d, J = 4.8 Hz, 2H), 8.10 (d, J = 7.2 Hz, 1H), 7.99 (d, J = 8.0 Hz, 1H), 7.55 (ddd, J = 8.2, 7.2, 1.2 Hz, 1H), 7.45-7.40 (m, 2H), 7.26-7.20 (m, 3H), 7.05 (dd, J = 7.2, 2.0 Hz, 2H), 6.48 (s, 1H), 5.57 (s, 2H), 5.51 (s, 2H), 2.73 (s, 3H). |
| AVG-091 | 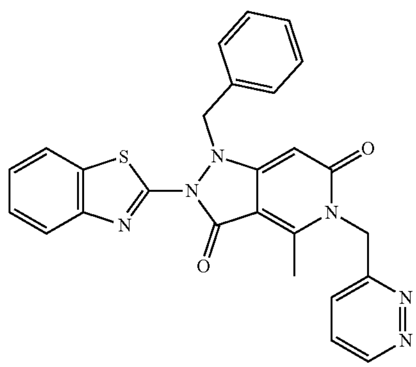 [SMILES: Cc1c2c(=O)n(-c3nc4ccccc4s3)n(Cc3ccccc3)c2cc(=O)n1Cc1cccnn1] | 481.2 | 2.51 | 9.00 | B | (CDCl$_3$) • 9.14 (dd, J = 4.8, 1.6 Hz, 1H), 7.97 (d, J = 8.4 Hz, 1H), 7.88 (d, J = 8.0 Hz, 1H), 7.74 (dd, J = 8.4, 1.6 Hz, 1H), 7.55-7.45 (m, 2H), 7.38 (ddd, J = 8.0, 8.0, 1.0 Hz, 1H), 7.26-7.22 (m, 1H), 7.19 (dd, J = 7.2, 6.0 Hz, 2H), 7.09 (d, J = 7.0 Hz, 2H), 6.17 (s, 1H), 5.61 (s, 2H), 5.42 (s, 2H), 3.06 (s, 3H). |
| AVG-092 | 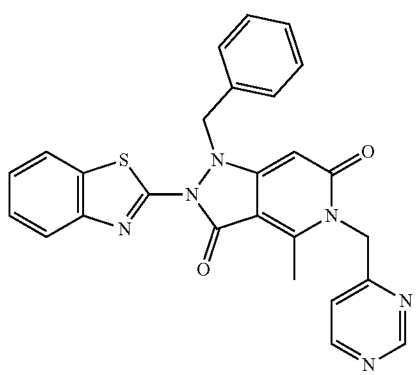 [SMILES: Cc1c2c(=O)n(-c3nc4ccccc4s3)n(Cc3ccccc3)c2cc(=O)n1Cc1ccncn1] | 481.2 | 2.56 | 9.20 | B | (CDCl$_3$) • 9.11 (d, J = 1.2 Hz, 1H), 8.71 (d, J = 5.2 Hz, 1H), 7.99 (d, J = 8.0 Hz, 1H), 7.88 (d, J = 7.4 Hz, 1H), 7.52 (ddd, J = 8.0, 7.2, 0.8 Hz, 1H), 7.39 (ddd, J = 8.4, 8.0, 1.2 Hz, 1H), 7.33 (dd, J = 5.2, 1.2 Hz, 1H), 7.26-7.23 (m, 1H), 7.20 (dd, J = 7.6, 7.2 Hz, 2H), 7.15-7.07 (m, 2H), 6.20 (s, 1H), 5.44 (s, 2H), 5.40 (s, 2H), 2.89 (s, 3H). |
| AVG-093 | 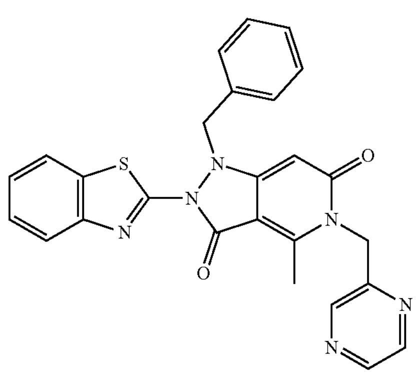 [SMILES: Cc1c2c(=O)n(-c3nc4ccccc4s3)n(Cc3ccccc3)c2cc(=O)n1Cc1cnccn1] | 481.1 | 2.60 | 9.76 | B | (CDCl$_3$) • 8.75 (d, J = 1.5 Hz, 1H), 8.51 (d, J = 2.4 Hz, 1H), 8.45 (dd, J = 2.4, 1.6 Hz, 1H), 7.98 (d, J = 8.4 Hz, 1H), 7.88 (d, J = 7.2 Hz, 1H), 7.51 (ddd, J = 8.2, 7.2, 0.8 Hz, 1H), 7.39 (ddd, J = 8.4, 8.0, 1.2 Hz, 1H), 7.25-7.23 (m, 1H), 7.20-7.17 (m, 2H), 7.11-7.08 (m, 2H), 6.17 (s, 1H), 5.45 (s, 2H), 5.42 (s, 2H), 2.97 (s, 3H). |

| Compound ID | Structure | M + 1 | Rt (min) (LCMS) | Rt (Min) (HPLC) | Method | 1HNMR (400 MHz) |
|---|---|---|---|---|---|---|
| AVG-094 | 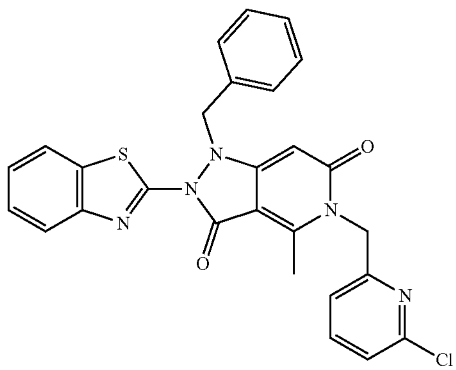 [SMILES: Cc1c2c(=O)n(-c3nc4ccccc4s3)n(Cc3ccccc3)c2cc(=O)n1Cc1cccc(Cl)n1] | 514.2 | 2.99 | 10.66 | B | (CDCl$_3$) • 7.98 (d, J = 8.0 Hz, 1H), 7.87 (d, J = 7.6 Hz, 1H), 7.63 (dd, J = 8.0, 7.6 Hz, 1H), 7.51 (dd, J = 8.0, 7.2 Hz, 1H), 7.39 (dd, J = 7.6 Hz, 1H), 7.25-7.17 (m, 5H), 7.10-7.08 (m, 2H), 6.20 (s, 1H), 5.43 (s, 2H), 5.41 (s, 2H), 2.92 (s, 3H). |
| AVG-095 | 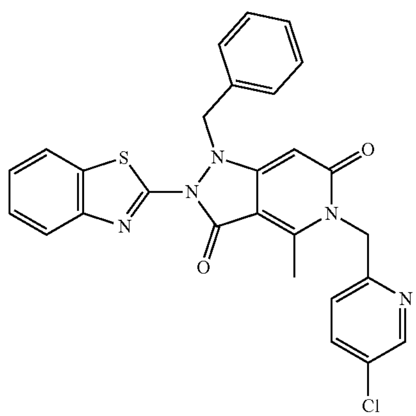 [SMILES: Cc1c2c(=O)n(-c3nc4ccccc4s3)n(Cc3ccccc3)c2cc(=O)n1Cc1ccc(Cl)cn1] | 514.2 | 3.03 | 10.8 | B | (DMSO-d$_6$) • 8.44 (d, J = 2.4 Hz, 1H), 7.98 (d, J = 8.0 Hz, 1H), 7.88 (d, J = 7.6 Hz, 1H), 7.65 (dd, J = 8.4, 2.4 Hz, 1H), 7.51 (ddd, J = 7.8, 7.6, 1.2 Hz, 1H), 7.39 (ddd, J = 7.6, 0.8 Hz, 1H), 7.34 (d, J = 8.4 Hz, 1H), 7.23-7.25 (m, 1H), 7.20-7.16 (m, 2H), 7.09 (d, J = 6.8 Hz, 2H), 6.18 (s, 1H), 5.42 (s, 2H), 5.40 (s, 2H), 2.93 (s, 3H). |
| AVG-096 | 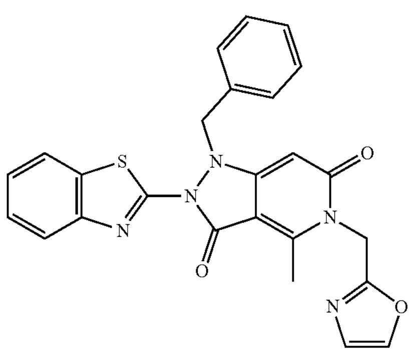 [SMILES: Cc1c2c(=O)n(-c3nc4ccccc4s3)n(Cc3ccccc3)c2cc(=O)n1Cc1ncco1] | 470.2 | 2.61 | 9.77 | B | (CDCl$_3$) • 7.98 (d, J = 8.0 Hz, 1H), 7.87 (d, J = 7.6 Hz, 1H), 7.63 (s, 1H), 7.51 (dd, J = 8.4, 7.2 Hz, 1H), 7.39 (dd, J = 8.0, 7.2 Hz, 1H), 7.25-7.23 (m, 1H), 7.21-7.17 (m, 2H), 7.12-7.08 (m, 3H), 6.20 (s, 1H), 5.48 (s, 2H), 5.43 (s, 2H), 2.92 (s, 3H). |
| AVG-097 | 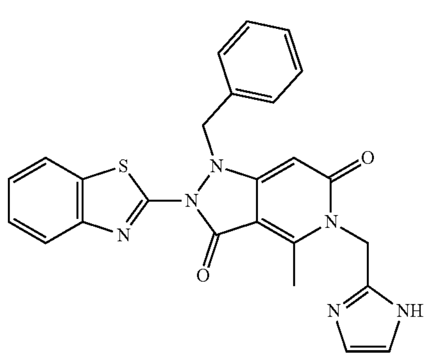 [SMILES: Cc1c2c(=O)n(-c3nc4ccccc4s3)n(Cc3ccccc3)c2cc(=O)n1Cc1ncc[nH]1] | 469.2 | 2.48 | 8.86 | B | (CDCl$_3$) • 12.23 (brs, 1H), 7.96 (d, J = 8.4 Hz, 1H), 7.87 (d, J = 7.6 Hz, 1H), 7.51 (ddd, J = 8.2, 7.0, 1.2 Hz, 1H), 7.38 (ddd, J = 8.0, 8.0, 0.8 Hz, 1H), 7.26-7.22 (m, 1H), 7.21-7.16 (m, 2H), 7.09-7.06 (m, 2H), 7.00 (s, 2H), 6.19 (s, 1H), 5.44 (s, 2H), 5.31 (s, 2H), 3.10 (s, 3H). |

| Compound ID | Structure | M + 1 | Rt (min) (LCMS) | Rt (Min) (HPLC) | Method | 1HNMR (400 MHz) |
|---|---|---|---|---|---|---|
| AVG-098 | 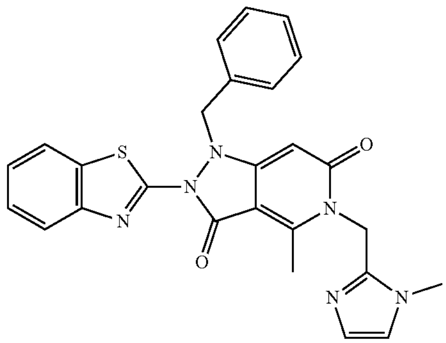 [SMILES: Cc1c2c(=O)n(-c3nc4ccccc4s3)n(Cc3ccccc3)c2cc(=O)n1Cc1nccn1C] | 483.2 | 2.67 | 9.09 | B | (DMSO-d$_6$) • 7.96 (d, J = 8.0 Hz, 1H), 7.87 (d, J = 7.6 Hz, 1H), 7.50 (ddd, J = 7.8, 7.6, 1.2 Hz, 1H), 7.38 (ddd, J = 7.6, 7.4, 0.8 Hz, 1H), 7.25-7.22 (m, 1H), 7.18 (dd, J = 7.6, 6.8 Hz, 2H), 7.10 (d, J = 7.2 Hz, 2H), 6.93 (d, J = 0.8 Hz, 1H), 6.82 (d, J = 1.2 Hz, 1H), 6.10 (s, 1H), 5.40 (s, 2H), 5.33 (s, 2H), 3.86 (s, 3H), 3.19 (s, 3H). |
| AVG-099 | 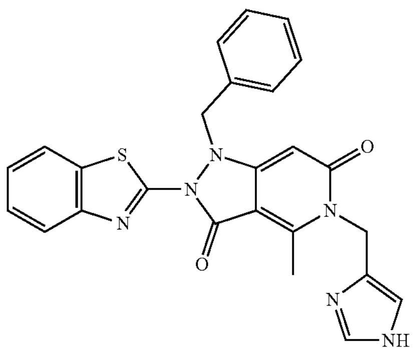 [SMILES: Cc1c2c(=O)n(-c3nc4ccccc4s3)n(Cc3ccccc3)c2cc(=O)n1Cc1c[nH]cn1] | 469.2 | 2.42 | 8.6 | B | (DMSO-d$_6$) • 12.03 (brs, 1H), 8.08 (d, J = 8.0 Hz, 1H), 7.96 (d, J = 8.0 Hz, 1H), 7.56 (s, 1H), 7.53 (dd, J = 8.0, 7.6 Hz, 1H), 7.41 (dd, J = 7.6 Hz, 1H), 7.23-7.19 (m, 3H), 7.03-7.01 (m, 3H), 6.42 (s, 1H), 5.53 (s, 2H), 5.17 (s, 2H), 3.03 (s, 3H). |
| AVG-100 | 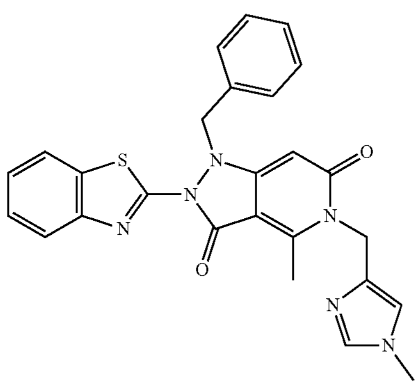 [SMILES: Cc1c2c(=O)n(-c3nc4ccccc4s3)n(Cc3ccccc3)c2cc(=O)n1Cc1cn(C)cn1] | 483.2 | 2.64 | 9.02 | B | (DMSO-d$_6$) • 7.96 (d, J = 8.0 Hz, 1H), 7.87 (d, J = 7.6 Hz, 1H), 7.50 (ddd, J = 7.8, 7.4, 1.2 Hz, 1H), 7.37 (ddd, J = 7.6, 0.8 Hz, 1H), 7.30 (s, 1H), 7.25-7.21 (m, 1H), 7.17 (dd, J = 7.6, 7.2 Hz, 2H), 7.08 (dd, J = 6.8, 1.6 Hz, 2H), 7.02 (s, 1H), 6.14 (s, 1H), 5.39 (s, 2H), 5.22 (s, 2H), 3.63 (s, 3H), 3.12 (s, 3H). |
| AVG-101 | 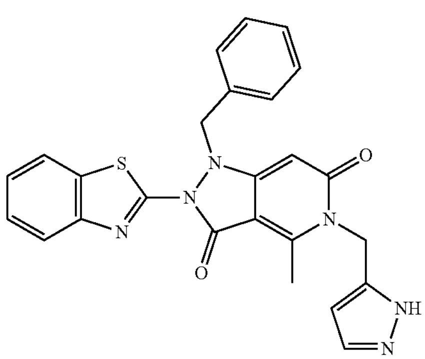 [SMILES: Cc1c2c(=O)n(-c3nc4ccccc4s3)n(Cc3ccccc3)c2cc(=O)n1Cc1ccn[nH]1] | 469.2 | 2.55 | 9.10 | B | (DMSO-d$_6$) • 12.73 (s, 1H), 8.08 (d, J = 7.6 Hz, 1H), 7.97 (d, J = 8.0 Hz, 1H), 7.68 (s, 1H), 7.53 (ddd, J = 8.4, 8.0, 1.2 Hz, 1H), 7.41 (ddd, J = 8.4, 8.0, 1.2 Hz, 1H), 7.31-7.10 (m, 3H), 7.03 (dd, J = 7.4, 1.9 Hz, 2H), 6.47 (s, 1H), 6.16 (s, 1H), 5.54 (s, 2H), 5.28 (s, 2H), 2.88 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-102 | 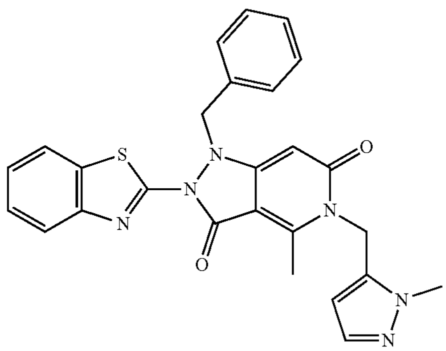 [SMILES: Cc1c2c(=O)n(-c3nc4ccccc4s3)n(Cc3ccccc3)c2cc(=O)n1Cc1ccnn1C] | 483.2 | 2.64 | 9.44 | B | (DMSO-d$_6$) • 8.10 (dd, J = 7.8, 0.6 Hz, 1H), 7.98 (d, J = 7.6 Hz, 1H), 7.54 (ddd, J = 8.4, 8.0, 1.2 Hz, 1H), 7.42 (ddd, J = 8.4, 8.0, 1.0 Hz, 1H), 7.30 (d, J = 2.0 Hz, 1H), 7.26-7.20 (m, 3H), 7.03 (dd, J = 8.2, 1.8 Hz, 2H), 6.54 (s, 1H), 5.75 (d, J = 2.0 Hz, 1H), 5.56 (s, 2H), 5.37 (s, 2H), 3.88 (s, 3H), 2.76 (s, 3H). |
| AVG-103 | | 483.2 | 2.72 | 9.63 | B | (DMSO-d$_6$) • 8.09 (d, J = 7.6 Hz, 1H), 7.97 (d, J = 7.6 Hz, 1H), 7.61 (d, J = 2.0 Hz, 1H), 7.54 (ddd, J = 8.4, 8.0, 1.0 Hz, 1H), 7.41 (dd, J = 8.0, 7.2 Hz, 1H), 7.24-7.18 (m, 3H), 7.02 (dd, J = 7.4, 1.8 Hz, 2H), 6.47 (s, 1H), 6.12 (d, J = 2.0 Hz, 1H), 5.54 (s, 2H), 5.23 (s, 2H), 3.76 (s, 3H), 2.88 (s, 3H). |
| AVG-103 | | 483.2 | 2.72 | 9.63 | B | (DMSO-d$_6$) • 8.09 (d, J = 7.6 Hz, 1H), 7.97 (d, J = 7.6 Hz, 1H), 7.61 (d, J = 2.0 Hz, 1H), 7.54 (ddd, J = 8.4, 8.0, 1.0 Hz, 1H), 7.41 (dd, J = 8.0, 7.2 Hz, 1H), 7.24-7.18 (m, 3H), 7.02 (dd, J = 7.4, 1.8 Hz, 2H), 6.47 (s, 1H), 6.12 (d, J = 2.0 Hz, 1H), 5.54 (s, 2H), 5.23 (s, 2H), 3.76 (s, 3H), 2.88 (s, 3H). |
| AVG-104 | 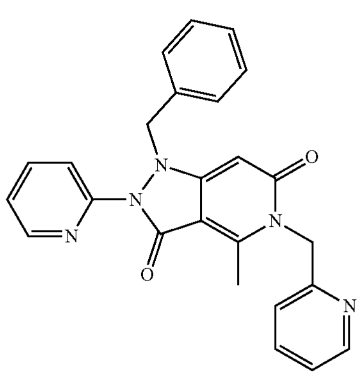 [SMILES: Cc1c2c(=O)n(-c3ccccn3)n(Cc3ccccc3)c2cc(=O)n1Cc1ccccn1] | 424.2 | 2.14 | 7.65 | B | (DMSO-d$_6$) • 8.60 (d, J = 3.6 Hz, 1H), 8.45 (d, J = 4.4 Hz, 1H), 7.97 (ddd, J = 9.2, 8.4, 2.0 Hz, 1H), 7.78 (ddd, J = 7.6, 7.6, 1.6 Hz, 1H), 7.67 (d, J = 8.0 Hz, 1H), 7.37-7.28 (m, 3H), 7.24-7.23 (m, 3H), 6.98-6.96 (m, 2H), 6.29 (s, 1H), 5.39 (s, 2H), 5.06 (s, 2H), 2.76 (s, 1H) |

-continued

| Compound ID | Structure | M + 1 | Rt (min) (LCMS) | Rt (Min) (HPLC) | Method | 1HNMR (400 MHz) |
|---|---|---|---|---|---|---|
| AVG-105 | 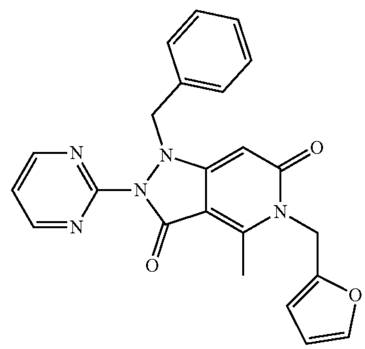 [SMILES: Cc1c2c(=O)n(-c3ncccn3)n(Cc3ccccc3)c2cc(=O)n1Cc1ccco1] | 414.2 | 1.97 | 7.04 | B | (CDCl₃) • 8.84 (d, J = 4.8 Hz, 2H), 7.34 (dd, J = 5.6, 0.8 Hz, 1H), 7.25-7.17 (m, 4H), 7.06 (dd, J = 7.6, 1.6 Hz, 2H), 6.40 (d, J = 3.6 Hz, 1H), 6.33 (dd, J = 3.2, 2.0 Hz, 1H), 6.03 (s, 1H), 5.30 (s, 2H), 4.90 (s, 2H), 2.99 (s, 3H). |
| AVG-106 | 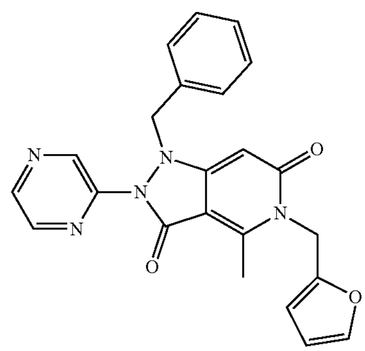 [SMILES: Cc1c2c(=O)n(-c3cnccn3)n(Cc3ccccc3)c2cc(=O)n1Cc1ccco1] | 414.2 | 2.20 | 7.9 | B | (DMSO-d₆) • 8.98 (d, J = 1.2 Hz, 1H), 8.66 (dd, J = 2.2, 1.4 Hz, 1H), 8.57 (d, J = 2.8 Hz, 1H), 7.60 (d, J = 0.8 Hz, 1H), 7.26-7.20 (m, 3H), 7.00-6.95 (m, 2H), 6.42 (dd, J = 3.2, 2.0 Hz, 1H), 6.35 (d, J = 3.2 Hz, 1H), 6.32 (s, 1H), 5.30 (s, 2H), 5.04 (s, 2H), 2.87 (s, 3H). |
| AVG-107 | 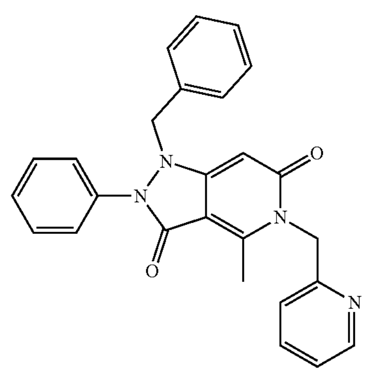 [SMILES: Cc1c2c(=O)n(-c3ccccc3)n(Cc3ccccc3)c2cc(=O)n1Cc1ccccn1] | 423.2 | 2.05 | 7.39 | B | ¹H NMR (400 MHz, DMSO-d₆) • 8.45 (dd, J = 3.2, 0.8 Hz, 1H), 7.78 (ddd, J = 7.6, 7.6, 2.0 Hz, 1H), 7.58-7.54 (m, 2H), 7.45-7.43 (m, 2H), 7.39-7.35 (m, 1H), 7.31-7.25 (m, 5H), 7.04-7.02 (m, 2H), 6.31 (s, 1H), 5.37 (s, 2H), 4.78 (s, 2H), 2.73 (s, 3H). |
| AVG-108 | 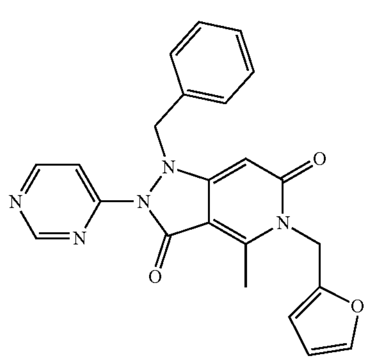 | 414.3 | 2.19 | 7.87 | B | (CDCl₃) • 9.13 (d, J = 0.8 Hz, 1H), 8.70 (d, J = 6.0 Hz, 1H), 7.99 (dd, J = 6.0, 0.8 Hz, 1H), 7.34 (dd, J = 1.6, 0.8 Hz, 1H), 7.28-7.18 (m, 3H), 7.01 (d, J = 3.2 Hz, 2H), 6.42 (dd, J = 3.6, 0.8 Hz, 1H), 6.34 (dd, J = 3.6, 2.0 Hz, 1H), 6.09 (s, 1H), 5.31 (s, 2H), 5.06 (s, 2H), 2.98 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-109 | 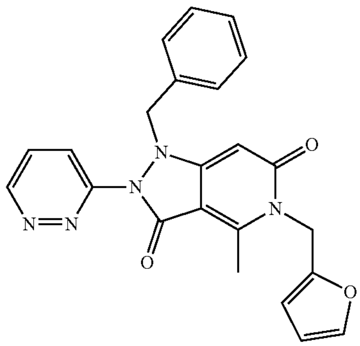 [SMILES: Cc1c2c(=O)n(-c3cccnn3)n(Cc3ccccc3)c2cc(=O)n1Cc1ccco1] | 414.2 | 2.17 | 7.85 | B | (CDCl$_3$) • 9.08 (dd, J = 4.8 Hz, 1.6 Hz, 1H), 8.09 (dd, J = 8.8 Hz, 1.6 Hz, 1H), 7.55 (dd, J = 9.0, 4.6 Hz, 1H), 7.34 (dd, J = 2.0, 0.8 Hz, 1H), 7.23-7.21 (m, 1H), 7.18-7.15 (m, 2H), 6.95 (d, J = 6.8 Hz, 2H), 6.43 (d, J = 3.6, 1H), 6.34 (dd, J = 3.2, 2.0 Hz, 1H), 6.12 (s, 1H), 5.32 (s, 2H), 5.09 (s, 2H), 2.99 (s, 3H). |
| AVG-110 | 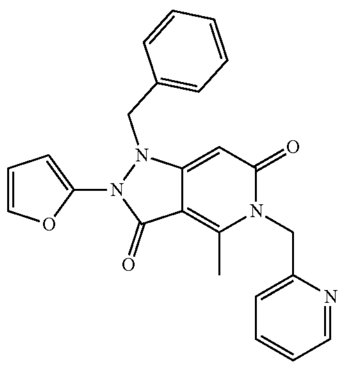 [SMILES: Cc1c2c(=O)n(-c3ccco3)n(Cc3ccccc3)c2cc(=O)n1Cc1ccccn1] | 413.3 | 2.22 | 7.96 | B | (CDCl$_3$) • 8.52 (d, J = 4.8 Hz, 1H), 7.65 (dd, J = 8.0, 7.6 Hz, 1H), 7.41 (s, 1H), 7.28-7.24 (m, 4H), 7.21-7.18 (m, 3H), 6.49 (dd, J = 3.2, 2.0 Hz, 1H), 6.46 (d, J = 3.6 Hz, 1H), 5.88 (s, 1H), 5.45 (s, 2H), 4.62 (s, 2H), 2.88 (s, 3H). |
| AVG-115 | 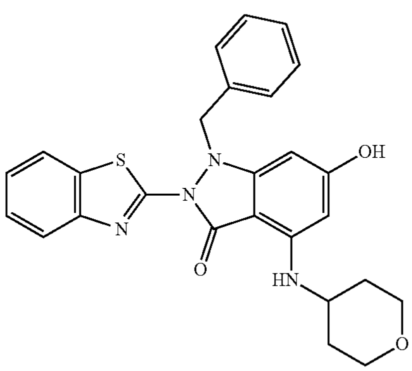 [SMILES: O=c1c2c(NC3CCOCC3)cc(O)cc2n(Cc2ccccc2)n1-c1nc2ccccc2s1] | 473.3 | 2.81 | 9.99 | B | (DMSO-d$_6$) • 10.39 (brs, 1H), 8.05 (d, J = 8.0 Hz, 1H), 7.94 (d, J = 8.0 Hz, 1H), 7.52 (dd, J = 8.0, 7.2 Hz, 1H), 7.38 (dd, J = 7.6, 7.2 Hz, 1H), 7.21-7.16 (m, 3H), 6.96-6.94 (m, 2H), 6.25 (s, 1H), 6.11 (d, J = 8.0 Hz, 1H), 5.85 (s, 1H), 5.45 (s, 2H), 3.88-3.85 (m, 2H), 3.57-3.50 (m, 1H), 3.46-3.41 (m, 2H), 1.93-1.89 (m, 2H), 1.52-1.42 (m, 2H). |
| AVG-119 | 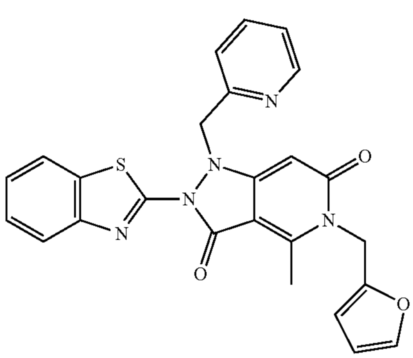 [SMILES: Cc1c2c(=O)n(-c3nc4ccccc4s3)n(Cc3ccccn3)c2cc(=O)n1Cc1ccco1] | 470.2 | 2.63 | 9.46 | B | (DMSO-d$_6$) • 8.37-8.34 (m, 1H), 8.04 (d, J = 7.6 Hz, 1H), 7.90 (d, J = 7.6 Hz, 1H), • 7.66 (ddd, J = 8.0, 7.6, 1.8 Hz, 1H), 7.62 (dd, J = 1.6, 0.8 Hz, 1H), • 7.50 (ddd, J = 8.2, 7.0, 1.0 Hz, 1H), • 7.37 (ddd, J = 8.4, 8.0, 1.2 Hz, 1H), 7.24-7.17 (m, 2H), 6.43 (dd, J = 3.2, 1.6 Hz, 1H), 6.37 (d, J = 3.2 Hz, 1H), 6.34 (s, 1H), 5.68 (s, 2H), 5.33 (s, 2H), 2.95 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-120 | 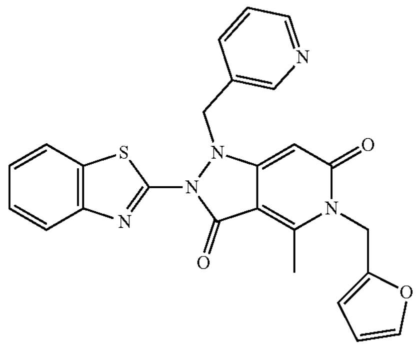 [SMILES: Cc1c2c(=O)n(-c3nc4ccccc4s3)n(Cc3cccnc3)c2cc(=O)n1Cc1ccco1] | 470.2 | 2.50 | 8.96 | B | (CDCl$_3$) • 8.50 (dd, J = 4.8, 1.6 Hz, 1H), 8.39 (d, J = 2.0 Hz, 1H), 7.96 (d, J = 8.0 Hz, 1H), 7.87 (d, J = 7.6 Hz, 1H), 7.49 (dd, J = 8.0, 8.0 Hz, 1H), 7.44-7.37 (m, 2H), 7.35-7.34 (m, 1H), 7.16-7.12 (m, 1H), 6.45 (d, J = 3.2, 1H), 6.34 (dd, J = 3.2, 2.0 Hz, 1H), 6.18 (s, 1H), 5.44 (s, 2H), 5.31 (s, 2H), 3.01 (s, 3H). |
| AVG-121 | 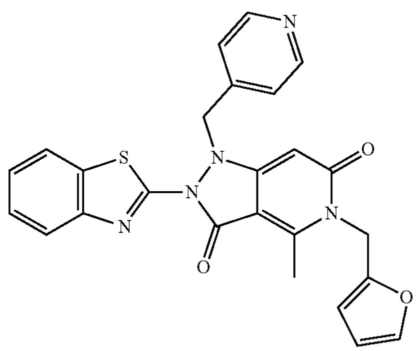 [SMILES: Cc1c2c(=O)n(-c3nc4ccccc4s3)n(Cc3ccncc3)c2cc(=O)n1Cc1ccco1] | 470.1 | 2.51 | 8.90 | B | (DMSO-d$_6$) • 8.45 (dd, J = 4.4, 1.2 Hz, 1H), 8.08 (d, J = 7.6 Hz, 1H), 7.92 (d, J = 8.0 Hz, 1H), 7.62-7.61 (m, 1H), 7.51 (ddd, J = 8.4, 8.4, 1.2 Hz, 1H), 7.40 (ddd, J = 8.4, 8.0, 1.2 Hz, 1H), 7.07 (dd, J = 4.4, 1.6 Hz, 2H), 6.44-6.37 (m, 3H), 5.58 (s, 2H), 5.32 (s, 2H), 2.92 (s, 3H) |
| AVG-122 | 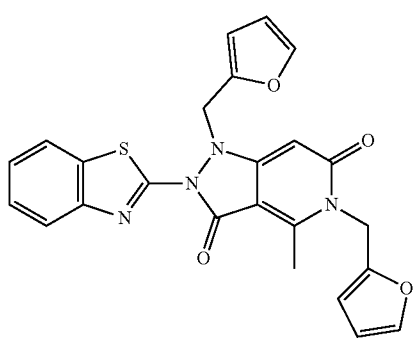 [SMILES: Cc1c2c(=O)n(-c3nc4ccccc4s3)n(Cc3ccco3)c2cc(=O)n1Cc1ccco1] | 459.1 | 2.71 | 10.11 | B | $^1$H NMR (400 MHz, DMSO-d$_6$) • 8.08 (d, J = 7.6 Hz, 1H), 7.94 (d, J = 8.0 Hz, 1H), 7.62 (d, J = 0.8 Hz, 1H), 7.53 (dd, J = 8.0, 7.2 Hz, 1H), 7.49 (d, J = 1.2 Hz, 1H), 7.42 (dd, J = 8.0, 7.2 Hz, 1H), 6.48 (s, 1H), 6.44 (dd, J = 3.0, 1.8 Hz, 1H), 6.39 (d, J = 2.8 Hz, 1H), 6.27 (dd, J = 3.0, 1.8 Hz, 1H), 6.10 (d, J = 3.2 Hz, 1H), 5.58 (s, 2H), 5.33 (s, 2H), 2.92 (s, 3H). |
| AVG-123 | 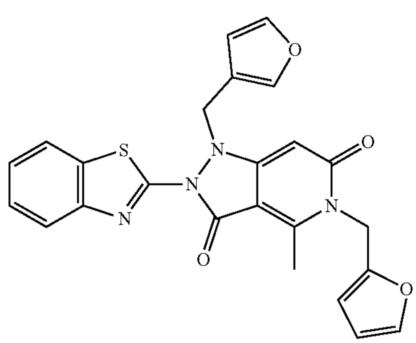 [SMILES: Cc1c2c(=O)n(-c3nc4ccccc4s3)n(Cc3ccoc3)c2cc(=O)n1Cc1ccco1] | 459.1 | 2.71 | 10.12 | B | $^1$H NMR (400 MHz, DMSO-d$_6$) • 8.09 (d, J = 8.0 Hz, 1H), 7.94 (d, J = 8.0 Hz, 1H), 7.61 (d, J = 1.2 Hz, 1H), 7.55-7.50 (m, 2H), 7.42-7.38 (m, 2H), 6.45 (s, 1H), 6.43 (dd, J = 3.0, 1.8 Hz, 1H), 6.38 (d, J = 3.2 Hz, 1H), 5.98 (s, 1H), 5.39 (s, 2H), 5.32 (s, 2H), 2.91 (s, 3H). |

| Compound ID | Structure | M + 1 | Rt (min) (LCMS) | Rt (Min) (HPLC) | Method | 1HNMR (400 MHz) |
|---|---|---|---|---|---|---|
| AVG-124 | 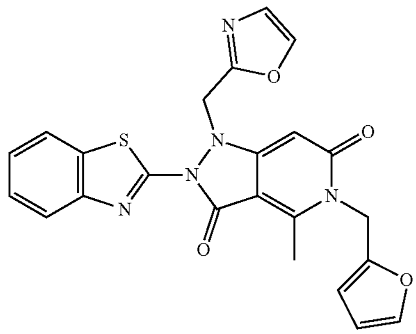 [SMILES: Cc1c2c(=O)n(-c3nc4ccccc4s3)n(Cc3ncco3)c2cc(=O)n1Cc1ccco1] | 460.2 | 2.61 | 9.28 | B | (CDCl₃) • 7.91 (d, J = 8.0 Hz, 1H), 7.84 (d, J = 8.0 Hz, 1H), 7.49-7.46 (m, 2H), 7.37-7.33 (m, 2H), 6.95 (s, 1H), 6.45 (d, J = 3.2 Hz, 1H), 6.34 (dd, J = 2.8, 2.0 Hz, 1H), 6.14 (s, 1H), 5.63 (s, 2H), 5.32 (s, 2H), 3.07 (s, 3H). |
| AVG-125 | 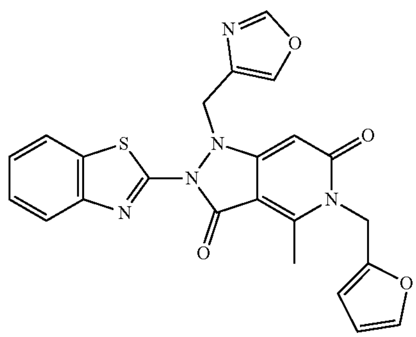 [SMILES: Cc1c2c(=O)n(-c3nc4ccccc4s3)n(Cc3cocn3)c2cc(=O)n1Cc1ccco1] | 460.1 | 2.56 | 9.13 | B | (CDCl₃) • 7.93 (d, J = 8.0 Hz, 1H), 7.85 (d, J = 7.6 Hz, 1H), 7.70 (s, 1H), 7.49-7.46 (m, 1H), 7.42 (s, 1H), 7.38-7.34 (m, 2H), 6.45 (d, J = 3.2 Hz, 1H), 6.34 (dd, J = 3.2, 1.6 Hz, 1H), 6.19 (s, 1H), 5.40 (s, 2H), 5.32 (s, 2H), 3.04 (s, 3H). |
| AVG-126 | 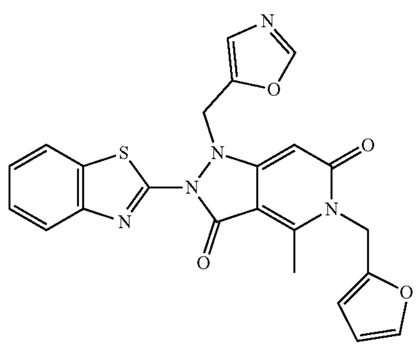 [SMILES: Cc1c2c(=O)n(-c3nc4ccccc4s3)n(Cc3cnco3)c2cc(=O)n1Cc1ccco1] | 460.2 | 2.54 | 9.15 | B | (CDCl₃) • 7.95 (d, J = 8.0 Hz, 1H), 7.88 (d, J = 7.6 Hz, 1H), 7.70 (s, 1H), 7.51 (dd, J = 8.4, 6.8 Hz, 1H), 7.40-7.35 (m, 2H), 6.86 (s, 1H), 6.46 (d, J = 2.8 Hz, 1H), 6.35 (dd, J = 3.2, 2.0 Hz, 1H), 6.18 (s, 1H), 5.53 (s, 2H), 5.33 (s, 2H), 3.04 (s, 3H). |
| AVG-127 | 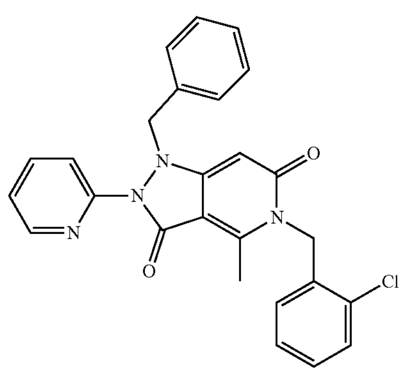 [SMILES: Cc1c2c(=O)n(-c3ccccn3)n(Cc3ccccc3)c2cc(=O)n1Cc1ccccc1Cl] | 457.2 | 2.65 | 9.40 | B | (CDCl₃) • 8.59 (d, J = 4.4 Hz, 1H), 7.86-7.76 (m, 2H), 7.40 (dd, J = 8.0, 0.8 Hz, 1H), 7.28-7.14 (m, 6H), 7.01 (d, J = 6.8 Hz, 2H), 6.67 (d, J = 6.8 Hz, 1H), 6.22 (s, 1H), 5.48 (s, 2H), 5.01 (s, 2H), 2.65 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-128 | 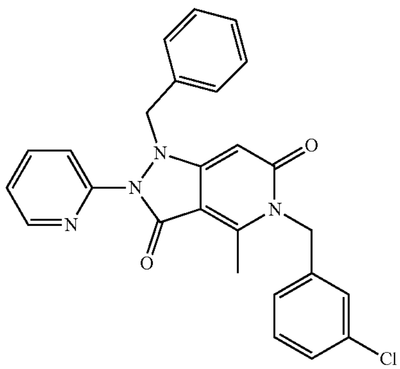 [SMILES: Cc1c2c(=O)n(-c3ccccn3)n(Cc3ccccc3)c2cc(=O)n1Cc1cccc(Cl)c1] | 457.1 | 2.56 | 9.60 | B | (CDCl$_3$) • 8.59-8.58 (m, 1H), 7.83 (ddd, J = 7.2, 7.2 Hz, 2.0 Hz, 1H), 7.77 (d, J = 8.4 Hz, 1H), 7.23-7.18 (m, 6H), 7.09 (s, 1H), 7.03-6.98 (m, 3H), 6.21 (s, 1H), 5.38 (s, 2H), 5.00 (s, 2H), 2.72 (s, 3H). |
| AVG-129 | 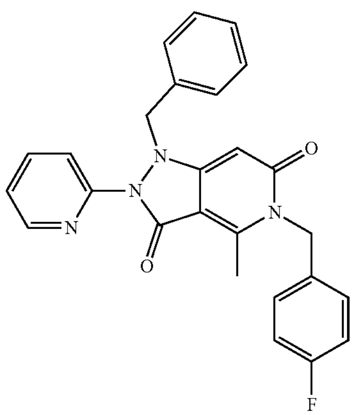 [SMILES: Cc1c2c(=O)n(-c3ccccn3)n(Cc3ccccc3)c2cc(=O)n1Cc1ccc(F)cc1] | 441.3 | 2.55 | 8.90 | B | (CDCl$_3$) • 8.59-8.57 (m, 1H), 7.85-7.75 (m, 2H), 7.25-7.17 (m, 4H), 7.15-7.11 (m, 2H), 7.04-6.97 (m, 4H), 6.19 (s, 1H), 5.37 (s, 2H), 5.00 (s, 2H), 2.73 (s, 3H). |
| AVG-130 | 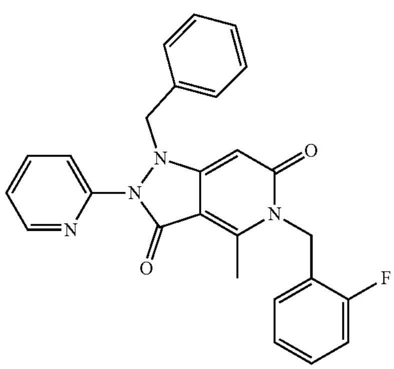 [SMILES: Cc1c2c(=O)n(-c3ccccn3)n(Cc3ccccc3)c2cc(=O)n1Cc1ccccc1F] | 441.2 | 2.55 | 8.93 | B | (DMSO-d$_6$) • 8.60 (dd, J = 4.8, 1.2 Hz, 1H), 7.97 (ddd, J = 7.8, 1.6 Hz, 1H), 7.66 (d, J = 8.0 Hz, 1H), 7.37-7.32 (m, 2H), 7.28-7.22 (m, 4H), 7.14 (dd, J = 7.6 Hz, 1H), 6.98-6.96 (m, 2H), 6.81 (dd, J = 7.8, 6.8 Hz, 1H), 6.38 (s, 1H), 5.35 (s, 2H), 5.09 (s, 2H), 2.69 (s, 3H). |
| AVG-131 | 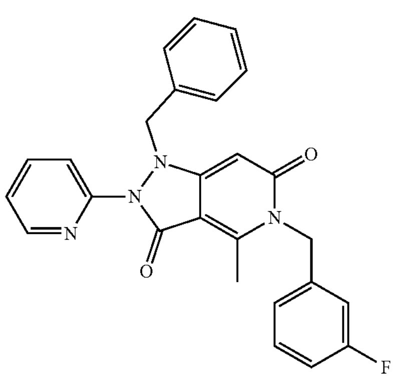 [SMILES: Cc1c2c(=O)n(-c3ccccn3)n(Cc3ccccc3)c2cc(=O)n1Cc1cccc(F)c1] | 441.3 | 2.56 | 9.11 | B | (CDCl$_3$) • 8.59-8.58 (m, 1H), 7.85-7.81 (m, 1H), 7.77 (d, J = 8.4 Hz, 1H), 7.32-7.18 (m, 5H), 7.00-6.94 (m, 3H), 6.91 (d, J = 8.0 Hz, 1H), 6.82 (d, J = 9.6 Hz, 1H), 6.21 (s, 1H), 5.40 (s, 2H), 5.00 (s, 2H), 2.72 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-132 | 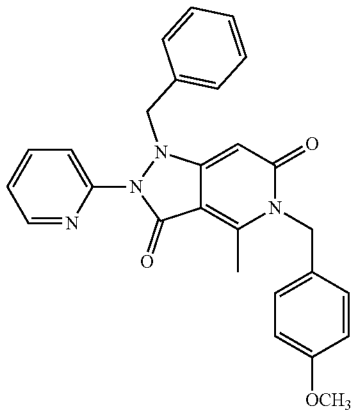 [SMILES: COc1ccc(Cn2c(C)c3c(=O)n(-c4ccccn4)n(Cc4ccccc4)c3cc2=O)cc1] | 453.3 | 2.52 | 8.94 | B | (CDCl$_3$) • 8.58 (d, J = 4.0 Hz, 1H), 7.82 (ddd, J = 6.8, 6.8, 1.8 Hz, 1H), 7.76 (d, J = 8.4 Hz, 1H), 7.24-7.17 (m, 4H), 7.10 (d, J = 8.8 Hz, 2H), 6.98 (d, J = 7.6 Hz, 2H), 6.84 (d, J = 8.8 Hz, 2H), 6.19 (s, 1H), 5.34 (s, 2H), 5.00 (s, 2H), 3.78 (s, 3H), 2.74 (s, 3H). |
| AVG-133 | 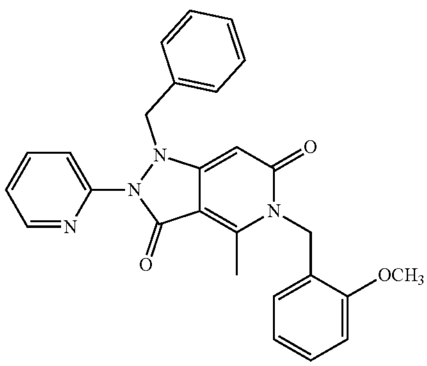 [SMILES: COc1ccccc1Cn1c(C)c2c(=O)n(-c3ccccn3)n(Cc3ccccc3)c2cc1=O] | 453.3 | 2.6 | 9.24 | B | (CDCl$_3$) • 8.59-8.58 (m, 1H), 7.85-7.80 (m, 2H), 7.78 (d, J = 8.4 Hz, 1H), 7.25-7.17 (m, 5H), 7.01-6.99 (m, 2H), 6.89-6.87 (m, 1H), 6.84 (d, J = 7.6 Hz, 1H), 6.67 (d, J = 6.8 Hz, 1 H), 6.21 (s, 1H), 5.39 (s, 2H), 5.00 (s, 2H), 3.87 (s, 3H), 2.67 (s, 3H). |
| AVG-134 | 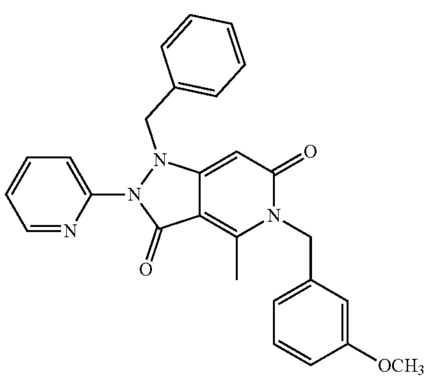 [SMILES: COc1cccc(Cn2c(C)c3c(=O)n(-c4ccccn4)n(Cc4ccccc4)c3cc2=O)c1] | 453.3 | 2.52 | 8.78 | B | (CDCl$_3$) • 8.59-8.57 (m, 1H), 7.85-7.76 (m, 2H), 7.25-7.16 (m, 5H), 6.99 (dd, J = 7.6, 1.6 Hz, 2H), 6.79 (dd, J = 8.2 Hz, 2.2 Hz, 1H), 6.68 (d, J = 7.6 Hz, 1H), 6.65 (s, 1H), 6.20 (s, 1H), 5.39 (s, 2H), 5.00 (s, 2H), 3.76 (s, 3H), 2.72 (s, 3H). |
| AVG-135 | 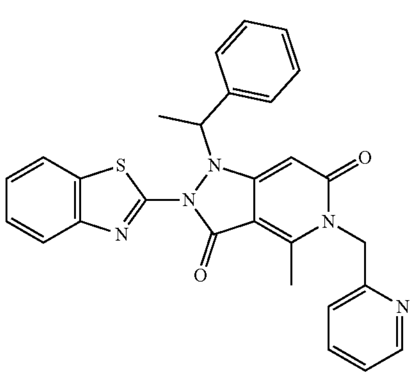 [SMILES: Cc1c2c(=O)n(-c3nc4ccccc4s3)n(C(C)c3ccccc3)c2cc(=O)n1Cc1ccccn1] | 494.1 | 2.75 | 10 | B | (DMSO-d$_6$) • 8.43 (d, J = 4.0 Hz, 1H), 8.11 (d, J = 7.6 Hz, 1H), 7.88 (d, J = 8.0 Hz, 1H), 7.79-7.74 (m, 3H), 7.53-7.47 (m, 3H), 7.44-7.38 (m, 2H), 7.32-7.26 (m, 2H), 6.19 (q, J = 6.8 Hz, 1H), 5.42 (d, J = 16.0 Hz, 1H), 5.32 (d, J = 16.4 Hz, 1H), 5.10 (s, 1H), 2.84 (s, 3H), 1.53 (d, J = 6.8 Hz, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-157 | 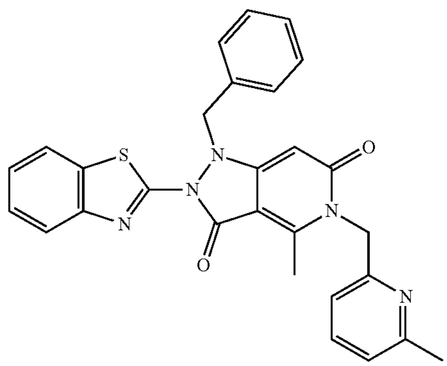 [SMILES: Cc1cccc(Cn2c(C)c3c(=O)n(-c4nc5ccccc5s4)n(Cc4ccccc4)c3cc2=O)n1] | 494.2 | 2.96 | 10.44 | B | (DMSO-d$_6$) • 7.99 (d, J = 8.0 Hz, 1H), 7.88 (d, J = 8.0 Hz, 1 H), 7.54-7.49 (m, 2H), 7.40-7.36 (m, 1H), 7.25-7.23 (m, 1H), 7.18 (dd, J = 7.6, 7.2 Hz, 2H), 7.09 (d, J = 6.8 Hz, 2H), 7.05 (d, J = 7.6 Hz, 1H), 6.99 (d, J = 7.6 Hz, 1H), 6.22 (s, 1H), 5.42 (s, 4H), 2.89 (s, 3H), 2.78 (s, 3H). |
| AVG-158 | 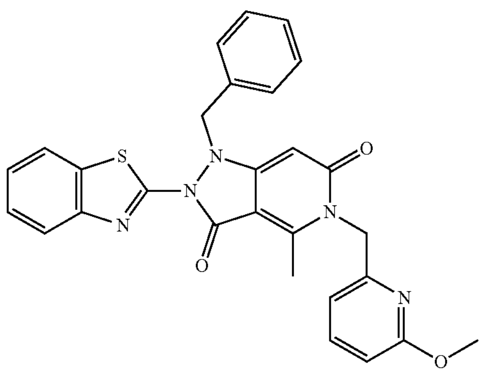 [SMILES: COc1cccc(Cn2c(C)c3c(=O)n(-c4nc5ccccc5s4)n(Cc4ccccc4)c3cc2=O)n1] | 510.2 | 3.05 | 10.72 | B | (CDCl$_3$) • 7.99 (d, J = 8.0 Hz, 1H), 7.88 (d, J = 7.6 Hz, 1H), 7.56-7.49 (m, 2H), 7.39 (ddd, J = 7.8, 7.4, 1.2 Hz, 1H), 7.26-7.21 (m, 1H), 7.16 (dd, J = 7.6, 7.2 Hz, 2H), 7.06 (dd, J = 7.6, 1.6 Hz, 2H), 6.89 (d, J = 6.8 Hz, 1H), 6.63 (d, J = 8.0 Hz, 1H), 6.20 (s, 1H), 5.42 (s, 2H), 5.36 (s, 2H), 3.68 (s, 3H), 2.96 (s, 3H). |
| AVG-159 | 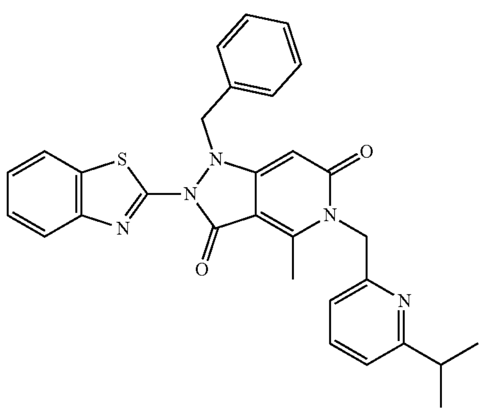 [SMILES: Cc1c2c(=O)n(-c3nc4ccccc4s3)n(Cc3ccccc3)c2cc(=O)n1Cc1cccc(C(C)C)n1] | 522.3 | 3.31 | 11.27 | B | (CDCl$_3$) • 7.99 (d, J = 8.0 Hz, 1H), 7.88 (d, J = 7.6 Hz, 1H), 7.57 (dd, J = 7.6, 7.6 Hz, 1H), 7.51 (dd, J = 8.0, 7.2 Hz, 1H), 7.38 (dd, J = 8.0, 7.2 Hz, 1H), 7.23-7.21 (m, 1H), 7.17-7.12 (m, 3H), 7.08-7.04 (m, 3H), 6.12 (s, 1H), 5.42 (s, 4H), 2.97 (s, 3H), 2.96-2.92 (m, 1H), 1.17 (d, J = 6.8 Hz, 6H). |
| AVG-160 | 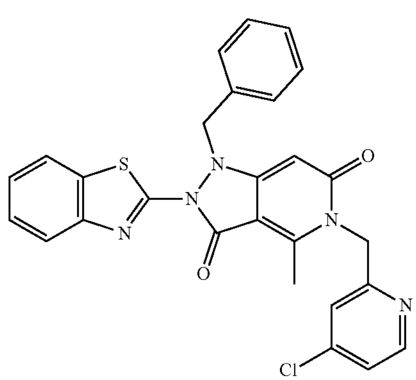 [SMILES: Cc1c2c(=O)n(-c3nc4ccccc4s3)n(Cc3ccccc3)c2cc(=O)n1Cc1cc(Cl)ccn1] | 514.2 | 2.87 | 10.76 | B | $^1$H NMR (400 MHz, DMSO-d$_6$) • 8.43 (d, J = 5.2 Hz, 1H), 8.10 (d, J = 8.0 Hz, 1H), 7.98 (d, J = 0.8 Hz, 1H), 7.56-7.52 (m, 2H), 7.47 (dd, J = 5.2, 2.0 Hz, 1H), 7.42 (ddd, J = 8.4, 7.6, 1.0 Hz, 1H), 7.27-7.20 (m, 3H), 7.04 (dd, J = 7.6, 2.0 Hz, 2H), 6.47 (s, 1H), 5.56 (s, 2H), 5.41 (s, 2H), 2.79 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-161 | 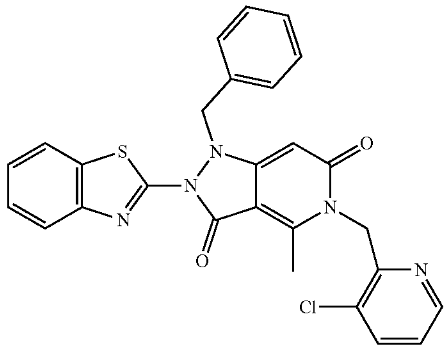 [SMILES: Cc1c2c(=O)n(-c3nc4ccccc4s3)n(Cc3ccccc3)c2cc(=O)n1Cc1ncccc1Cl] | 514.1 | 2.89 | 10.79 | B | (DMSO-d$_6$) • 8.36 (d, J = 4.8 Hz, 1H), 8.10 (d, J = 8.4 Hz, 1H), 8.02-7.97 (m, 2H), 7.56 (dd, J = 8.0, 6.8 Hz, 1H), 7.44-7.37 (m, 2H), 7.25-7.21 (m, 3H), 7.06-7.04 (m, 2H), 6.48 (s, 1H), 5.57 (s, 2H), 5.52 (s, 2H), 2.71 (s, 3H) |
| AVG-162 | 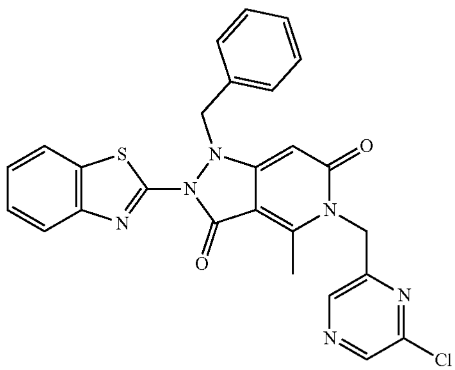 [SMILES: Cc1c2c(=O)n(-c3nc4ccccc4s3)n(Cc3ccccc3)c2cc(=O)n1Cc1cncc(Cl)n1] | 515.1 | 2.85 | 10.57 | B | (DMSO-d$_6$) • 8.74 (s, 1H), 8.73 (s, 1H), 8.10 (d, J = 8.0 Hz, 1H), 7.98 (d, J = 8.0 Hz, 1H), 7.54 (dd, J = 7.6, 7.2 Hz, 1H), 7.42 (dd, J = 7.6, 7.2 Hz, 1H), 7.28-7.17 (m, 3H), 7.02 (d, J = 6.4 Hz, 2H), 6.51 (s, 1H), 5.56 (s, 2H), 5.47 (s, 2H), 2.82 (s, 3H). |
| AVG-163 | 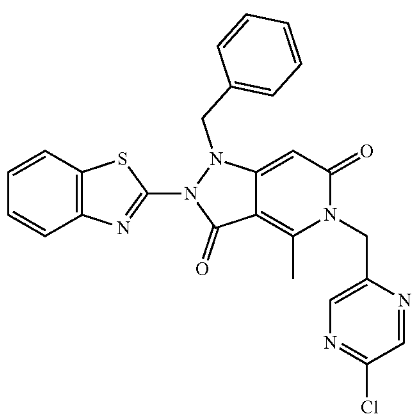 [SMILES: Cc1c2c(=O)n(-c3nc4ccccc4s3)n(Cc3ccccc3)c2cc(=O)n1Cc1cnc(Cl)cn1] | 515.2 | 3.03 | 10.56 | B | (DMSO-d$_6$) • 8.69 (s, 1H), 8.65 (s, 1H), 8.10 (d, J = 7.6 Hz, 1H), 7.98 (d, J = 8.0 Hz, 1H), 7.54 (ddd, J = 8.4, 8.4, 1.2 Hz, 1H), 7.42 (ddd, J = 8.0, 8.0, 0.8 Hz, 1H), 7.26-7.21 (m, 3H), 7.04-7.02 (m, 2H), 6.48 (s, 1H), 5.56 (s, 2H), 5.47 (s, 2H), 2.83 (s, 3H) |
| AVG-164 | 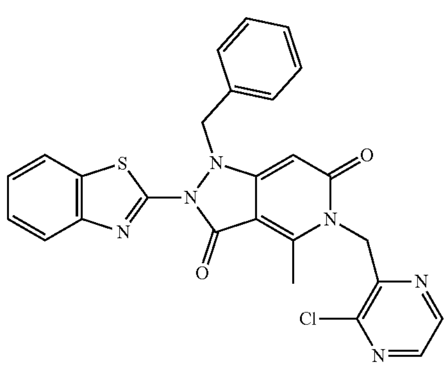 [SMILES: Cc1c2c(=O)n(-c3nc4ccccc4s3)n(Cc3ccccc3)c2cc(=O)n1Cc1nccnc1Cl] | 515.2 | 2.93 | 10.23 | B | (CDCl$_3$) • 8.32 (s, 2H), 7.99 (d, J = 8.0 Hz, 1H), 7.88 (d, J = 8.0 Hz, 1H), 7.52 (dd, J = 8.0, 7.2 Hz, 1H), 7.39 (dd, J = 7.6, 7.6 Hz, 1H), 7.25-7.22 (m, 1H), 7.20 (dd, J = 7.6, 7.2 Hz, 2H), 7.12 (d, J = 7.2 Hz, 2H), 6.21 (s, 1H), 5.57 (s, 2H), 5.44 (s, 2H), 2.74 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-165 | 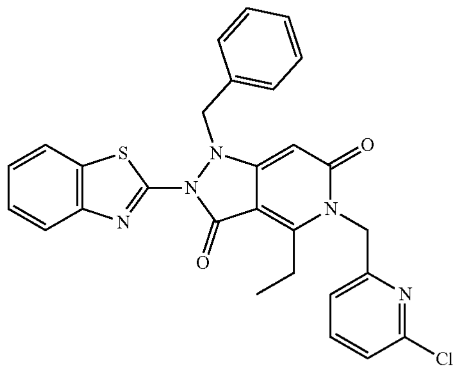 [SMILES: CCc1c2c(=O)n(-c3nc4ccccc4s3)n(Cc3ccccc3)c2cc(=O)n1Cc1cccc(Cl)n1] | 528.2 | 3 | 11.15 | B | (CDCl$_3$) • 7.98 (d, J = 8.0 Hz, 1H), 7.87 (d, J = 7.6 Hz, 1H), 7.62 (dd, J = 8.0, 7.6 Hz, 1H), 7.51 (dd, J = 7.6, 7.2 Hz, 1H), 7.38 (dd, J = 7.6 Hz, 1H), 7.26-7.23 (m, 2H), 7.21-7.09 (m, 5H), 6.19 (s, 1H), 5.43 (s, 2H), 5.41 (s, 2H), 3.33 (q, J = 7.6 Hz, 2H), 1.24 (t, J = 7.6 Hz, 3H). |
| AVG-166 | 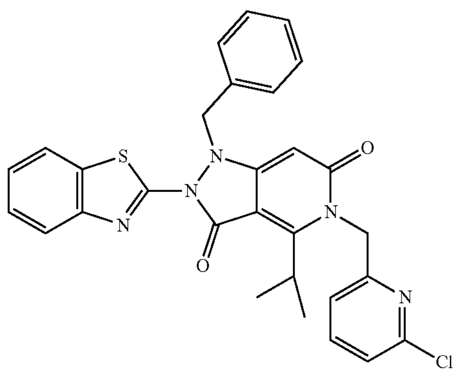 [SMILES: CC(C)c1c2c(=O)n(-c3nc4ccccc4s3)n(Cc3ccccc3)c2cc(=O)n1Cc1cccc(Cl)n1] | 542.2 | 3.35 | 11.55 | B | (DMSO-d$_6$) • 8.08 (d, J = 7.6 Hz, 1H), 7.97 (d, J = 8.4 Hz, 1H), 7.92-7.85 (m, 1H), 7.54 (dd, J = 8.0, 7.6 Hz, 1H), 7.46-7.38 (m, 3H), 7.28-7.20 (m, 3H), 7.04-7.02 (m, 2H), 6.52 (s, 1H), 5.64 (brs, 2H), 5.54 (s, 2H), 2.58-2.52 (m, 1H), 1.31 -1.23 (m, 6H) |
| AVG-168 | 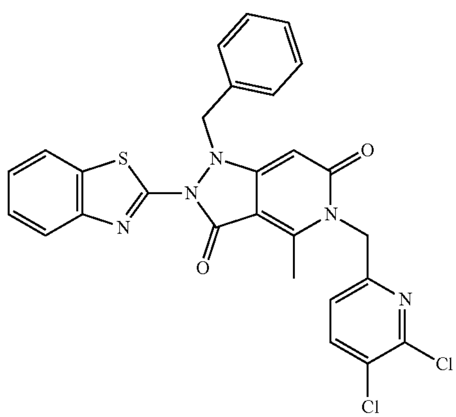 [SMILES: Cc1c2c(=O)n(-c3nc4ccccc4s3)n(Cc3ccccc3)c2cc(=O)n1Cc1ccc(Cl)c(Cl)n1] | 548.1 | 3.31 | 11.40 | B | (CDCl$_3$) • 7.98 (d, J = 8.0 Hz, 1H), 7.88 (d, J = 8.0 Hz, 1H), 7.74 (d, J = 8.0 Hz, 1H), 7.39 (ddd, J = 7.8, 7.6, 1.0 Hz, 1H), 7.38 (ddd, J = 7.8, 7.4, 1.2 Hz, 1H), 7.29-7.26 (m, 1H), 7.25-7.23 (m, 1H), 7.20-7.16 (m, 2H), 7.09 (d, J = 7.2 Hz, 2H), 6.17 (s, 1H), 5.42 (s, 2H), 5.36 (s, 2H), 2.95 (s, 3H). |
| AVG-169 | 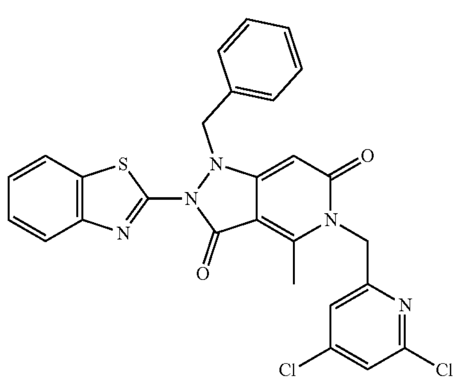 [SMILES: Cc1c2c(=O)n(-c3nc4ccccc4s3)n(Cc3ccccc3)c2cc(=O)n1Cc1cc(Cl)cc(Cl)n1] | 548.1 | 3.114 | 11.45 | B | (CDCl$_3$) • 7.99 (d, J = 8.0 Hz, 1H), 7.88 (d, J = 8.0 Hz, 1H), 7.52 (ddd, J = 8.4, 8.0, 1.0 Hz, 1H), 7.39 (ddd, J = 8.0, 8.0, 0.8 Hz, 1H), 7.29 (d, J = 1.6 Hz, 1H), 7.26-7.22 (m, 2H), 7.21-7.09 (m, 2H), 7.11-7.07 (m, 2H), 6.20 (s, 1H), 5.43 (s, 2H), 5.37 (s, 2H), 2.92 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-170 | 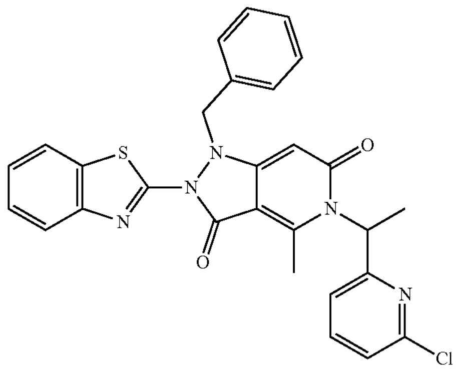 [SMILES: Cc1c2c(=O)n(-c3nc4ccccc4s3)n(Cc3ccccc3)c2cc(=O)n1C(C)c1cccc(Cl)n1] | 528.2 | 3.19 | 11 | B | (DMSO-d$_6$) • 8.09 (d, J = 8.0 Hz, 1H), 7.97 (d, J = 8.0 Hz, 1H), 7.84 (dd, J = 8.0, 7.8 Hz, 1H), 7.54 (ddd, J = 7.8, 1.2 Hz, 1H), 7.44-7.35 (m, 3H), 7.28-7.20 (m, 3H), 7.03 (d, J = 6.4 Hz, 2H), 6.31 (s, 1H), 5.76 (brs, 1H), 5.52 (s, 2H), 2.89 (s, 3H), 1.87 (d, J = 6.8 Hz, 3H). |
| AVG-171 | 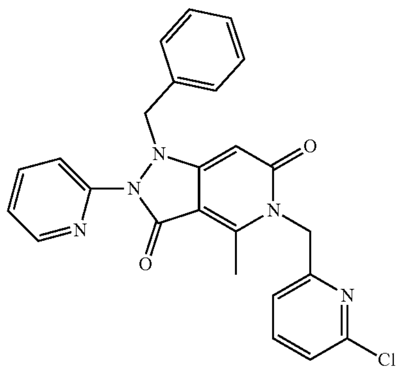 [SMILES: Cc1c2c(=O)n(-c3ccccn3)n(Cc3ccccc3)c2cc(=O)n1Cc1cccc(Cl)n1] | 458.2 | 2.46 | 8.79 | B | (CDCl$_3$) • 8.58 (dd, J = 4.8 Hz, 0.8 Hz, 1H), 7.85-7.76 (m, 2H), 7.61 (dd, J = 8.0, 7.6 Hz, 1H), 7.26-7.14 (m, 6H), 6.97 (d, J = 7.2 Hz, 2H), 6.14 (s, 1H), 5.42 (s, 2H), 4.99 (s, 2H), 2.88 (s, 3H). |
| AVG-172 | 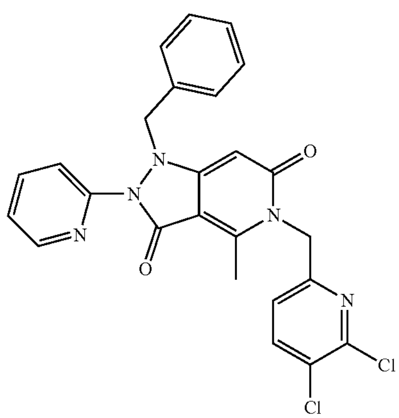 [SMILES: Cc1c2c(=O)n(-c3ccccn3)n(Cc3ccccc3)c2cc(=O)n1Cc1ccc(Cl)c(Cl)n1] | 492.1 | 2.76 | 9.56 | B | (CDCl$_3$) • 8.57 (d, J = 4.0 Hz, 1H), 7.85-7.75 (m, 2H), 7.72 (d, J = 8.0 Hz, 1H), 7.24-7.16 (m, 5H), 6.97 (d, J = 7.2 Hz, 2H), 6.11 (s, 1H), 5.37 (s, 2H), 4.99 (s, 2H), 2.90 (s, 3H). |
| AVG-173 | 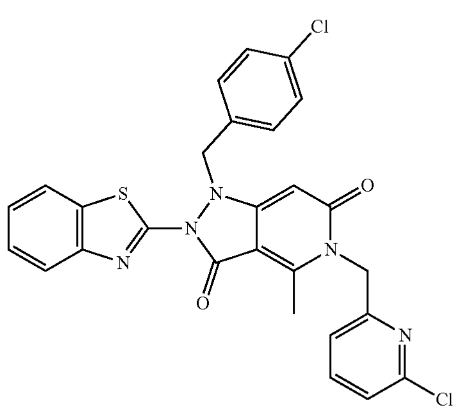 [SMILES: Cc1c2c(=O)n(-c3nc4ccccc4s3)n(Cc3ccc(Cl)cc3)c2cc(=O)n1Cc1cccc(Cl)n1] | 548.0 | 3.11 | 11.44 | B | (CDCl$_3$) • 7.97 (d, J = 8.0 Hz, 1H), 7.88 (d, J = 7.6 Hz, 1H), 7.64 (dd, J = 8.0, 7.6 Hz, 1H), 7.52 (ddd, J = 7.2, 6.8, 1.2 Hz, 1H), 7.39 (ddd, J = 8.0, 7.2, 1.2 Hz, 1H), 7.25-7.23 (m, 2H), 7.17 (d, J = 8.4 Hz, 2H), 7.04 (d, J = 8.4 Hz, 2H), 6.17 (s, 1H), 5.41 (s, 2H), 5.39 (s, 2H), 2.94 (s, 3H). |

| Compound ID | Structure | M + 1 | Rt (min) (LCMS) | Rt (Min) (HPLC) | Method | 1HNMR (400 MHz) |
|---|---|---|---|---|---|---|
| AVG-174 | 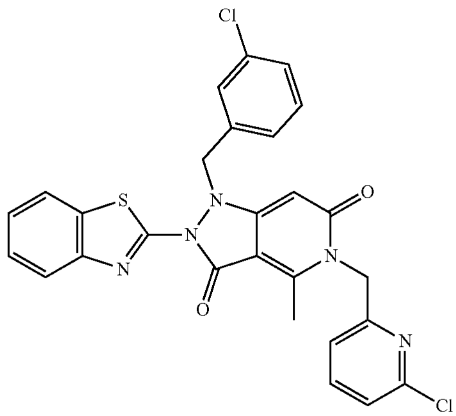 [SMILES: Cc1c2c(=O)n(-c3nc4ccccc4s3)n(Cc3cccc(Cl)c3)c2cc(=O)n1Cc1cccc(Cl)n1] | 548.2 | 3.23 | 11.10 | B | (CDCl$_3$) • 7.96 (d, J = 8.0 Hz, 1H), 7.88 (d, J = 8.0 Hz, 1H), 7.63 (dd, J = 8.0, 7.6 Hz, 1H), 7.51 (dd, J = 7.8, 7.6 Hz, 1H), 7.39 (dd, J = 7.4, 7.2 Hz, 1H), 7.26-7.13 (m, 5H), 7.01 (d, J = 7.6 Hz, 1H), 6.14 (s, 1H), 5.42 (s, 2H), 5.38 (s, 2H), 2.95 (s, 3H) |
| AVG-175 | 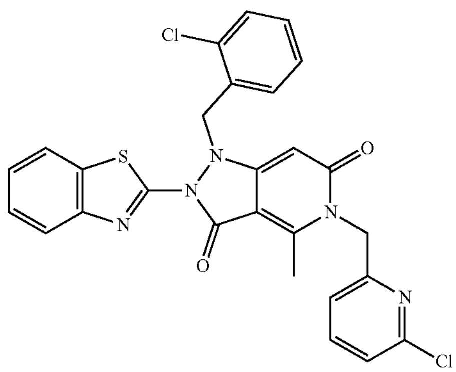 [SMILES: Cc1c2c(=O)n(-c3nc4ccccc4s3)n(Cc3ccccc3Cl)c2cc(=O)n1Cc1cccc(Cl)n1] | 548.2 | 3.23 | 11.14 | B | (DMSO-d$_6$) • 8.06 (d, J = 7.6 Hz, 1H), 7.88-7.85 (m, 2H), 7.50 (dd, J = 8.0, 7.2 Hz, 1H), 7.45-7.33 (m, 4H), 7.30-7.26 (m, 1H), 7.24-7.22 (m, 2H), 6.29 (s, 1H), 5.69 (s, 2H), 5.41 (s, 2H), 2.84 (s, 3H). |
| AVG-176 | 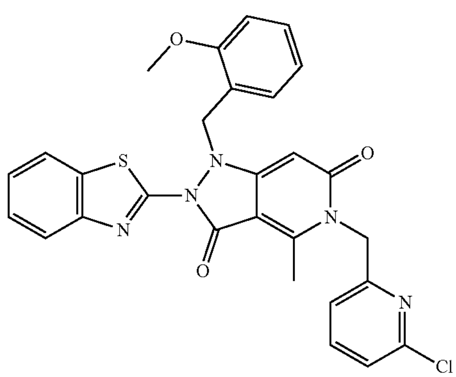 [SMILES: COc1ccccc1Cn1c2cc(=O)n(Cc3cccc(Cl)n3)c(C)c2c(=O)n1-c1nc2ccccc2s1] | 544.2 | 3.04 | 10.56 | B | (DMSO-d$_6$) • 8.05 (d, J = 7.6 Hz, 1H), 7.96 (d, J = 8.0 Hz, 1H), 7.88 (dd, J = 8.0, 7.6 Hz, 1H), 7.53 (ddd J = 8.4, 8.4, 1.4 Hz, 1H), 7.44 (d, J = 8.0 Hz, 1H), 7.39-7.35 (m, 2H), 7.19 (ddd, J = 9.2, 8.0, 2.0 Hz, 1H), 7.00 (dd, J = 7.6, 1.6 Hz, 1H), 6.87 (d, J = 8.0 Hz, 1H), 6.70 (dd, J = 7.6, 7.6 Hz, 1H), 6.36 (s, 1H), 5.45 (s, 2H), 5.41 (s, 2H), 3.36 (s, 3H), 2.79 (s, 3H). |

| Compound ID | Structure | M + 1 | Rt (min) (LCMS) | Rt (Min) (HPLC) | Method | 1HNMR (400 MHz) |
|---|---|---|---|---|---|---|
| AVG-177 | 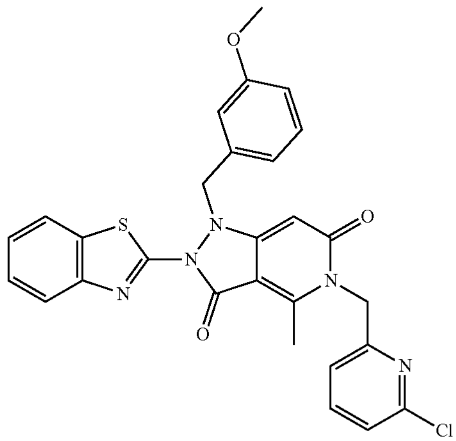 [SMILES: COc1cccc(Cn2c3cc(=O)n(Cc4cccc(Cl)n4)c(C)c3c(=O)n2-c2nc3ccccc3s2)c1] | 544.2 | 3.07 | 10.65 | B | (CDCl$_3$) • 7.97 (d, J = 8.0 Hz, 1H), 7.87 (d, J = 8.0 Hz, 1H), 7.62 (dd, J = 8.0, 7.6 Hz, 1H), 7.51 (dd, J = 8.0, 7.6 Hz, 1H), 7.38 (dd, J = 7.6, 7.2 Hz, 1H), 7.26-7.20 (m, 2H), 7.10 (dd, J = 8.0, 7.6 Hz, 1H), 6.78 (dd, J = 8.2, 2.2 Hz, 1H), 6.68 (d, J = 7.6 Hz, 1H), 6.64 (s, 1H), 6.18 (s, 1H), 5.41 (s, 2H), 5.38 (s, 2H), 3.60 (s, 3H), 2.94 (s, 3H). |
| AVG-178 | 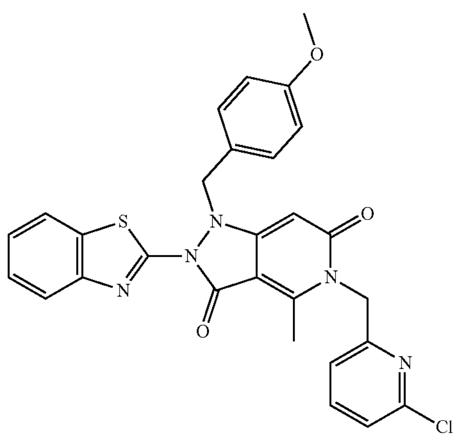 [SMILES: COc1ccc(Cn2c3cc(=O)n(Cc4cccc(Cl)n4)c(C)c3c(=O)n2-c2nc3ccccc3s2)cc1] | 544.2 | 3.05 | 10.53 | B | (CDCl$_3$) • 7.99 (d, J = 8.0 Hz, 1H), 7.88 (d, J = 8.0 Hz, 1H), 7.63 (dd, J = 8.0, 7.6 Hz, 1H), 7.52 (dd, J = 7.6, 6.8 Hz, 1H), 7.39 (dd, J = 8.0, 7.2 Hz, 1H), 7.24-7.21 (m, 2H), 6.98 (d, J = 8.4 Hz, 2H), 6.68 (d, J = 8.4 Hz, 2H), 6.22 (s, 1H), 5.41 (s, 2H), 5.36 (s, 2H), 3.72 (s, 3H), 2.92 (s, 3H). |
| AVG-183 | 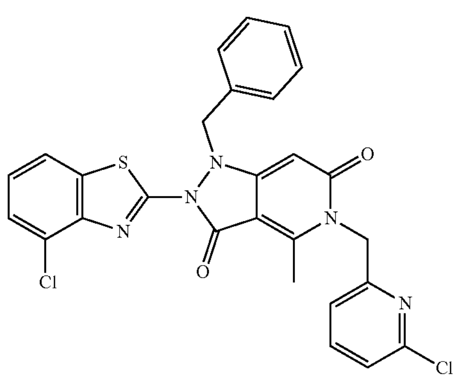 [SMILES: Cc1c2c(=O)n(-c3nc4c(Cl)cccc4s3)n(Cc3ccccc3)c2cc(=O)n1Cc1cccc(Cl)n1] | 548.1 | 3.30 | 11.44 | B | (CDCl$_3$) • 7.75 (d, J = 8.0 Hz, 1H), 7.64 (dd, J = 8.0, 7.6 Hz, 1H), 7.53 (d, J = 8.0 Hz, 1H), 7.32-7.26 (m, 2H), 7.25-7.23 (m, 2H), 7.22-7.16 (m, 4H), 6.17 (s, 1H), 5.50 (s, 2H), 5.42 (s, 2H), 2.95 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-184 | 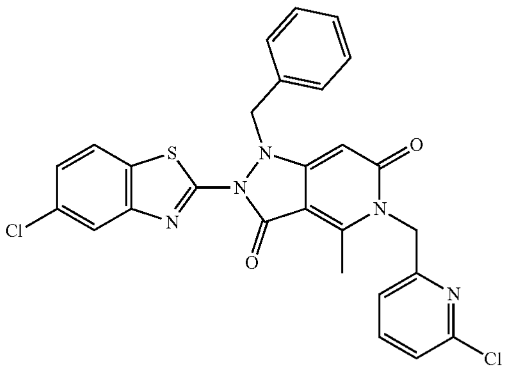 [SMILES: Cc1c2c(=O)n(-c3nc4cc(Cl)ccc4s3)n(Cc3ccccc3)c2cc(=O)n1Cc1cccc(Cl)n1] | 548.1 | 3.33 | 11.29 | B | (DMSO-d$_6$) • 8.13 (d, J = 8.4 Hz, 1H), 8.07 (d, J = 2.0 Hz, 1H), 7.87 (dd, J = 8.0, 7.6 Hz, 1H), 7.48-7.43 (m, 2H), 7.34 (d, J = 7.6 Hz, 1H), 7.25-7.20 (m, 3H), 7.02 (d, J = 6.0 Hz, 2H), 6.52 (s, 1H), 5.55 (s, 2H), 5.40 (s, 2H), 2.78 (s, 3H). |
| AVG-185 | 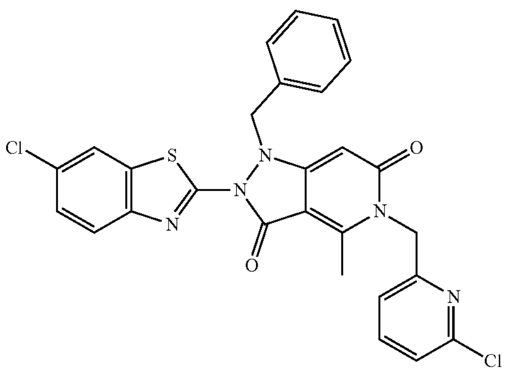 [SMILES: Cc1c2c(=O)n(-c3nc4ccc(Cl)cc4s3)n(Cc3ccccc3)c2cc(=O)n1Cc1cccc(Cl)n1] | 548.1 | 3.34 | 11.33 | B | (DMSO-d$_6$) • 8.25 (d, J = 2.0 Hz, 1H), 7.98 (d, J = 8.4 Hz, 1H), 7.87 (dd, J = 8.0, 7.6 Hz, 1H), 7.57 (dd, J = 8.4, 2.0 Hz, 1H), 7.44 (d, J = 8.0 Hz, 1H), 7.33 (d, J = 7.6 Hz, 1H), 7.26-7.21 (m, 3H), 7.03 (d, J = 6.0 Hz, 2H), 6.51 (s, 1H), 5.54 (s, 2H), 5.40 (s, 2H), 2.78 (s, 3H). |
| AVG-186 | 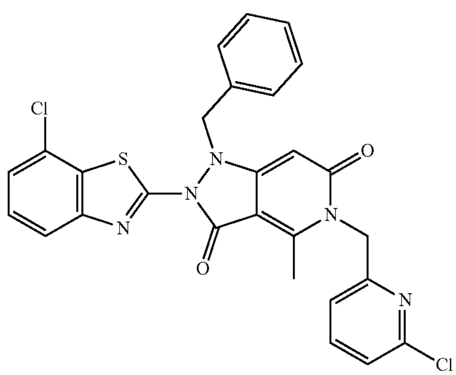 [SMILES: Cc1c2c(=O)n(-c3nc4cccc(Cl)c4s3)n(Cc3ccccc3)c2cc(=O)n1Cc1cccc(Cl)n1] | 550.2 | 3.43 | 11.85 | B | (DMSO-d$_6$) • 7.98 (dd, J = 8.0, 0.8 Hz, 1H), 7.87 (dd, J = 8.0, 7.6 Hz, 1H), 7.59 (dd, J = 8.0, 7.6 Hz, 1H), 7.53 (dd, J = 7.6, 0.8 Hz, 1H), 7.33 (d, J = 8.0 Hz, 1H), 7.23 (d, J = 7.2 Hz, 1H), 7.23-7.22 (m, 3H), 7.06-7.04 (m, 2H) 6.51 (s, 1H), 5.55 (s, 2H), 5.41 (s, 2H), 2.78 (s, 3H) |
| AVG-187 | 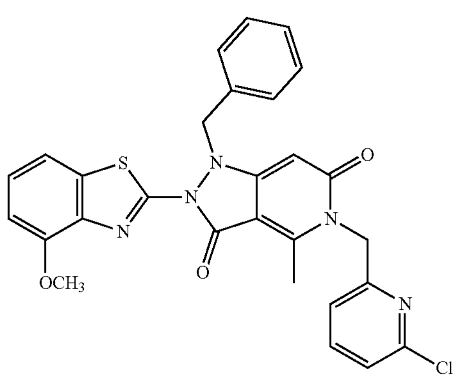 [SMILES: COc1cccc2sc(-n3c(=O)c4c(C)n(Cc5cccc(Cl)n5)c(=O)cc4n3Cc3ccccc3)nc12] | 544.2 | 3.04 | 10.63 | B | (DMSO-d$_6$) • 7.87 (dd, J = 8.0, 8.0 Hz, 1H), 7.63 (d, J = 8.0 Hz, 1H), 7.44 (d, J = 8.0 Hz, 1H), 7.38-7.32 (m, 2H), 7.29-7.12 (m, 3H), 7.10 (d, J = 8.0 Hz, 1H), 7.03-7.01 (m, 2H), 6.52 (s, 1H), 5.56 (s, 2H), 5.40 (s, 2H), 4.01 (s, 3H), 2.77 (s, 3H) |

| Compound ID | Structure | M + 1 | Rt (min) (LCMS) | Rt (Min) (HPLC) | Method | 1HNMR (400 MHz) |
|---|---|---|---|---|---|---|
| AVG-188 | 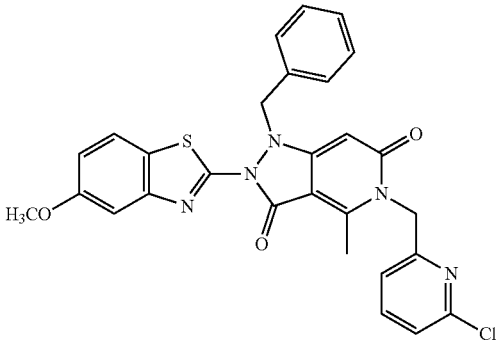 [SMILES: COc1ccc2sc(-n3c(=O)c4c(C)n(Cc5cccc(Cl)n5)c(=O)cc4n3Cc3ccccc3)nc2c1] | 544.2 | 3.08 | 10.73 | B | (DMSO-d$_6$) • 7.94 (d, J = 8.8 Hz, 1H), 7.87 (dd, J = 8.0, 7.6 Hz, 1H), 7.55 (d, J = 7.6 Hz, 1H), 7.44 (d, J = 8.0 Hz, 1H), 7.32 (d, J = 7.6 Hz, 1H), 7.26-7.22 (m, 3H), 7.06-7.02 (m, 3H), 6.51 (s, 1H), 5.57 (s, 2H), 5.40 (s, 2H), 3.87 (s, 3H), 2.78 (s, 3H) |
| AVG-189 | 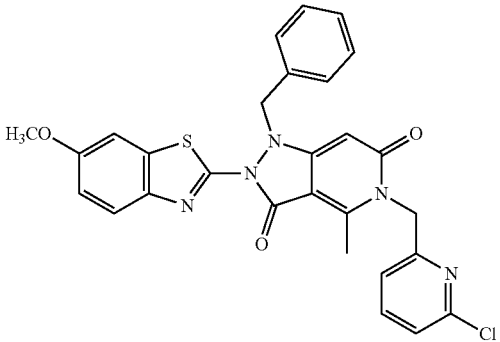 [SMILES: COc1ccc2nc(-n3c(=O)c4c(C)n(Cc5cccc(Cl)n5)c(=O)cc4n3Cc3ccccc3)sc2c1] | 544.2 | 3.02 | 10.41 | B | (CDCl$_3$) • 7.86 (d, J = 9.2 Hz, 1H), 7.63 (dd, J = 8.0, 7.6 Hz, 1H), 7.34 (d, J = 2.4 Hz, 1H), 7.25-7.22 (m, 2H), 7.22-7.15 (m, 3H), 7.12-7.06 (m, 3H), 6.19 (s, 1H), 5.40 (s, 4H), 3.90 (s, 3H), 2.91 (s, 3H). |
| AVG-191 | 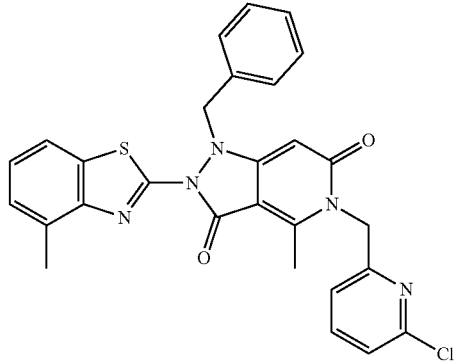 [SMILES: Cc1cccc2sc(-n3c(=O)c4c(C)n(Cc5cccc(Cl)n5)c(=O)cc4n3Cc3ccccc3)nc12] | 528.2 | 3.32 | 11.5 | B | (CDCl$_3$) • 7.71-7.69 (m, 1H), 7.63 (dd, J = 8.0 Hz, 1H), 7.32-7.26 (m, 2H), 7.26-7.15 (m, 7H), 6.15 (s, 1H), 5.47 (s, 2H), 5.41 (s, 2H), 2.94 (s, 3H), 2.74 (s, 3H). |
| AVG-192 | 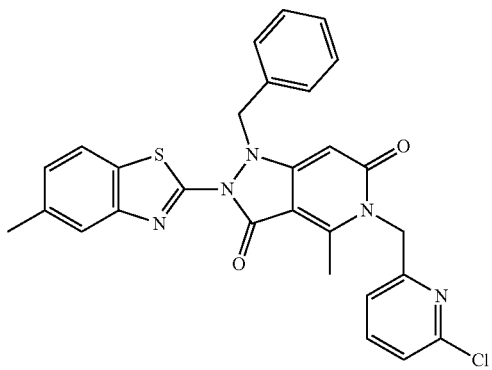 [SMILES: Cc1ccc2sc(-n3c(=O)c4c(C)n(Cc5cccc(Cl)n5)c(=O)cc4n3Cc3ccccc3)nc2c1] | 528.2 | 3.29 | 11.35 | B | (CDCl$_3$) • 7.79 (s, 1H), 7.74 (d, J = 8.0 Hz, 1H), 7.62 (dd, J = 7.6, 7.6 Hz, 1H), 7.24-7.16 (m, 6H), 7.09 (d, J = 7.2 Hz, 2H), 6.19 (s, 1H), 5.41 (s, 4H), 2.92 (s, 3H), 2.53 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-194 | 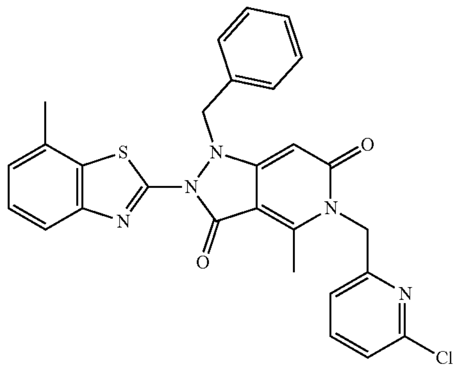 [SMILES: Cc1cccc2nc(-n3c(=O)c4c(C)n(Cc5cccc(Cl)n5)c(=O)cc4n3Cc3ccccc3)sc12] | 528.2 | 3.27 | 11.38 | B | (DMSO-d$_6$) • 7.89-7.82 (m, 2H), 7.49-7.43 (m, 2H), 7.33 (d, J = 7.6 Hz, 1H), 7.26-7.21 (m, 4H), 7.03 (d, J = 6.4 Hz, 2H), 6.52 (s, 1H), 5.56 (s, 2H), 5.40 (s, 2H), 2.78 (s, 3H), 2.55 (s, 3H). |
| AVG-195 | 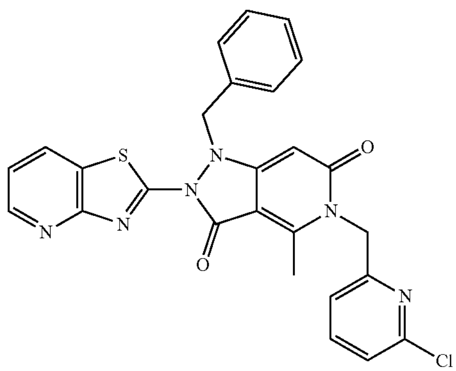 [SMILES: Cc1c2c(=O)n(-c3nc4ncccc4s3)n(Cc3ccccc3)c2cc(=O)n1Cc1cccc(Cl)n1] | 515.2 | 2.61 | 9.21 | B | (CDCl$_3$) • 8.65 (dd, J = 4.8, 2.0 Hz, 1H), 8.57 (dd, J = 8.0, 2.0 Hz, 1H), 7.87 (dd, J = 8.0, 7.6 Hz, 1H), 7.45-7.41 (m, 2H), 7.34 (d, J = 7.6 Hz, 1H), 7.27-7.22 (m, 3H), 7.06 (dd, J = 6.0, 2.0 Hz, 2H), 6.50 (s, 1H), 5.57 (s, 2H), 5.41 (s, 2H), 2.78 (s, 3H). |
| AVG-196 | 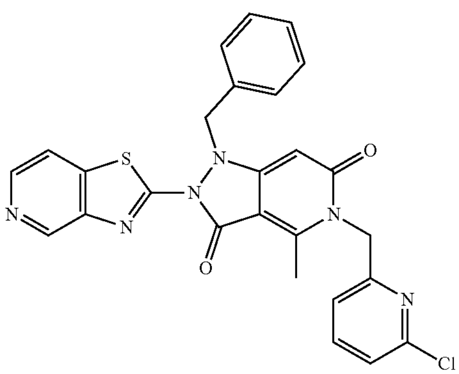 [SMILES: Cc1c2c(=O)n(-c3nc4cnccc4s3)n(Cc3ccccc3)c2cc(=O)n1Cc1cccc(Cl)n1] | 515.2 | 2.18 | 7.06 | B | (DMSO-d$_6$) • 9.23 (s, 1H), 8.50 (d, J = 5.6 Hz, 1H), 8.17 (d, J = 5.6 Hz, 1H), 7.87 (dd, J = 8.0, 7.6 Hz, 1H), 7.44 (d, J = 8.4 Hz, 1H), 7.34 (d, J = 8.4 Hz, 1H), 7.29-7.19 (m, 3H), 7.04 (d, J = 6.4 Hz, 2H), 6.53 (s, 1H), 5.56 (s, 2H), 5.41 (s, 2H), 2.78 (s, 3H). |
| AVG-197 | 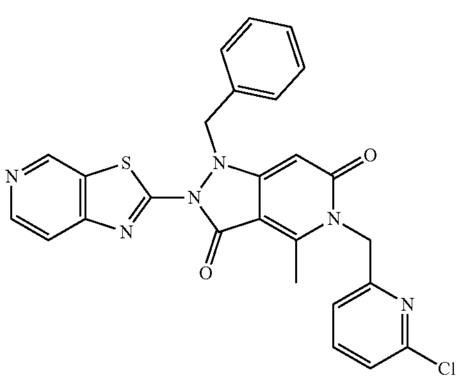 [SMILES: Cc1c2c(=O)n(-c3nc4ccncc4s3)n(Cc3ccccc3)c2cc(=O)n1Cc1cccc(Cl)n1] | 515.1 | 2.64 | 9.15 | B | (CDCl$_3$) • 9.14 (s, 1H), 8.67 (d, J = 5.2 Hz, 1H), 7.84 (d, J = 5.2 Hz, 1H), 7.64 (dd, J = 8.0, 7.2 Hz, 1H), 7.26-7.25 (m, 3H), 7.22-7.18 (m, 2H), 7.09 (d, J = 6.8 Hz, 2H), 6.18 (s, 1H), 5.41 (s, 4H), 2.95 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-198 | 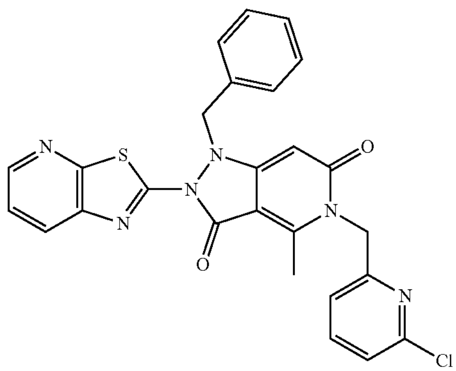 [SMILES: Cc1c2c(=O)n(-c3nc4cccnc4s3)n(Cc3ccccc3)c2cc(=O)n1Cc1cccc(Cl)n1] | 515.2 | 2.77 | 9.79 | B | (DMSO-d$_6$) • 8.56 (dd, J = 4.8, 1.2 Hz, 1H), 8.36 (dd, J = 8.0, 1.2 Hz, 1H), 7.87 (dd, J = 8.0, 7.6 Hz, 1H), 7.61 (dd, J = 8.2, 4.6 Hz, 1H), 7.44 (d, J = 7.6 Hz, 1H), 7.34 (d, J = 7.6 Hz, 1H), 7.28-7.19 (m, 3H), 7.10-7.01 (m, 2H), 6.52 (s, 1H), 5.54 (s, 2H), 5.41 (s, 2H), 2.78 (s, 3H). |
| AVG-199 | 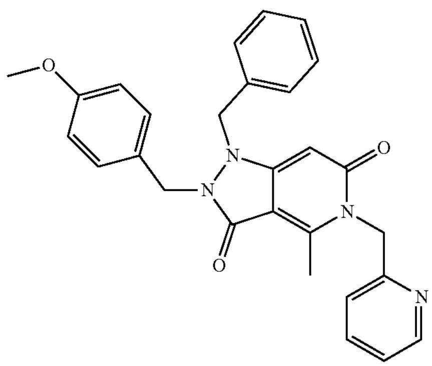 [SMILES: COc1ccc(Cn2c(=O)c3c(C)n(Cc4ccccn4)c(=O)cc3n2Cc2ccccc2)cc1] | 467.3 | 2.34 | 8.38 | B | (CDCl$_3$) • 8.53 (dd, J = 4.8, 0.8 Hz, 1H), 7.64 (ddd, J = 7.8, 7.6, 2.0 Hz, 1H), 7.28-7.25 (m, 4H), 7.21-7.18 (m, 1H), 7.11 (d, J = 8.8 Hz, 2H), 7.09-7.06 (m, 2H), 6.82 (d, J = 8.4 Hz, 2H), 5.81 (s, 1H), 5.45 (s, 2H), 4.85 (s, 2H), 4.65 (s, 2H), 3.79 (s, 3H), 2.93 (s, 3H). |
| AVG-200 | 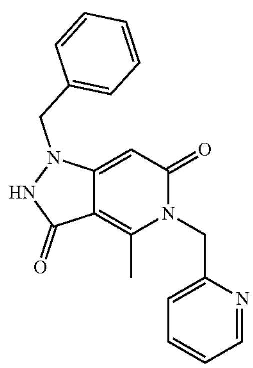 [SMILES: Cc1c2c(=O)[nH]n(Cc3ccccc3)c2cc(=O)n1Cc1ccccn1] | 347.3 | 1.43 | 5.22 | B | (DMSO-d$_6$) 8.45 (d, J = 8.8 Hz, 1H), 7.76 (ddd, J = 7.8, 7.6, 2.0 Hz, 1H), 7.36-7.32 (m, 2H), 7.29-7.24 (m, 5H), 5.91 (s, 1H), 5.36 (s, 2H), 4.86 (s, 2H), 2.69 (s, 3H). |
| AVG-201 | 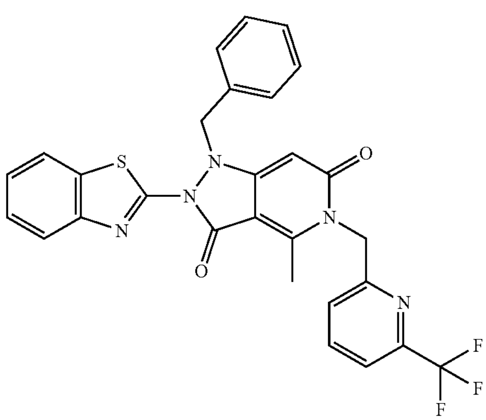 [SMILES: Cc1c2c(=O)n(-c3nc4ccccc4s3)n(Cc3ccccc3)c2cc(=O)n1Cc1cccc(C(F)(F)F)n1] | 548.2 | 3.18 | 11.04 | B | (CDCl$_3$) • 7.98 (d, J = 8.0 Hz, 1H), 7.89-7.85 (m, 2H), 7.62-7.60 (m, 2H), 7.51 (dd, J = 7.2, 7.2 Hz, 1H), 7.39 (dd, J = 7.2, 7.2 Hz, 1H), 7.25-7.23 (m, 1H), 7.17 (dd, J = 7.6, 7.2 Hz, 2H), 7.07 (d, J = 7.2 Hz, 2H), 6.19 (s, 1H), 5.49 (s, 2H), 5.42 (s, 2H), 2.98 (s, 3H). |

| Compound ID | Structure | M + 1 | Rt (min) (LCMS) | Rt (Min) (HPLC) | Method | 1HNMR (400 MHz) |
|---|---|---|---|---|---|---|
| AVG-203 | 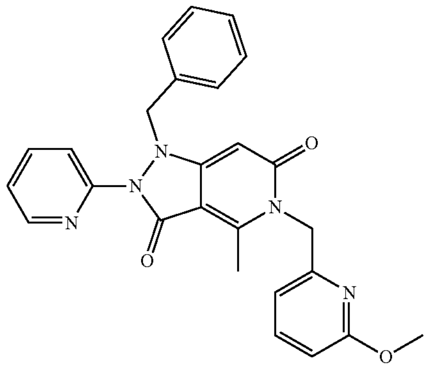 [SMILES: COc1cccc(Cn2c(C)c3c(=O)n(-c4ccccn4)n(Cc4ccccc4)c3cc2=O)n1] | 454.2 | 2.37 | 8.83 | B | (CDCl$_3$) • 8.58 (dd, J = 5.0 Hz, 1.0 Hz, 1H), 7.85-7.77 (m, 2H), 7.52 (dd, J = 8.4, 7.6 Hz, 1H), 7.25-7.20 (m, 2H), 7.18-7.14 (m, 2H), 6.95 (dd, J = 7.8, 1.2 Hz, 2H), 6.85 (d, J = 7.6 Hz, 1H), 6.62 (d, J = 8.4 Hz, 1H), 6.15 (s, 1H), 5.36 (s, 2H), 4.99 (s, 2H), 3.71 (s, 3H), 2.91 (s, 3H). |
| AVG-204 | 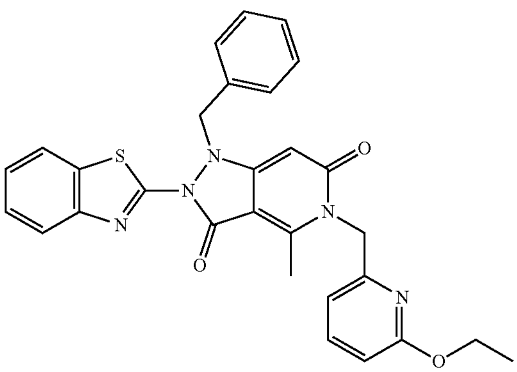 [SMILES: CCOc1cccc(Cn2c(C)c3c(=O)n(-c4nc5ccccc5s4)n(Cc4ccccc4)c3cc2=O)n1] | 524.2 | 3.06 | 11.24 | B | (DMSO-d$_6$) • 8.10 (d, J = 7.6 Hz, 1H), 7.98 (d, J = 8.0 Hz, 1H), 7.68 (dd, J = 8.0, 8.0 Hz, 1H), 7.54 (dd, J = 7.6, 7.2 Hz, 1H), 7.42 (dd, J = 7.6, 7.2 Hz, 1H), 7.30-7.15 (m, 3H), 7.02 (d, J = 7.2 Hz, 2H), 6.92 (d, J = 6.8 Hz, 1H), 6.67 (d, J = 8.0 Hz, 1H), 6.50 (s, 1H), 5.56 (s, 2H), 5.33 (s, 2H), 3.99 (q, J = 6.8 Hz, 2H), 2.82 (s, 3H), 1.07 (t, J = 6.8 Hz, 3H). |
| AVG-205 | 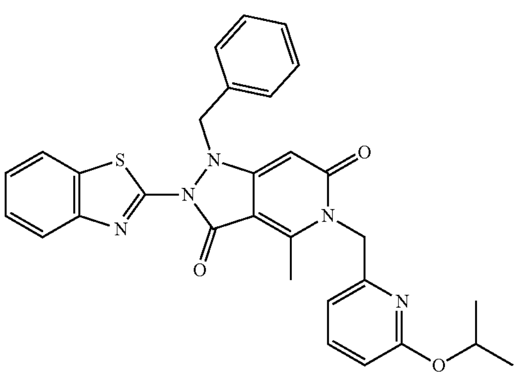 [SMILES: Cc1c2c(=O)n(-c3nc4ccccc4s3)n(Cc3ccccc3)c2cc(=O)n1Cc1cccc(OC(C)C)n1] | 538.3 | 3.35 | 11.58 | B | (CDCl$_3$) • 7.98 (d, J = 8.0 Hz, 1H), 7.87 (d, J = 8.0 Hz, 1H), 7.54-7.49 (m, 2H), 7.39 (ddd, J = 8.0, 8.0, 0.8 Hz, 1H), 7.26-7.21 (m, 1H), 7.18-7.14 (m, 2H), 7.08-7.06 (m, 2H), 6.86 (d, J = 7.2 Hz, 1H), 6.56 (d, J = 8.0 Hz, 1H), 6.19 (s, 1H), 5.42 (s, 2H), 5.33 (s, 2H), 5.01-4.92 (m, 1H), 2.96 (s, 3H), 1.18 (d, J = 6.4 Hz, 6H). |
| AVG-206 | 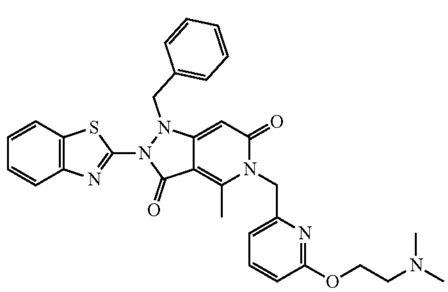 [SMILES: Cc1c2c(=O)n(-c3nc4ccccc4s3)n(Cc3ccccc3)c2cc(=O)n1Cc1cccc(OCCN(C)C)n1] | 567.2 | 2.37 | 7.89 | B | (DMSO-d$_6$) • 8.10 (d, J = 7.6 Hz, 1H), 7.98 (d, J = 8.0 Hz, 1H), 7.68 (dd, J = 8.0, 7.6 Hz, 1H), 7.54 (ddd, J = 8.4, 8.0, 1.2 Hz, 1H), 7.42 (ddd, J = 8.4, 8.0, 1.2 Hz, 1H), 7.26-7.18 (m, 3H), 7.03 (dd, J = 7.6, 1.6 Hz, 2H), 6.94 (d, J = 7.6 Hz, 1H), 6.68 (d, J = 8.4 Hz, 1H), 6.49 (s, 1H), 5.56 (s, 2H), 5.34 (s, 2H), 4.06 (t, J = 6.0 Hz, 2H), 2.81 (s, 3H), 2.34 (t, J = 5.8 Hz, 2H), 1.99 (s, 6H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-207 | 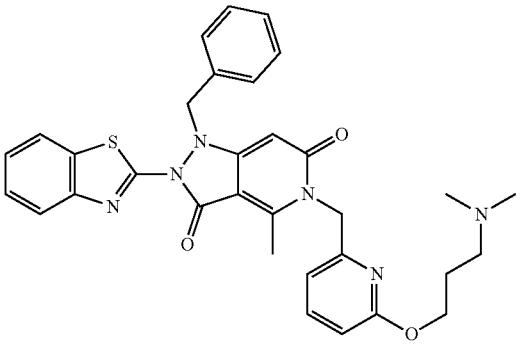 [SMILES: Cc1c2c(=O)n(-c3nc4ccccc4s3)n(Cc3ccccc3)c2cc(=O)n1Cc1cccc(OCCCN(C)C)n1] | 581.3 | 2.91 | 10.47 | B | (CDCl$_3$) • 7.98 (d, J = 8.0 Hz, 1H), 7.80 (d, J = 8.0 Hz, 1H), 7.55-7.49 (m, 2H), 7.39 (dd, J = 7.2 Hz, 1H), 7.26-7.22 (m, 1H), 7.19-7.15 (m, 2H), 7.10-7.07 (m, 2H), 6.84 (d, J = 6.8 Hz, 1H), 6.62 (d, J = 8.0 Hz, 1H), 6.20 (s, 1H), 5.42 (s, 2H), 5.34 (s, 2H), 4.12 (t, J = 6.4 Hz, 2H), 2.94 (s, 3H), 2.41 (t, J = 7.2 Hz, 2H), 2.26 (s, 6H), 1.90-1.83 (m, 2H). |
| AVG-208 | 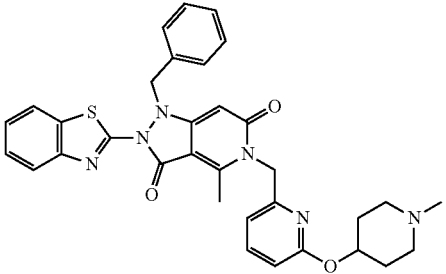 [SMILES: Cc1c2c(=O)n(-c3nc4ccccc4s3)n(Cc3ccccc3)c2cc(=O)n1Cc1cccc(OC2CCN(C)CC2)n1] | 593.3 | 2.91 | 10.26 | B | (DMSO-d$_6$) • 8.09 (d, J = 7.6 Hz, 1H), 7.97 (d, J = 8.0 Hz, 1H), 7.68 (dd, J = 8.0, 7.6 Hz, 1H), 7.53 (dd, J = 8.4, 8.0 Hz, 1H), 7.41 (dd, J = 8.0, 7.2 Hz, 1H), 7.29-7.19 (m, 3H), 7.10-7.00 (m, 3H), 6.62 (d, J = 8.4 Hz, 1H), 6.45 (s, 1H), 5.55 (s, 2H), 5.36 (s, 2H), 4.38-4.28 (m, 1H), 2.83 (s, 3H), 2.37-2.31 (m, 2H), 1.68-1.56 (m, 5H), 1.57-1.45 (m, 2H), 1.40-1.32 (m, 2H). |
| AVG-209 | 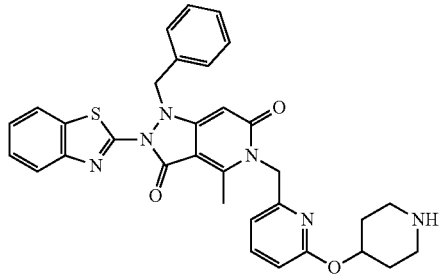 [SMILES: Cc1c2c(=O)n(-c3nc4ccccc4s3)n(Cc3ccccc3)c2cc(=O)n1Cc1cccc(OC2CCNCC2)n1] | 579.3 | 2.77 | 9.48 | B | (DMSO-d$_6$) • 8.09 (d, J = 8.0 Hz, 1H), 7.98 (d, J = 8.0 Hz, 1H), 7.67 (dd, J = 8.0, 7.6 Hz, 1H), 7.54 (dd, J = 8.0, 7.2 Hz, 1H), 7.42 (dd, J = 7.6 Hz, 1H), 7.25-7.19 (m, 3H), 7.04-7.02 (m, 2H), 6.98 (d, J = 7.2 Hz, 1H), 6.63 (d, J = 8.4 Hz, 1H), 6.44 (s, 1H), 5.55 (s, 2H), 5.32 (s, 2H), 4.56-4.50 (m, 1H), 2.87 (s, 3H), 2.67-2.63 (m, 2H), 2.24-2.17 (m, 2H), 1.75 (brs, 1H), 1.68-1.65 (m, 2H), 1.27-1.20 (m, 2H). |
| AVG-210 | 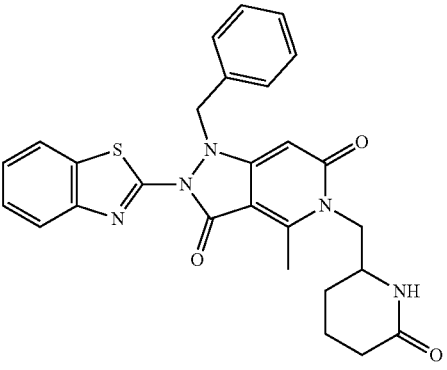 [SMILES: Cc1c2c(=O)n(-c3nc4ccccc4s3)n(Cc3ccccc3)c2cc(=O)n1CC1CCCC(=O)N1] | 500.3 | 2.55 | 9.00 | B | (CDCl$_3$) • 7.99 (d, J = 8.0 Hz, 1H), 7.89 (d, J = 8.0 Hz, 1H), 7.52 (ddd, J = 8.0, 7.6, 1.2 Hz, 1H), 7.40 (dd, J = 7.2, 7.2 Hz, 1H), 7.26-7.24 (m, 1H), 7.20 (dd, J = 7.2, 7.2 Hz, 2H), 7.09 (d, J = 7.2 Hz, 2H), 6.17 (s, 1H), 6.11 (s, 1H), 5.48 (d, J = 14.8 Hz, 1H), 5.40 (d, J = 14.8 Hz, 1H), 4.21-4.06 (m, 2H), 3.95-3.75 (m, 1H), 2.84 (s, 3H), 2.42-2.34 (m, 2H), 2.05-1.94 (m, 2H), 1.80-1.75 (m, 1H), 1.64-1.58 (m, 1H). |

| Compound ID | Structure | M + 1 | Rt (min) (LCMS) | Rt (Min) (HPLC) | Method | 1HNMR (400 MHz) |
|---|---|---|---|---|---|---|
| AVG-212 | 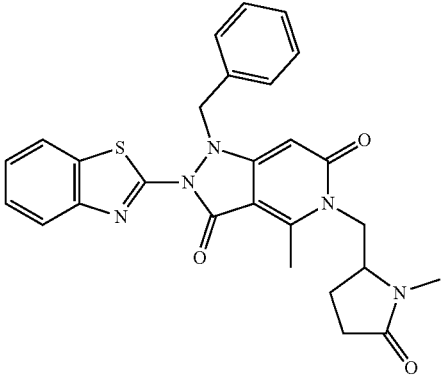 [SMILES: Cc1c2c(=O)n(-c3nc4ccccc4s3)n(Cc3ccccc3)c2cc(=O)n1CC1CCC(=O)N1C] | 500.2 | 2.46 | 9.09 | B | (DMSO-d$_6$) • 8.10 (d, J = 7.6 Hz, 1H), 7.98 (d, J = 8.0 Hz, 1H), 7.54 (ddd, J = 8.0, 7.2, 0.8 Hz, 1H), 7.42 (ddd, J = 8.0, 6.8, 1.2 Hz, 1H), 7.26-7.14 (m, 3H), 7.00 (d, J = 6.8 Hz, 2H), 6.54 (s, 1H), 5.56 (d, J = 15.2 Hz, 1H), 5.51 (d, J = 14.8 Hz, 1H), 4.28-4.16 (m, 2H), 4.03-3.95 (m, 1H), 2.79 (s, 3H), 2.49 (s, 3H), 2.48-2.40 (m, 1H), 2.16-1.96 (m, 2H), 1.79-1.70 (m, 1H). |
| AVG-213 | 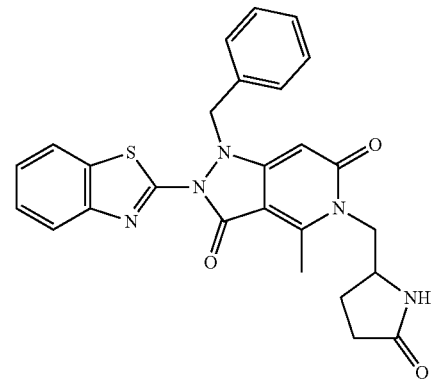 [SMILES: Cc1c2c(=O)n(-c3nc4ccccc4s3)n(Cc3ccccc3)c2cc(=O)n1CC1CCC(=O)N1] | 486.2 | 2.48 | 8.75 | B | (DMSO-d$_6$) • 8.08 (d, J = 8.0 Hz, 1H), 7.97 (d, J = 8.0 Hz, 1H), 7.89 (s, 1H), 7.54 (dd, J = 7.6, 7.2 Hz, 1H), 7.41 (dd, J = 7.6, 7.2 Hz, 1H), 7.24-7.19 (m, 3H), 7.05-7.03 (m, 2H), 6.45 (s, 1H), 5.61 (d, J = 15.2 Hz, 1H), 5.49 (d, J = 14.8 Hz, 1H), 4.17-4.13(m, 1H), 3.97-3.95 (m, 2H), 2.77 (s, 3H), 2.33-2.27 (m, 2H), 2.16-2.08 (m, 2H), 1.81-1.76 (m, 1H) |
| AVG-213 | 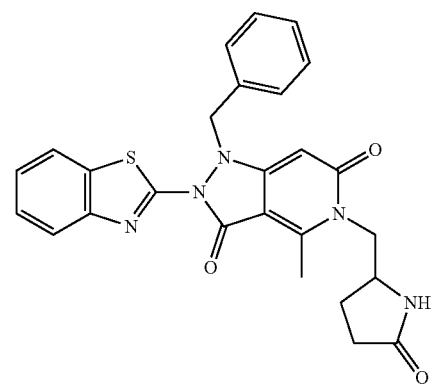 [SMILES: Cc1c2c(=O)n(-c3nc4ccccc4s3)n(Cc3ccccc3)c2cc(=O)n1CC1CCC(=O)N1] | 486.2 | 2.48 | 8.75 | B | (DMSO-d$_6$) • 8.08 (d, J = 8.0 Hz, 1H), 7.97 (d, J = 8.0 Hz, 1H), 7.89 (s, 1H), 7.54 (dd, J = 7.6, 7.2 Hz, 1H), 7.41 (dd, J = 7.6, 7.2 Hz, 1H), 7.24-7.19 (m, 3H), 7.05-7.03 (m, 2H), 6.45 (s, 1H), 5.61 (d, J = 15.2 Hz, 1H), 5.49 (d, J = 14.8 Hz, 1H), 4.17-4.13(m, 1H), 3.97-3.95 (m, 2H), 2.77 (s, 3H), 2.33-2.27 (m, 2H), 2.16-2.08 (m, 2H), 1.81-1.76 (m, 1H) |
| AVG-214 | 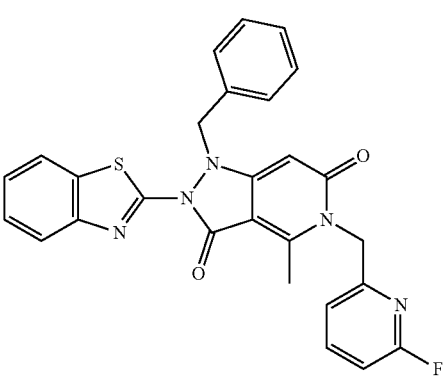 [SMILES: Cc1c2c(=O)n(-c3nc4ccccc4s3)n(Cc3ccccc3)c2cc(=O)n1Cc1cccc(F)n1] | 498.1 | 2.99 | 10.51 | B | (CDCl$_3$) • 7.98 (d, J = 8.0 Hz, 1H), 7.87 (d, J = 8.0 Hz, 1H), 7.77 (dd, J = 15.6, 8.0 Hz, 1H), 7.51 (dd, J = 7.6, 7.2 Hz, 1H), 7.39 (dd, J = 8.0, 7.6 Hz, 1H), 7.25-7.23 (m, 1H), 7.21-7.16 (m, 3H), 7.11-7.08 (m, 2H), 6.85 (dd, J = 8.0, 2.4 Hz, 1H), 6.19 (s, 1H), 5.42 (s, 2H), 5.38 (s, 2H), 2.92 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-225 | 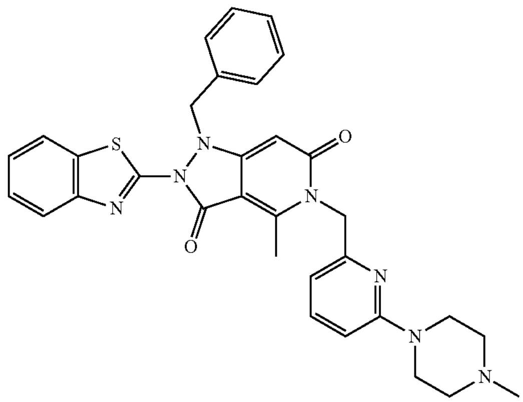 [SMILES: Cc1c2c(=O)n(-c3nc4ccccc4s3)n(Cc3ccccc3)c2cc(=O)n1Cc1cccc(N2CCN(C)CC2)n1] | 578.3 | 2.95 | 10.39 | B | (DMSO-d$_6$) • 8.09 (d, J = 8.0 Hz, 1H), 7.98 (d, J = 8.0 Hz, 1H), 7.56-7.48 (m, 2H), 7.42 (ddd, J = 8.4, 8.0, 1.2 Hz, 1H), 7.25-7.20 (m, 3H), 7.02 (dd, J = 7.8, 1.4 Hz, 2H), 6.71 (d, J = 8.4 Hz, 1H), 6.51-6.49 (m, 2H), 5.56 (s, 2H), 5.26 (s, 2H), 3.31 (t, J = 4.4 Hz, 4H), 2.78 (s, 3H), 2.25 (t, J = 4.4 Hz, 4H), 2.15 (s, 3H). |
| AVG-227 | 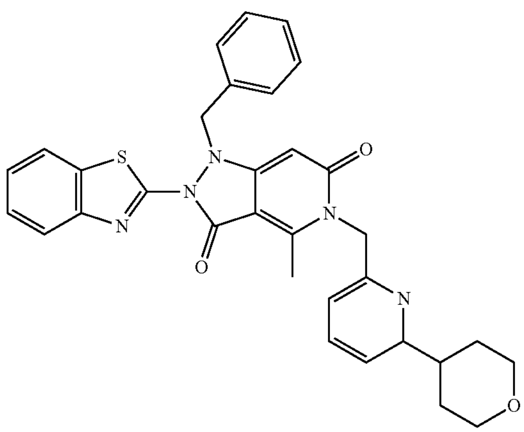 [SMILES: Cc1c2c(=O)n(-c3nc4ccccc4s3)n(Cc3ccccc3)c2cc(=O)n1CC1=CC=CC(C2CCOCC2)N1] | 564.3 | 3.06 | 10.68 | B | (CDCl$_3$) • 7.98 (d, J = 8.0 Hz, 1H), 7.87 (d, J = 8.0 Hz, 1H), 7.60 (dd, J = 8.0, 7.6 Hz, 1H), 7.51 (dd, J = 7.6, 7.2 Hz, 1H), 7.38 (dd, J = 7.6 Hz, 1H), 7.26-7.22 (m, 1H), 7.19-7.15 (m, 3H), 7.10-7.05 (m, 3H), 6.19 (s, 1H), 5.42 (s, 4H), 4.06-4.02 (m, 2H), 3.54-3.46 (m, 2H), 2.97 (s, 3H), 2.97-2.80 (m, 1H), 1.81-1.75 (m, 4H). |
| AVG-228 | 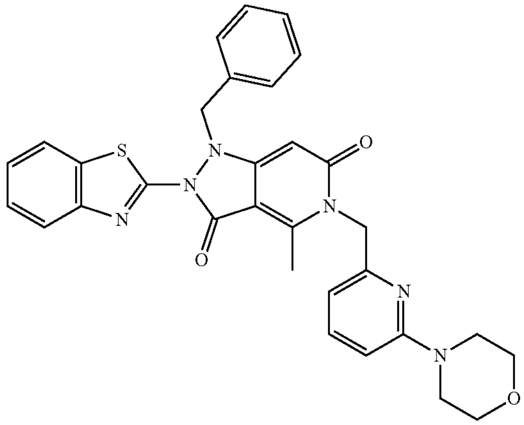 [SMILES: Cc1c2c(=O)n(-c3nc4ccccc4s3)n(Cc3ccccc3)c2cc(=O)n1Cc1cccc(N2CCOCC2)n1] | 565.3 | 3.04 | 10.64 | B | (DMSO-d$_6$) • 8.09 (d, J = 7.6 Hz, 1H), 7.98 (d, J = 8.4 Hz, 1H), 7.57-7.51 (m, 2H), 7.41 (dd, J = 8.0, 7.2 Hz, 1H), 7.29-7.17 (m, 3H), 7.02 (d, J = 6.8 Hz, 2H), 6.73 (d, J = 8.4 Hz, 1H), 6.56 (d, J = 7.2 Hz, 1H), 6.49 (s, 1H), 5.56 (s, 2H), 5.26 (s, 2H), 3.58 (t, J = 4.6 Hz, 1H), 3.28 (t, J = 4.4 Hz, 1H), 2.79 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-229 | 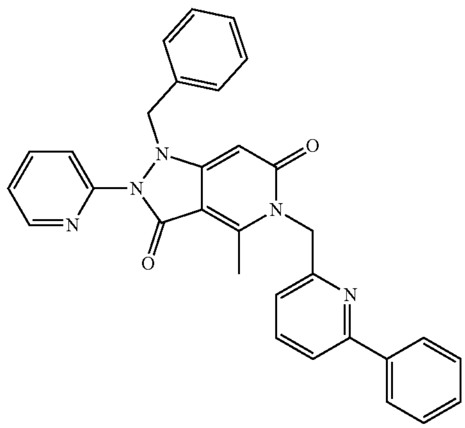 [SMILES: Cc1c2c(=O)n(-c3ccccn3)n(Cc3ccccc3)c2cc(=O)n1Cc1cccc(-c2ccccc2)n1] | 500.3 | 2.81 | 9.8 | B | (CDCl$_3$) • 8.59-8.57 (m, 1H), 7.92-7.89 (m, 2H), 7.84-7.77 (m, 2H), 7.72 (dd, J = 8.0, 7.6 Hz, 1H), 7.65-7.62 (m, 1H), 7.45-7.37 (m, 3H), 7.24-7.19 (m, 3H), 7.16-7.12 (m, 2H), 6.97-6.95 (m, 2H), 6.16 (s, 1H), 5.52 (s, 2H), 4.99 (s, 2H), 2.98 (s, 3H). |
| AVG-230 | 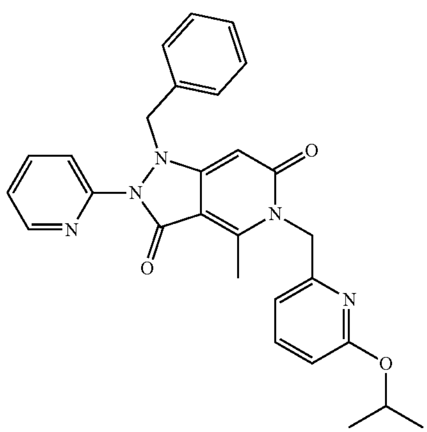 [SMILES: Cc1c2c(=O)n(-c3ccccn3)n(Cc3ccccc3)c2cc(=O)n1Cc1cccc(OC(C)C)n1] | 482.2 | 2.61 | 9.67 | B | (DMSO-d$_6$) • 8.59 (dd, J = 4.8, 0.8 Hz, 1H), 7.96 (ddd, J = 8.0, 7.6, 1.6 Hz, 1H), 7.70-7.62 (m, 2H), 7.35 (dd, J = 6.8, 6.8 Hz, 1H), 7.27-7.17 (m, 3H), 6.94 (dd, J = 7.4, 1.4 Hz, 2H), 6.88 (d, J = 7.6 Hz, 1H), 6.60 (d, J = 8.4 Hz, 1H), 6.28 (s, 1H), 5.30 (s, 2H), 5.06 (s, 2H), 4.87-4.78 (m, 1H), 2.80 (s, 3H), 1.09 (d, J = 6.0 Hz, 6H). |
| AVG-231 | 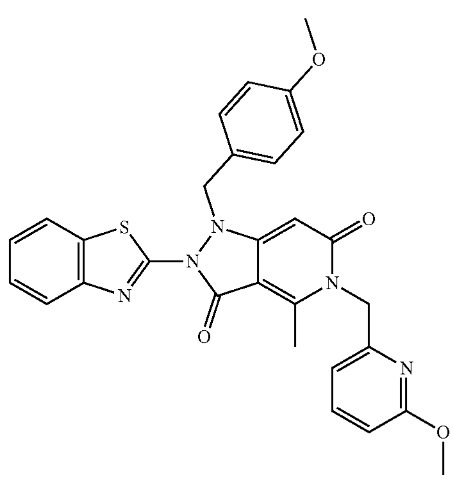 [SMILES: COc1ccc(Cn2c3cc(=O)n(Cc4cccc(OC)n4)c(C)c3c(=O)n2-c2nc3ccccc3s2)cc1] | 540.3 | 3.12 | 10.79 | B | (CDCl$_3$) • 7.99 (d, J = 8.0 Hz, 1H), 7.88 (d, J = 8.0 Hz, 1H), 7.56-7.52 (m, 2H), 7.40 (dd, J = 7.2, 7.2 Hz, 1H), 6.96 (d, J = 8.8 Hz, 2H), 6.89 (d, J = 7.6 Hz, 1H), 6.67-6.62 (m, 3H), 6.21 (s, 1H), 5.35 (s, 4H), 3.72 (s, 3H), 3.68 (s, 3H), 2.95 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-232 | 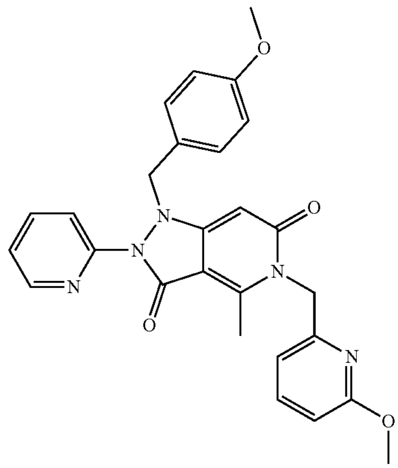 [SMILES: COc1ccc(Cn2c3cc(=O)n(Cc4cccc(OC)n4)c(C)c3c(=O)n2-c2ccccn2)cc1] | 484.2 | 2.48 | 8.75 | B | (DMSO-d$_6$) • 8.59 (d, J = 3.6 Hz, 1H), 7.98 (ddd, J = 8.0, 7.6, 1.6 Hz, 1H), 7.73-7.65 (m, 2H), 7.35 (dd, J = 7.2, 5.2 Hz, 1H), 6.90-6.92 (m, 3H), 6.76 (d, J = 8.8 Hz, 2H), 6.70 (d, J = 8.0 Hz, 2H), 6.32 (s, 1H), 5.31 (s, 2H), 4.99 (s, 2H), 3.68 (s, 3H), 3.59 (s, 3H), 2.78 (s, 3H). |
| AVG-233 | 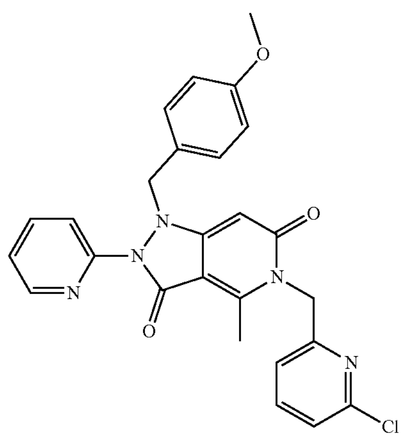 [SMILES: COc1ccc(Cn2c3cc(=O)n(Cc4cccc(Cl)n4)c(C)c3c(=O)n2-c2ccccn2)cc1] | 488.2 | 2.45 | 8.71 | B | (CDCl$_3$) • 8.58 (d, J = 5.6 Hz, 1H), 7.86-7.77 (m, 2H), 7.61 (dd, J = 8.0, 7.6 Hz, 1H), 7.25-7.20 (m, 2H), 7.15 (d, J = 7.6 Hz, 1H), 6.87 (d, J = 8.4 Hz, 2H), 6.69 (d, J = 8.8 Hz, 2H), 6.16 (s, 1H), 5.42 (s, 2H), 4.93 (s, 2H), 3.74 (s, 3H), 2.86 (s, 3H). |
| AVG-234 | 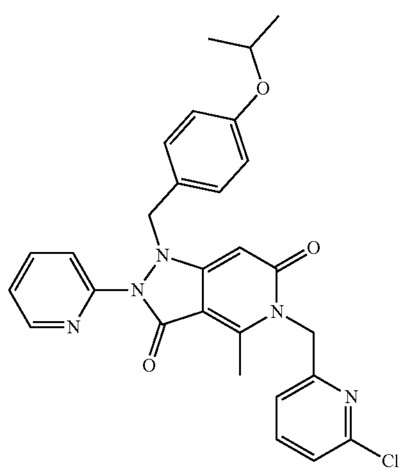 [SMILES: Cc1c2c(=O)n(-c3ccccn3)n(Cc3ccc(OC(C)C)cc3)c2cc(=O)n1Cc1cccc(Cl)n1] | 516.3 | 2.79 | 9.66 | B | (DMSO-d$_6$) • 8.59 (dd, J = 5.0, 1.0 Hz, 1H), 7.97 (ddd, J = 8.0, 7.6, 1.6 Hz, 1H), 7.85 (dd, J = 8.0, 7.6 Hz, 1H), 7.68 (d, J = 8.4 Hz, 1H), 7.43 (d, J = 7.6 Hz, 1H), 7.38-7.33 (m 1H), 7.28 (d, J = 7.6 Hz, 1H), 6.84 (d, J = 8.4 Hz, 2H), 6.73 (d, J = 8.8 Hz, 2H), 6.31 (s, 1H), 5.37 (s, 2H), 4.98 (s, 2H), 4.56-4.46 (m, 1H), 2.75 (s, 3H), 1.19 (d, J = 5.6 Hz, 6H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-239 | 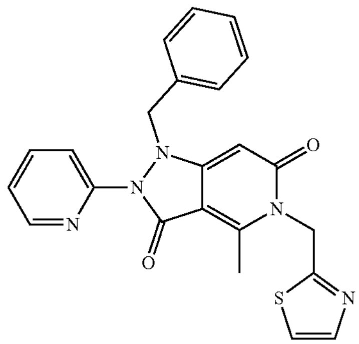 [SMILES: Cc1c2c(=O)n(-c3ccccn3)n(Cc3ccccc3)c2cc(=O)n1Cc1nccs1] | 430.2 | 2.25 | 7.89 | B | (DMSO-d$_6$) • 8.59 (dd, J = 4.8, 1.2 Hz, 1H), 7.96 (ddd, J = 7.8, 7.8, 2.0 Hz, 1H), 7.73 (dd, J = 8.4, 7.6 Hz, 1H), 7.64 (d, J = 8.0 Hz, 1H), 7.35 (ddd, J = 6.4, 6.0, 1.1 Hz, 1H), 7.23-7.20 (m, 3H), 6.96-6.94 (m, 2H), 6.34 (s, 1H), 5.56 (s, 2H), 5.07 (s, 2H), 2.88 (s, 3H) |
| AVG-242 | 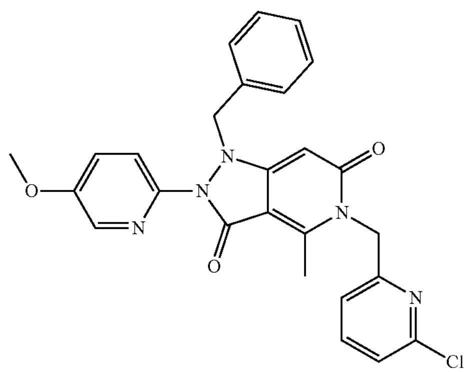 [SMILES: COc1ccc(-n2c(=O)c3c(C)n(Cc4cccc(Cl)n4)c(=O)cc3n2Cc2ccccc2)nc1] | 488.2 | 2.57 | 8.86 | B | (CDCl$_3$) • 8.24 (d, J = 2.8 Hz, 1H), 7.62-7.58 (m, 2H), 7.36 (dd, J = 9.0, 3.0 Hz, 1H), 7.24-7.14 (m, 5H), 6.98 (d, J = 6.8 Hz, 2H), 6.11 (s, 1H), 5.42 (s, 2H), 4.91 (s, 2H), 3.92 (s, 3H), 2.87 (s, 3H). |
| AVG-243 | 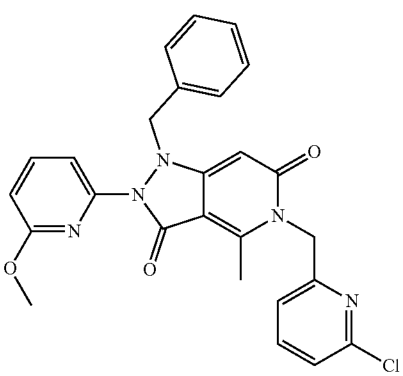 [SMILES: COc1cccc(-n2c(=O)c3c(C)n(Cc4cccc(Cl)n4)c(=O)cc3n2Cc2ccccc2)n1] | 488.2 | 2.80 | 9.70 | B | (CDCl$_3$) • 7.70 (dd, J = 8.0 Hz, 1H), 7.60 (dd, J = 8.0, 7.6 Hz, 1H), 7.36 (d, J = 7.6 Hz, 1H), 7.25-7.16 (m, 4H), 7.17 (d, J = 7.6 Hz, 1H), 7.08 (dd, J = 7.8, 1.4 Hz, 2H), 6.64 (d, J = 8.0 Hz, 1H), 6.01 (s, 1H), 5.41 (s, 2H), 4.99 (s, 2H), 3.90 (s, 3H), 2.89 (s, 3H). |
| AVG-245 | 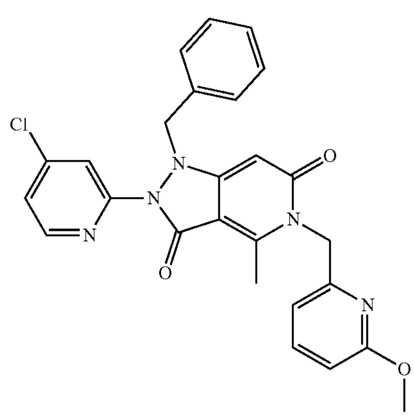 [SMILES: COc1cccc(Cn2c(C)c3c(=O)n(-c4cc(Cl)ccn4)n(Cc4ccccc4)c3cc2=O)n1] | 488.1 | 2.57 | 9.58 | B | (DMSO-d$_6$) • 8.51 (d, J = 5.6 Hz, 1H), 7.67 (dd, J = 8.0, 7.6 Hz, 1H), 7.61 (d, J = 1.6 Hz, 1H), 7.56 (dd, J = 5.4, 1.8 Hz, 1H), 7.30-7.20 (m, 3H), 7.02 (dd, J = 7.6, 1.6 Hz, 2H), 6.85 (d, J = 7.2 Hz, 1H), 6.69 (d, J = 8.4 Hz, 1H), 6.41 (s, 1H), 5.30 (s, 2H), 4.85 (s, 2H), 3.54 (s, 3H), 2.75 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-247 | 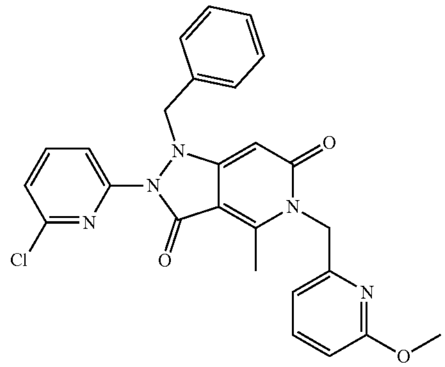 [SMILES: COc1cccc(Cn2c(C)c3c(=O)n(-c4cccc(Cl)n4)n(Cc4ccccc4)c3cc2=O)n1] | 488.2 | 2.88 | 9.99 | B | (CDCl$_3$) • 7.82-7.71 (m, 2H), 7.52 (dd, J = 8.0, 7.6 Hz, 1H), 7.25-7.14 (m, 4H), 7.02 (d, J = 7.2 Hz, 2H), 6.86 (d, J = 7.2 Hz, 1H), 6.62 (d, J = 8.4 Hz, 1H), 6.09 (s, 1H), 5.36 (s, 2H), 5.00 (s, 2H), 3.72 (s, 3H), 2.92 (s, 3H). |
| AVG-250 | 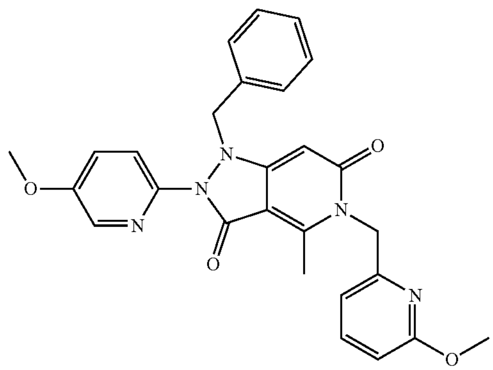 | 484.3 | 2.56 | 8.86 | B | (CDCl$_3$) • 8.25 (d, J = 2.8 Hz, 1H), 7.63 (d, J = 9.2 Hz, 1H), 7.52 (dd, J = 7.2, 7.2 Hz, 1H), 7.37 (dd, J = 9.6, 2.8 Hz, 1H), 7.22 (d, J = 7.6 Hz, 1H), 7.17 (dd, J = 7.2, 7.2 Hz, 2H), 6.97 (d, J = 6.8 Hz, 2H), 6.84 (d, J = 7.2 Hz, 1H), 6.61 (d, J = 8.0 Hz, 1H), 6.11 (s, 1H), 5.36 (s, 2H), 4.91 (s, 3H), 3.92 (s, 3H), 3.72 (s, 3H), 2.91 (s, 3H). |
| AVG-251 | 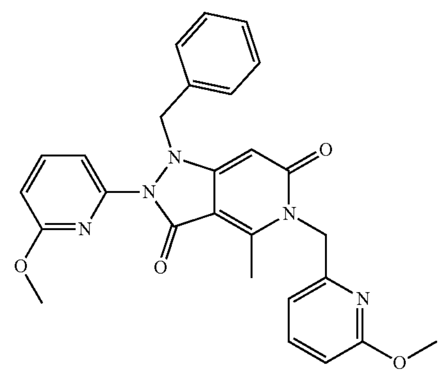 [SMILES: COc1cccc(Cn2c(C)c3c(=O)n(-c4cccc(OC)n4)n(Cc4ccccc4)c3cc2=O)n1] | 484.2 | 2.81 | 9.74 | B | (CDCl$_3$) • 7.70 (dd, J = 8.0 Hz, 1H), 7.51 (dd, J = 8.4, 7.9 Hz, 1H), 7.38 (d, J = 8.0 Hz, 1H), 7.25-7.17 (m, 3H), 7.06 (dd, J = 7.4, 1.2 Hz, 2H), 6.85 (d, J = 7.2 Hz, 1H), 6.65-6.60 (m, 2H), 6.02 (s, 1H), 5.35 (s, 2H), 4.99 (s, 2H), 3.92 (s, 3H), 3.74 (s, 3H), 2.94 (s, 3H). |
| AVG-252 | 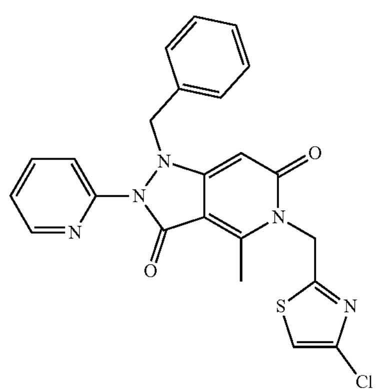 [SMILES: Cc1c2c(=O)n(-c3ccccn3)n(Cc3ccccc3)c2cc(=O)n1Cc1nc(Cl)cs1] | 464.1 | 2.55 | 8.9 | B | (DMSO-d$_6$) • 8.59 (dd, J = 5.2, 1.2 Hz, 1H), 7.96 (ddd, J = 8.2, 7.6, 2.0 Hz, 1H), 7.72 (s, 1H), 7.64 (d, J = 8.4 Hz, 1 H), 7.37-7.34 (m, 1H), 7.23-7.20 (m, 3H), 6.96-6.93 (m, 2H), 6.35 (s, 1H), 5.51 (s, 2H), 5.08 (s, 2H), 2.86 (s, 3H). |

-continued

| Compound ID | Structure | M + 1 | Rt (min) (LCMS) | Rt (Min) (HPLC) | Method | 1HNMR (400 MHz) |
|---|---|---|---|---|---|---|
| AVG-253 | 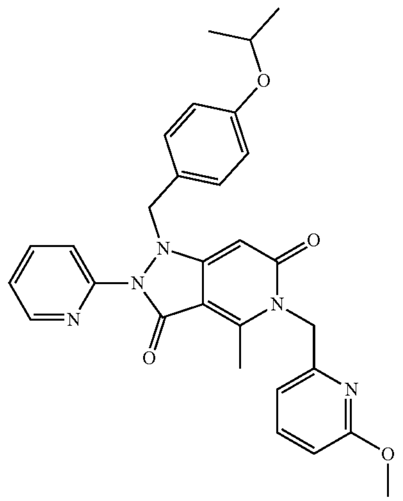 [SMILES: COc1cccc(Cn2c(C)c3c(=O)n(-c4ccccn4)n(Cc4ccc(OC(C)C)cc4)c3cc2=O)n1] | 512.3 | 2.61 | 9.66 | B | (DMSO-d₆) • 8.59 (d, J = 4.4 Hz, 1H), 7.97 (ddd, J = 8.0, 7.6, 2.0 Hz, 1H), 7.73-7.64 (m, 2H), 7.35 (dd, J = 7.6, 7.6 Hz, 1H), 6.90-6.80 (m, 3H), 6.76-6.68 (m, 3H), 6.31 (s, 1H), 5.31 (s, 2H), 4.97 (s, 2H), 4.56-4.47 (m, 1H), 3.59 (s, 3H), 2.79 (s, 3H), 1.20 (d, J = 6.0 Hz, 6H). |
| AVG-254 | 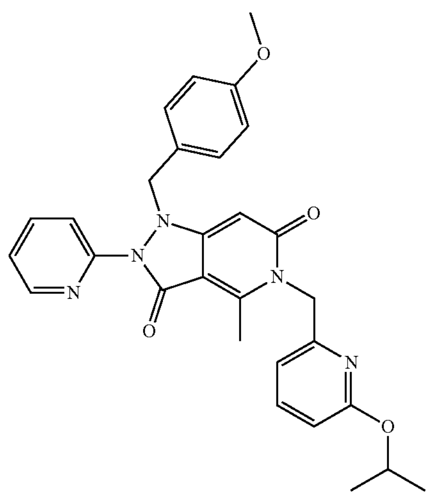 [SMILES: COc1ccc(Cn2c3cc(=O)n(Cc4cccc(OC(C)C)n4)c(C)c3c(=O)n2-c2ccccn2)cc1] | 512.3 | 2.78 | 9.62 | B | (CDCl₃) • 8.58 (d, J = 8.8 Hz, 1H), 7.86-7.79 (m, 2H), 7.50 (dd, J = 8.0, 7.5 Hz, 1H), 7.23-7.20 (m, 1H), 6.86 (d, J = 8.4 Hz, 2H), 6.81 (d, J = 7.2 Hz, 1H), 6.67 (d, J = 8.8 Hz, 2H), 6.55 (d, J = 8.0 Hz, 1H), 6.14 (s, 1H), 5.33 (s, 2H), 5.03-4.99 (m, 1H), 4.92 (s, 2H), 3.73 (s, 3H), 2.91 (s, 3H), 1.20 (d, J = 6.0 Hz, 6H). |
| AVG-256 | 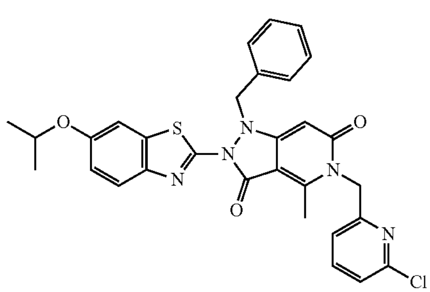 [SMILES: Cc1c2c(=O)n(-c3nc4ccc(OC(C)C)cc4s3)n(Cc3ccccc3)c2cc(=O)n1Cc1cccc(Cl)n1] | 572.2 | 3.33 | 11.44 | B | (CDCl₃) • 7.84 (d, J = 8.8 Hz, 1H), 7.62 (dd, J = 8.0, 7.6 Hz, 1H), 7.33 (d, J = 2.4 Hz, 1H), 7.26-7.16 (m, 5H), 7.10-7.06 (m, 3H), 6.19 (s, 1H), 5.40 (s, 2H), 5.39 (s, 2H), 4.65-4.56 (m, 1H), 2.91 (s, 3H), 1.39 (d, J = 6.0 Hz, 6H). |

| Compound ID | Structure | M + 1 | Rt (min) (LCMS) | Rt (Min) (HPLC) | Method | 1HNMR (400 MHz) |
|---|---|---|---|---|---|---|
| AVG-258 | 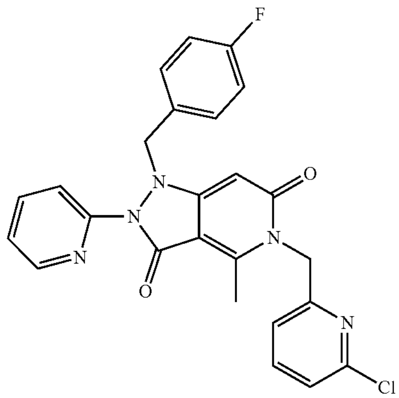 [SMILES: Cc1c2c(=O)n(-c3ccccn3)n(Cc3ccc(F)cc3)c2cc(=O)n1Cc1cccc(Cl)n1] | 476.2 | 2.60 | 8.98 | B | (CDCl$_3$) • 8.58-8.55 (m, 1H), 7.86-7.79 (m, 2H), 7.61 (dd, J = 7.6 Hz, 1H), 7.26-7.20 (m, 2H), 7.17 (d, J = 7.6 Hz, 1H), 6.99-6.94 (m, 2H), 6.90-6.85 (m, 2H), 6.12 (s, 1H), 5.42 (s, 2H), 4.96 (s, 2H), 2.89 (s, 3H). |

Example 5: Potency Range of Certain Compounds (EC50 Values)

The potency range of selected compounds (EC50 values) was tested and the results are provided below:

1. EC50 Values for a Series:

| Compound # | Potency Range* |
|---|---|
| AVG-001 | C |
| AVG-001-b | C |
| AVG-006 | C |
| AVG-006b | C |
| AVG-065 | D |
| AVG-065b | C |
| AVG-066 | D |
| AVG-067 | E |
| AVG-068 | C |
| AVG-069 | E |
| AVG-116 | C |
| AVG-117 | D |
| AVG-179 | E |
| AVG-180 | D |
| AVG-180b | D |
| AVG-181 | C |

*Potency Ranges (EC50 values)
A >0.01-0.10 μM
B >0.10-1.00 μM
C >1.00-10.00 μM
D >10.00-20.00 μM
E >20.00 μM 2. EC50 Values for B Series:

| Compound # | Potency Range* |
|---|---|
| AVG-021 | C |
| AVG-022 | B |
| AVG-023 | E |
| AVG-024 | C |
| AVG-025 | C |
| AVG-026 | C |
| AVG-027 | D |
| AVG-028 | C |
| AVG-029 | E |
| AVG-031 | B |
| AVG-032 | E |
| AVG-033 | C |
| AVG-034 | C |
| AVG-035 | C |
| AVG-036 | B |
| AVG-037 | E |
| AVG-038 | E |
| AVG-039 | D |
| AVG-040 | C |
| AVG-041 | C |
| AVG-042 | C |
| AVG-043 | D |
| AVG-070 | C |
| AVG-071 | C |
| AVG-072 | C |
| AVG-073 | C |
| AVG-074 | D |
| AVG-075 | C |
| AVG-076 | D |
| AVG-077 | B |
| AVG-078 | B |
| AVG-079 | E |
| AVG-080 | C |
| AVG-081 | D |
| AVG-082 | C |
| AVG-088 | C |
| AVG-089 | C |
| AVG-090 | D |
| AVG-091 | C |
| AVG-092 | C |
| AVG-093 | B |
| AVG-094 | B |
| AVG-095 | C |
| AVG-096 | C |
| AVG-097 | C |
| AVG-098 | C |
| AVG-099 | C |
| AVG-100 | E |
| AVG-101 | C |
| AVG-102 | C |
| AVG-103 | C |
| AVG-104 | C |
| AVG-105 | E |
| AVG-106 | C |
| AVG-107 | C |
| AVG-108 | C |
| AVG-109 | C |
| AVG-110 | D |
| AVG-119 | C |

-continued

| Compound # | Potency Range* |
|---|---|
| AVG-120 | C |
| AVG-121 | C |
| AVG-122 | C |
| AVG-123 | D |
| AVG-124 | C |
| AVG-125 | E |
| AVG-126 | C |
| AVG-127 | B |
| AVG-128 | B |
| AVG-129 | B |
| AVG-130 | B |
| AVG-131 | B |
| AVG-132 | C |
| AVG-133 | B |
| AVG-134 | B |
| AVG-135 | D |
| AVG-157 | B |
| AVG-158 | B |
| AVG-159 | A |
| AVG-160 | C |
| AVG-161 | C |
| AVG-162 | D |
| AVG-163 | C |
| AVG-164 | E |
| AVG-165 | C |
| AVG-166 | C |
| AVG-168 | B |
| AVG-169 | B |
| AVG-170 | C |
| AVG-171 | A |
| AVG-172 | B |
| AVG-173 | B |
| AVG-174 | C |
| AVG-175 | C |
| AVG-176 | B |
| AVG-177 | B |
| AVG-178 | A |
| AVG-183 | A |
| AVG-184 | C |
| AVG-185 | B |
| AVG-187 | B |
| AVG-188 | B |
| AVG-189 | A |
| AVG-191 | B |
| AVG-192 | B |
| AVG-193 | B |
| AVG-194 | B |
| AVG-195 | A |
| AVG-196 | D |
| AVG-197 | A |
| AVG-198 | B |
| AVG-199 | D |
| AVG-200 | E |
| AVG-201 | B |
| AVG-203 | A |
| AVG-204 | B |
| AVG-205 | B |
| AVG-206 | C |
| AVG-207 | C |
| AVG-208 | C |
| AVG-210 | D |
| AVG-212 | D |
| AVG-213 | C |
| AVG-214 | B |
| AVG-225 | B |
| AVG-227 | B |
| AVG-228 | B |
| AVG-229 | B |
| AVG-230 | B |
| AVG-231 | A |
| AVG-232 | A |
| AVG-233 | A |
| AVG-234 | B |
| AVG-239 | C |
| AVG-245 | B |
| AVG-252 | B |
| AVG-253 | B |
| AVG-254 | B |
| AVG-256 | A |
| AVG-257 | D |

*Potency Ranges (EC50 values)
A >0.01-0.10 μM
B >0.10-1.00 μM
C >1.00-10.00 μM
D >10.00-20.00 μM
E >20.00 μM The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method of inhibiting RSV, comprising administering to a patient in need thereof, an effective amount of a compound of Formula 1b:

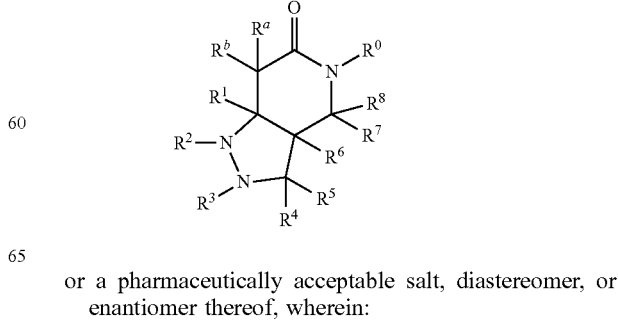

[Formula 1b]

or a pharmaceutically acceptable salt, diastereomer, or enantiomer thereof, wherein:

R⁰ is a monocyclic or bicyclic heteroaryl-alkyl having at least three carbon atoms and to three heteroatoms selected from the group consisting of O, S, and N, wherein said heteroaryl is substituted with Cl, F, or methoxy;

R¹ and R$^b$ together form a double bond;

R² is phenyl-alkyl, wherein the phenyl is optionally substituted with methoxy;

R³ is a monocyclic or bicyclic heteroaryl having one to three heteroatoms selected from the group consisting of O, S, and N, wherein the heteroaryl is optionally substituted with alkoxy, alkyl, oxycycloalkyl, Cl, or F;

R⁴ and R⁵ together form a carbonyl;

R⁶ and R⁸ together form a double bond;

R⁷ is alkyl or aryl optionally substituted with —R$^c$ or —OR$^c$; and

R$^a$ is selected from the group consisting of —R$^c$, —OR$^c$, —N(R$^c$)₂, —SR$^c$, —SO₂R$^c$, —SO₂N(R$^c$)₂; —C(O)R$^c$, OC(O)R$^c$, —COOR$^c$, —C(O)N(R$^c$)₂, —OC(O)N(R$^c$)₂, —N(R$^c$)C(O), —N(R$^c$)C(O)N(R$^c$)₂, —F, —Cl, —Br, —I, —CN, and —NO₂;

wherein R$^c$ is selected from the group consisting of hydrogen, C₁₋₈ alkyl, C₃₋₈ cycloalkyl, a monocyclic or bicyclic heterocyclyl having from two to eight carbon atoms and one to three heteroatoms selected from the group consisting of O, S, and N, C₆₋₁₂ aryl, a monocyclic or bicyclic heteroaryl having from three to twelve carbon atoms and one to three heteroatoms selected from the group consisting of O, S, and N, C₁₋₈alkyl-C₃₋₈cycloalkyl, a monocyclic or bicyclic heterocyclyl-alkyl having from three to sixteen carbon atoms and one to three heteroatoms selected from the group consisting of O, S, and N, C₁₋₈alkyl-C₆₋₁₂aryl, and a monocyclic or bicyclic heteroaryl-alkyl having from four to twenty carbon atoms and one to three heteroatoms selected from the group consisting of O, S, and N.

2. The method according to claim 1, wherein R⁷ is C₆ aryl.

3. The method according to claim 1, wherein R⁷ has the formula:

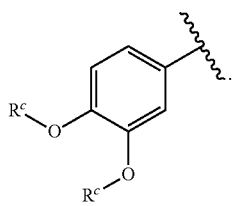

4. The method according to claim 1, wherein R⁷ has the formula:

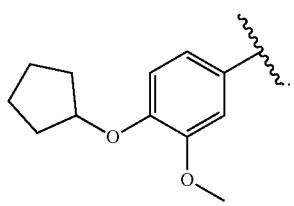 [SMILES: *c1ccc(OC2CCCC2)c(OC)c1]

5. The method according to claim 1, wherein R³ is a monocyclic or bicyclic heteroaryl having from three to twelve carbon atoms.

6. The method according to claim 1, wherein R$^a$ is hydrogen.

7. The method according to claim 1, wherein R⁷ is C₁₋₈ alkyl.

8. The method according to claim 1, wherein R⁷ is methyl.

9. The method according to claim 1, wherein R² is an unsubstituted phenyl-alkyl.

10. The method according to claim 1, wherein R⁰ is CH₂-heteroaryl.

11. The method according to claim 1, wherein R⁰ is CH₂-furan-2-yl.

12. The method according to claim 1, wherein R³ has the formula:

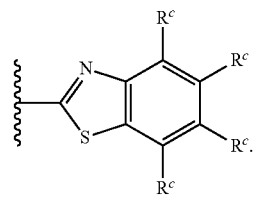

13. The method according to claim 1, wherein R³ has the formula:

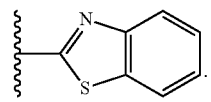 [SMILES: *c1nc2ccccc2s1]

14. A method of treating an RSV infection, comprising administering to a patient in need thereof an effective amount of a compound of Formula 1b:

[Formula 1b]

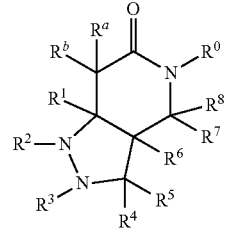

or a pharmaceutically acceptable salt, diastereomer, or enantiomer thereof, wherein:

R⁰ is a monocyclic or bicyclic heteroaryl-alkyl having at least three carbon atoms and one to three heteroatoms selected from the group consisting of O, S, and N, wherein said heteroaryl is substituted with Cl, F, or methoxy, R¹ and R$^b$ together form a double bond;

R² is a phenyl-alkyl, wherein the phenyl is optionally substituted with methoxy;

R³ is a monocyclic or bicyclic heteroaryl having one to three heteroatoms selected from the group consisting of O, S, and N, wherein the heteroaryl is optionally substituted with alkoxy, alkyl, oxycycloalkyl, Cl, or F;

R⁴ and R⁵ together form a carbonyl;

R⁶ and W together form a double bond;

R⁷ is alkyl or aryl optionally substituted with —R$^c$ or —OR$^c$; and $R^a$ is selected from the group consisting of —$R^c$, —$OR^{c1}$, —$N(R^c)_2$, —$SR^c$, —$SO_2R^c$, —$SO_2N(R^c)_2$—$C(O)R^c$, $OC(O)R^c$, —$COOR^c$, —$C(O)N(R^c)_2$, —$OC(O)N(R^c)_2$, —$N(R^c)C(O)$, —$N(R^c)C(O)N(R^c)_2$, —F, —Cl, —Br, —I, —CN, and —$NO_2$;

wherein $R^c$ is selected from the group consisting of hydrogen, $C_{1-8}$ alkyl, $C_{3-8}$ cycloalkyl, a monocyclic or bicyclic heterocyclyl having from two to eight carbon atoms and one to three heteroatoms selected from the group consisting of O, S, and N, $C_{6-12}$ aryl, a monocyclic or bicyclic heteroaryl having from three to twelve carbon atoms and one to three heteroatoms selected from the group consisting of O, S, and N, $C_{1-8}$alkyl-$C_{3-8}$cycloalkyl, a monocyclic or bicyclic heterocyclyl-alkyl having from three to sixteen carbon atoms and one to three heteroatoms selected from the group consisting of 0, S, and N, $C_{1-8}$alkyl-$C_{6-12}$aryl, and a monocyclic or bicyclic heteroaryl-alkyl having from four to twenty carbon atoms and one to three heteroatoms selected from the group consisting of O, S, and N.

15. The method of treating an RSV infection according to claim 14 wherein the compound is administered via a route of administration selected from the group consisting of buccal, oral, intravenous, inhalation, intradermal, intramuscular, topical, subcutaneous, rectal, vaginal, parenteral, pulmonary, intranasal, and ophthalmic.

16. A compound of Formula 1b:

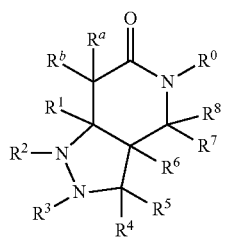

[Formula 1b]

or a pharmaceutically acceptable salt, diastereomer, or enantiomer thereof, wherein:

$R^0$ is a monocyclic or bicyclic heteroaryl-alkyl having at least three carbon atoms and one to three heteroatoms selected from the group consisting of O, S, and N, wherein said heteroaryl is substituted with Cl, F, or methoxy, $R^1$ and $R^b$ together form a double bond;

$R^2$ is a phenyl-alkyl, wherein the phenyl is optionally substituted with methoxy;

$R^3$ is a monocyclic or bicyclic heteroaryl having one to three heteroatoms selected from the group consisting of O, S, and N, wherein the heteroaryl is optionally substituted with alkoxy, alkyl, oxycycloalkyl, Cl, or F;

$R^4$ and $R^5$ together form a carbonyl;

$R^6$ and W together form a double bond;

$R^7$ is alkyl or aryl optionally substituted with —$R^c$ or —$OR^c$; and $R^a$ is selected from the group consisting of —$R^c$, —$OR^{c1}$, —$N(R^c)_2$, —$SR^c$, —$SO_2R^c$, —$SO_2N(R^c)_2$—$C(O)R^c$, $OC(O)R^c$, —$COOR^c$, —$C(O)N(R^c)_2$, —$OC(O)N(R^c)_2$, —$N(R^c)C(O)$, —$N(R^c)C(O)N(R^c)_2$, —F, —Cl, —Br, —I, —CN, and —$NO_2$;

wherein $R^c$ is selected from the group consisting of hydrogen, $C_{1-8}$ alkyl, $C_{3-8}$ cycloalkyl, a monocyclic or bicyclic heterocyclyl having from two to eight carbon atoms and one to three heteroatoms selected from the group consisting of O, S, and N, $C_{6-12}$ aryl, a monocyclic or bicyclic heteroaryl having from three to twelve carbon atoms and one to three heteroatoms selected from the group consisting of O, S, and N, $C_{1-8}$alkyl-$C_{3-8}$cycloalkyl, a monocyclic or bicyclic heterocyclyl-alkyl having from three to sixteen carbon atoms and one to three heteroatoms selected from the group consisting of 0, S, and N, $C_{1-8}$alkyl-$C_{6-12}$aryl, and a monocyclic or bicyclic heteroaryl-alkyl having from four to twenty carbon atoms and one to three heteroatoms selected from the group consisting of O, S, and N.

17. The compound according to claim 16 wherein the compound is selected from the group consisting of:

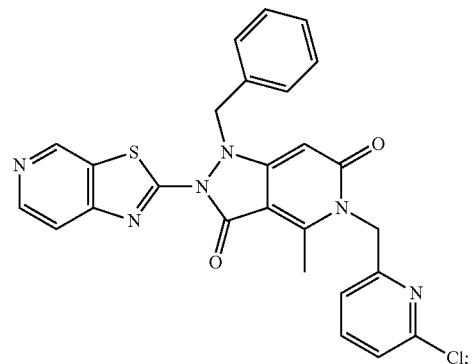

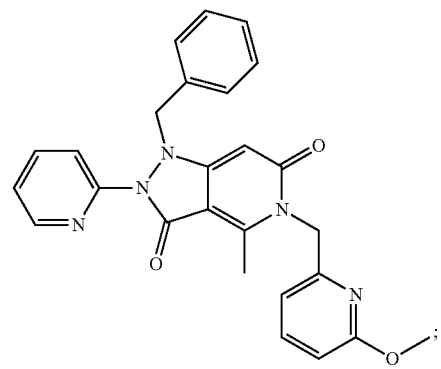

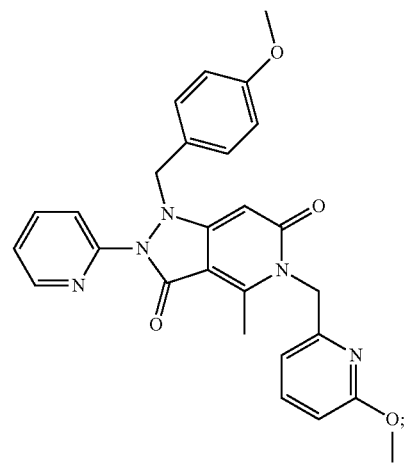

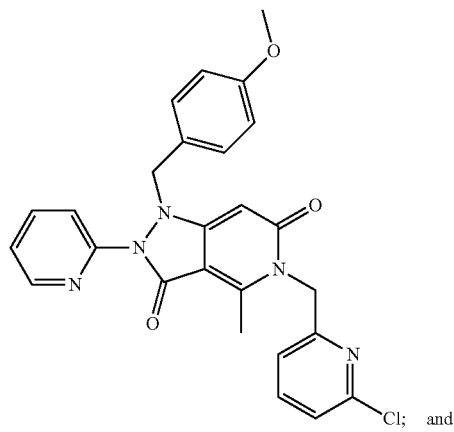
and
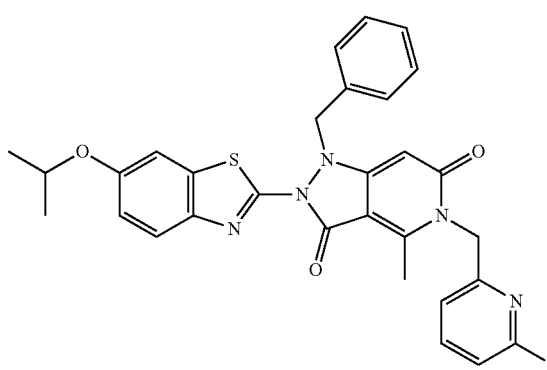
18. A pharmaceutical composition comprising the compound of claim 16 and a pharmaceutically acceptable carrier, vehicle, or excipient.
19. The pharmaceutical composition according to claim 18 wherein the compound is selected from the group consisting of:
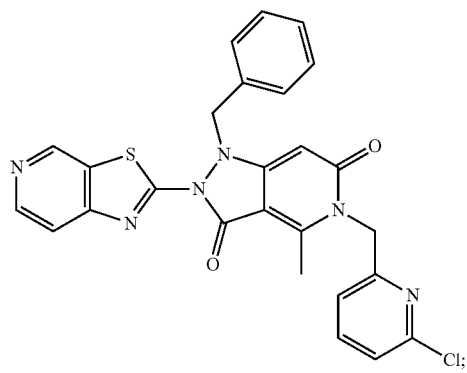
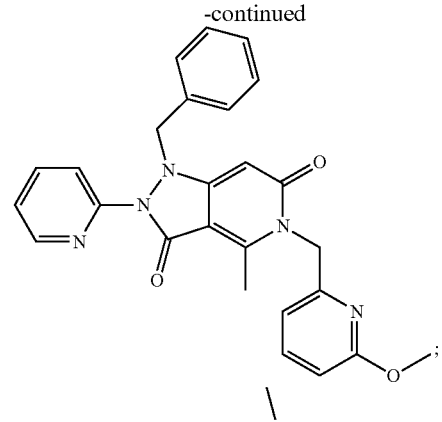
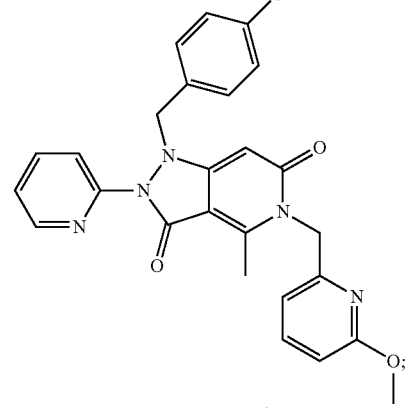
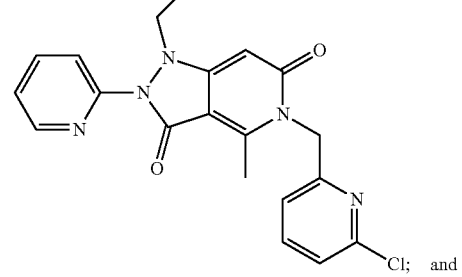
and
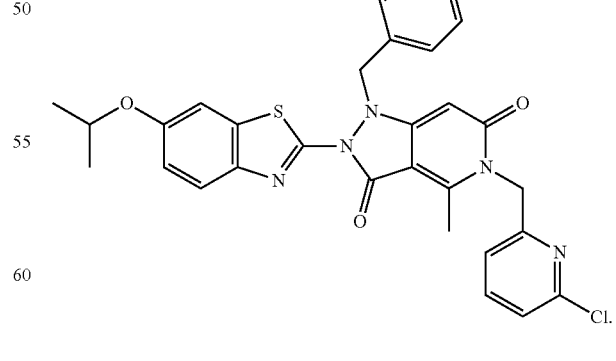
* * * * *